United States Patent
Vogt et al.

(10) Patent No.: US 10,966,426 B2
(45) Date of Patent: Apr. 6, 2021

(54) HERBICIDAL COMPOSITIONS COMPRISING PHENYLPYRIMIDINES

(71) Applicant: BASF SE, Ludwigshafen am Rhein (DE)

(72) Inventors: Florian Vogt, Ludwigshafen (DE); Matthias Witschel, Ludwigshafen (DE); Tobias Seiser, Limburgerhof (DE); Thomas Seitz, Ludwigshafen (DE); Gerd Kraemer, Limburgerhof (DE); Peter Dombo, Limburgerhof (DE)

(73) Assignee: BASF SE, Ludwigshafen (DE)

( * ) Notice: Subject to any disclaimer, the term of this patent is extended or adjusted under 35 U.S.C. 154(b) by 71 days.

(21) Appl. No.: 16/318,969

(22) PCT Filed: Jul. 7, 2017

(86) PCT No.: PCT/EP2017/067065
§ 371 (c)(1),
(2) Date: Jan. 18, 2019

(87) PCT Pub. No.: WO2018/015180
PCT Pub. Date: Jan. 25, 2018

(65) Prior Publication Data
US 2019/0297886 A1 Oct. 3, 2019

(30) Foreign Application Priority Data

Jul. 20, 2016 (EP) .................................... 16180303

(51) Int. Cl.
| | | |
|---|---|---|
| *A01N 25/02* | (2006.01) | |
| *A01N 25/08* | (2006.01) | |
| *A01N 25/32* | (2006.01) | |
| *A01N 43/54* | (2006.01) | |
| *A01N 43/70* | (2006.01) | |
| *A01N 43/56* | (2006.01) | |
| *A01N 43/80* | (2006.01) | |
| *A01N 43/82* | (2006.01) | |
| *A01N 43/88* | (2006.01) | |
| *A01N 43/84* | (2006.01) | |
| *A01N 47/06* | (2006.01) | |
| *A01N 47/12* | (2006.01) | |
| *A01N 47/30* | (2006.01) | |
| *A01N 47/36* | (2006.01) | |
| *C07D 239/26* | (2006.01) | |

(52) U.S. Cl.
CPC ............. *A01N 43/54* (2013.01); *A01N 25/32* (2013.01); *C07D 239/26* (2013.01); *A01N 25/02* (2013.01); *A01N 25/08* (2013.01)

(58) Field of Classification Search
None
See application file for complete search history.

(56) References Cited

U.S. PATENT DOCUMENTS 10,420,341 B2 * 9/2019 Vogt ..................... C07D 239/30

FOREIGN PATENT DOCUMENTS

| EP | 136976 A | * | 4/1985 |
|---|---|---|---|
| WO | 1997006150 A1 | | 2/1997 |
| WO | 2000073278 A2 | | 12/2000 |
| WO | 2016120116 A1 | | 8/2016 |
| WO | 20160120355 A2 | | 8/2016 |
| WO | 2018019552 A1 | | 2/2018 |
| WO | 2018019554 A1 | | 2/2018 |
| WO | 2018019555 A1 | | 2/2018 |
| WO | 2018019574 A1 | | 2/2018 |
| WO | 2018019765 A1 | | 2/2018 |
| WO | 2018019860 A1 | | 2/2018 |

OTHER PUBLICATIONS

The Agrochemical Handbook, 3rd edition, Royal Society of Chemistry, 1991, Cinmethylin (Year: 1991).*
European Search Report for EP Patent Application No. 16180303.6, dated Oct. 13, 2016, 3 pages.
International Search Report for PCT Patent Application No. PCT/EP2017/067065, dated Aug. 7, 2017, 3 pages.

* cited by examiner

*Primary Examiner* — Alton N Pryor
(74) *Attorney, Agent, or Firm* — Marshall, Gerstein & Borun LLP

(57) ABSTRACT

The present invention relates to herbicidal compositions comprising at least one phenylpyrimidine of formula (I)

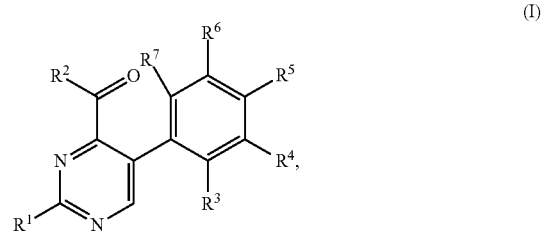

or their agriculturally acceptable salts or derivatives, wherein the variables are defined according to the description,
and at least one further compound selected from herbicidally active compounds and safeners.

18 Claims, No Drawings

HERBICIDAL COMPOSITIONS COMPRISING PHENYLPYRIMIDINES

This application is a National Stage application of International Application No. PCT/EP2017/067065, filed Jul. 7, 2017. This application also claims priority under 35 U.S.C. § 119 to European Patent Application No. 16180303.6, filed Jul. 20, 2016.

The present invention relates to herbicidal compositions comprising at least one phenylpyrimidine of formula (I) and at least one further compound selected from herbicidally active compounds and safeners.

In the case of crop protection compositions, it is desirable in principle to increase the specific activity of an active compound and the reliability of the effect. It is particularly desirable for the crop protection composition to control the harmful plants effectively, but at the same time to be compatible with the useful plants in question. Also desirable is a broad spectrum of activity allowing the simultaneous control of harmful plants. Frequently, this cannot be achieved using a single herbicidally active compound.

With many highly effective herbicides, there is the problem that their compatibility with useful plants, in particular dicotyledonous crop plants, such as cotton, oilseed rape and graminaceous plants, such as barley, millet, corn, rice, wheat and sugar cane, is not always satisfactory, i.e. in addition to the harmful plants, the crop plants, too, are damaged on a scale which cannot be tolerated. By reducing the application rates, the useful plants are spared; however, naturally, the extent of the control of harmful plants decreases, too.

Frequently, it is a problem that herbicides can only be applied within a narrow time frame in order to achieve the desired herbicidal action, which time frame may be unpredictably influenced by weather conditions.

It is known that special combinations of different specifically active herbicides result in enhanced activity of an herbicide component in the sense of a synergistic effect. In this manner, it is possible to reduce the application rates of herbicidally active compounds required for controlling the harmful plants.

Furthermore, it is known that in some cases joint application of specifically acting herbicides with organic active compounds, some of which may also have herbicidal activity, allows better crop plant compatibility to be achieved. In these cases, the active compounds act as antidotes or antagonists and are also referred to as safeners, since they reduce or even prevent damage to the crop plants.

Some compounds having a 5-phenyl pyrimidine moiety have been described for example in WO 2000/073278 as being antagonists of the Neurokinin 1 receptor and thus having pharmaceutical properties.

It is an object of the present invention to provide herbicidal compositions which are highly active against unwanted harmful plants. At the same time, the compositions should have good compatibility with useful plants. In addition, the compositions according to the invention should have a broad spectrum of activity.

This and further objects are achieved by the herbicidal compositions below.

Accordingly, the present invention relates to herbicidal compositions comprising:

A) at least one phenylpyrimidine of formula (I)

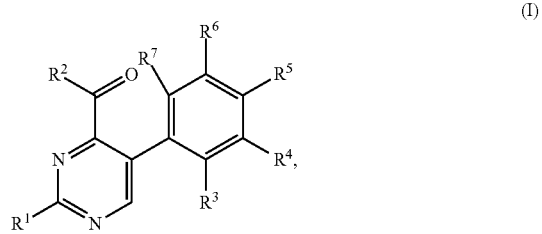

wherein in formula (I) the variables have the following meanings:

$R^1$ $C_1$-$C_6$-alkyl, $C_1$-$C_6$-haloalkyl, hydroxy-$C_1$-$C_6$-alkyl, $C_2$-$C_6$-alkenyl, $C_2$-$C_6$-haloalkenyl, $C_2$-$C_6$-alkynyl, $C_3$-$C_6$-haloalkynyl, $C_1$-$C_6$-alkoxy-$C_1$-$C_6$-alkyl, $C_1$-$C_6$-alkoxy, $C_3$-$C_6$-alkenyloxy, $C_3$-$C_6$-haloalkenyloxy, $C_3$-$C_6$-alkynyloxy, $C_3$-$C_6$-haloalkynyloxy, $C_1$-$C_6$-haloalkoxy, $C_3$-$C_6$-cycloalkoxy, $C_3$-$C_6$-halocycloalkoxy, $C_3$-$C_6$-cycloalkenyloxy, $C_3$-$C_6$-halocycloalkenyloxy, $C_1$-$C_6$-alkylthio, $C_1$-$C_6$-haloalkylthio, ($C_1$-$C_6$-alkyl)amino, di($C_1$-$C_6$-alkyl)amino, $C_1$-$C_6$-alkylsulfinyl, $C_1$-$C_6$-alkylsulfonyl, $C_3$-$C_6$-cycloalkyl, $C_3$-$C_6$-cycloalkenyl, $C_3$-$C_6$-halocycloalkyl, $C_3$-$C_6$-halocycloalkenyl, [1-($C_1$-$C_6$-alkyl)]-$C_3$-$C_6$-cycloalkyl, [1-($C_2$-$C_6$-alkenyl)]-$C_3$-$C_6$-cycloalkyl, [1-($C_2$-$C_6$-alkynyl)]-$C_3$-$C_6$-cycloalkyl, [1-($C_1$-$C_6$-haloalkyl)]-$C_3$-$C_6$-cycloalkyl, [1-($C_2$-$C_6$-haloalkenyl)]-$C_3$-$C_6$-cycloalkyl, [1-($C_3$-$C_6$-haloalkynyl)]-$C_3$-$C_6$-cycloalkyl, $C_3$-$C_6$-cycloalkyl-$C_1$-$C_6$-alkyl, $C_3$-$C_6$-cycloalkyl-$C_1$-$C_6$-haloalkyl, $C_3$-$C_6$-cycloalkyl-$C_1$-$C_6$-alkoxy, $C_3$-$C_6$-cycloalkyl-$C_1$-$C_6$-haloalkoxy, phenyl, 5- or 6-membered heteroaryl, or 3- to 6-membered heterocyclyl, wherein the cycloalkyl, phenyl, heteroaryl and heterocyclyl substituents independently of one another are unsubstituted or substituted by one to five substituents selected from the group consisting of halogen, CN, $NO_2$, $C_1$-$C_6$-alkyl, $C_1$-$C_6$-haloalkyl, $C_1$-$C_6$-alkoxy or $C_1$-$C_6$-haloalkoxy;

$R^2$ H, halogen, $C_1$-$C_6$-alkyl, $C_1$-$C_6$-haloalkyl, $C_1$-$C_6$-alkylcarbonyl-$C_1$-$C_6$-alkyl, $C_1$-$C_6$-alkoxycarbonyl-$C_1$-$C_6$-alkyl, $C_1$-$C_6$-haloalkylcarbonyl-$C_1$-$C_6$-alkyl, $C_1$-$C_6$-haloalkoxycarbonyl-$C_1$-$C_6$-alkyl, $C_1$-$C_6$-alkylcarbonyl-$C_1$-$C_6$-haloalkyl, $C_1$-$C_6$-alkoxycarbonyl-$C_1$-$C_6$-haloalkyl, $C_1$-$C_6$-haloalkylcarbonyl-$C_1$-$C_6$-haloalkyl, $C_1$-$C_6$-haloalkoxycarbonyl-$C_1$-$C_6$-haloalkyl, OH, $C_1$-$C_6$-alkoxy, $C_1$-$C_6$-alkoxy-$C_1$-$C_6$-alkoxy, $C_1$-$C_6$-haloalkoxy-$C_1$-$C_6$-alkoxy, $C_1$-$C_6$-alkoxy-$C_1$-$C_6$-haloalkoxy, $C_1$-$C_6$-haloalkoxy-$C_1$-$C_6$-haloalkoxy, $C_1$-$C_6$-alkoxy-$C_1$-$C_6$-alkoxy-$C_1$-$C_6$-alkoxy, $C_1$-$C_6$-haloalkoxy, $C_1$-$C_6$-cyanoalkoxy, $C_1$-$C_6$-hydroxyalkoxy, $C_3$-$C_6$-alkenyloxy, $C_2$-$C_3$-alkenyloxy-$C_1$-$C_6$-alkoxy, $C_3$-$C_6$-haloalkenyloxy-$C_1$-$C_6$-haloalkoxy, $C_3$-$C_6$-alkenyloxy-$C_1$-$C_6$-haloalkoxy, $C_3$-$C_6$-haloalkenyloxy, $C_3$-$C_6$-alkynyloxy, $C_3$-$C_6$-haloalkynyloxy, $C_3$-$C_6$-alkynyloxy-$C_1$-$C_6$-alkoxy, $C_3$-$C_6$-haloalkynyloxy-$C_1$-$C_6$-haloalkoxy, $C_3$-$C_6$-alkynyloxy-$C_1$-$C_6$-haloalkoxy, $C_3$-$C_6$-alkynyloxy-$C_3$-$C_6$-alkenyloxy, $C_3$-$C_6$-haloalkynyloxy-$C_3$-$C_6$-alkenyloxy, $C_3$-$C_6$-alkynyloxy-$C_3$-$C_6$-haloalkenyloxy, $C_3$-$C_6$-haloalkynyloxy-$C_3$-$C_6$-haloalkenyloxy, $C_3$-$C_6$-alkynyloxy-$C_3$-$C_6$-alkynyloxy, $C_3$-$C_6$-haloalkynyloxy-$C_3$-$C_6$-alkynyloxy, $C_3$-$C_6$-alkynyloxy-$C_3$-$C_6$-haloalkynyloxy, $C_3$-$C_6$-haloalkynyloxy-$C_3$-$C_6$-haloalkynyloxy, ($C_1$-$C_6$-alkyl)carbonyl-$C_1$-$C_6$-alkoxy, ($C_1$-$C_6$-haloalkyl)carbonyl-$C_1$-$C_6$-haloalkoxy, ($C_1$-$C_6$-haloalkyl)carbonyl-$C_1$-$C_6$-alkoxy, ($C_1$-$C_6$-alkyl)carbonyl-$C_1$-$C_6$-haloalkoxy, ($C_1$-$C_6$- alkoxy)carbonyl-$C_1$-$C_6$-alkoxy, ($C_1$-$C_6$-haloalkoxy)carbonyl-$C_1$-$C_6$-alkoxy, ($C_1$-$C_6$-alkoxy)carbonyl-$C_1$-$C_6$-haloalkoxy, ($C_1$-$C_6$-haloalkoxy)carbonyl-$C_1$-$C_6$-haloalkoxy, ($C_1$-$C_6$-alkoxy-$C_1$-$C_6$-alkyl)carbonyl-$C_1$-$C_6$-alkoxy, ($C_1$-$C_6$-haloalkoxy-$C_1$-$C_6$-alkyl)carbonyl-$C_1$-$C_6$-alkoxy, ($C_1$-$C_6$-alkoxy-$C_1$-$C_6$-haloalkyl)carbonyl-$C_1$-$C_6$-alkoxy, ($C_1$-$C_6$-alkoxy-$C_1$-$C_6$-alkyl)carbonyl-$C_1$-$C_6$-haloalkoxy, ($C_1$-$C_6$-haloalkoxy-$C_1$-$C_6$-haloalkyl)carbonyl-$C_1$-$C_6$-alkoxy, ($C_1$-$C_6$-haloalkoxy-$C_1$-$C_6$-alkyl)carbonyl-$C_1$-$C_6$-haloalkoxy, ($C_1$-$C_6$-alkoxy-$C_1$-$C_6$-haloalkyl)carbonyl-$C_1$-$C_6$-haloalkoxy, ($C_1$-$C_6$-haloalkoxy-$C_1$-$C_6$-haloalkyl)carbonyl-$C_1$-$C_6$-haloalkoxy, ($C_1$-$C_6$-alkylthio)carbonyl-$C_1$-$C_6$-alkoxy, ($C_1$-$C_6$-haloalkylthio)carbonyl-$C_1$-$C_6$-alkoxy, ($C_1$-$C_6$-alkylthio)carbonyl-$C_1$-$C_6$-haloalkoxy, ($C_1$-$C_6$-haloalkylthio)carbonyl-$C_1$-$C_6$-haloalkoxy, ($C_1$-$C_6$-alkylthio-$C_1$-$C_6$-alkyl)carbonyl-$C_1$-$C_6$-alkoxy, ($C_1$-$C_6$-haloalkylthio-$C_1$-$C_6$-alkyl)carbonyl-$C_1$-$C_6$-alkoxy, ($C_1$-$C_6$-alkylthio-$C_1$-$C_6$-haloalkyl)carbonyl-$C_1$-$C_6$-alkoxy, ($C_1$-$C_6$-alkylthio-$C_1$-$C_6$-alkyl)carbonyl-$C_1$-$C_6$-haloalkoxy, ($C_1$-$C_6$-haloalkylthio-$C_1$-$C_6$-haloalkyl)carbonyl-$C_1$-$C_6$-alkoxy, ($C_1$-$C_6$-haloalkylthio-$C_1$-$C_6$-alkyl)carbonyl-$C_1$-$C_6$-haloalkoxy, ($C_1$-$C_6$-alkylthio-$C_1$-$C_6$-haloalkyl)carbonyl-$C_1$-$C_6$-haloalkoxy, ($C_1$-$C_6$-haloalkylthio-$C_1$-$C_6$-haloalkyl)carbonyl-$C_1$-$C_6$-haloalkoxy, $C_3$-$C_6$-cycloalkoxy, $C_3$-$C_6$-halocycloalkoxy, ($C_3$-$C_6$-cycloalkyl)$C_1$-$C_6$-alkoxy, ($C_3$-$C_6$-halocycloalkyl)$C_1$-$C_6$-alkoxy, ($C_3$-$C_6$-cycloalkyl)$C_1$-$C_6$-haloalkoxy, ($C_3$-$C_6$-halocycloalkyl)$C_1$-$C_6$-haloalkoxy, aminocarbonyl-$C_1$-$C_6$-alkoxy, aminocarbonyl-$C_1$-$C_6$-haloalkoxy, N—($C_1$-$C_6$-alkyl)-aminocarbonyl-$C_1$-$C_6$-alkoxy, N—($C_1$-$C_6$-alkyl)-aminocarbonyl-$C_1$-$C_6$-haloalkoxy, N,N-di($C_1$-$C_6$-alkyl)-aminocarbonyl-$C_1$-$C_6$-alkoxy, N,N-di($C_1$-$C_6$-alkyl)-aminocarbonyl-$C_1$-$C_6$-haloalkoxy, (di(phenyl)C=N—O, (phenyl)($C_1$-$C_6$-alkyl)C=N—O, [di($C_1$-$C_6$-alkyl)]C=N—O, ($C_1$-$C_6$-alkyl)$_3$-silyl-$C_1$-$C_6$-alkoxy, $C_1$-$C_6$-alkylthio, $C_1$-$C_6$-haloalkylthio, $C_1$-$C_6$-alkoxy-$C_1$-$C_6$-alkylthio, $C_1$-$C_6$-haloalkoxy-$C_1$-$C_6$-alkylthio, $C_1$-$C_6$-alkoxy-$C_1$-$C_6$-haloalkylthio, $C_1$-$C_6$-haloalkoxy-$C_1$-$C_6$-haloalkylthio, $C_1$-$C_6$-alkoxy-$C_1$-$C_6$-alkoxy-$C_1$-$C_6$-alkylthio, $C_1$-$C_6$-cyanoalkylthio, $C_2$-$C_6$-alkenylthio, $C_2$-$C_6$-haloalkenylthio, $C_3$-$C_6$-alkenyloxy-$C_1$-$C_6$-alkylthio, $C_3$-$C_6$-haloalkenyloxy-$C_1$-$C_6$-alkylthio, $C_3$-$C_6$-alkenyloxy-$C_1$-$C_6$-haloalkylthio, $C_3$-$C_6$-haloalkenyloxy-$C_1$-$C_6$-haloalkylthio, $C_2$-$C_6$-alkynylthio, $C_2$-$C_6$-haloalkynylthio, $C_3$-$C_6$-alkynyloxy-$C_1$-$C_6$-alkylthio, $C_3$-$C_6$-haloalkynyloxy-$C_1$-$C_6$-haloalkylthio, $C_3$-$C_6$-alkynyloxy-$C_1$-$C_6$-haloalkylthio, $C_3$-$C_6$-alkynyloxy-$C_2$-$C_6$-alkenylthio, $C_3$-$C_6$-haloalkynyloxy-$C_2$-$C_6$-alkenylthio, $C_3$-$C_6$-alkynyloxy-$C_2$-$C_6$-haloalkenylthio, $C_3$-$C_6$-haloalkynyloxy-$C_2$-$C_6$-haloalkenylthio, $C_3$-$C_6$-alkynyloxy-$C_2$-$C_6$-alkynylthio, $C_3$-$C_6$-haloalkynyloxy-$C_2$-$C_6$-alkynylthio, $C_3$-$C_6$-alkynyloxy-$C_2$-$C_6$-haloalkynylthio, $C_3$-$C_6$-haloalkynyloxy-$C_2$-$C_6$-haloalkynylthio, ($C_1$-$C_6$-alkyl)carbonyl-$C_1$-$C_6$-alkylthio, ($C_1$-$C_6$-haloalkyl)carbonyl-$C_1$-$C_6$-alkylthio, ($C_1$-$C_6$-alkyl)carbonyl-$C_1$-$C_6$-haloalkylthio, ($C_1$-$C_6$-haloalkyl)carbonyl-$C_1$-$C_6$-haloalkylthio, ($C_1$-$C_6$-alkoxy)carbonyl-$C_1$-$C_6$-alkylthio, ($C_1$-$C_6$-haloalkoxy)carbonyl-$C_1$-$C_6$-alkylthio, ($C_1$-$C_6$-alkoxy)carbonyl-$C_1$-$C_6$-haloalkylthio, ($C_1$-$C_6$-haloalkoxy)carbonyl-$C_1$-$C_6$-haloalkylthio, ($C_1$-$C_6$-alkoxy-$C_1$-$C_6$-alkyl)carbonyl-$C_1$-$C_6$-alkylthio, ($C_1$-$C_6$-haloalkoxy-$C_1$-$C_6$-alkyl)carbonyl-$C_1$-$C_6$-alkylthio, ($C_1$-$C_6$-alkoxy-$C_1$-$C_6$-haloalkyl)carbonyl-$C_1$-$C_6$-alkylthio, ($C_1$-$C_6$-alkoxy-$C_1$-$C_6$-alkyl)carbonyl-$C_1$-$C_6$-haloalkylthio, ($C_1$-$C_6$-haloalkoxy-$C_1$-$C_6$-haloalkyl)carbonyl-$C_1$-$C_6$-alkylthio, ($C_1$-$C_6$-haloalkoxy-$C_1$-$C_6$-alkyl)carbonyl-$C_1$-$C_6$-haloalkylthio, ($C_1$-$C_6$-alkoxy-$C_1$-$C_6$-haloalkyl)carbonyl-$C_1$-$C_6$-haloalkylthio, ($C_1$-$C_6$-haloalkoxy-$C_1$-$C_6$-haloalkyl)carbonyl-$C_1$-$C_6$-haloalkylthio, ($C_1$-$C_6$-alkylthio)carbonyl-$C_1$-$C_6$-alkylthio, ($C_1$-$C_6$-haloalkylthio)carbonyl-$C_1$-$C_6$-alkylthio, ($C_1$-$C_6$-alkylthio)carbonyl-$C_1$-$C_6$-haloalkylthio, ($C_1$-$C_6$-haloalkylthio)carbonyl-$C_1$-$C_6$-haloalkylthio, ($C_1$-$C_6$-alkylthio-$C_1$-$C_6$-alkyl)carbonyl-$C_1$-$C_6$-alkylthio, ($C_1$-$C_6$-haloalkylthio-$C_0$-$C_6$-alkyl)carbonyl-$C_1$-$C_6$-alkylthio, ($C_1$-$C_6$-alkylthio-$C_1$-$C_6$-haloalkyl)carbonyl-$C_1$-$C_6$-alkylthio, ($C_1$-$C_6$-alkylthio-$C_1$-$C_6$-alkyl)carbonyl-$C_1$-$C_6$-haloalkylthio, ($C_1$-$C_6$-haloalkylthio-$C_1$-$C_6$-haloalkyl)carbonyl-$C_1$-$C_6$-alkylthio, ($C_1$-$C_6$-haloalkylthio-$C_1$-$C_6$-alkyl)carbonyl-$C_1$-$C_6$-haloalkylthio, ($C_1$-$C_6$-alkylthio-$C_1$-$C_6$-haloalkyl)carbonyl-$C_1$-$C_6$-haloalkylthio, ($C_1$-$C_6$-haloalkylthio-$C_1$-$C_6$-haloalkyl)carbonyl-$C_1$-$C_6$-haloalkylthio, $C_3$-$C_6$-cycloalkylthio, $C_3$-$C_6$-halocycloalkylthio, ($C_3$-$C_6$-cycloalkyl)$C_1$-$C_6$-alkylthio, ($C_3$-$C_6$-cycloalkyl)$C_1$-$C_6$-haloalkylthio, ($C_3$-$C_6$-halocycloalkyl)$C_1$-$C_6$-alkylthio, ($C_3$-$C_6$-halocycloalkyl)$C_1$-$C_6$-haloalkylthio, aminocarbonyl-$C_1$-$C_6$-alkylthio, aminocarbonyl-$C_1$-$C_6$-haloalkylthio, N—($C_1$-$C_6$-alkyl)-aminocarbonyl-$C_1$-$C_6$-alkylthio, N—($C_1$-$C_6$-haloalkyl)-aminocarbonyl-$C_1$-$C_6$-alkylthio, N—($C_1$-$C_6$-alkyl)-aminocarbonyl-$C_1$-$C_6$-haloalkylthio, N—($C_1$-$C_6$-haloalkyl)-aminocarbonyl-$C_1$-$C_6$-haloalkylthio, N,N-di($C_1$-$C_6$-alkyl)-aminocarbonyl-$C_1$-$C_6$-alkylthio, N,N-di($C_1$-$C_6$-haloalkyl)-aminocarbonyl-$C_1$-$C_6$-alkylthio, N,N-di($C_1$-$C_6$-alkyl)-aminocarbonyl-$C_1$-$C_6$-haloalkylthio, N,N-di($C_1$-$C_6$-haloalkyl)-aminocarbonyl-$C_1$-$C_6$-haloalkylthio, $NH_2$, ($C_1$-$C_6$-alkyl)amino, hydroxyamino, ($C_1$-$C_6$-alkoxy)amino, ($C_3$-$C_6$-cycloalkoxy)amino, ($C_1$-$C_6$-alkyl)sulfinylamino, ($C_1$-$C_6$-alkyl)sulfonylamino, (amino)sulfinylamino, [($C_1$-$C_6$-alkyl)amino]sulfinylamino, (amino)sulfonylamino, [($C_1$-$C_6$-alkyl)amino]sulfonylamino, [di($C_1$-$C_6$-alkyl)amino]sulfonylamino, di($C_1$-$C_6$-alkyl)amino, (hydroxy)($C_1$-$C_6$-alkyl)amino, (hydroxy)($C_1$-$C_6$-cycloalkyl)amino, ($C_1$-$C_6$-alkoxy)($C_1$-$C_6$-alkyl)amino, ($C_1$-$C_6$-alkoxy)($C_3$-$C_6$-cycloalkyl)amino, ($C_3$-$C_6$-cycloalkoxy)($C_1$-$C_6$-alkyl)amino, ($C_3$-$C_6$-cycloalkoxy)($C_3$-$C_6$-cycloalkyl)amino, [($C_1$-$C_6$-alkyl)sulfinyl]($C_1$-$C_6$-alkyl)amino, [($C_1$-$C_6$-alkyl)sulfonyl]($C_1$-$C_6$-alkyl)amino, [di($C_1$-$C_6$-alkyl)amino]sulfinylamino, [di($C_1$-$C_6$-alkyl)amino]sulfonylamino, phenyloxy, phenyl-$C_1$-$C_6$-alkoxy, phenylthio, phenyl-$C_1$-$C_6$-alkylthio, phenylamino, ($C_1$-$C_6$-alkyl)(phenyl)amino, (heteroaryl)oxy, heteroaryl-$C_1$-$C_6$-alkoxy, (heterocyclyl)oxy, heterocyclyl-$C_1$-$C_6$-alkoxy, wherein the phenyl, heteroaryl and heterocyclyl substituents independently from one another are unsubstituted or substituted by one to five substituents selected from the group consisting of halogen, CN, $NO_2$, $C_1$-$C_6$-alkyl, $C_1$-$C_6$-haloalkyl, $C_1$-$C_6$-alkoxy or $C_1$-$C_6$-haloalkoxy;

$R^3$ halogen, CN, $NO_2$, $C_1$-$C_6$-alkyl, $C_1$-$C_6$-haloalkyl, $C_1$-$C_6$-alkylcarbonyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy, $C_1$-$C_6$-haloalkoxy, $C_3$-$C_6$-alkenyloxy, $C_3$-$C_6$-haloalkenyloxy, $C_3$-$C_6$-alkynyloxy, $C_3$-$C_6$-haloalkynyloxy, $C_1$-$C_6$-alkoxy-$C_1$-$C_6$-alkoxy, hydroxycarbonyl, $C_1$-$C_6$-alkoxycarbonyl, $C_1$-$C_6$-alkylthio, $C_1$-$C_6$-haloalkylthio, $NH_2$, ($C_1$-$C_6$-alkyl)amino, di($C_1$-$C_6$-alkyl)amino, ($C_1$-$C_6$-alkyl)sulfinyl, ($C_1$-$C_6$-alkyl)sulfonyl, $C_3$-$C_6$-cycloalkyl, ($C_3$-$C_6$-cycloalkyl)oxy or phenyl;

wherein the cycloalkyl, (cycloalkyl)oxy, or phenyl substituents independently from one another are unsubstituted or substituted by one to five substituents selected from the group consisting of halogen, CN, $NO_2$, $C_1$-$C_6$-alkyl, $C_1$-$C_6$-haloalkyl, $C_1$-$C_6$-alkoxy or $C_1$-$C_6$-haloalkoxy;
and $R^4$, $R^5$, $R^6$ and $R^7$ independently of one another H, halogen, CN, $NO_2$, $C_1$-$C_6$-alkyl, $C_1$-$C_6$-haloalkyl, $C_1$-$C_6$-alkylcarbonyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy, $C_1$-$C_6$-haloalkoxy, $C_3$-$C_6$-alkenyloxy, $C_3$-$C_6$-haloalkenyloxy, $C_3$-$C_6$-alkynyloxy, $C_3$-$C_6$-haloalkynyloxy, $C_1$-$C_6$-alkoxy-$C_1$-$C_6$-alkoxy, hydroxycarbonyl, $C_1$-$C_6$-alkoxycarbonyl, $C_1$-$C_6$-alkylthio, $C_1$-$C_6$-haloalkylthio, $NH_2$, ($C_1$-$C_6$-alkyl)amino, di($C_1$-$C_6$-alkyl)amino, ($C_1$-$C_6$-alkyl)sulfinyl, ($C_1$-$C_6$-alkyl)sulfonyl, $C_3$-$C_6$-cycloalkyl, ($C_3$-$C_6$-cycloalkyl)oxy or phenyl;
  wherein the cycloalkyl, (cycloalkyl)oxy, or phenyl substituents independently from one another are unsubstituted or substituted by one to five substituents selected from the group consisting of halogen, CN, $NO_2$, $C_1$-$C_6$-alkyl, $C_1$-$C_6$-haloalkyl, $C_1$-$C_6$-alkoxy or $C_1$-$C_6$-haloalkoxy;
  including agriculturally acceptable salts or derivatives of the compounds of formula (I) having a carboxyl group;
and at least one further active compound selected from
B) herbicides of class b1) to b15):
  b1) lipid biosynthesis inhibitors;
  b2) acetolactate synthase inhibitors (ALS inhibitors);
  b3) photosynthesis inhibitors;
  b4) protoporphyrinogen-IX oxidase inhibitors,
  b5) bleacher herbicides;
  b6) enolpyruvyl shikimate 3-phosphate synthase inhibitors (EPSP inhibitors);
  b7) glutamine synthetase inhibitors;
  b8) 7,8-dihydropteroate synthase inhibitors (DHP inhibitors);
  b9) mitosis inhibitors;
  b10) inhibitors of the synthesis of very long chain fatty acids (VLCFA inhibitors);
  b11) cellulose biosynthesis inhibitors;
  b12) decoupler herbicides;
  b13) auxinic herbicides;
  b14) auxin transport inhibitors; and
  b15) other herbicides selected from the group consisting of bromobutide, chlorflurenol, chlorflurenol-methyl, cinmethylin, cumyluron, dalapon, dazomet, difenzoquat, difenzoquat-metilsulfate, dimethipin, DSMA, dymron, endothal and its salts, etobenzanid, flamprop, flamprop-isopropyl, flamprop-methyl, flamprop-M-isopropyl, flamprop-M-methyl, flurenol, flurenol-butyl, flurprimidol, fosamine, fosamine-ammonium, indanofan, indaziflam, maleic hydrazide, mefluidide, metam, methiozolin, methyl azide, methyl bromide, methyldymron, methyl iodide, MSMA, oleic acid, oxaziclomefone, pelargonic acid, pyributicarb, quinoclamine, triaziflam, tridiphane and 6-chloro-3-(2-cyclopropyl-6-methylphenoxy)-4-pyridazinol and its salts and esters;
including their agriculturally acceptable salts or derivatives.

In one embodiment of the present invention the compositions according to the present invention comprise at least one pyrimidine compound of formula (I) (component A) and at least one further active compound selected from herbicides B, preferably herbicides B of class b1) to b15), and safeners C (component C).

The invention relates in particular to compositions in the form of herbicidal active agrochemical compositions comprising a herbicidally effective amount of an active compound combination comprising at least one phenylpyrimidine of formula (I) and at least one further compound selected from the herbicides B and the safeners C, as defined above, and also at least one liquid and/or solid carrier and/or one or more surfactants and, if desired, one or more further auxiliaries customary for agrochemical compositions.

The invention also relates to compositions in the form of a agrochemical composition formulated as a 1-component composition comprising an active compound combination comprising at least one phenylpyrimidine of formula (I) and at least one further active compound selected from the herbicides B and the safeners C, and at least one solid or liquid carrier and/or one or more surfactants and, if desired, one or more further auxiliaries customary for agrochemical compositions.

The invention also relates to compositions in the form of a agrochemical composition formulated as a 2-component composition comprising a first component comprising at least one phenylpyrimidine of formula (I), a solid or liquid carrier and/or one or more surfactants, and a second component comprising at least one further active compound selected from the herbicides B and safeners C, a solid or liquid carrier and/or one or more surfactants, where additionally both components may also comprise further auxiliaries customary for agrochemical compositions.

Surprisingly, the compositions according to the invention comprising at least one phenylpyrimidine of formula (I) and at least one herbicide B have better herbicidal activity, i.e. better activity against harmful plants, than would have been expected based on the herbicidal activity observed for the individual compounds, or a broader activity spectrum. The herbicidal activity to be expected for mixtures based on the individual compound can be calculated using Colby's formula (see below). If the activity observed exceeds the expected additive activity of the individual compounds, synergism is said to be present.

Moreover, the time frame, within which the desired herbicidal action can be achieved, may be expanded by the compositions according to the invention comprising at least one phenylpyrimidine of formula (I) and at least one herbicide B and optionally a safener C. This allows a more flexibly timed application of the compositions according to the present invention in comparison with the single compounds.

The compositions according to the invention comprising both at least phenylpyrimidine of formula (I) and at least one of the compounds mentioned under C also have good herbicidal activity against harmful plants and better compatibility with useful plants.

Surprisingly, the compositions according to the invention comprising at least one phenylpyrimidine of formula (I), at least one herbicide B and at least one of the compounds mentioned under C have better herbicidal activity, i.e. better activity against harmful plants, than would have been expected based on the herbicidal activity observed for the individual compounds, or a broader activity spectrum, and show better compatibility with useful plants than compositions comprising only one compound I and one herbicide B.

The invention furthermore relates to a method for controlling unwanted vegetation, in particular where crop plants are cultivated.

The invention also relates to a method for the desiccation or defoliation of plants.

As used herein, the terms "controlling" and "combating" are synonyms.

As used herein, the terms "undesirable vegetation" and "harmful plants" are synonyms.

If the phenylpyrimidines of formula (I), the herbicidal compounds B and/or the safeners C as described herein are capable of forming geometrical isomers, for example E/Z isomers, it is possible to use both, the pure isomers and mixtures thereof, in the compositions according to the invention.

If the phenylpyrimidines of formula (I), the herbicidal compounds B and/or the safeners C as described herein have one or more centers of chirality and, as a consequence, are present as enantiomers or diastereomers, it is possible to use both, the pure enantiomers and diastereomers and their mixtures, in the compositions according to the invention.

If the phenylpyrimidines of formula (I), the herbicidal compounds B and/or the safeners C as described herein have ionizable functional groups, they can also be employed in the form of their agriculturally acceptable salts. Suitable are, in general, the salts of those cations and the acid addition salts of those acids whose cations and anions, respectively, have no adverse effect on the activity of the active compounds.

Preferred cations are the ions of the alkali metals, preferably of lithium, sodium and potassium, of the alkaline earth metals, preferably of calcium and magnesium, and of the transition metals, preferably of manganese, copper, zinc and iron, further ammonium and substituted ammonium in which one to four hydrogen atoms are replaced by $C_1$-$C_4$-alkyl, hydroxy-$C_1$-$C_4$-alkyl, $C_1$-$C_4$-alkoxy-$C_1$-$C_4$-alkyl, hydroxy-$C_1$-$C_4$-alkoxy-$C_1$-$C_4$-alkyl, phenyl or benzyl, preferably ammonium, methylammonium, isopropylammonium, dimethylammonium, diisopropylammonium, trimethylammonium, heptylammonium, dodecylammonium, tetradecylammonium, tetramethylammonium, tetraethylammonium, tetrabutylammonium, 2-hydroxyethylammonium (olamine salt), 2-(2-hydroxyeth-1-oxy)eth-1-ylammonium (diglycolamine salt), di(2-hydroxyeth-1-yl)ammonium (diolamine salt), tris(2-hydroxyethyl)ammonium (trolamine salt), tris(2-hydroxypropyl)ammonium, benzyltrimethylammonium, benzyltriethylammonium, N,N,N-trimethylethanolammonium (choline salt), furthermore phosphonium ions, sulfonium ions, preferably tri($C_1$-$C_4$-alkyl)sulfonium, such as trimethylsulfonium, and sulfoxonium ions, preferably tri($C_1$-$C_4$-alkyl)sulfoxonium, and finally the salts of polybasic amines such as N,N-bis-(3-aminopropyl)methylamine and diethylenetriamine.

Anions of useful acid addition salts are primarily chloride, bromide, fluoride, iodide, hydrogensulfate, methylsulfate, sulfate, dihydrogenphosphate, hydrogenphosphate, nitrate, bicarbonate, carbonate, hexafluorosilicate, hexafluorophosphate, benzoate and also the anions of $C_1$-$C_4$-alkanoic acids, preferably formate, acetate, propionate and butyrate.

Phenylpyrimidines of formula (I), herbicidal compounds B and/or safeners C as described herein having a carboxyl group can be employed in the form of the acid, in the form of an agriculturally suitable salt as mentioned above or else in the form of an agriculturally acceptable derivative, for example as amides, such as mono- and di-$C_1$-$C_6$-alkylamides or arylamides, as esters, for example as allyl esters, propargyl esters, $C_1$-$C_{10}$-alkyl esters, alkoxyalkyl esters, tefuryl ((tetrahydrofuran-2-yl)methyl) esters and also as thioesters, for example as $C_1$-$C_{10}$-alkylthio esters. Preferred mono- and di-$C_1$-$C_6$-alkylamides are the methyl and the dimethylamides. Preferred arylamides are, for example, the anilides and the 2-chloroanilides. Preferred alkyl esters are, for example, the methyl, ethyl, propyl, isopropyl, butyl, isobutyl, pentyl, mexyl (1-methylhexyl), meptyl (1-methylheptyl), heptyl, octyl or isooctyl (2-ethylhexyl) esters. Preferred $C_1$-$C_4$-alkoxy-$C_1$-$C_4$-alkyl esters are the straight-chain or branched $C_1$-$C_4$-alkoxy ethyl esters, for example the 2-methoxyethyl, 2-ethoxyethyl, 2-butoxyethyl (butotyl), 2-butoxypropyl or 3-butoxypropyl ester. An example of a straight-chain or branched $C_1$-$C_{10}$-alkylthio ester is the ethylthio ester.

Further embodiments of the present invention are evident from the claims, the description and the examples. It is to be understood that the features mentioned above and still to be illustrated below of the subject matter of the invention can be applied not only in the combination given in each particular case but also in other combinations, without leaving the scope of the invention.

The organic moieties mentioned in the definition of the variables $R^1$ to $R^7$, are—like the term halogen—collective terms for individual enumerations of the individual group members. The term halogen denotes in each case fluorine, chlorine, bromine or iodine. All hydrocarbon chains, for example all alkyl, alkenyl, alkynyl, alkoxy chains can be straight-chain or branched, the prefix $C_n$-$C_m$ denoting in each case the possible number of carbon atoms in the group.

Examples of such meanings are:

$C_1$-$C_4$-alkyl: for example $CH_3$, $C_2H_5$, n-propyl, CH($CH_3$)$_2$, n-butyl, CH($CH_3$)—$C_2H_5$, $CH_2$—CH($CH_3$)$_2$ and C($CH_3$)$_3$;

$C_1$-$C_6$-alkyl: $C_1$-$C_4$-alkyl as mentioned above, and also, for example, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably methyl, ethyl, n-propyl, 1-methylethyl, n-butyl, 1,1-dimethylethyl, n-pentyl or n-hexyl;

$C_1$-$C_4$-haloalkyl: $C_1$-$C_4$-alkyl as mentioned above which is partially or fully substituted by fluorine, chlorine, bromine and/or iodine, for example, chloromethyl, dichloromethyl, trichloromethyl, fluoromethyl, difluoromethyl, trifluoromethyl, chlorofluoromethyl, dichlorofluoromethyl, chlorodifluoromethyl, bromomethyl, iodomethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl, nonafluorobutyl, 1,1,2,2,-tetrafluoroethyl and 1-trifluoromethyl-1,2,2,2-tetrafluoroethyl;

$C_1$-$C_6$-haloalkyl: $C_1$-$C_4$-haloalkyl as mentioned above, and also, for example, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl and dodecafluorohexyl;

$C_3$-$C_6$-cycloalkyl: monocyclic saturated hydrocarbons having 3 to 6 ring members, such as cyclopropyl, cyclobutyl, cyclopentyl and cyclohexyl;

$C_2$-$C_6$-alkenyl: for example ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1l-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl; —$C_2$-$C_6$-haloalkenyl: a $C_2$-$C_6$-alkenyl substituent as mentioned above which is partially or fully substituted by fluorine, chlorine, bromine and/or iodine, for example 2-chloroprop-2-en-1-yl, 3-chloroprop-2-en-1-yl, 2,3-dichloroprop-2-en-1-yl, 3,3-dichloroprop-2-en-1-yl, 2,3,3-trichloro-2-en-1-yl, 2,3-dichlorobut-2-en-1-yl, 2-bromoprop-2-en-1-yl, 3-bromoprop-2-en-1-yl, 2,3-dibromoprop-2-en-1-yl, 3,3-dibromoprop-2-en-1-yl, 2,3,3-tribromo-2-en-1-yl or 2,3-dibromobut-2-en-1-yl; —$C_3$-$C_6$-alkynyl: for example 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

$C_2$-$C_6$-alkynyl: $C_3$-$C_6$-alkynyl as mentioned above and also ethynyl;

$C_3$-$C_6$-haloalkynyl: a $C_3$-$C_6$-alkynyl radical as mentioned above which is partially or fully substituted by fluorine, chlorine, bromine and/or iodine, for example 1,1-difluoroprop-2-yn-1-yl, 3-chloroprop-2-yn-1-yl, 3-bromoprop-2-yn-1-yl, 3-iodoprop-2-yn-1-yl, 4-fluorobut-2-yn-1-yl, 4-chlorobut-2-yn-1-yl, 1,1-difluorobut-2-yn-1-yl, 4-iodobut-3-yn-1-yl, 5-fluoropent-3-yn-1-yl, 5-iodopent-4-yn-1-yl, 6-fluorohex-4-yn-1-yl or 6-iodohex-5-yn-1-yl;

$C_1$-$C_4$-alkoxy: for example methoxy, ethoxy, propoxy, 1-methylethoxy butoxy, 1-methylpropoxy, 2-methylpropoxy and 1,1-dimethylethoxy;

$C_1$-$C_6$-alkoxy: $C_1$-$C_4$-alkoxy as mentioned above, and also, for example, pentoxy, 1-methylbutoxy, 2-methylbutoxy, 3-methoxybutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy.

$C_1$-$C_4$-haloalkoxy: a $C_1$-$C_4$-alkoxy radical as mentioned above which is partially or fully substituted by fluorine, chlorine, bromine and/or iodine, i.e., for example, fluoromethoxy, difluoromethoxy, trifluoromethoxy, chlorodifluoromethoxy, bromodifluoromethoxy, 2-fluoroethoxy, 2-chloroethoxy, 2-bromomethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy and nonafluorobutoxy;

$C_1$-$C_6$-haloalkoxy: a $C_1$-$C_4$-haloalkoxy as mentioned above, and also, for example, 5-fluoropentoxy, 5-chloropentoxy, 5-bromopentoxy, 5-iodopentoxy, undecafluoropentoxy, 6-fluorohexoxy, 6-chlorohexoxy, 6-bromohexoxy, 6-iodohexoxy and dodecafluorohexoxy;

$C_1$-$C_4$-alkylthio: for example methylthio, ethylthio, propylthio, 1-methylethylthio, butylthio, 1-methylpropylthio, 2-methylpropylthio and 1,1-dimethylethylthio;

$C_1$-$C_6$-alkylthio: $C_1$-$C_4$-alkylthio as mentioned above, and also, for example, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio;

($C_1$-$C_4$-alkyl)amino: for example methylamino, ethylamino, propylamino, 1-methylethylamino, butylamino, 1-methylpropylamino, 2-methylpropylamino or 1,1-dimethylethylamino;

($C_1$-$C_6$-alkyl)amino: ($C_1$-$C_4$-alkylamino) as mentioned above, and also, for example, pentylamino, 1-methylbutylamino, 2-methylbutylamino, 3-methylbutylamino, 2,2-dimethylpropylamino, 1-ethylpropylamino, hexylamino, 1,1-dimethylpropylamino, 1,2-dimethylpropylamino, 1-methylpentylamino, 2-methylpentylamino, 3-methylpentylamino, 4-methylpentylamino, 1,1-dimethylbutylamino, 1,2-dimethylbutylamino, 1,3-dimethylbutylamino, 2,2-dimethylbutylamino, 2,3-dimethylbutyl-amino 3,3-dimethylbutylamino, 1-ethylbutylamino, 2-ethylbutylamino, 1,1,2-trimethylpropylamino, 1,2,2- trimethyl-propylamino, 1-ethyl-1-methylpropylamino or 1-ethyl-2-methylpropylamino;

di($C_1$-$C_4$-alkyl)amino: for example N,N-dimethylamino, N,N-diethylamino, N,N-di(1-methylethyl)amino, N,N-dipropylamino, N,N-dibutylamino, N,N-di(1-methylpropyl)amino, N,N-di(2-methylpropyl)amino, N,N-di(1,1-dimethylethyl)amino, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl)amino, N-(1,1-dimethylethyl)-N-methylamino, N-ethyl-N-propylamino, N-ethyl-N-(1-methylethyl)amino, N-butyl-N-ethylamino, N-ethyl-N-(1-methylpropyl)amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)amino, N-(1-methylethyl)-N-(2-methylpropyl)amino, N-(1,1-dimethylethyl)-N-(1-methylethyl)amino, N-butyl-N-(1-methylpropyl)amino, N-butyl-N-(2-methylpropyl)amino, N-butyl-N-(1,1-dimethylethyl)amino, N-(1-methylpropyl)-N-(2-methylpropyl)amino, N-(1,1-dimethylethyl)-N-(1-methylpropyl)amino or N-(1,1-dimethylethyl)-N-(2-methylpropyl)amino;

di($C_1$-$C_6$-alkyl)amino: di($C_1$-$C_4$-alkyl)amino as mentioned above, and also, for example, N-methyl-N-pentylamino, N-methyl-N-(1-methylbutyl)amino, N-methyl-N-(2-methylbutyl)amino, N-methyl-N-(3-methylbutyl)amino, N-methyl-N-(2,2-dimethylpropyl)amino, N-methyl-N-(1-ethylpropyl)amino, N-methyl-N-hexylamino, N-methyl-N-(1,1-dimethylpropyl)amino, N-methyl-N-(1,2-dimethylpropyl)amino, N-methyl-N-(1-methylpentyl)amino, N-methyl-N-(2-methylpentyl)amino, N-methyl-N-(3-methylpentyl)amino, N-methyl-N-(4-methylpentyl)amino, N-methyl-N-(1,1-dimethylbutyl)amino, N-methyl-N-(1,2-dimethylbutyl)amino, N-methyl-N-(1,3-dimethylbutyl)amino, N-methyl-N-(2,2-dimethylbutyl)amino, N-methyl-N-(2,3-dimethylbutyl)amino, N-methyl-N-(3,3-dimethylbutyl)amino, N-methyl-N-(1-ethyl butyl)amino, N-methyl-N-(2-ethylbutyl)amino, N-methyl-N-(1,1,2-trimethylpropyl)amino, N-methyl-N-(1,2,2-trimethylpropyl)amino, N-methyl-N-(1-ethyl-1-methylpropyl)amino, N-methyl-N-(1-ethyl-2-methylpropyl)amino, N-ethyl-N-pentylamino, N-ethyl-N-(1-methylbutyl)amino, N-ethyl-N-(2-methylbutyl)amino, N-ethyl-N-(3-methylbutyl)amino, N-ethyl-N-(2,2-dimethylpropyl)amino, N-ethyl-N-(1-ethylpropyl)amino, N-ethyl-N-hexylamino, N-ethyl-N-(1,1-dimethylpropyl)amino, N-ethyl-N-(1,2-dimethylpropyl)amino, N-ethyl-N-(1-methylpentyl)amino, N-ethyl-N-(2-methylpentyl)amino, N-ethyl-N-(3-methylpentyl)amino, N-ethyl-N-(4-methylpentyl)amino, N-ethyl-N-(1,1-dimethylbutyl)amino, N-ethyl-N-(1,2-dimethylbutyl)amino, N-ethyl-N-(1,3-dimethylbutyl)amino, N-ethyl-N-(2,2-dimethylbutyl)amino, N-ethyl-N-(2,3-dimethylbutyl)amino, N-ethyl-N-(3,3-dimethylbutyl)amino, N-ethyl-N-(1-ethylbutyl)amino, N-ethyl-N-(2-ethylbutyl)amino, N-ethyl-N-(1,1,2-trimethylpropyl)amino, N-ethyl-N-(1,2,2-trimethylpropyl)amino, N-ethyl-N-(1-ethyl-1-methylpropyl)amino, N-ethyl-N-(1-ethyl-2-methylpropyl)amino, N-propyl-N-pentylamino, N-butyl-N-pentylamino, N,N-dipentylamino, N-propyl-N-hexylamino, N-butyl-N-hexylamino, N-pentyl-N-hexylamino or N,N-dihexylamino;

$C_1$-$C_6$-alkylsulfinyl ($C_1$-$C_6$-Alkyl-S(=O)—): for example methylsulfinyl, ethylsulfinyl, propylsulfinyl, 1-methylethylsulfinyl, butylsulfinyl, 1-methylpropylsulfinyl, 2-methyl propylsulfinyl, 1,1-dimethylethylsulfinyl, pentylsulfinyl, 1-methylbutylsulfinyl, 2-methylbutylsulfinyl, 3-methylbutylsulfinyl, 2,2-dimethylpropylsulfinyl, 1-ethylpropylsulfinyl, 1,1-dimethylpropylsulfinyl, 1,2-dimethylpropylsulfinyl, hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutyl-sulfinyl, 2,2-dimethylbutylsulfinyl, 2,3-dimethylbutylsulfinyl, 3,3-dimethylbutyl-sulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl and 1-ethyl-2-methylpropylsulfinyl;

$C_1$-$C_6$-alkylsulfonyl ($C_1$-$C_6$-alkyl-S(O)$_2$—): for example methylsulfonyl, ethylsulfonyl, propylsulfonyl, 1-methylethylsulfonyl, butylsulfonyl, 1-methylpropylsulfonyl, 2-methyl-propylsulfonyl, 1,1-dimethylethylsulfonyl, pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethyl-propylsulfonyl, 1,2,2-trimethylpropylsulfonyl, 1-ethyl-1-methylpropylsulfonyl and 1-ethyl-2-methylpropylsulfonyl;

$C_3$-$C_6$-cycloalkyl: a monocyclic saturated hydrocarbon having 3 to 6 ring members, such as cyclopropyl, cyclobutyl, cyclopentyl and cyclohexyl;

$C_3$-$C_6$-cycloalkenyl: 1-cyclopropenyl, 2-cyclopropenyl, 1-cyclobutenyl, 2-cyclobutenyl, 1-cyclopentenyl, 2-cyclopentenyl, 1,3-cyclopentadienyl, 1,4-cyclopentadienyl, 2,4-cyclopentadienyl, 1-cyclohexenyl, 2-cyclohexenyl, 3-cyclohexenyl, 1,3-cyclohexadienyl, 1,4-cyclohexadienyl, 2,5-cyclohexadienyl;

heterocyclyl: a 3- to 6-membered heterocyclyl: a saturated or partial unsaturated cycle having three to six ring members which comprises apart from carbon atoms one to four nitrogen atoms, or one or two oxygen atoms, or one or two sulfur atoms, or one to three nitrogen atoms and an oxygen atom, or one to three nitrogen atoms and a sulfur atom, or one sulfur and one oxygen atom, for example three- or four-membered heterocycles like 2-oxiranyl, 2-aziridinyl, 2-thiiranyl, 2-oxetanyl, 3-oxetanyl, 2-thietanyl, 3-thietanyl, 1-azetidinyl, 2-azetidinyl, 1-azetinyl, 2-azetinyl;

five-membered saturated heterocycles like 2-tetrahydrofuranyl, 3-tetrahydrofuranyl, 2-tetrahydrothienyl, 3-tetrahydrothienyl, 1-pyrrolidinyl, 2-pyrrolidinyl, 3-pyrrolidinyl, 3-isoxazolidinyl, 4-isoxazolidinyl, 5-isoxazolidinyl, 2-isothiazolidinyl, 3-isothiazolidinyl, 4-isothiazolidinyl, 5-isothiazolidinyl, 1-pyrazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 1-imidazolidinyl, 2-imidazolidinyl, 4-imidazolidinyl, 3-oxazolidinyl, 1,2,4-oxadiazolidin-3-yl, 1,2,4-oxadiazolidin-5-yl, 3-thiazolidinyl, 1,2,4-thiadiazolidin-3-yl, 1,2,4- thiadiazolidin-5-yl, 1,2,4-triazolidin-3-yl, 1,2,4-oxadiazolidin-2-yl, 1,2,4-oxadiazolidin-4-yl, 1,3,4-oxadiazolidin-2-yl, 1,2,4-thiadiazolidin-2-yl, 1,2,4-thiadiazolidin-4-yl, 1,3,4-thiadiazolidin-2-yl, 1,2,4-triazolidin-1-yl, 1,3,4-triazolidin-2-yl;

five-membered partial unsaturated heterocycles like 2,3-dihydrofur-2-yl, 2,3-dihydrofur-3-yl, 2,4-dihydrofur-2-yl, 2,4-dihydrofur-3-yl, dioxolan-2-yl, 1,3-dioxol-2-yl, 2,3-dihydrothien-2-yl, 2,3-dihydrothien-3-yl, 2,4-dihydrothien-2-yl, 2,4-dihydrothien-3-yl, 4,5-dihydropyrrol-1-yl, 4,5-dihydropyrrol-2-yl, 4,5-dihydropyrrol-3-yl, 2,5-dihydropyrrol-1-yl, 2,5-dihydropyrrol-2-yl, 2,5-dihydropyrrol-3-yl, 2,3-dihydroisoxazol-1-yl, 2,3-dihydroisoxazol-3-yl, 2,3-dihydroisoxazol-4-yl, 2,3-dihydroisoxazol-5-yl, 2,5-dihydroisoxazol-3-yl, 2,5-dihydroisoxazol-4-yl, 2,5-dihydroisoxazol-5-yl, 4,5-dihydroisoxazol-2-yl, 4,5-dihydroisoxazol-3-yl, 4,5-dihydroisoxazol-4-yl, 4,5-dihydroisoxazol-5-yl, 2,3-dihydroisothiazol-1-yl, 2,3-dihydroisothiazol-3-yl, 2,3-dihydroisothiazol-4-yl, 2,3-dihydroisothiazol-5-yl, 2,5-dihydroisothiazol-3-yl, 2,5-dihydroisothiazol-4-yl, 2,5-dihydroisothiazol-5-yl, 4,5-dihydroisothiazol-1-yl, 4,5-dihydroisothiazol-3-yl, 4,5-dihydroisothiazol-4-yl, 4,5-dihydroisothiazol-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydroimidazol-1-yl, 2,3-dihydroimidazol-2-yl, 2,3-dihydroimidazol-3-yl, 2,3-dihydroimidazol-4-yl, 2,3-dihydroimidazol-5-yl, 4,5-dihydroimidazol-1-yl, 4,5-dihydroimidazol-2-yl, 4,5-dihydroimidazol-4-yl, 4,5-dihydroimidazol-5-yl, 2,5-dihydroimidazol-1-yl, 2,5-dihydroimidazol-2-yl, 2,5-dihydroimidazol-4-yl, 2,5-dihydroimidazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 2,3-dihydrothiazol-2-yl, 2,3-dihydrothiazol-3-yl, 2,3-dihydrothiazol-4-yl, 2,3-dihydrothiazol-5-yl, 3,4-dihydrothiazol-2-yl, 3,4-dihydrothiazol-3-yl, 3,4-dihydrothiazol-4-yl, 3,4-dihydrothiazol-5-yl, 3,4-dihydrothiazol-2-yl, 3,4-dihydrothiazol-3-yl, 3,4-dihydrothiazol-4-yl; six-membered saturated heterocycles like 1-piperidinyl, 2-piperidinyl, 3-piperidinyl, 4-piperidinyl, 1,3-dioxan-5-yl, 1,4-dioxanyl, 1,3-dithian-5-yl, 1,3-dithianyl, 1,3-oxathian-5-yl, 1,4-oxathianyl, 2-tetrahydropyranyl, 3-tetrahydopyranyl, 4-tetrahydropyranyl, 2-tetrahydrothiopyranyl, 3-tetrahydrothiopyranyl, 4-tetrahydrothiopyranyl, 1-hexahydropyridazinyl, 3-hexahydropyridazinyl, 4-hexahydropyridazinyl, 1-hexahydropyrimidinyl, 2-hexahydropyrimidinyl, 4-hexahydropyrimidinyl, 5-hexahydropyrimidinyl, 1-piperazinyl, 2-piperazinyl, 1,3,5-hexahydrotriazin-1-yl, 1,3,5-hexahydrotriazin-2-yl, 1,2,4-hexahydrotriazin-1-yl, 1,2,4-hexahydrotriazin-3-yl, tetrahydro-1,3-oxazin-1-yl, tetrahydro-1,3-oxazin-2-yl, tetrahydro-1,3-oxazin-6-yl, 1-morpholinyl, 2-morpholinyl, 3-morpholinyl;

six-membered partial unsaturated heterocycles like 2H-pyran-2-yl, 2H-pyran-3-yl, 2H-pyran-4-yl, 2H-pyran-5-yl, 2H-pyran-6-yl, 2H-thiopyran-2-yl, 2H-thiopyran-3-yl, 2H-thiopyran-4-yl, 2H-thiopyran-5-yl, 2H-thiopyran-6-yl, 5,6-dihydro-4H-1,3-oxazin-2-yl.

heteroaryl: a 5- or 6-membered heteroaryl: monocyclic aromatic heteroaryl having 5 to 6 ring members which, in addition to carbon atoms, contains 1 to 4 nitrogen atoms, or 1 to 3 nitrogen atoms and an oxygen or sulfur atom, or an oxygen or a sulfur atom, for example 5-membered aromatic rings like furyl (for example 2-furyl, 3-furyl), thienyl (for example 2-thienyl, 3-thienyl), pyrrolyl (for example pyrrol-2-yl, pyrrol-3-yl), pyrazolyl (for example pyrazol-3-yl, pyrazol-4-yl), isoxazolyl (for example isoxazol-3-yl, isoxazol-4-yl, isoxazol-5-yl), isothiazolyl (for example isothiazol-3-yl, isothiazol-4-yl, isothiazol-5-yl), imidazolyl (for example imidazole-2-yl, imidazole-4-yl), oxazolyl (for example oxazol-2-yl, oxazol-4-yl, oxazol-5-yl), thiazolyl (for example thiazol-2-yl, thiazol-4-yl, thiazol-5-yl), oxadiazolyl (for example 1,2,3-oxadiazol-4-yl, 1,2,3-oxadiazol-5-yl, 1,2,4-oxadiazol-3-yl, 1,2,4-oxadiazol-5-yl, 1,3,4-oxadiazol-2-yl), thiadiazolyl (for example 1,2,3-thiadiazol-4-yl, 1,2,3-thiadiazol-5-yl, 1,2,4-thiadiazol-3-yl, 1,2,4-thiadiazol-5-yl, 1,3,4-thiadiazolyl-2-yl), triazolyl (for example 1,2,3-triazol-4-yl, 1,2,4-triazol-3-yl); 1-tetrazolyl; 6-membered aromatic rings like pyridyl (for example pyridine-2-yl, pyridine-3-yl, pyridine-4-yl), pyrazinyl (for example pyridazin-3-yl, pyridazin-4-yl), pyrimidinyl (for example pyrimidin-2-yl, pyrimidin-4-yl, pyrimidin-5-yl), pyrazin-2-yl, triazinyl (for example 1,3,5-triazin-2-yl, 1,2,4-triazin-3-yl, 1,2,4-triazin-5-yl, 1,2,4-triazin-6-yl).

The preferred embodiments of the invention mentioned herein below have to be understood as being preferred either independently from each other or in combination with one another.

Particular groups of preferred embodiments relate to compositions comprising at least one, preferably exactly one, phenylpyrimidine of formula (I), wherein the variables, either independently of one another or in combination with one another, have the following meanings:

Preferred are the compositions, which comprise as active component A at least one, preferably exactly one, phenylpyrimidine of formula (I), wherein $R^1$ is $C_1$-$C_6$-alkyl, $C_1$-$C_6$-alkoxy, $C_1$-$C_6$-haloalkoxy, $C_3$-$C_6$-alkenyloxy, $C_3$-$C_6$-haloalkenyloxy $C_3$-$C_6$-alkynyloxy, $C_3$-$C_6$-haloalkynyloxy, $C_1$-$C_6$-alkylthio, $C_3$-$C_6$-cycloalkyl or phenyl, wherein the cycloalkyl or phenyl substituent is unsubstituted;

particularly preferred $C_1$-$C_6$-alkyl, $C_1$-$C_6$-alkoxy or $C_3$-$C_6$-cycloalkyl, wherein the cycloalkyl substituent is unsubstituted;

especially preferred $C_3$-$C_6$-cycloalkyl, wherein the cycloalkyl substituent is unsubstituted; also especially preferred $C_2H_5$, i-$C_3H_7$, i-$C_4H_9$, $OCH_3$, c-$C_3H_5$ or c-$C_4H_9$;

more preferred $C_2H_5$, $OCH_3$ or c-$C_3H_5$;

most preferred c-$C_3H_5$.

Also preferred are the compositions, which comprise as active component A at least one, preferably exactly one, phenylpyrimidine of formula (I), wherein $R^1$ is $C_1$-$C_6$-alkyl, $C_1$-$C_6$-alkoxy, $C_1$-$C_6$-haloalkoxy, $C_3$-$C_6$-alkenyloxy, $C_3$-$C_6$-alkynyloxy, $C_1$-$C_6$-alkylthio or $C_3$-$C_6$-cycloalkyl, wherein the cycloalkyl substituent is unsubstituted;

particularly preferred $C_1$-$C_6$-alkyl, $C_1$-$C_6$-alkoxy or $C_3$-$C_6$-cycloalkyl, wherein the cycloalkyl substituent is unsubstituted;

especially preferred $C_3$-$C_6$-cycloalkyl, wherein the cycloalkyl substituent is unsubstituted;

also especially preferred $C_2H_5$, i-$C_3H_7$, i-$C_4H_9$, $OCH_3$, c-$C_3H_5$ or c-$C_4H_9$;

more preferred $C_2H_5$, $OCH_3$ or c-$C_3H_5$;

most preferred c-$C_3H_5$.

Also preferred are the compositions, which comprise as active component A at least one, preferably exactly one, phenylpyrimidine of formula (I), wherein
$R^1$ is $C_1$-$C_6$-alkyl, $C_1$-$C_6$-alkoxy, $C_1$-$C_6$-haloalkoxy or $C_3$-$C_6$-cycloalkyl.

Also preferred are the compositions, which comprise as active component A at least one, preferably exactly one, phenylpyrimidine of formula (I), wherein
$R^2$ is OH, $C_1$-$C_6$-alkoxy, $C_1$-$C_6$-haloalkoxy, $C_3$-$C_6$-alkenyloxy, $C_3$-$C_6$-haloalkenyloxy, $C_3$-$C_6$-alkynyloxy, $C_3$-$C_6$-haloalkynyloxy, $C_1$-$C_6$-alkoxyamino, hydroxyamino, ($C_1$-$C_6$-alkoxy)carbonyl-$C_1$-$C_6$-alkoxy, $C_1$-$C_6$-alkylthio, ($C_1$-$C_6$-alkoxy)carbonyl-$C_1$-$C_6$-alkylthio, $NH_2$, ($C_1$-$C_6$-alkyl)amino, ($C_1$-$C_6$-alkyl)sulfonylamino, [di($C_1$-$C_6$-alkyl)amino]sulfonylamino, phenyloxy, phenyl-$C_1$-$C_6$-alkoxy or phenyl-$C_1$-$C_6$-alkylthio,
wherein the phenyl substituent is unsubstituted;
preferably OH, $C_1$-$C_6$-alkoxy, $C_1$-$C_6$-haloalkoxy, $C_3$-$C_6$-alkynyloxy, ($C_1$-$C_6$-alkoxy)carbonyl-$C_1$-$C_6$-alkoxy, $C_1$-$C_6$-alkylthio, ($C_1$-$C_6$-alkoxy)carbonyl-$C_1$-$C_6$-alkylthio, $C_1$-$C_6$-alkoxyamino, hydroxyamino, ($C_1$-$C_6$-alkyl)sulfonylamino, [di($C_1$-$C_6$-alkyl)amino]sulfonylamino, phenyloxy, phenyl-$C_1$-$C_6$-alkoxy or phenyl-$C_1$-$C_6$-alkylthio,
wherein the phenyl substituent is unsubstituted;
particularly preferred OH, $C_1$-$C_6$-alkoxy, $C_1$-$C_6$-haloalkoxy, $C_3$-$C_6$-alkynyloxy, $C_1$-$C_6$-alkylthio, $C_1$-$C_6$-alkoxyamino, phenyloxy or phenyl-$C_1$-$C_6$-alkoxy,
wherein the phenyl substituent is unsubstituted;
also particularly preferred OH, $C_1$-$C_6$-alkoxy, $C_1$-$C_6$-haloalkoxy, $C_3$-$C_6$-alkynyloxy or $C_1$-$C_6$-alkoxyamino;
especially preferred $C_1$-$C_6$-alkoxy, $C_3$-$C_6$-alkynyloxy, $C_1$-$C_6$-haloalkoxy or $C_1$-$C_6$-alkoxyamino;
also especially preferred OH, $C_1$-$C_6$-alkoxy or $C_1$-$C_6$-haloalkoxy;
more preferred OH or $C_1$-$C_6$-alkoxy,
most preferred OH,
also most preferred $C_1$-$C_6$-alkoxy.

Also preferred are the compositions, which comprise as active component A at least one, preferably exactly one, phenylpyrimidine of formula (I), wherein
$R^2$ is OH, $C_1$-$C_6$-alkoxy, $C_1$-$C_6$-haloalkoxy, $C_3$-$C_6$-alkenyloxy, $C_3$-$C_6$-alkynyloxy, hydroxyamino ($C_1$-$C_6$-alkoxy)amino, (hydroxy)($C_1$-$C_6$-alkyl)amino or ($C_1$-$C_6$-alkoxy)($C_1$-$C_6$-alkyl)amino;
preferably is OH, $C_1$-$C_6$-alkoxy, or $C_3$-$C_6$-alkynyloxy or $C_1$-$C_6$-alkoxyamino.

Also preferred are the compositions, which comprise as active component A at least one, preferably exactly one, phenylpyrimidine of formula (I), wherein
$R^3$ is halogen, CN, $NO_2$, $C_1$-$C_6$-alkyl, $C_1$-$C_6$-haloalkyl, $C_1$-$C_6$-alkoxy or $C_3$-$C_6$-cycloalkyl;
also preferred halogen, CN, $C_1$-$C_6$-alkyl, $C_1$-$C_6$-haloalkyl or $C_1$-$C_6$-alkoxy,
particularly preferred halogen, CN, $C_1$-$C_6$-alkyl or $C_1$-$C_6$-alkoxy;
especially preferred halogen or $CH_3$;
also especially preferred halogen;
more preferred Cl, Br or I;
most preferred Br or I;
also most preferred Cl or Br.

Also preferred are the compositions, which comprise as active component A at least one, preferably exactly one, phenylpyrimidine of formula (I), wherein
$R^3$ is halogen, $C_1$-$C_6$-alkyl or $C_1$-$C_6$-haloalkyl.

Also preferred are the compositions, which comprise as active component A at least one, preferably exactly one, phenylpyrimidine of formula (I), wherein
$R^4$, $R^5$, $R^6$ and $R^7$ independently of one another are H, halogen, CN, $NO_2$, $C_1$-$C_6$-alkyl, $C_1$-$C_6$-haloalkyl, $C_1$-$C_6$-alkylcarbonyl, $C_2$-$C_6$-alkenyl, $C_1$-$C_6$-alkoxy, $C_1$-$C_6$-haloalkoxy, $C_1$-$C_6$-alkoxy-$C_1$-$C_6$-alkoxy, hydroxycarbonyl, $C_1$-$C_6$-alkoxycarbonyl, $C_1$-$C_6$-alkylthio, $C_1$-$C_6$-haloalkylthio, $NH_2$, ($C_1$-$C_6$-alkyl)amino, di($C_1$-$C_6$-alkyl)amino, ($C_1$-$C_6$-alkyl)sulfinyl, ($C_1$-$C_6$-alkyl)sulfonyl, $C_3$-$C_6$-cycloalkyl, ($C_3$-$C_6$-cycloalkyl)oxy or phenyl;
wherein the cycloalkyl, (cycloalkyl)oxy, or phenyl substituents independently from one another are unsubstituted or substituted by one to five substituents selected from the group consisting of halogen, CN, $NO_2$, $C_1$-$C_6$-alkyl, $C_1$-$C_6$-haloalkyl, $C_1$-$C_6$-alkoxy or $C_1$-$C_6$-haloalkoxy.

Also preferred are the compositions, which comprise as active component A at least one, preferably exactly one, phenylpyrimidine of formula (I), wherein
$R^4$, $R^5$, $R^6$ and $R^7$ independently of one another are H, halogen or $C_1$-$C_6$-haloalkyl;
preferably are H, F, Cl or $CF_3$.

Also preferred are the compositions, which comprise as active component A at least one, preferably exactly one, phenylpyrimidine of formula (I), wherein
$R^4$ is H, halogen, CN, $C_1$-$C_6$-alkyl, $C_1$-$C_6$-haloalkyl or $C_1$-$C_6$-alkoxy;
particularly preferred H, halogen or $C_1$-$C_6$-alkyl,
especially preferred H or halogen;
more preferred H or F;
most preferred H;
also most preferred F.

Also preferred are the compositions, which comprise as active component A at least one, preferably exactly one, phenylpyrimidine of formula (I), wherein
$R^5$ is H, halogen, CN, $C_1$-$C_6$-alkyl, $C_1$-$C_6$-haloalkyl or $C_1$-$C_6$-alkoxy;
particularly preferred H, halogen, $C_1$-$C_6$-alkyl $C_1$-$C_6$-haloalkyl or $C_1$-$C_6$-alkoxy;
especially preferred H, halogen, $C_1$-$C_6$-haloalkyl or $C_1$-$C_6$-alkoxy;
more preferred H or halogen;
also more preferred H, F, Cl, $CF_3$ or $OCH_3$;
most preferred H, F or $CF_3$;
also most preferred H or F;
also most preferred H;
also most preferred F;
also most preferred $CF_3$.

Also preferred are the compositions, which comprise as active component A at least one, preferably exactly one, phenylpyrimidine of formula (I), wherein
$R^6$ is H, halogen, $C_1$-$C_6$-alkyl, $C_1$-$C_6$-haloalkyl or $C_1$-$C_6$-alkoxy;
particularly preferred H, halogen, $C_1$-$C_6$-alkyl or $C_1$-$C_6$-haloalkyl;
especially preferred H, halogen or $CF_3$;
more preferred H or halogen;
also more preferred H or $CF_3$;
most preferred H or F;
also most preferred H;
also most preferred F;
also most preferred $CF_3$.

Also preferred are the compositions, which comprise as active component A at least one, preferably exactly one, phenylpyrimidine of formula (I), wherein $R^7$ is H, halogen, CN, $C_1$-$C_6$-alkyl or $C_1$-$C_6$-alkoxy;
particularly preferred H, halogen, $C_1$-$C_6$-alkyl or $C_1$-$C_6$-alkoxy;
especially preferred H, halogen or $C_1$-$C_6$-alkyl;
more preferred H, F, Cl or $CH_3$;
most preferred H, F or Cl;
also most preferred $CH_3$;
also most preferred H;

Also preferred are the compositions, which comprise as active component A at least one, preferably exactly one, phenylpyrimidine of formula (I), wherein
$R^1$ is preferably $C_1$-$C_6$-alkyl, $C_1$-$C_6$-alkoxy or $C_3$-$C_6$-cycloalkyl,
wherein the cycloalkyl substituent is unsubstituted;
particularly preferred $C_3$-$C_6$-cycloalkyl,
wherein the cycloalkyl substituent is unsubstituted;
$R^2$ is preferably OH, $C_1$-$C_6$-alkoxy, $C_1$-$C_6$-haloalkoxy, $C_3$-$C_6$-alkynyloxy, or $C_1$-$C_6$-alkoxyamino;
particularly preferred $C_1$-$C_6$-alkoxy, $C_3$-$C_6$-alkynyloxy, $C_1$-$C_6$-haloalkoxy, or $C_1$-$C_6$-alkoxyamino;
also particularly preferred OH or $C_1$-$C_6$-alkoxy,
more preferred OH;
also more preferred $C_1$-$C_6$-alkoxy;
$R^3$ is preferably halogen, CN, $C_1$-$C_6$-alkyl, $C_1$-$C_6$-haloalkyl or $C_1$-$C_6$-alkoxy;
particularly preferred halogen or $CH_3$;
$R^4$ is preferably H;
$R^5$ is preferably H or halogen;
$R^6$ is preferably H or halogen
also preferably H or $CF_3$;
particularly preferred $CF_3$;
$R^7$ is H, halogen, $C_1$-$C_6$-alkyl, $C_1$-$C_6$-alkoxy.

Also preferred are the compositions, which comprise as active component A at least one, preferably exactly one, phenylpyrimidine of formula (I), wherein
$R^1$ is $C_1$-$C_6$-alkyl, $C_1$-$C_6$-alkoxy, $C_1$-$C_6$-haloalkoxy or $C_3$-$C_6$-cycloalkyl;
$R^2$ is OH, $C_1$-$C_6$-alkoxy, $C_1$-$C_6$-haloalkoxy, $C_3$-$C_6$-alkenyloxy, $C_3$-$C_6$-alkynyloxy, hydroxyamino ($C_1$-$C_6$-alkoxy)amino, (hydroxy)($C_1$-$C_6$-alkyl)amino or ($C_1$-$C_6$-alkoxy)($C_1$-$C_6$-alkyl)amino;
$R^3$ is halogen, $C_1$-$C_6$-alkyl or $C_1$-$C_6$-haloalkyl; and
$R^4$, $R^5$, $R^6$ and $R^7$ independently of one another are H, halogen or $C_1$-$C_6$-haloalkyl.

Also preferred are the compositions, which comprise as active component A at least one, preferably exactly one, phenylpyrimidine of formula (I), wherein
$R^1$ is $C_3$-$C_6$-cycloalkyl;
$R^2$ is OH, $C_1$-$C_6$-alkoxy, $C_3$-$C_6$-alkynyloxy or $C_1$-$C_6$-alkoxyamino;
$R^3$ is halogen; and
$R^4$, $R^5$, $R^6$ and $R^7$ independently of one another are H, F, Cl or $CF_3$.

Also preferred are the compositions, which comprise as active component A at least one, preferably exactly one, phenylpyrimidine of formula (I), wherein
$R^1$ is $C_3$-$C_6$-cycloalkyl;
$R^2$ is OH or $C_1$-$C_6$-alkoxy;
$R^3$ is halogen; and
$R^4$, $R^5$, $R^6$ and $R^7$ independently of one another are H or halogen.

Also preferred are the compositions, which comprise as active component A at least one, preferably exactly one, phenylpyrimidine of formula (I), wherein
$R^1$ is $C_3$-$C_6$-cycloalkyl;
$R^2$ is OH or $C_1$-$C_6$-alkoxy;
$R^3$ is halogen;

$R^4$, $R^6$ and $R^7$ are H;
$R^5$ is H or halogen.

more preferred are the compositions, which comprise as active component A at least one, preferably exactly one, phenylpyrimidine of formula (I), wherein
$R^1$ is $C_1$-$C_3H_5$;
$R^2$ is OH or $OCH_3$;
$R^3$ is Cl;
$R^4$, $R^6$ and $R^7$ are H;
$R^5$ is H or F.

Particular preference is given to the compositions, which comprise as active component A at least one, preferably exactly one, phenylpyrimidine of formula (I.a) (corresponds to phenylpyrimidines of formula (I) wherein $R^2$ is OH and $R^4$ is H),

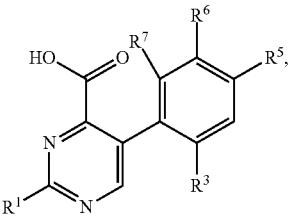

(I.a)

wherein the variables $R^1$, $R^3$, $R^5$, $R^6$ and $R^7$ have the meanings, in particular the preferred meanings, as defined above.

Special preference is given to the compositions, which comprise as active component A at least one, preferably exactly one, phenylpyrimidine of the formulae (I.a.1) to (I.a.1344) of Table (I), where the definitions of the variables $R^1$, $R^2$, $R^3$, $R^5$, $R^6$ and $R^7$ are of particular importance for the compounds according to the invention not only in combination with one another but in each case also on their own:

TABLE (I)

| No. | $R^1$ | $R^3$ | $R^5$ | $R^6$ | $R^7$ |
|---|---|---|---|---|---|
| I.a.1. | c-$C_3H_5$ | F | H | H | H |
| I.a.2. | c-$C_3H_5$ | F | H | H | F |
| I.a.3. | c-$C_3H_5$ | F | H | H | Cl |
| I.a.4. | c-$C_3H_5$ | F | H | H | Br |
| I.a.5. | c-$C_3H_5$ | F | H | H | $CH_3$ |
| I.a.6. | c-$C_3H_5$ | F | H | H | $OCH_3$ |
| I.a.7. | c-$C_3H_5$ | F | H | F | H |
| I.a.8. | c-$C_3H_5$ | F | H | F | F |
| I.a.9. | c-$C_3H_5$ | F | H | F | Cl |
| I.a.10. | c-$C_3H_5$ | F | H | F | Br |
| I.a.11. | c-$C_3H_5$ | F | H | F | $CH_3$ |
| I.a.12. | c-$C_3H_5$ | F | H | F | $OCH_3$ |
| I.a.13. | c-$C_3H_5$ | F | F | H | H |
| I.a.14. | c-$C_3H_5$ | F | F | H | F |
| I.a.15. | c-$C_3H_5$ | F | F | H | Cl |
| I.a.16. | c-$C_3H_5$ | F | F | H | Br |
| I.a.17. | c-$C_3H_5$ | F | F | H | $CH_3$ |
| I.a.18. | c-$C_3H_5$ | F | F | H | $OCH_3$ |
| I.a.19. | c-$C_3H_5$ | F | F | F | H |
| I.a.20. | c-$C_3H_5$ | F | F | F | F |
| I.a.21. | c-$C_3H_5$ | F | F | F | Cl |
| I.a.22. | c-$C_3H_5$ | F | F | F | Br |
| I.a.23. | c-$C_3H_5$ | F | F | F | $CH_3$ |
| I.a.24. | c-$C_3H_5$ | F | F | F | $OCH_3$ |
| I.a.25. | c-$C_3H_5$ | Cl | H | H | H |
| I.a.26. | c-$C_3H_5$ | Cl | H | H | F |
| I.a.27. | c-$C_3H_5$ | Cl | H | H | Cl |
| I.a.28. | c-$C_3H_5$ | Cl | H | H | Br |
| I.a.29. | c-$C_3H_5$ | Cl | H | H | $CH_3$ |
| I.a.30. | c-$C_3H_5$ | Cl | H | H | $OCH_3$ |

TABLE (I)-continued

| No. | $R^1$ | $R^3$ | $R^5$ | $R^6$ | $R^7$ |
|---|---|---|---|---|---|
| I.a.31. | c-$C_3H_5$ | Cl | H | F | H |
| I.a.32. | c-$C_3H_5$ | Cl | H | F | F |
| I.a.33. | c-$C_3H_5$ | Cl | H | F | Cl |
| I.a.34. | c-$C_3H_5$ | Cl | H | F | Br |
| I.a.35. | c-$C_3H_5$ | Cl | H | F | $CH_3$ |
| I.a.36. | c-$C_3H_5$ | Cl | H | F | $OCH_3$ |
| I.a.37. | c-$C_3H_5$ | Cl | F | H | H |
| I.a.38. | c-$C_3H_5$ | Cl | F | H | F |
| I.a.39. | c-$C_3H_5$ | Cl | F | H | Cl |
| I.a.40. | c-$C_3H_5$ | Cl | F | H | Br |
| I.a.41. | c-$C_3H_5$ | Cl | F | H | $CH_3$ |
| I.a.42. | c-$C_3H_5$ | Cl | F | H | $OCH_3$ |
| I.a.43. | c-$C_3H_5$ | Cl | F | F | H |
| I.a.44. | c-$C_3H_5$ | Cl | F | F | F |
| I.a.45. | c-$C_3H_5$ | Cl | F | F | Cl |
| I.a.46. | c-$C_3H_5$ | Cl | F | F | Br |
| I.a.47. | c-$C_3H_5$ | Cl | F | F | $CH_3$ |
| I.a.48. | c-$C_3H_5$ | Cl | F | F | $OCH_3$ |
| I.a.49. | c-$C_3H_5$ | Br | H | H | H |
| I.a.50. | c-$C_3H_5$ | Br | H | H | F |
| I.a.51. | c-$C_3H_5$ | Br | H | H | Cl |
| I.a.52. | c-$C_3H_5$ | Br | H | H | Br |
| I.a.53. | c-$C_3H_5$ | Br | H | H | $CH_3$ |
| I.a.54. | c-$C_3H_5$ | Br | H | H | $OCH_3$ |
| I.a.55. | c-$C_3H_5$ | Br | H | F | H |
| I.a.56. | c-$C_3H_5$ | Br | H | F | F |
| I.a.57. | c-$C_3H_5$ | Br | H | F | Cl |
| I.a.58. | c-$C_3H_5$ | Br | H | F | Br |
| I.a.59. | c-$C_3H_5$ | Br | H | F | $CH_3$ |
| I.a.60. | c-$C_3H_5$ | Br | H | F | $OCH_3$ |
| I.a.61. | c-$C_3H_5$ | Br | F | H | H |
| I.a.62. | c-$C_3H_5$ | Br | F | H | F |
| I.a.63. | c-$C_3H_5$ | Br | F | H | Cl |
| I.a.64. | c-$C_3H_5$ | Br | F | H | Br |
| I.a.65. | c-$C_3H_5$ | Br | F | H | $CH_3$ |
| I.a.66. | c-$C_3H_5$ | Br | F | H | $OCH_3$ |
| I.a.67. | c-$C_3H_5$ | Br | F | F | H |
| I.a.68. | c-$C_3H_5$ | Br | F | F | F |
| I.a.69. | c-$C_3H_5$ | Br | F | F | Cl |
| I.a.70. | c-$C_3H_5$ | Br | F | F | Br |
| I.a.71. | c-$C_3H_5$ | Br | F | F | $CH_3$ |
| I.a.72. | c-$C_3H_5$ | Br | F | F | $OCH_3$ |
| I.a.73. | c-$C_3H_5$ | I | H | H | H |
| I.a.74. | c-$C_3H_5$ | I | H | H | F |
| I.a.75. | c-$C_3H_5$ | I | H | H | Cl |
| I.a.76. | c-$C_3H_5$ | I | H | H | Br |
| I.a.77. | c-$C_3H_5$ | I | H | H | $CH_3$ |
| I.a.78. | c-$C_3H_5$ | I | H | H | $OCH_3$ |
| I.a.79. | c-$C_3H_5$ | I | H | F | H |
| I.a.80. | c-$C_3H_5$ | I | H | F | F |
| I.a.81. | c-$C_3H_5$ | I | H | F | Cl |
| I.a.82. | c-$C_3H_5$ | I | H | F | Br |
| I.a.83. | c-$C_3H_5$ | I | H | F | $CH_3$ |
| I.a.84. | c-$C_3H_5$ | I | H | F | $OCH_3$ |
| I.a.85. | c-$C_3H_5$ | I | F | H | H |
| I.a.86. | c-$C_3H_5$ | I | F | H | F |
| I.a.87. | c-$C_3H_5$ | I | F | H | Cl |
| I.a.88. | c-$C_3H_5$ | I | F | H | Br |
| I.a.89. | c-$C_3H_5$ | I | F | H | $CH_3$ |
| I.a.90. | c-$C_3H_5$ | I | F | H | $OCH_3$ |
| I.a.91. | c-$C_3H_5$ | I | F | F | H |
| I.a.92. | c-$C_3H_5$ | I | F | F | F |
| I.a.93. | c-$C_3H_5$ | I | F | F | Cl |
| I.a.94. | c-$C_3H_5$ | I | F | F | Br |
| I.a.95. | c-$C_3H_5$ | I | F | F | $CH_3$ |
| I.a.96. | c-$C_3H_5$ | I | F | F | $OCH_3$ |
| I.a.97. | c-$C_3H_5$ | $CH_3$ | H | H | H |
| I.a.98. | c-$C_3H_5$ | $CH_3$ | H | H | F |
| I.a.99. | c-$C_3H_5$ | $CH_3$ | H | H | Cl |
| I.a.100. | c-$C_3H_5$ | $CH_3$ | H | H | Br |
| I.a.101. | c-$C_3H_5$ | $CH_3$ | H | H | $CH_3$ |
| I.a.102. | c-$C_3H_5$ | $CH_3$ | H | H | $OCH_3$ |
| I.a.103. | c-$C_3H_5$ | $CH_3$ | H | F | H |
| I.a.104. | c-$C_3H_5$ | $CH_3$ | H | F | F |
| I.a.105. | c-$C_3H_5$ | $CH_3$ | H | F | Cl |
| I.a.106. | c-$C_3H_5$ | $CH_3$ | H | F | Br |
| I.a.107. | c-$C_3H_5$ | $CH_3$ | H | F | $CH_3$ |
| I.a.108. | c-$C_3H_5$ | $CH_3$ | H | F | $OCH_3$ |
| I.a.109. | c-$C_3H_5$ | $CH_3$ | F | H | H |
| I.a.110. | c-$C_3H_5$ | $CH_3$ | F | H | F |
| I.a.111. | c-$C_3H_5$ | $CH_3$ | F | H | Cl |
| I.a.112. | c-$C_3H_5$ | $CH_3$ | F | H | Br |
| I.a.113. | c-$C_3H_5$ | $CH_3$ | F | H | $CH_3$ |
| I.a.114. | c-$C_3H_5$ | $CH_3$ | F | H | $OCH_3$ |
| I.a.115. | c-$C_3H_5$ | $CH_3$ | F | F | H |
| I.a.116. | c-$C_3H_5$ | $CH_3$ | F | F | F |
| I.a.117. | c-$C_3H_5$ | $CH_3$ | F | F | Cl |
| I.a.118. | c-$C_3H_5$ | $CH_3$ | F | F | Br |
| I.a.119. | c-$C_3H_5$ | $CH_3$ | F | F | $CH_3$ |
| I.a.120. | c-$C_3H_5$ | $CH_3$ | F | F | $OCH_3$ |
| I.a.121. | c-$C_3H_5$ | $OCH_3$ | H | H | H |
| I.a.122. | c-$C_3H_5$ | $OCH_3$ | H | H | F |
| I.a.123. | c-$C_3H_5$ | $OCH_3$ | H | H | Cl |
| I.a.124. | c-$C_3H_5$ | $OCH_3$ | H | H | Br |
| I.a.125. | c-$C_3H_5$ | $OCH_3$ | H | H | $CH_3$ |
| I.a.126. | c-$C_3H_5$ | $OCH_3$ | H | H | $OCH_3$ |
| I.a.127. | c-$C_3H_5$ | $OCH_3$ | H | F | H |
| I.a.128. | c-$C_3H_5$ | $OCH_3$ | H | F | F |
| I.a.129. | c-$C_3H_5$ | $OCH_3$ | H | F | Cl |
| I.a.130. | c-$C_3H_5$ | $OCH_3$ | H | F | Br |
| I.a.131. | c-$C_3H_5$ | $OCH_3$ | H | F | $CH_3$ |
| I.a.132. | c-$C_3H_5$ | $OCH_3$ | H | F | $OCH_3$ |
| I.a.133. | c-$C_3H_5$ | $OCH_3$ | F | H | H |
| I.a.134. | c-$C_3H_5$ | $OCH_3$ | F | H | F |
| I.a.135. | c-$C_3H_5$ | $OCH_3$ | F | H | Cl |
| I.a.136. | c-$C_3H_5$ | $OCH_3$ | F | H | Br |
| I.a.137. | c-$C_3H_5$ | $OCH_3$ | F | H | $CH_3$ |
| I.a.138. | c-$C_3H_5$ | $OCH_3$ | F | H | $OCH_3$ |
| I.a.139. | c-$C_3H_5$ | $OCH_3$ | F | F | H |
| I.a.140. | c-$C_3H_5$ | $OCH_3$ | F | F | F |
| I.a.141. | c-$C_3H_5$ | $OCH_3$ | F | F | Cl |
| I.a.142. | c-$C_3H_5$ | $OCH_3$ | F | F | Br |
| I.a.143. | c-$C_3H_5$ | $OCH_3$ | F | F | $CH_3$ |
| I.a.144. | c-$C_3H_5$ | $OCH_3$ | F | F | $OCH_3$ |
| I.a.145. | c-$C_3H_5$ | $CF_3$ | H | H | H |
| I.a.146. | c-$C_3H_5$ | $CF_3$ | H | H | F |
| I.a.147. | c-$C_3H_5$ | $CF_3$ | H | H | Cl |
| I.a.148. | c-$C_3H_5$ | $CF_3$ | H | H | Br |
| I.a.149. | c-$C_3H_5$ | $CF_3$ | H | H | $CH_3$ |
| I.a.150. | c-$C_3H_5$ | $CF_3$ | H | H | $OCH_3$ |
| I.a.151. | c-$C_3H_5$ | $CF_3$ | H | F | H |
| I.a.152. | c-$C_3H_5$ | $CF_3$ | H | F | F |
| I.a.153. | c-$C_3H_5$ | $CF_3$ | H | F | Cl |
| I.a.154. | c-$C_3H_5$ | $CF_3$ | H | F | Br |
| I.a.155. | c-$C_3H_5$ | $CF_3$ | H | F | $CH_3$ |
| I.a.156. | c-$C_3H_5$ | $CF_3$ | H | F | $OCH_3$ |
| I.a.157. | c-$C_3H_5$ | $CF_3$ | F | H | H |
| I.a.158. | c-$C_3H_5$ | $CF_3$ | F | H | F |
| I.a.159. | c-$C_3H_5$ | $CF_3$ | F | H | Cl |
| I.a.160. | c-$C_3H_5$ | $CF_3$ | F | H | Br |
| I.a.161. | c-$C_3H_5$ | $CF_3$ | F | H | $CH_3$ |
| I.a.162. | c-$C_3H_5$ | $CF_3$ | F | H | $OCH_3$ |
| I.a.163. | c-$C_3H_5$ | $CF_3$ | F | F | H |
| I.a.164. | c-$C_3H_5$ | $CF_3$ | F | F | F |
| I.a.165. | c-$C_3H_5$ | $CF_3$ | F | F | Cl |
| I.a.166. | c-$C_3H_5$ | $CF_3$ | F | F | Br |
| I.a.167. | c-$C_3H_5$ | $CF_3$ | F | F | $CH_3$ |
| I.a.168. | c-$C_3H_5$ | $CF_3$ | F | F | $OCH_3$ |
| I.a.169. | c-$C_4H_7$ | F | H | H | H |
| I.a.170. | c-$C_4H_7$ | F | H | H | F |
| I.a.171. | c-$C_4H_7$ | F | H | H | Cl |
| I.a.172. | c-$C_4H_7$ | F | H | H | Br |
| I.a.173. | c-$C_4H_7$ | F | H | H | $CH_3$ |
| I.a.174. | c-$C_4H_7$ | F | H | H | $OCH_3$ |
| I.a.175. | c-$C_4H_7$ | F | H | F | H |
| I.a.176. | c-$C_4H_7$ | F | H | F | F |
| I.a.177. | c-$C_4H_7$ | F | H | F | Cl |
| I.a.178. | c-$C_4H_7$ | F | H | F | Br |
| I.a.179. | c-$C_4H_7$ | F | H | F | $CH_3$ |
| I.a.180. | c-$C_4H_7$ | F | H | F | $OCH_3$ |
| I.a.181. | c-$C_4H_7$ | F | F | H | H |
| I.a.182. | c-$C_4H_7$ | F | F | H | F |
| I.a.183. | c-$C_4H_7$ | F | F | H | Cl |
| I.a.184. | c-$C_4H_7$ | F | F | H | Br |
| I.a.185. | c-$C_4H_7$ | F | F | H | $CH_3$ |
| I.a.186. | c-$C_4H_7$ | F | F | H | $OCH_3$ |

TABLE (I)-continued

| No. | R¹ | R³ | R⁵ | R⁶ | R⁷ |
| --- | --- | --- | --- | --- | --- |
| I.a.187. | c-C₄H₇ | F | F | F | H |
| I.a.188. | c-C₄H₇ | F | F | F | F |
| I.a.189. | c-C₄H₇ | F | F | F | Cl |
| I.a.190. | c-C₄H₇ | F | F | F | Br |
| I.a.191. | c-C₄H₇ | F | F | F | CH₃ |
| I.a.192. | c-C₄H₇ | F | F | F | OCH₃ |
| I.a.193. | c-C₄H₇ | Cl | H | H | H |
| I.a.194. | c-C₄H₇ | Cl | H | H | F |
| I.a.195. | c-C₄H₇ | Cl | H | H | Cl |
| I.a.196. | c-C₄H₇ | Cl | H | H | Br |
| I.a.197. | c-C₄H₇ | Cl | H | H | CH₃ |
| I.a.198. | c-C₄H₇ | Cl | H | H | OCH₃ |
| I.a.199. | c-C₄H₇ | Cl | H | F | H |
| I.a.200. | c-C₄H₇ | Cl | H | F | F |
| I.a.201. | c-C₄H₇ | Cl | H | F | Cl |
| I.a.202. | c-C₄H₇ | Cl | H | F | Br |
| I.a.203. | c-C₄H₇ | Cl | H | F | CH₃ |
| I.a.204. | c-C₄H₇ | Cl | H | F | OCH₃ |
| I.a.205. | c-C₄H₇ | Cl | F | H | H |
| I.a.206. | c-C₄H₇ | Cl | F | H | F |
| I.a.207. | c-C₄H₇ | Cl | F | H | Cl |
| I.a.208. | c-C₄H₇ | Cl | F | H | Br |
| I.a.209. | c-C₄H₇ | Cl | F | H | CH₃ |
| I.a.210. | c-C₄H₇ | Cl | F | H | OCH₃ |
| I.a.211. | c-C₄H₇ | Cl | F | F | H |
| I.a.212. | c-C₄H₇ | Cl | F | F | F |
| I.a.213. | c-C₄H₇ | Cl | F | F | Cl |
| I.a.214. | c-C₄H₇ | Cl | F | F | Br |
| I.a.215. | c-C₄H₇ | Cl | F | F | CH₃ |
| I.a.216. | c-C₄H₇ | Cl | F | F | OCH₃ |
| I.a.217. | c-C₄H₇ | Br | H | H | H |
| I.a.218. | c-C₄H₇ | Br | H | H | F |
| I.a.219. | c-C₄H₇ | Br | H | H | Cl |
| I.a.220. | c-C₄H₇ | Br | H | H | Br |
| I.a.221. | c-C₄H₇ | Br | H | H | CH₃ |
| I.a.222. | c-C₄H₇ | Br | H | H | OCH₃ |
| I.a.223. | c-C₄H₇ | Br | H | F | H |
| I.a.224. | c-C₄H₇ | Br | H | F | F |
| I.a.225. | c-C₄H₇ | Br | H | F | Cl |
| I.a.226. | c-C₄H₇ | Br | H | F | Br |
| I.a.227. | c-C₄H₇ | Br | H | F | CH₃ |
| I.a.228. | c-C₄H₇ | Br | H | F | OCH₃ |
| I.a.229. | c-C₄H₇ | Br | F | H | H |
| I.a.230. | c-C₄H₇ | Br | F | H | F |
| I.a.231. | c-C₄H₇ | Br | F | H | Cl |
| I.a.232. | c-C₄H₇ | Br | F | H | Br |
| I.a.233. | c-C₄H₇ | Br | F | H | CH₃ |
| I.a.234. | c-C₄H₇ | Br | F | H | OCH₃ |
| I.a.235. | c-C₄H₇ | Br | F | F | H |
| I.a.236. | c-C₄H₇ | Br | F | F | F |
| I.a.237. | c-C₄H₇ | Br | F | F | Cl |
| I.a.238. | c-C₄H₇ | Br | F | F | Br |
| I.a.239. | c-C₄H₇ | Br | F | F | CH₃ |
| I.a.240. | c-C₄H₇ | Br | F | F | OCH₃ |
| I.a.241. | c-C₄H₇ | I | H | H | H |
| I.a.242. | c-C₄H₇ | I | H | H | F |
| I.a.243. | c-C₄H₇ | I | H | H | Cl |
| I.a.244. | c-C₄H₇ | I | H | H | Br |
| I.a.245. | c-C₄H₇ | I | H | H | CH₃ |
| I.a.246. | c-C₄H₇ | I | H | H | OCH₃ |
| I.a.247. | c-C₄H₇ | I | H | F | H |
| I.a.248. | c-C₄H₇ | I | H | F | F |
| I.a.249. | c-C₄H₇ | I | H | F | Cl |
| I.a.250. | c-C₄H₇ | I | H | F | Br |
| I.a.251. | c-C₄H₇ | I | H | F | CH₃ |
| I.a.252. | c-C₄H₇ | I | H | F | OCH₃ |
| I.a.253. | c-C₄H₇ | I | F | H | H |
| I.a.254. | c-C₄H₇ | I | F | H | F |
| I.a.255. | c-C₄H₇ | I | F | H | Cl |
| I.a.256. | c-C₄H₇ | I | F | H | Br |
| I.a.257. | c-C₄H₇ | I | F | H | CH₃ |
| I.a.258. | c-C₄H₇ | I | F | H | OCH₃ |
| I.a.259. | c-C₄H₇ | I | F | F | H |
| I.a.260. | c-C₄H₇ | I | F | F | F |
| I.a.261. | c-C₄H₇ | I | F | F | Cl |
| I.a.262. | c-C₄H₇ | I | F | F | Br |
| I.a.263. | c-C₄H₇ | I | F | F | CH₃ |
| I.a.264. | c-C₄H₇ | I | F | F | OCH₃ |
| I.a.265. | c-C₄H₇ | CH₃ | H | H | H |
| I.a.266. | c-C₄H₇ | CH₃ | H | H | F |
| I.a.267. | c-C₄H₇ | CH₃ | H | H | Cl |
| I.a.268. | c-C₄H₇ | CH₃ | H | H | Br |
| I.a.269. | c-C₄H₇ | CH₃ | H | H | CH₃ |
| I.a.270. | c-C₄H₇ | CH₃ | H | H | OCH₃ |
| I.a.271. | c-C₄H₇ | CH₃ | H | F | H |
| I.a.272. | c-C₄H₇ | CH₃ | H | F | F |
| I.a.273. | c-C₄H₇ | CH₃ | H | F | Cl |
| I.a.274. | c-C₄H₇ | CH₃ | H | F | Br |
| I.a.275. | c-C₄H₇ | CH₃ | H | F | CH₃ |
| I.a.276. | c-C₄H₇ | CH₃ | H | F | OCH₃ |
| I.a.277. | c-C₄H₇ | CH₃ | F | H | H |
| I.a.278. | c-C₄H₇ | CH₃ | F | H | F |
| I.a.279. | c-C₄H₇ | CH₃ | F | H | Cl |
| I.a.280. | c-C₄H₇ | CH₃ | F | H | Br |
| I.a.281. | c-C₄H₇ | CH₃ | F | H | CH₃ |
| I.a.282. | c-C₄H₇ | CH₃ | F | H | OCH₃ |
| I.a.283. | c-C₄H₇ | CH₃ | F | F | H |
| I.a.284. | c-C₄H₇ | CH₃ | F | F | F |
| I.a.285. | c-C₄H₇ | CH₃ | F | F | Cl |
| I.a.286. | c-C₄H₇ | CH₃ | F | F | Br |
| I.a.287. | c-C₄H₇ | CH₃ | F | F | CH₃ |
| I.a.288. | c-C₄H₇ | CH₃ | F | F | OCH₃ |
| I.a.289. | c-C₄H₇ | OCH₃ | H | H | H |
| I.a.290. | c-C₄H₇ | OCH₃ | H | H | F |
| I.a.291. | c-C₄H₇ | OCH₃ | H | H | Cl |
| I.a.292. | c-C₄H₇ | OCH₃ | H | H | Br |
| I.a.293. | c-C₄H₇ | OCH₃ | H | H | CH₃ |
| I.a.294. | c-C₄H₇ | OCH₃ | H | H | OCH₃ |
| I.a.295. | c-C₄H₇ | OCH₃ | H | F | H |
| I.a.296. | c-C₄H₇ | OCH₃ | H | F | F |
| I.a.297. | c-C₄H₇ | OCH₃ | H | F | Cl |
| I.a.298. | c-C₄H₇ | OCH₃ | H | F | Br |
| I.a.299. | c-C₄H₇ | OCH₃ | H | F | CH₃ |
| I.a.300. | c-C₄H₇ | OCH₃ | H | F | OCH₃ |
| I.a.301. | c-C₄H₇ | OCH₃ | F | H | H |
| I.a.302. | c-C₄H₇ | OCH₃ | F | H | F |
| I.a.303. | c-C₄H₇ | OCH₃ | F | H | Cl |
| I.a.304. | c-C₄H₇ | OCH₃ | F | H | Br |
| I.a.305. | c-C₄H₇ | OCH₃ | F | H | CH₃ |
| I.a.306. | c-C₄H₇ | OCH₃ | F | H | OCH₃ |
| I.a.307. | c-C₄H₇ | OCH₃ | F | F | H |
| I.a.308. | c-C₄H₇ | OCH₃ | F | F | F |
| I.a.309. | c-C₄H₇ | OCH₃ | F | F | Cl |
| I.a.310. | c-C₄H₇ | OCH₃ | F | F | Br |
| I.a.311. | c-C₄H₇ | OCH₃ | F | F | CH₃ |
| I.a.312. | c-C₄H₇ | OCH₃ | F | F | OCH₃ |
| I.a.313. | c-C₄H₇ | CF₃ | H | H | H |
| I.a.314. | c-C₄H₇ | CF₃ | H | H | F |
| I.a.315. | c-C₄H₇ | CF₃ | H | H | Cl |
| I.a.316. | c-C₄H₇ | CF₃ | H | H | Br |
| I.a.317. | c-C₄H₇ | CF₃ | H | H | CH₃ |
| I.a.318. | c-C₄H₇ | CF₃ | H | H | OCH₃ |
| I.a.319. | c-C₄H₇ | CF₃ | H | F | H |
| I.a.320. | c-C₄H₇ | CF₃ | H | F | F |
| I.a.321. | c-C₄H₇ | CF₃ | H | F | Cl |
| I.a.322. | c-C₄H₇ | CF₃ | H | F | Br |
| I.a.323. | c-C₄H₇ | CF₃ | H | F | CH₃ |
| I.a.324. | c-C₄H₇ | CF₃ | H | F | OCH₃ |
| I.a.325. | c-C₄H₇ | CF₃ | F | H | H |
| I.a.326. | c-C₄H₇ | CF₃ | F | H | F |
| I.a.327. | c-C₄H₇ | CF₃ | F | H | Cl |
| I.a.328. | c-C₄H₇ | CF₃ | F | H | Br |
| I.a.329. | c-C₄H₇ | CF₃ | F | H | CH₃ |
| I.a.330. | c-C₄H₇ | CF₃ | F | H | OCH₃ |
| I.a.331. | c-C₄H₇ | CF₃ | F | F | H |
| I.a.332. | c-C₄H₇ | CF₃ | F | F | F |
| I.a.333. | c-C₄H₇ | CF₃ | F | F | Cl |
| I.a.334. | c-C₄H₇ | CF₃ | F | F | Br |
| I.a.335. | c-C₄H₇ | CF₃ | F | F | CH₃ |
| I.a.336. | c-C₄H₇ | CF₃ | F | F | OCH₃ |
| I.a.337. | C₂H₅ | F | H | H | H |
| I.a.338. | C₂H₅ | F | H | H | F |
| I.a.339. | C₂H₅ | F | H | H | Cl |
| I.a.340. | C₂H₅ | F | H | H | Br |
| I.a.341. | C₂H₅ | F | H | H | CH₃ |
| I.a.342. | C₂H₅ | F | H | H | OCH₃ |

TABLE (I)-continued

| No. | $R^1$ | $R^3$ | $R^5$ | $R^6$ | $R^7$ |
|---|---|---|---|---|---|
| I.a.343. | $C_2H_5$ | F | H | F | H |
| I.a.344. | $C_2H_5$ | F | H | F | F |
| I.a.345. | $C_2H_5$ | F | H | F | Cl |
| I.a.346. | $C_2H_5$ | F | H | F | Br |
| I.a.347. | $C_2H_5$ | F | H | F | $CH_3$ |
| I.a.348. | $C_2H_5$ | F | H | F | $OCH_3$ |
| I.a.349. | $C_2H_5$ | F | F | H | H |
| I.a.350. | $C_2H_5$ | F | F | H | F |
| I.a.351. | $C_2H_5$ | F | F | H | Cl |
| I.a.352. | $C_2H_5$ | F | F | H | Br |
| I.a.353. | $C_2H_5$ | F | F | H | $CH_3$ |
| I.a.354. | $C_2H_5$ | F | F | H | $OCH_3$ |
| I.a.355. | $C_2H_5$ | F | F | F | H |
| I.a.356. | $C_2H_5$ | F | F | F | F |
| I.a.357. | $C_2H_5$ | F | F | F | Cl |
| I.a.358. | $C_2H_5$ | F | F | F | Br |
| I.a.359. | $C_2H_5$ | F | F | F | $CH_3$ |
| I.a.360. | $C_2H_5$ | F | F | F | $OCH_3$ |
| I.a.361. | $C_2H_5$ | Cl | H | H | H |
| I.a.362. | $C_2H_5$ | Cl | H | H | F |
| I.a.363. | $C_2H_5$ | Cl | H | H | Cl |
| I.a.364. | $C_2H_5$ | Cl | H | H | Br |
| I.a.365. | $C_2H_5$ | Cl | H | H | $CH_3$ |
| I.a.366. | $C_2H_5$ | Cl | H | H | $OCH_3$ |
| I.a.367. | $C_2H_5$ | Cl | H | F | H |
| I.a.368. | $C_2H_5$ | Cl | H | F | F |
| I.a.369. | $C_2H_5$ | Cl | H | F | Cl |
| I.a.370. | $C_2H_5$ | Cl | H | F | Br |
| I.a.371. | $C_2H_5$ | Cl | H | F | $CH_3$ |
| I.a.372. | $C_2H_5$ | Cl | H | F | $OCH_3$ |
| I.a.373. | $C_2H_5$ | Cl | F | H | H |
| I.a.374. | $C_2H_5$ | Cl | F | H | F |
| I.a.375. | $C_2H_5$ | Cl | F | H | Cl |
| I.a.376. | $C_2H_5$ | Cl | F | H | Br |
| I.a.377. | $C_2H_5$ | Cl | F | H | $CH_3$ |
| I.a.378. | $C_2H_5$ | Cl | F | H | $OCH_3$ |
| I.a.379. | $C_2H_5$ | Cl | F | F | H |
| I.a.380. | $C_2H_5$ | Cl | F | F | F |
| I.a.381. | $C_2H_5$ | Cl | F | F | Cl |
| I.a.382. | $C_2H_5$ | Cl | F | F | Br |
| I.a.383. | $C_2H_5$ | Cl | F | F | $CH_3$ |
| I.a.384. | $C_2H_5$ | Cl | F | F | $OCH_3$ |
| I.a.385. | $C_2H_5$ | Br | H | H | H |
| I.a.386. | $C_2H_5$ | Br | H | H | F |
| I.a.387. | $C_2H_5$ | Br | H | H | Cl |
| I.a.388. | $C_2H_5$ | Br | H | H | Br |
| I.a.389. | $C_2H_5$ | Br | H | H | $CH_3$ |
| I.a.390. | $C_2H_5$ | Br | H | H | $OCH_3$ |
| I.a.391. | $C_2H_5$ | Br | H | F | H |
| I.a.392. | $C_2H_5$ | Br | H | F | F |
| I.a.393. | $C_2H_5$ | Br | H | F | Cl |
| I.a.394. | $C_2H_5$ | Br | H | F | Br |
| I.a.395. | $C_2H_5$ | Br | H | F | $CH_3$ |
| I.a.396. | $C_2H_5$ | Br | H | F | $OCH_3$ |
| I.a.397. | $C_2H_5$ | Br | F | H | H |
| I.a.398. | $C_2H_5$ | Br | F | H | F |
| I.a.399. | $C_2H_5$ | Br | F | H | Cl |
| I.a.400. | $C_2H_5$ | Br | F | H | Br |
| I.a.401. | $C_2H_5$ | Br | F | H | $CH_3$ |
| I.a.402. | $C_2H_5$ | Br | F | H | $OCH_3$ |
| I.a.403. | $C_2H_5$ | Br | F | F | H |
| I.a.404. | $C_2H_5$ | Br | F | F | F |
| I.a.405. | $C_2H_5$ | Br | F | F | Cl |
| I.a.406. | $C_2H_5$ | Br | F | F | Br |
| I.a.407. | $C_2H_5$ | Br | F | F | $CH_3$ |
| I.a.408. | $C_2H_5$ | Br | F | F | $OCH_3$ |
| I.a.409. | $C_2H_5$ | I | H | H | H |
| I.a.410. | $C_2H_5$ | I | H | H | F |
| I.a.411. | $C_2H_5$ | I | H | H | Cl |
| I.a.412. | $C_2H_5$ | I | H | H | Br |
| I.a.413. | $C_2H_5$ | I | H | H | $CH_3$ |
| I.a.414. | $C_2H_5$ | I | H | H | $OCH_3$ |
| I.a.415. | $C_2H_5$ | I | H | F | H |
| I.a.416. | $C_2H_5$ | I | H | F | F |
| I.a.417. | $C_2H_5$ | I | H | F | Cl |
| I.a.418. | $C_2H_5$ | I | H | F | Br |
| I.a.419. | $C_2H_5$ | I | H | F | $CH_3$ |
| I.a.420. | $C_2H_5$ | I | H | F | $OCH_3$ |
| I.a.421. | $C_2H_5$ | I | F | H | H |
| I.a.422. | $C_2H_5$ | I | F | H | F |
| I.a.423. | $C_2H_5$ | I | F | H | Cl |
| I.a.424. | $C_2H_5$ | I | F | H | Br |
| I.a.425. | $C_2H_5$ | I | F | H | $CH_3$ |
| I.a.426. | $C_2H_5$ | I | F | H | $OCH_3$ |
| I.a.427. | $C_2H_5$ | I | F | F | H |
| I.a.428. | $C_2H_5$ | I | F | F | F |
| I.a.429. | $C_2H_5$ | I | F | F | Cl |
| I.a.430. | $C_2H_5$ | I | F | F | Br |
| I.a.431. | $C_2H_5$ | I | F | F | $CH_3$ |
| I.a.432. | $C_2H_5$ | I | F | F | $OCH_3$ |
| I.a.433. | $C_2H_5$ | $CH_3$ | H | H | H |
| I.a.434. | $C_2H_5$ | $CH_3$ | H | H | F |
| I.a.435. | $C_2H_5$ | $CH_3$ | H | H | Cl |
| I.a.436. | $C_2H_5$ | $CH_3$ | H | H | Br |
| I.a.437. | $C_2H_5$ | $CH_3$ | H | H | $CH_3$ |
| I.a.438. | $C_2H_5$ | $CH_3$ | H | H | $OCH_3$ |
| I.a.439. | $C_2H_5$ | $CH_3$ | H | F | H |
| I.a.440. | $C_2H_5$ | $CH_3$ | H | F | F |
| I.a.441. | $C_2H_5$ | $CH_3$ | H | F | Cl |
| I.a.442. | $C_2H_5$ | $CH_3$ | H | F | Br |
| I.a.443. | $C_2H_5$ | $CH_3$ | H | F | $CH_3$ |
| I.a.444. | $C_2H_5$ | $CH_3$ | H | F | $OCH_3$ |
| I.a.445. | $C_2H_5$ | $CH_3$ | F | H | H |
| I.a.446. | $C_2H_5$ | $CH_3$ | F | H | F |
| I.a.447. | $C_2H_5$ | $CH_3$ | F | H | Cl |
| I.a.448. | $C_2H_5$ | $CH_3$ | F | H | Br |
| I.a.449. | $C_2H_5$ | $CH_3$ | F | H | $CH_3$ |
| I.a.450. | $C_2H_5$ | $CH_3$ | F | H | $OCH_3$ |
| I.a.451. | $C_2H_5$ | $CH_3$ | F | F | H |
| I.a.452. | $C_2H_5$ | $CH_3$ | F | F | F |
| I.a.453. | $C_2H_5$ | $CH_3$ | F | F | Cl |
| I.a.454. | $C_2H_5$ | $CH_3$ | F | F | Br |
| I.a.455. | $C_2H_5$ | $CH_3$ | F | F | $CH_3$ |
| I.a.456. | $C_2H_5$ | $CH_3$ | F | F | $OCH_3$ |
| I.a.457. | $C_2H_5$ | $OCH_3$ | H | H | H |
| I.a.458. | $C_2H_5$ | $OCH_3$ | H | H | F |
| I.a.459. | $C_2H_5$ | $OCH_3$ | H | H | Cl |
| I.a.460. | $C_2H_5$ | $OCH_3$ | H | H | Br |
| I.a.461. | $C_2H_5$ | $OCH_3$ | H | H | $CH_3$ |
| I.a.462. | $C_2H_5$ | $OCH_3$ | H | H | $OCH_3$ |
| I.a.463. | $C_2H_5$ | $OCH_3$ | H | F | H |
| I.a.464. | $C_2H_5$ | $OCH_3$ | H | F | F |
| I.a.465. | $C_2H_5$ | $OCH_3$ | H | F | Cl |
| I.a.466. | $C_2H_5$ | $OCH_3$ | H | F | Br |
| I.a.467. | $C_2H_5$ | $OCH_3$ | H | F | $CH_3$ |
| I.a.468. | $C_2H_5$ | $OCH_3$ | H | F | $OCH_3$ |
| I.a.469. | $C_2H_5$ | $OCH_3$ | F | H | H |
| I.a.470. | $C_2H_5$ | $OCH_3$ | F | H | F |
| I.a.471. | $C_2H_5$ | $OCH_3$ | F | H | Cl |
| I.a.472. | $C_2H_5$ | $OCH_3$ | F | H | Br |
| I.a.473. | $C_2H_5$ | $OCH_3$ | F | H | $CH_3$ |
| I.a.474. | $C_2H_5$ | $OCH_3$ | F | H | $OCH_3$ |
| I.a.475. | $C_2H_5$ | $OCH_3$ | F | F | H |
| I.a.476. | $C_2H_5$ | $OCH_3$ | F | F | F |
| I.a.477. | $C_2H_5$ | $OCH_3$ | F | F | Cl |
| I.a.478. | $C_2H_5$ | $OCH_3$ | F | F | Br |
| I.a.479. | $C_2H_5$ | $OCH_3$ | F | F | $CH_3$ |
| I.a.480. | $C_2H_5$ | $OCH_3$ | F | F | $OCH_3$ |
| I.a.481. | $C_2H_5$ | $CF_3$ | H | H | H |
| I.a.482. | $C_2H_5$ | $CF_3$ | H | H | F |
| I.a.483. | $C_2H_5$ | $CF_3$ | H | H | Cl |
| I.a.484. | $C_2H_5$ | $CF_3$ | H | H | Br |
| I.a.485. | $C_2H_5$ | $CF_3$ | H | H | $CH_3$ |
| I.a.486. | $C_2H_5$ | $CF_3$ | H | H | $OCH_3$ |
| I.a.487. | $C_2H_5$ | $CF_3$ | H | F | H |
| I.a.488. | $C_2H_5$ | $CF_3$ | H | F | F |
| I.a.489. | $C_2H_5$ | $CF_3$ | H | F | Cl |
| I.a.490. | $C_2H_5$ | $CF_3$ | H | F | Br |
| I.a.491. | $C_2H_5$ | $CF_3$ | H | F | $CH_3$ |
| I.a.492. | $C_2H_5$ | $CF_3$ | H | F | $OCH_3$ |
| I.a.493. | $C_2H_5$ | $CF_3$ | F | H | H |
| I.a.494. | $C_2H_5$ | $CF_3$ | F | H | F |
| I.a.495. | $C_2H_5$ | $CF_3$ | F | H | Cl |
| I.a.496. | $C_2H_5$ | $CF_3$ | F | H | Br |
| I.a.497. | $C_2H_5$ | $CF_3$ | F | H | $CH_3$ |
| I.a.498. | $C_2H_5$ | $CF_3$ | F | H | $OCH_3$ |

TABLE (I)-continued

| No. | R¹ | R³ | R⁵ | R⁶ | R⁷ |
|---|---|---|---|---|---|
| I.a.499. | C₂H₅ | CF₃ | F | F | H |
| I.a.500. | C₂H₅ | CF₃ | F | F | F |
| I.a.501. | C₂H₅ | CF₃ | F | F | Cl |
| I.a.502. | C₂H₅ | CF₃ | F | F | Br |
| I.a.503. | C₂H₅ | CF₃ | F | F | CH₃ |
| I.a.504. | C₂H₅ | CF₃ | F | F | OCH₃ |
| I.a.505. | OCH₃ | F | H | H | H |
| I.a.506. | OCH₃ | F | H | H | F |
| I.a.507. | OCH₃ | F | H | H | Cl |
| I.a.508. | OCH₃ | F | H | H | Br |
| I.a.509. | OCH₃ | F | H | H | CH₃ |
| I.a.510. | OCH₃ | F | H | H | OCH₃ |
| I.a.511. | OCH₃ | F | H | F | H |
| I.a.512. | OCH₃ | F | H | F | F |
| I.a.513. | OCH₃ | F | H | F | Cl |
| I.a.514. | OCH₃ | F | H | F | Br |
| I.a.515. | OCH₃ | F | H | F | CH₃ |
| I.a.516. | OCH₃ | F | H | F | OCH₃ |
| I.a.517. | OCH₃ | F | F | H | H |
| I.a.518. | OCH₃ | F | F | H | F |
| I.a.519. | OCH₃ | F | F | H | Cl |
| I.a.520. | OCH₃ | F | F | H | Br |
| I.a.521. | OCH₃ | F | F | H | CH₃ |
| I.a.522. | OCH₃ | F | F | H | OCH₃ |
| I.a.523. | OCH₃ | F | F | F | H |
| I.a.524. | OCH₃ | F | F | F | F |
| I.a.525. | OCH₃ | F | F | F | Cl |
| I.a.526. | OCH₃ | F | F | F | Br |
| I.a.527. | OCH₃ | F | F | F | CH₃ |
| I.a.528. | OCH₃ | F | F | F | OCH₃ |
| I.a.529. | OCH₃ | Cl | H | H | H |
| I.a.530. | OCH₃ | Cl | H | H | F |
| I.a.531. | OCH₃ | Cl | H | H | Cl |
| I.a.532. | OCH₃ | Cl | H | H | Br |
| I.a.533. | OCH₃ | Cl | H | H | CH₃ |
| I.a.534. | OCH₃ | Cl | H | H | OCH₃ |
| I.a.535. | OCH₃ | Cl | H | F | H |
| I.a.536. | OCH₃ | Cl | H | F | F |
| I.a.537. | OCH₃ | Cl | H | F | Cl |
| I.a.538. | OCH₃ | Cl | H | F | Br |
| I.a.539. | OCH₃ | Cl | H | F | CH₃ |
| I.a.540. | OCH₃ | Cl | H | F | OCH₃ |
| I.a.541. | OCH₃ | Cl | F | H | H |
| I.a.542. | OCH₃ | Cl | F | H | F |
| I.a.543. | OCH₃ | Cl | F | H | Cl |
| I.a.544. | OCH₃ | Cl | F | H | Br |
| I.a.545. | OCH₃ | Cl | F | H | CH₃ |
| I.a.546. | OCH₃ | Cl | F | H | OCH₃ |
| I.a.547. | OCH₃ | Cl | F | F | H |
| I.a.548. | OCH₃ | Cl | F | F | F |
| I.a.549. | OCH₃ | Cl | F | F | Cl |
| I.a.550. | OCH₃ | Cl | F | F | Br |
| I.a.551. | OCH₃ | Cl | F | F | CH₃ |
| I.a.552. | OCH₃ | Cl | F | F | OCH₃ |
| I.a.553. | OCH₃ | Br | H | H | H |
| I.a.554. | OCH₃ | Br | H | H | F |
| I.a.555. | OCH₃ | Br | H | H | Cl |
| I.a.556. | OCH₃ | Br | H | H | Br |
| I.a.557. | OCH₃ | Br | H | H | CH₃ |
| I.a.558. | OCH₃ | Br | H | H | OCH₃ |
| I.a.559. | OCH₃ | Br | H | F | H |
| I.a.560. | OCH₃ | Br | H | F | F |
| I.a.561. | OCH₃ | Br | H | F | Cl |
| I.a.562. | OCH₃ | Br | H | F | Br |
| I.a.563. | OCH₃ | Br | H | F | CH₃ |
| I.a.564. | OCH₃ | Br | H | F | OCH₃ |
| I.a.565. | OCH₃ | Br | F | H | H |
| I.a.566. | OCH₃ | Br | F | H | F |
| I.a.567. | OCH₃ | Br | F | H | Cl |
| I.a.568. | OCH₃ | Br | F | H | Br |
| I.a.569. | OCH₃ | Br | F | H | CH₃ |
| I.a.570. | OCH₃ | Br | F | H | OCH₃ |
| I.a.571. | OCH₃ | Br | F | F | H |
| I.a.572. | OCH₃ | Br | F | F | F |
| I.a.573. | OCH₃ | Br | F | F | Cl |
| I.a.574. | OCH₃ | Br | F | F | Br |
| I.a.575. | OCH₃ | Br | F | F | CH₃ |
| I.a.576. | OCH₃ | Br | F | F | OCH₃ |
| I.a.577. | OCH₃ | I | H | H | H |
| I.a.578. | OCH₃ | I | H | H | F |
| I.a.579. | OCH₃ | I | H | H | Cl |
| I.a.580. | OCH₃ | I | H | H | Br |
| I.a.581. | OCH₃ | I | H | H | CH₃ |
| I.a.582. | OCH₃ | I | H | H | OCH₃ |
| I.a.583. | OCH₃ | I | H | F | H |
| I.a.584. | OCH₃ | I | H | F | F |
| I.a.585. | OCH₃ | I | H | F | Cl |
| I.a.586. | OCH₃ | I | H | F | Br |
| I.a.587. | OCH₃ | I | H | F | CH₃ |
| I.a.588. | OCH₃ | I | H | F | OCH₃ |
| I.a.589. | OCH₃ | I | F | H | H |
| I.a.590. | OCH₃ | I | F | H | F |
| I.a.591. | OCH₃ | I | F | H | Cl |
| I.a.592. | OCH₃ | I | F | H | Br |
| I.a.593. | OCH₃ | I | F | H | CH₃ |
| I.a.594. | OCH₃ | I | F | H | OCH₃ |
| I.a.595. | OCH₃ | I | F | F | H |
| I.a.596. | OCH₃ | I | F | F | F |
| I.a.597. | OCH₃ | I | F | F | Cl |
| I.a.598. | OCH₃ | I | F | F | Br |
| I.a.599. | OCH₃ | I | F | F | CH₃ |
| I.a.600. | OCH₃ | I | F | F | OCH₃ |
| I.a.601. | OCH₃ | CH₃ | H | H | H |
| I.a.602. | OCH₃ | CH₃ | H | H | F |
| I.a.603. | OCH₃ | CH₃ | H | H | Cl |
| I.a.604. | OCH₃ | CH₃ | H | H | Br |
| I.a.605. | OCH₃ | CH₃ | H | H | CH₃ |
| I.a.606. | OCH₃ | CH₃ | H | H | OCH₃ |
| I.a.607. | OCH₃ | CH₃ | H | F | H |
| I.a.608. | OCH₃ | CH₃ | H | F | F |
| I.a.609. | OCH₃ | CH₃ | H | F | Cl |
| I.a.610. | OCH₃ | CH₃ | H | F | Br |
| I.a.611. | OCH₃ | CH₃ | H | F | CH₃ |
| I.a.612. | OCH₃ | CH₃ | H | F | OCH₃ |
| I.a.613. | OCH₃ | CH₃ | F | H | H |
| I.a.614. | OCH₃ | CH₃ | F | H | F |
| I.a.615. | OCH₃ | CH₃ | F | H | Cl |
| I.a.616. | OCH₃ | CH₃ | F | H | Br |
| I.a.617. | OCH₃ | CH₃ | F | H | CH₃ |
| I.a.618. | OCH₃ | CH₃ | F | H | OCH₃ |
| I.a.619. | OCH₃ | CH₃ | F | F | H |
| I.a.620. | OCH₃ | CH₃ | F | F | F |
| I.a.621. | OCH₃ | CH₃ | F | F | Cl |
| I.a.622. | OCH₃ | CH₃ | F | F | Br |
| I.a.623. | OCH₃ | CH₃ | F | F | CH₃ |
| I.a.624. | OCH₃ | CH₃ | F | F | OCH₃ |
| I.a.625. | OCH₃ | OCH₃ | H | H | H |
| I.a.626. | OCH₃ | OCH₃ | H | H | F |
| I.a.627. | OCH₃ | OCH₃ | H | H | Cl |
| I.a.628. | OCH₃ | OCH₃ | H | H | Br |
| I.a.629. | OCH₃ | OCH₃ | H | H | CH₃ |
| I.a.630. | OCH₃ | OCH₃ | H | H | OCH₃ |
| I.a.631. | OCH₃ | OCH₃ | H | F | H |
| I.a.632. | OCH₃ | OCH₃ | H | F | F |
| I.a.633. | OCH₃ | OCH₃ | H | F | Cl |
| I.a.634. | OCH₃ | OCH₃ | H | F | Br |
| I.a.635. | OCH₃ | OCH₃ | H | F | CH₃ |
| I.a.636. | OCH₃ | OCH₃ | H | F | OCH₃ |
| I.a.637. | OCH₃ | OCH₃ | F | H | H |
| I.a.638. | OCH₃ | OCH₃ | F | H | F |
| I.a.639. | OCH₃ | OCH₃ | F | H | Cl |
| I.a.640. | OCH₃ | OCH₃ | F | H | Br |
| I.a.641. | OCH₃ | OCH₃ | F | H | CH₃ |
| I.a.642. | OCH₃ | OCH₃ | F | H | OCH₃ |
| I.a.643. | OCH₃ | OCH₃ | F | F | H |
| I.a.644. | OCH₃ | OCH₃ | F | F | F |
| I.a.645. | OCH₃ | OCH₃ | F | F | Cl |
| I.a.646. | OCH₃ | OCH₃ | F | F | Br |
| I.a.647. | OCH₃ | OCH₃ | F | F | CH₃ |
| I.a.648. | OCH₃ | OCH₃ | F | F | OCH₃ |
| I.a.649. | OCH₃ | CF₃ | H | H | H |
| I.a.650. | OCH₃ | CF₃ | H | H | F |
| I.a.651. | OCH₃ | CF₃ | H | H | Cl |
| I.a.652. | OCH₃ | CF₃ | H | H | Br |
| I.a.653. | OCH₃ | CF₃ | H | H | CH₃ |
| I.a.654. | OCH₃ | CF₃ | H | H | OCH₃ |

TABLE (I)-continued

| No. | R¹ | R³ | R⁵ | R⁶ | R⁷ |
|---|---|---|---|---|---|
| I.a.655. | OCH₃ | CF₃ | H | F | H |
| I.a.656. | OCH₃ | CF₃ | H | F | F |
| I.a.657. | OCH₃ | CF₃ | H | F | Cl |
| I.a.658. | OCH₃ | CF₃ | H | F | Br |
| I.a.659. | OCH₃ | CF₃ | H | F | CH₃ |
| I.a.660. | OCH₃ | CF₃ | H | F | OCH₃ |
| I.a.661. | OCH₃ | CF₃ | F | H | H |
| I.a.662. | OCH₃ | CF₃ | F | H | F |
| I.a.663. | OCH₃ | CF₃ | F | H | Cl |
| I.a.664. | OCH₃ | CF₃ | F | H | Br |
| I.a.665. | OCH₃ | CF₃ | F | H | CH₃ |
| I.a.666. | OCH₃ | CF₃ | F | H | OCH₃ |
| I.a.667. | OCH₃ | CF₃ | F | F | H |
| I.a.668. | OCH₃ | CF₃ | F | F | F |
| I.a.669. | OCH₃ | CF₃ | F | F | Cl |
| I.a.670. | OCH₃ | CF₃ | F | F | Br |
| I.a.671. | OCH₃ | CF₃ | F | F | CH₃ |
| I.a.672. | OCH₃ | CF₃ | F | F | OCH₃ |
| I.a.673. | c-C₃H₅ | F | CF₃ | H | H |
| I.a.674. | c-C₃H₅ | F | CF₃ | H | F |
| I.a.675. | c-C₃H₅ | F | CF₃ | H | Cl |
| I.a.676. | c-C₃H₅ | F | CF₃ | H | Br |
| I.a.677. | c-C₃H₅ | F | CF₃ | H | CH₃ |
| I.a.678. | c-C₃H₅ | F | CF₃ | H | OCH₃ |
| I.a.679. | c-C₃H₅ | F | CF₃ | F | H |
| I.a.680. | c-C₃H₅ | F | CF₃ | F | F |
| I.a.681. | c-C₃H₅ | F | CF₃ | F | Cl |
| I.a.682. | c-C₃H₅ | F | CF₃ | F | Br |
| I.a.683. | c-C₃H₅ | F | CF₃ | F | CH₃ |
| I.a.684. | c-C₃H₅ | F | CF₃ | F | OCH₃ |
| I.a.685. | c-C₃H₅ | Cl | CF₃ | H | H |
| I.a.686. | c-C₃H₅ | Cl | CF₃ | H | F |
| I.a.687. | c-C₃H₅ | Cl | CF₃ | H | Cl |
| I.a.688. | c-C₃H₅ | Cl | CF₃ | H | Br |
| I.a.689. | c-C₃H₅ | Cl | CF₃ | H | CH₃ |
| I.a.690. | c-C₃H₅ | Cl | CF₃ | H | OCH₃ |
| I.a.691. | c-C₃H₅ | Cl | CF₃ | F | H |
| I.a.692. | c-C₃H₅ | Cl | CF₃ | F | F |
| I.a.693. | c-C₃H₅ | Cl | CF₃ | F | Cl |
| I.a.694. | c-C₃H₅ | Cl | CF₃ | F | Br |
| I.a.695. | c-C₃H₅ | Cl | CF₃ | F | CH₃ |
| I.a.696. | c-C₃H₅ | Cl | CF₃ | F | OCH₃ |
| I.a.697. | c-C₃H₅ | Br | CF₃ | H | H |
| I.a.698. | c-C₃H₅ | Br | CF₃ | H | F |
| I.a.699. | c-C₃H₅ | Br | CF₃ | H | Cl |
| I.a.700. | c-C₃H₅ | Br | CF₃ | H | Br |
| I.a.701. | c-C₃H₅ | Br | CF₃ | H | CH₃ |
| I.a.702. | c-C₃H₅ | Br | CF₃ | H | OCH₃ |
| I.a.703. | c-C₃H₅ | Br | CF₃ | F | H |
| I.a.704. | c-C₃H₅ | Br | CF₃ | F | F |
| I.a.705. | c-C₃H₅ | Br | CF₃ | F | Cl |
| I.a.706. | c-C₃H₅ | Br | CF₃ | F | Br |
| I.a.707. | c-C₃H₅ | Br | CF₃ | F | CH₃ |
| I.a.708. | c-C₃H₅ | Br | CF₃ | F | OCH₃ |
| I.a.709. | c-C₃H₅ | I | CF₃ | H | H |
| I.a.710. | c-C₃H₅ | I | CF₃ | H | F |
| I.a.711. | c-C₃H₅ | I | CF₃ | H | Cl |
| I.a.712. | c-C₃H₅ | I | CF₃ | H | Br |
| I.a.713. | c-C₃H₅ | I | CF₃ | H | CH₃ |
| I.a.714. | c-C₃H₅ | I | CF₃ | H | OCH₃ |
| I.a.715. | c-C₃H₅ | I | CF₃ | F | H |
| I.a.716. | c-C₃H₅ | I | CF₃ | F | F |
| I.a.717. | c-C₃H₅ | I | CF₃ | F | Cl |
| I.a.718. | c-C₃H₅ | I | CF₃ | F | Br |
| I.a.719. | c-C₃H₅ | I | CF₃ | F | CH₃ |
| I.a.720. | c-C₃H₅ | I | CF₃ | F | OCH₃ |
| I.a.721. | c-C₃H₅ | CH₃ | CF₃ | H | H |
| I.a.722. | c-C₃H₅ | CH₃ | CF₃ | H | F |
| I.a.723. | c-C₃H₅ | CH₃ | CF₃ | H | Cl |
| I.a.724. | c-C₃H₅ | CH₃ | CF₃ | H | Br |
| I.a.725. | c-C₃H₅ | CH₃ | CF₃ | H | CH₃ |
| I.a.726. | c-C₃H₅ | CH₃ | CF₃ | H | OCH₃ |
| I.a.727. | c-C₃H₅ | CH₃ | CF₃ | F | H |
| I.a.728. | c-C₃H₅ | CH₃ | CF₃ | F | F |
| I.a.729. | c-C₃H₅ | CH₃ | CF₃ | F | Cl |
| I.a.730. | c-C₃H₅ | CH₃ | CF₃ | F | Br |
| I.a.731. | c-C₃H₅ | CH₃ | CF₃ | F | CH₃ |
| I.a.732. | c-C₃H₅ | CH₃ | CF₃ | F | OCH₃ |
| I.a.733. | c-C₃H₅ | OCH₃ | CF₃ | H | H |
| I.a.734. | c-C₃H₅ | OCH₃ | CF₃ | H | F |
| I.a.735. | c-C₃H₅ | OCH₃ | CF₃ | H | Cl |
| I.a.736. | c-C₃H₅ | OCH₃ | CF₃ | H | Br |
| I.a.737. | c-C₃H₅ | OCH₃ | CF₃ | H | CH₃ |
| I.a.738. | c-C₃H₅ | OCH₃ | CF₃ | H | OCH₃ |
| I.a.739. | c-C₃H₅ | OCH₃ | CF₃ | F | H |
| I.a.740. | c-C₃H₅ | OCH₃ | CF₃ | F | F |
| I.a.741. | c-C₃H₅ | OCH₃ | CF₃ | F | Cl |
| I.a.742. | c-C₃H₅ | OCH₃ | CF₃ | F | Br |
| I.a.743. | c-C₃H₅ | OCH₃ | CF₃ | F | CH₃ |
| I.a.744. | c-C₃H₅ | OCH₃ | CF₃ | F | OCH₃ |
| I.a.745. | c-C₃H₅ | CF₃ | CF₃ | H | H |
| I.a.746. | c-C₃H₅ | CF₃ | CF₃ | H | F |
| I.a.747. | c-C₃H₅ | CF₃ | CF₃ | H | Cl |
| I.a.748. | c-C₃H₅ | CF₃ | CF₃ | H | Br |
| I.a.749. | c-C₃H₅ | CF₃ | CF₃ | H | CH₃ |
| I.a.750. | c-C₃H₅ | CF₃ | CF₃ | H | OCH₃ |
| I.a.751. | c-C₃H₅ | CF₃ | CF₃ | F | H |
| I.a.752. | c-C₃H₅ | CF₃ | CF₃ | F | F |
| I.a.753. | c-C₃H₅ | CF₃ | CF₃ | F | Cl |
| I.a.754. | c-C₃H₅ | CF₃ | CF₃ | F | Br |
| I.a.755. | c-C₃H₅ | CF₃ | CF₃ | F | CH₃ |
| I.a.756. | c-C₃H₅ | CF₃ | CF₃ | F | OCH₃ |
| I.a.757. | c-C₄H₇ | F | CF₃ | H | H |
| I.a.758. | c-C₄H₇ | F | CF₃ | H | F |
| I.a.759. | c-C₄H₇ | F | CF₃ | H | Cl |
| I.a.760. | c-C₄H₇ | F | CF₃ | H | Br |
| I.a.761. | c-C₄H₇ | F | CF₃ | H | CH₃ |
| I.a.762. | c-C₄H₇ | F | CF₃ | H | OCH₃ |
| I.a.763. | c-C₄H₇ | F | CF₃ | F | H |
| I.a.764. | c-C₄H₇ | F | CF₃ | F | F |
| I.a.765. | c-C₄H₇ | F | CF₃ | F | Cl |
| I.a.766. | c-C₄H₇ | F | CF₃ | F | Br |
| I.a.767. | c-C₄H₇ | F | CF₃ | F | CH₃ |
| I.a.768. | c-C₄H₇ | F | CF₃ | F | OCH₃ |
| I.a.769. | c-C₄H₇ | Cl | CF₃ | H | H |
| I.a.770. | c-C₄H₇ | Cl | CF₃ | H | F |
| I.a.771. | c-C₄H₇ | Cl | CF₃ | H | Cl |
| I.a.772. | c-C₄H₇ | Cl | CF₃ | H | Br |
| I.a.773. | c-C₄H₇ | Cl | CF₃ | H | CH₃ |
| I.a.774. | c-C₄H₇ | Cl | CF₃ | H | OCH₃ |
| I.a.775. | c-C₄H₇ | Cl | CF₃ | F | H |
| I.a.776. | c-C₄H₇ | Cl | CF₃ | F | F |
| I.a.777. | c-C₄H₇ | Cl | CF₃ | F | Cl |
| I.a.778. | c-C₄H₇ | Cl | CF₃ | F | Br |
| I.a.779. | c-C₄H₇ | Cl | CF₃ | F | CH₃ |
| I.a.780. | c-C₄H₇ | Cl | CF₃ | F | OCH₃ |
| I.a.781. | c-C₄H₇ | Br | CF₃ | H | H |
| I.a.782. | c-C₄H₇ | Br | CF₃ | H | F |
| I.a.783. | c-C₄H₇ | Br | CF₃ | H | Cl |
| I.a.784. | c-C₄H₇ | Br | CF₃ | H | Br |
| I.a.785. | c-C₄H₇ | Br | CF₃ | H | CH₃ |
| I.a.786. | c-C₄H₇ | Br | CF₃ | H | OCH₃ |
| I.a.787. | c-C₄H₇ | Br | CF₃ | F | H |
| I.a.788. | c-C₄H₇ | Br | CF₃ | F | F |
| I.a.789. | c-C₄H₇ | Br | CF₃ | F | Cl |
| I.a.790. | c-C₄H₇ | Br | CF₃ | F | Br |
| I.a.791. | c-C₄H₇ | Br | CF₃ | F | CH₃ |
| I.a.792. | c-C₄H₇ | Br | CF₃ | F | OCH₃ |
| I.a.793. | c-C₄H₇ | I | CF₃ | H | H |
| I.a.794. | c-C₄H₇ | I | CF₃ | H | F |
| I.a.795. | c-C₄H₇ | I | CF₃ | H | Cl |
| I.a.796. | c-C₄H₇ | I | CF₃ | H | Br |
| I.a.797. | c-C₄H₇ | I | CF₃ | H | CH₃ |
| I.a.798. | c-C₄H₇ | I | CF₃ | H | OCH₃ |
| I.a.799. | c-C₄H₇ | I | CF₃ | F | H |
| I.a.800. | c-C₄H₇ | I | CF₃ | F | F |
| I.a.801. | c-C₄H₇ | I | CF₃ | F | Cl |
| I.a.802. | c-C₄H₇ | I | CF₃ | F | Br |
| I.a.803. | c-C₄H₇ | I | CF₃ | F | CH₃ |
| I.a.804. | c-C₄H₇ | I | CF₃ | F | OCH₃ |
| I.a.805. | c-C₄H₇ | CH₃ | CF₃ | H | H |
| I.a.806. | c-C₄H₇ | CH₃ | CF₃ | H | F |
| I.a.807. | c-C₄H₇ | CH₃ | CF₃ | H | Cl |
| I.a.808. | c-C₄H₇ | CH₃ | CF₃ | H | Br |
| I.a.809. | c-C₄H₇ | CH₃ | CF₃ | H | CH₃ |
| I.a.810. | c-C₄H₇ | CH₃ | CF₃ | H | OCH₃ |

TABLE (I)-continued

| No. | $R^1$ | $R^3$ | $R^5$ | $R^6$ | $R^7$ |
|---|---|---|---|---|---|
| I.a.811. | c-$C_4H_7$ | $CH_3$ | $CF_3$ | F | H |
| I.a.812. | c-$C_4H_7$ | $CH_3$ | $CF_3$ | F | F |
| I.a.813. | c-$C_4H_7$ | $CH_3$ | $CF_3$ | F | Cl |
| I.a.814. | c-$C_4H_7$ | $CH_3$ | $CF_3$ | F | Br |
| I.a.815. | c-$C_4H_7$ | $CH_3$ | $CF_3$ | F | $CH_3$ |
| I.a.816. | c-$C_4H_7$ | $CH_3$ | $CF_3$ | F | $OCH_3$ |
| I.a.817. | c-$C_4H_7$ | $OCH_3$ | $CF_3$ | H | H |
| I.a.818. | c-$C_4H_7$ | $OCH_3$ | $CF_3$ | H | F |
| I.a.819. | c-$C_4H_7$ | $OCH_3$ | $CF_3$ | H | Cl |
| I.a.820. | c-$C_4H_7$ | $OCH_3$ | $CF_3$ | H | Br |
| I.a.821. | c-$C_4H_7$ | $OCH_3$ | $CF_3$ | H | $CH_3$ |
| I.a.822. | c-$C_4H_7$ | $OCH_3$ | $CF_3$ | H | $OCH_3$ |
| I.a.823. | c-$C_4H_7$ | $OCH_3$ | $CF_3$ | F | H |
| I.a.824. | c-$C_4H_7$ | $OCH_3$ | $CF_3$ | F | F |
| I.a.825. | c-$C_4H_7$ | $OCH_3$ | $CF_3$ | F | Cl |
| I.a.826. | c-$C_4H_7$ | $OCH_3$ | $CF_3$ | F | Br |
| I.a.827. | c-$C_4H_7$ | $OCH_3$ | $CF_3$ | F | $CH_3$ |
| I.a.828. | c-$C_4H_7$ | $OCH_3$ | $CF_3$ | F | $OCH_3$ |
| I.a.829. | c-$C_4H_7$ | $CF_3$ | $CF_3$ | H | H |
| I.a.830. | c-$C_4H_7$ | $CF_3$ | $CF_3$ | H | F |
| I.a.831. | c-$C_4H_7$ | $CF_3$ | $CF_3$ | H | Cl |
| I.a.832. | c-$C_4H_7$ | $CF_3$ | $CF_3$ | H | Br |
| I.a.833. | c-$C_4H_7$ | $CF_3$ | $CF_3$ | H | $CH_3$ |
| I.a.834. | c-$C_4H_7$ | $CF_3$ | $CF_3$ | H | $OCH_3$ |
| I.a.835. | c-$C_4H_7$ | $CF_3$ | $CF_3$ | F | H |
| I.a.836. | c-$C_4H_7$ | $CF_3$ | $CF_3$ | F | F |
| I.a.837. | c-$C_4H_7$ | $CF_3$ | $CF_3$ | F | Cl |
| I.a.838. | c-$C_4H_7$ | $CF_3$ | $CF_3$ | F | Br |
| I.a.839. | c-$C_4H_7$ | $CF_3$ | $CF_3$ | F | $CH_3$ |
| I.a.840. | c-$C_4H_7$ | $CF_3$ | $CF_3$ | F | $OCH_3$ |
| I.a.841. | $C_2H_5$ | F | $CF_3$ | H | H |
| I.a.842. | $C_2H_5$ | F | $CF_3$ | H | F |
| I.a.843. | $C_2H_5$ | F | $CF_3$ | H | Cl |
| I.a.844. | $C_2H_5$ | F | $CF_3$ | H | Br |
| I.a.845. | $C_2H_5$ | F | $CF_3$ | H | $CH_3$ |
| I.a.846. | $C_2H_5$ | F | $CF_3$ | H | $OCH_3$ |
| I.a.847. | $C_2H_5$ | F | $CF_3$ | F | H |
| I.a.848. | $C_2H_5$ | F | $CF_3$ | F | F |
| I.a.849. | $C_2H_5$ | F | $CF_3$ | F | Cl |
| I.a.850. | $C_2H_5$ | F | $CF_3$ | F | Br |
| I.a.851. | $C_2H_5$ | F | $CF_3$ | F | $CH_3$ |
| I.a.852. | $C_2H_5$ | F | $CF_3$ | F | $OCH_3$ |
| I.a.853. | $C_2H_5$ | Cl | $CF_3$ | H | H |
| I.a.854. | $C_2H_5$ | Cl | $CF_3$ | H | F |
| I.a.855. | $C_2H_5$ | Cl | $CF_3$ | H | Cl |
| I.a.856. | $C_2H_5$ | Cl | $CF_3$ | H | Br |
| I.a.857. | $C_2H_5$ | Cl | $CF_3$ | H | $CH_3$ |
| I.a.858. | $C_2H_5$ | Cl | $CF_3$ | H | $OCH_3$ |
| I.a.859. | $C_2H_5$ | Cl | $CF_3$ | F | H |
| I.a.860. | $C_2H_5$ | Cl | $CF_3$ | F | F |
| I.a.861. | $C_2H_5$ | Cl | $CF_3$ | F | Cl |
| I.a.862. | $C_2H_5$ | Cl | $CF_3$ | F | Br |
| I.a.863. | $C_2H_5$ | Cl | $CF_3$ | F | $CH_3$ |
| I.a.864. | $C_2H_5$ | Cl | $CF_3$ | F | $OCH_3$ |
| I.a.865. | $C_2H_5$ | Br | $CF_3$ | H | H |
| I.a.866. | $C_2H_5$ | Br | $CF_3$ | H | F |
| I.a.867. | $C_2H_5$ | Br | $CF_3$ | H | Cl |
| I.a.868. | $C_2H_5$ | Br | $CF_3$ | H | Br |
| I.a.869. | $C_2H_5$ | Br | $CF_3$ | H | $CH_3$ |
| I.a.870. | $C_2H_5$ | Br | $CF_3$ | H | $OCH_3$ |
| I.a.871. | $C_2H_5$ | Br | $CF_3$ | F | H |
| I.a.872. | $C_2H_5$ | Br | $CF_3$ | F | F |
| I.a.873. | $C_2H_5$ | Br | $CF_3$ | F | Cl |
| I.a.874. | $C_2H_5$ | Br | $CF_3$ | F | Br |
| I.a.875. | $C_2H_5$ | Br | $CF_3$ | F | $CH_3$ |
| I.a.876. | $C_2H_5$ | Br | $CF_3$ | F | $OCH_3$ |
| I.a.877. | $C_2H_5$ | I | $CF_3$ | H | H |
| I.a.878. | $C_2H_5$ | I | $CF_3$ | H | F |
| I.a.879. | $C_2H_5$ | I | $CF_3$ | H | Cl |
| I.a.880. | $C_2H_5$ | I | $CF_3$ | H | Br |
| I.a.881. | $C_2H_5$ | I | $CF_3$ | H | $CH_3$ |
| I.a.882. | $C_2H_5$ | I | $CF_3$ | H | $OCH_3$ |
| I.a.883. | $C_2H_5$ | I | $CF_3$ | F | H |
| I.a.884. | $C_2H_5$ | I | $CF_3$ | F | F |
| I.a.885. | $C_2H_5$ | I | $CF_3$ | F | Cl |
| I.a.886. | $C_2H_5$ | I | $CF_3$ | F | Br |
| I.a.887. | $C_2H_5$ | I | $CF_3$ | F | $CH_3$ |
| I.a.888. | $C_2H_5$ | I | $CF_3$ | F | $OCH_3$ |
| I.a.889. | $C_2H_5$ | $CH_3$ | $CF_3$ | H | H |
| I.a.890. | $C_2H_5$ | $CH_3$ | $CF_3$ | H | F |
| I.a.891. | $C_2H_5$ | $CH_3$ | $CF_3$ | H | Cl |
| I.a.892. | $C_2H_5$ | $CH_3$ | $CF_3$ | H | Br |
| I.a.893. | $C_2H_5$ | $CH_3$ | $CF_3$ | H | $CH_3$ |
| I.a.894. | $C_2H_5$ | $CH_3$ | $CF_3$ | H | $OCH_3$ |
| I.a.895. | $C_2H_5$ | $CH_3$ | $CF_3$ | F | H |
| I.a.896. | $C_2H_5$ | $CH_3$ | $CF_3$ | F | F |
| I.a.897. | $C_2H_5$ | $CH_3$ | $CF_3$ | F | Cl |
| I.a.898. | $C_2H_5$ | $CH_3$ | $CF_3$ | F | Br |
| I.a.899. | $C_2H_5$ | $CH_3$ | $CF_3$ | F | $CH_3$ |
| I.a.900. | $C_2H_5$ | $CH_3$ | $CF_3$ | F | $OCH_3$ |
| I.a.901. | $C_2H_5$ | $OCH_3$ | $CF_3$ | H | H |
| I.a.902. | $C_2H_5$ | $OCH_3$ | $CF_3$ | H | F |
| I.a.903. | $C_2H_5$ | $OCH_3$ | $CF_3$ | H | Cl |
| I.a.904. | $C_2H_5$ | $OCH_3$ | $CF_3$ | H | Br |
| I.a.905. | $C_2H_5$ | $OCH_3$ | $CF_3$ | H | $CH_3$ |
| I.a.906. | $C_2H_5$ | $OCH_3$ | $CF_3$ | H | $OCH_3$ |
| I.a.907. | $C_2H_5$ | $OCH_3$ | $CF_3$ | F | H |
| I.a.908. | $C_2H_5$ | $OCH_3$ | $CF_3$ | F | F |
| I.a.909. | $C_2H_5$ | $OCH_3$ | $CF_3$ | F | Cl |
| I.a.910. | $C_2H_5$ | $OCH_3$ | $CF_3$ | F | Br |
| I.a.911. | $C_2H_5$ | $OCH_3$ | $CF_3$ | F | $CH_3$ |
| I.a.912. | $C_2H_5$ | $OCH_3$ | $CF_3$ | F | $OCH_3$ |
| I.a.913. | $C_2H_5$ | $CF_3$ | $CF_3$ | H | H |
| I.a.914. | $C_2H_5$ | $CF_3$ | $CF_3$ | H | F |
| I.a.915. | $C_2H_5$ | $CF_3$ | $CF_3$ | H | Cl |
| I.a.916. | $C_2H_5$ | $CF_3$ | $CF_3$ | H | Br |
| I.a.917. | $C_2H_5$ | $CF_3$ | $CF_3$ | H | $CH_3$ |
| I.a.918. | $C_2H_5$ | $CF_3$ | $CF_3$ | H | $OCH_3$ |
| I.a.919. | $C_2H_5$ | $CF_3$ | $CF_3$ | F | H |
| I.a.920. | $C_2H_5$ | $CF_3$ | $CF_3$ | F | F |
| I.a.921. | $C_2H_5$ | $CF_3$ | $CF_3$ | F | Cl |
| I.a.922. | $C_2H_5$ | $CF_3$ | $CF_3$ | F | Br |
| I.a.923. | $C_2H_5$ | $CF_3$ | $CF_3$ | F | $CH_3$ |
| I.a.924. | $C_2H_5$ | $CF_3$ | $CF_3$ | F | $OCH_3$ |
| I.a.925. | $OCH_3$ | F | $CF_3$ | H | H |
| I.a.926. | $OCH_3$ | F | $CF_3$ | H | F |
| I.a.927. | $OCH_3$ | F | $CF_3$ | H | Cl |
| I.a.928. | $OCH_3$ | F | $CF_3$ | H | Br |
| I.a.929. | $OCH_3$ | F | $CF_3$ | H | $CH_3$ |
| I.a.930. | $OCH_3$ | F | $CF_3$ | H | $OCH_3$ |
| I.a.931. | $OCH_3$ | F | $CF_3$ | F | H |
| I.a.932. | $OCH_3$ | F | $CF_3$ | F | F |
| I.a.933. | $OCH_3$ | F | $CF_3$ | F | Cl |
| I.a.934. | $OCH_3$ | F | $CF_3$ | F | Br |
| I.a.935. | $OCH_3$ | F | $CF_3$ | F | $CH_3$ |
| I.a.936. | $OCH_3$ | F | $CF_3$ | F | $OCH_3$ |
| I.a.937. | $OCH_3$ | Cl | $CF_3$ | H | H |
| I.a.938. | $OCH_3$ | Cl | $CF_3$ | H | F |
| I.a.939. | $OCH_3$ | Cl | $CF_3$ | H | Cl |
| I.a.940. | $OCH_3$ | Cl | $CF_3$ | H | Br |
| I.a.941. | $OCH_3$ | Cl | $CF_3$ | H | $CH_3$ |
| I.a.942. | $OCH_3$ | Cl | $CF_3$ | H | $OCH_3$ |
| I.a.943. | $OCH_3$ | Cl | $CF_3$ | F | H |
| I.a.944. | $OCH_3$ | Cl | $CF_3$ | F | F |
| I.a.945. | $OCH_3$ | Cl | $CF_3$ | F | Cl |
| I.a.946. | $OCH_3$ | Cl | $CF_3$ | F | Br |
| I.a.947. | $OCH_3$ | Cl | $CF_3$ | F | $CH_3$ |
| I.a.948. | $OCH_3$ | Cl | $CF_3$ | F | $OCH_3$ |
| I.a.949. | $OCH_3$ | Br | $CF_3$ | H | H |
| I.a.950. | $OCH_3$ | Br | $CF_3$ | H | F |
| I.a.951. | $OCH_3$ | Br | $CF_3$ | H | Cl |
| I.a.952. | $OCH_3$ | Br | $CF_3$ | H | Br |
| I.a.953. | $OCH_3$ | Br | $CF_3$ | H | $CH_3$ |
| I.a.954. | $OCH_3$ | Br | $CF_3$ | H | $OCH_3$ |
| I.a.955. | $OCH_3$ | Br | $CF_3$ | F | H |
| I.a.956. | $OCH_3$ | Br | $CF_3$ | F | F |
| I.a.957. | $OCH_3$ | Br | $CF_3$ | F | Cl |
| I.a.958. | $OCH_3$ | Br | $CF_3$ | F | Br |
| I.a.959. | $OCH_3$ | Br | $CF_3$ | F | $CH_3$ |
| I.a.960. | $OCH_3$ | Br | $CF_3$ | F | $OCH_3$ |
| I.a.961. | $OCH_3$ | I | $CF_3$ | H | H |
| I.a.962. | $OCH_3$ | I | $CF_3$ | H | F |
| I.a.963. | $OCH_3$ | I | $CF_3$ | H | Cl |
| I.a.964. | $OCH_3$ | I | $CF_3$ | H | Br |
| I.a.965. | $OCH_3$ | I | $CF_3$ | H | $CH_3$ |
| I.a.966. | $OCH_3$ | I | $CF_3$ | H | $OCH_3$ |

TABLE (I)-continued

| No. | R¹ | R³ | R⁵ | R⁶ | R⁷ |
|---|---|---|---|---|---|
| I.a.967. | OCH$_3$ | I | CF$_3$ | F | H |
| I.a.968. | OCH$_3$ | I | CF$_3$ | F | F |
| I.a.969. | OCH$_3$ | I | CF$_3$ | F | Cl |
| I.a.970. | OCH$_3$ | I | CF$_3$ | F | Br |
| I.a.971. | OCH$_3$ | I | CF$_3$ | F | CH$_3$ |
| I.a.972. | OCH$_3$ | I | CF$_3$ | F | OCH$_3$ |
| I.a.973. | OCH$_3$ | CH$_3$ | CF$_3$ | H | H |
| I.a.974. | OCH$_3$ | CH$_3$ | CF$_3$ | H | F |
| I.a.975. | OCH$_3$ | CH$_3$ | CF$_3$ | H | Cl |
| I.a.976. | OCH$_3$ | CH$_3$ | CF$_3$ | H | Br |
| I.a.977. | OCH$_3$ | CH$_3$ | CF$_3$ | H | CH$_3$ |
| I.a.978. | OCH$_3$ | CH$_3$ | CF$_3$ | H | OCH$_3$ |
| I.a.979. | OCH$_3$ | CH$_3$ | CF$_3$ | F | H |
| I.a.980. | OCH$_3$ | CH$_3$ | CF$_3$ | F | F |
| I.a.981. | OCH$_3$ | CH$_3$ | CF$_3$ | F | Cl |
| I.a.982. | OCH$_3$ | CH$_3$ | CF$_3$ | F | Br |
| I.a.983. | OCH$_3$ | CH$_3$ | CF$_3$ | F | CH$_3$ |
| I.a.984. | OCH$_3$ | CH$_3$ | CF$_3$ | F | OCH$_3$ |
| I.a.985. | OCH$_3$ | OCH$_3$ | CF$_3$ | H | H |
| I.a.986. | OCH$_3$ | OCH$_3$ | CF$_3$ | H | F |
| I.a.987. | OCH$_3$ | OCH$_3$ | CF$_3$ | H | Cl |
| I.a.988. | OCH$_3$ | OCH$_3$ | CF$_3$ | H | Br |
| I.a.989. | OCH$_3$ | OCH$_3$ | CF$_3$ | H | CH$_3$ |
| I.a.990. | OCH$_3$ | OCH$_3$ | CF$_3$ | H | OCH$_3$ |
| I.a.991. | OCH$_3$ | OCH$_3$ | CF$_3$ | F | H |
| I.a.992. | OCH$_3$ | OCH$_3$ | CF$_3$ | F | F |
| I.a.993. | OCH$_3$ | OCH$_3$ | CF$_3$ | F | Cl |
| I.a.994. | OCH$_3$ | OCH$_3$ | CF$_3$ | F | Br |
| I.a.995. | OCH$_3$ | OCH$_3$ | CF$_3$ | F | CH$_3$ |
| I.a.996. | OCH$_3$ | OCH$_3$ | CF$_3$ | F | OCH$_3$ |
| I.a.997. | OCH$_3$ | CF$_3$ | CF$_3$ | H | H |
| I.a.998. | OCH$_3$ | CF$_3$ | CF$_3$ | H | F |
| I.a.999. | OCH$_3$ | CF$_3$ | CF$_3$ | H | Cl |
| I.a.1000. | OCH$_3$ | CF$_3$ | CF$_3$ | H | Br |
| I.a.1001. | OCH$_3$ | CF$_3$ | CF$_3$ | H | CH$_3$ |
| I.a.1002. | OCH$_3$ | CF$_3$ | CF$_3$ | H | OCH$_3$ |
| I.a.1003. | OCH$_3$ | CF$_3$ | CF$_3$ | F | H |
| I.a.1004. | OCH$_3$ | CF$_3$ | CF$_3$ | F | F |
| I.a.1005. | OCH$_3$ | CF$_3$ | CF$_3$ | F | Cl |
| I.a.1006. | OCH$_3$ | CF$_3$ | CF$_3$ | F | Br |
| I.a.1007. | OCH$_3$ | CF$_3$ | CF$_3$ | F | CH$_3$ |
| I.a.1008. | OCH$_3$ | CF$_3$ | CF$_3$ | F | OCH$_3$ |
| I.a.1009. | c-C$_3$H$_5$ | F | H | CF$_3$ | H |
| I.a.1010. | c-C$_3$H$_5$ | F | H | CF$_3$ | F |
| I.a.1011. | c-C$_3$H$_5$ | F | H | CF$_3$ | Cl |
| I.a.1012. | c-C$_3$H$_5$ | F | H | CF$_3$ | Br |
| I.a.1013. | c-C$_3$H$_5$ | F | H | CF$_3$ | CH$_3$ |
| I.a.1014. | c-C$_3$H$_5$ | F | H | CF$_3$ | OCH$_3$ |
| I.a.1015. | c-C$_3$H$_5$ | F | F | CF$_3$ | H |
| I.a.1016. | c-C$_3$H$_5$ | F | F | CF$_3$ | F |
| I.a.1017. | c-C$_3$H$_5$ | F | F | CF$_3$ | Cl |
| I.a.1018. | c-C$_3$H$_5$ | F | F | CF$_3$ | Br |
| I.a.1019. | c-C$_3$H$_5$ | F | F | CF$_3$ | CH$_3$ |
| I.a.1020. | c-C$_3$H$_5$ | F | F | CF$_3$ | OCH$_3$ |
| I.a.1021. | c-C$_3$H$_5$ | Cl | H | CF$_3$ | H |
| I.a.1022. | c-C$_3$H$_5$ | Cl | H | CF$_3$ | F |
| I.a.1023. | c-C$_3$H$_5$ | Cl | H | CF$_3$ | Cl |
| I.a.1024. | c-C$_3$H$_5$ | Cl | H | CF$_3$ | Br |
| I.a.1025. | c-C$_3$H$_5$ | Cl | H | CF$_3$ | CH$_3$ |
| I.a.1026. | c-C$_3$H$_5$ | Cl | H | CF$_3$ | OCH$_3$ |
| I.a.1027. | c-C$_3$H$_5$ | Cl | F | CF$_3$ | H |
| I.a.1028. | c-C$_3$H$_5$ | Cl | F | CF$_3$ | F |
| I.a.1029. | c-C$_3$H$_5$ | Cl | F | CF$_3$ | Cl |
| I.a.1030. | c-C$_3$H$_5$ | Cl | F | CF$_3$ | Br |
| I.a.1031. | c-C$_3$H$_5$ | Cl | F | CF$_3$ | CH$_3$ |
| I.a.1032. | c-C$_3$H$_5$ | Cl | F | CF$_3$ | OCH$_3$ |
| I.a.1033. | c-C$_3$H$_5$ | Br | H | CF$_3$ | H |
| I.a.1034. | c-C$_3$H$_5$ | Br | H | CF$_3$ | F |
| I.a.1035. | c-C$_3$H$_5$ | Br | H | CF$_3$ | Cl |
| I.a.1036. | c-C$_3$H$_5$ | Br | H | CF$_3$ | Br |
| I.a.1037. | c-C$_3$H$_5$ | Br | H | CF$_3$ | CH$_3$ |
| I.a.1038. | c-C$_3$H$_5$ | Br | H | CF$_3$ | OCH$_3$ |
| I.a.1039. | c-C$_3$H$_5$ | Br | F | CF$_3$ | H |
| I.a.1040. | c-C$_3$H$_5$ | Br | F | CF$_3$ | F |
| I.a.1041. | c-C$_3$H$_5$ | Br | F | CF$_3$ | Cl |
| I.a.1042. | c-C$_3$H$_5$ | Br | F | CF$_3$ | Br |
| I.a.1043. | c-C$_3$H$_5$ | Br | F | CF$_3$ | CH$_3$ |
| I.a.1044. | c-C$_3$H$_5$ | Br | F | CF$_3$ | OCH$_3$ |
| I.a.1045. | c-C$_3$H$_5$ | I | H | CF$_3$ | H |
| I.a.1046. | c-C$_3$H$_5$ | I | H | CF$_3$ | F |
| I.a.1047. | c-C$_3$H$_5$ | I | H | CF$_3$ | Cl |
| I.a.1048. | c-C$_3$H$_5$ | I | H | CF$_3$ | Br |
| I.a.1049. | c-C$_3$H$_5$ | I | H | CF$_3$ | CH$_3$ |
| I.a.1050. | c-C$_3$H$_5$ | I | H | CF$_3$ | OCH$_3$ |
| I.a.1051. | c-C$_3$H$_5$ | I | F | CF$_3$ | H |
| I.a.1052. | c-C$_3$H$_5$ | I | F | CF$_3$ | F |
| I.a.1053. | c-C$_3$H$_5$ | I | F | CF$_3$ | Cl |
| I.a.1054. | c-C$_3$H$_5$ | I | F | CF$_3$ | Br |
| I.a.1055. | c-C$_3$H$_5$ | I | F | CF$_3$ | CH$_3$ |
| I.a.1056. | c-C$_3$H$_5$ | I | F | CF$_3$ | OCH$_3$ |
| I.a.1057. | c-C$_3$H$_5$ | CH$_3$ | H | CF$_3$ | H |
| I.a.1058. | c-C$_3$H$_5$ | CH$_3$ | H | CF$_3$ | F |
| I.a.1059. | c-C$_3$H$_5$ | CH$_3$ | H | CF$_3$ | Cl |
| I.a.1060. | c-C$_3$H$_5$ | CH$_3$ | H | CF$_3$ | Br |
| I.a.1061. | c-C$_3$H$_5$ | CH$_3$ | H | CF$_3$ | CH$_3$ |
| I.a.1062. | c-C$_3$H$_5$ | CH$_3$ | H | CF$_3$ | OCH$_3$ |
| I.a.1063. | c-C$_3$H$_5$ | CH$_3$ | F | CF$_3$ | H |
| I.a.1064. | c-C$_3$H$_5$ | CH$_3$ | F | CF$_3$ | F |
| I.a.1065. | c-C$_3$H$_5$ | CH$_3$ | F | CF$_3$ | Cl |
| I.a.1066. | c-C$_3$H$_5$ | CH$_3$ | F | CF$_3$ | Br |
| I.a.1067. | c-C$_3$H$_5$ | CH$_3$ | F | CF$_3$ | CH$_3$ |
| I.a.1068. | c-C$_3$H$_5$ | CH$_3$ | F | CF$_3$ | OCH$_3$ |
| I.a.1069. | c-C$_3$H$_5$ | OCH$_3$ | H | CF$_3$ | H |
| I.a.1070. | c-C$_3$H$_5$ | OCH$_3$ | H | CF$_3$ | F |
| I.a.1071. | c-C$_3$H$_5$ | OCH$_3$ | H | CF$_3$ | Cl |
| I.a.1072. | c-C$_3$H$_5$ | OCH$_3$ | H | CF$_3$ | Br |
| I.a.1073. | c-C$_3$H$_5$ | OCH$_3$ | H | CF$_3$ | CH$_3$ |
| I.a.1074. | c-C$_3$H$_5$ | OCH$_3$ | H | CF$_3$ | OCH$_3$ |
| I.a.1075. | c-C$_3$H$_5$ | OCH$_3$ | F | CF$_3$ | H |
| I.a.1076. | c-C$_3$H$_5$ | OCH$_3$ | F | CF$_3$ | F |
| I.a.1077. | c-C$_3$H$_5$ | OCH$_3$ | F | CF$_3$ | Cl |
| I.a.1078. | c-C$_3$H$_5$ | OCH$_3$ | F | CF$_3$ | Br |
| I.a.1079. | c-C$_3$H$_5$ | OCH$_3$ | F | CF$_3$ | CH$_3$ |
| I.a.1080. | c-C$_3$H$_5$ | OCH$_3$ | F | CF$_3$ | OCH$_3$ |
| I.a.1081. | c-C$_3$H$_5$ | CF$_3$ | H | CF$_3$ | H |
| I.a.1082. | c-C$_3$H$_5$ | CF$_3$ | H | CF$_3$ | F |
| I.a.1083. | c-C$_3$H$_5$ | CF$_3$ | H | CF$_3$ | Cl |
| I.a.1084. | c-C$_3$H$_5$ | CF$_3$ | H | CF$_3$ | Br |
| I.a.1085. | c-C$_3$H$_5$ | CF$_3$ | H | CF$_3$ | CH$_3$ |
| I.a.1086. | c-C$_3$H$_5$ | CF$_3$ | H | CF$_3$ | OCH$_3$ |
| I.a.1087. | c-C$_3$H$_5$ | CF$_3$ | F | CF$_3$ | H |
| I.a.1088. | c-C$_3$H$_5$ | CF$_3$ | F | CF$_3$ | F |
| I.a.1089. | c-C$_3$H$_5$ | CF$_3$ | F | CF$_3$ | Cl |
| I.a.1090. | c-C$_3$H$_5$ | CF$_3$ | F | CF$_3$ | Br |
| I.a.1091. | c-C$_3$H$_5$ | CF$_3$ | F | CF$_3$ | CH$_3$ |
| I.a.1092. | c-C$_3$H$_5$ | CF$_3$ | F | CF$_3$ | OCH$_3$ |
| I.a.1093. | c-C$_4$H$_7$ | F | H | CF$_3$ | H |
| I.a.1094. | c-C$_4$H$_7$ | F | H | CF$_3$ | F |
| I.a.1095. | c-C$_4$H$_7$ | F | H | CF$_3$ | Cl |
| I.a.1096. | c-C$_4$H$_7$ | F | H | CF$_3$ | Br |
| I.a.1097. | c-C$_4$H$_7$ | F | H | CF$_3$ | CH$_3$ |
| I.a.1098. | c-C$_4$H$_7$ | F | H | CF$_3$ | OCH$_3$ |
| I.a.1099. | c-C$_4$H$_7$ | F | F | CF$_3$ | H |
| I.a.1100. | c-C$_4$H$_7$ | F | F | CF$_3$ | F |
| I.a.1101. | c-C$_4$H$_7$ | F | F | CF$_3$ | Cl |
| I.a.1102. | c-C$_4$H$_7$ | F | F | CF$_3$ | Br |
| I.a.1103. | c-C$_4$H$_7$ | F | F | CF$_3$ | CH$_3$ |
| I.a.1104. | c-C$_4$H$_7$ | F | F | CF$_3$ | OCH$_3$ |
| I.a.1105. | c-C$_4$H$_7$ | Cl | H | CF$_3$ | H |
| I.a.1106. | c-C$_4$H$_7$ | Cl | H | CF$_3$ | F |
| I.a.1107. | c-C$_4$H$_7$ | Cl | H | CF$_3$ | Cl |
| I.a.1108. | c-C$_4$H$_7$ | Cl | H | CF$_3$ | Br |
| I.a.1109. | c-C$_4$H$_7$ | Cl | H | CF$_3$ | CH$_3$ |
| I.a.1110. | c-C$_4$H$_7$ | Cl | H | CF$_3$ | OCH$_3$ |
| I.a.1111. | c-C$_4$H$_7$ | Cl | F | CF$_3$ | H |
| I.a.1112. | c-C$_4$H$_7$ | Cl | F | CF$_3$ | F |
| I.a.1113. | c-C$_4$H$_7$ | Cl | F | CF$_3$ | Cl |
| I.a.1114. | c-C$_4$H$_7$ | Cl | F | CF$_3$ | Br |
| I.a.1115. | c-C$_4$H$_7$ | Cl | F | CF$_3$ | CH$_3$ |
| I.a.1116. | c-C$_4$H$_7$ | Cl | F | CF$_3$ | OCH$_3$ |
| I.a.1117. | c-C$_4$H$_7$ | Br | H | CF$_3$ | H |
| I.a.1118. | c-C$_4$H$_7$ | Br | H | CF$_3$ | F |
| I.a.1119. | c-C$_4$H$_7$ | Br | H | CF$_3$ | Cl |
| I.a.1120. | c-C$_4$H$_7$ | Br | H | CF$_3$ | Br |
| I.a.1121. | c-C$_4$H$_7$ | Br | H | CF$_3$ | CH$_3$ |
| I.a.1122. | c-C$_4$H$_7$ | Br | H | CF$_3$ | OCH$_3$ |

TABLE (I)-continued

| No. | R¹ | R³ | R⁵ | R⁶ | R⁷ |
|---|---|---|---|---|---|
| I.a.1123. | c-C₄H₇ | Br | F | CF₃ | H |
| I.a.1124. | c-C₄H₇ | Br | F | CF₃ | F |
| I.a.1125. | c-C₄H₇ | Br | F | CF₃ | Cl |
| I.a.1126. | c-C₄H₇ | Br | F | CF₃ | Br |
| I.a.1127. | c-C₄H₇ | Br | F | CF₃ | CH₃ |
| I.a.1128. | c-C₄H₇ | Br | F | CF₃ | OCH₃ |
| I.a.1129. | c-C₄H₇ | I | H | CF₃ | H |
| I.a.1130. | c-C₄H₇ | I | H | CF₃ | F |
| I.a.1131. | c-C₄H₇ | I | H | CF₃ | Cl |
| I.a.1132. | c-C₄H₇ | I | H | CF₃ | Br |
| I.a.1133. | c-C₄H₇ | I | H | CF₃ | CH₃ |
| I.a.1134. | c-C₄H₇ | I | H | CF₃ | OCH₃ |
| I.a.1135. | c-C₄H₇ | I | F | CF₃ | H |
| I.a.1136. | c-C₄H₇ | I | F | CF₃ | F |
| I.a.1137. | c-C₄H₇ | I | F | CF₃ | Cl |
| I.a.1138. | c-C₄H₇ | I | F | CF₃ | Br |
| I.a.1139. | c-C₄H₇ | I | F | CF₃ | CH₃ |
| I.a.1140. | c-C₄H₇ | I | F | CF₃ | OCH₃ |
| I.a.1141. | c-C₄H₇ | CH₃ | H | CF₃ | H |
| I.a.1142. | c-C₄H₇ | CH₃ | H | CF₃ | F |
| I.a.1143. | c-C₄H₇ | CH₃ | H | CF₃ | Cl |
| I.a.1144. | c-C₄H₇ | CH₃ | H | CF₃ | Br |
| I.a.1145. | c-C₄H₇ | CH₃ | H | CF₃ | CH₃ |
| I.a.1146. | c-C₄H₇ | CH₃ | H | CF₃ | OCH₃ |
| I.a.1147. | c-C₄H₇ | CH₃ | F | CF₃ | H |
| I.a.1148. | c-C₄H₇ | CH₃ | F | CF₃ | F |
| I.a.1149. | c-C₄H₇ | CH₃ | F | CF₃ | Cl |
| I.a.1150. | c-C₄H₇ | CH₃ | F | CF₃ | Br |
| I.a.1151. | c-C₄H₇ | CH₃ | F | CF₃ | CH₃ |
| I.a.1152. | c-C₄H₇ | CH₃ | F | CF₃ | OCH₃ |
| I.a.1153. | c-C₄H₇ | OCH₃ | H | CF₃ | H |
| I.a.1154. | c-C₄H₇ | OCH₃ | H | CF₃ | F |
| I.a.1155. | c-C₄H₇ | OCH₃ | H | CF₃ | Cl |
| I.a.1156. | c-C₄H₇ | OCH₃ | H | CF₃ | Br |
| I.a.1157. | c-C₄H₇ | OCH₃ | H | CF₃ | CH₃ |
| I.a.1158. | c-C₄H₇ | OCH₃ | H | CF₃ | OCH₃ |
| I.a.1159. | c-C₄H₇ | OCH₃ | F | CF₃ | H |
| I.a.1160. | c-C₄H₇ | OCH₃ | F | CF₃ | F |
| I.a.1161. | c-C₄H₇ | OCH₃ | F | CF₃ | Cl |
| I.a.1162. | c-C₄H₇ | OCH₃ | F | CF₃ | Br |
| I.a.1163. | c-C₄H₇ | OCH₃ | F | CF₃ | CH₃ |
| I.a.1164. | c-C₄H₇ | OCH₃ | F | CF₃ | OCH₃ |
| I.a.1165. | c-C₄H₇ | CF₃ | H | CF₃ | H |
| I.a.1166. | c-C₄H₇ | CF₃ | H | CF₃ | F |
| I.a.1167. | c-C₄H₇ | CF₃ | H | CF₃ | Cl |
| I.a.1168. | c-C₄H₇ | CF₃ | H | CF₃ | Br |
| I.a.1169. | c-C₄H₇ | CF₃ | H | CF₃ | CH₃ |
| I.a.1170. | c-C₄H₇ | CF₃ | H | CF₃ | OCH₃ |
| I.a.1171. | c-C₄H₇ | CF₃ | F | CF₃ | H |
| I.a.1172. | c-C₄H₇ | CF₃ | F | CF₃ | F |
| I.a.1173. | c-C₄H₇ | CF₃ | F | CF₃ | Cl |
| I.a.1174. | c-C₄H₇ | CF₃ | F | CF₃ | Br |
| I.a.1175. | c-C₄H₇ | CF₃ | F | CF₃ | CH₃ |
| I.a.1176. | c-C₄H₇ | CF₃ | F | CF₃ | OCH₃ |
| I.a.1177. | C₂H₅ | F | H | CF₃ | H |
| I.a.1178. | C₂H₅ | F | H | CF₃ | F |
| I.a.1179. | C₂H₅ | F | H | CF₃ | Cl |
| I.a.1180. | C₂H₅ | F | H | CF₃ | Br |
| I.a.1181. | C₂H₅ | F | H | CF₃ | CH₃ |
| I.a.1182. | C₂H₅ | F | H | CF₃ | OCH₃ |
| I.a.1183. | C₂H₅ | F | F | CF₃ | H |
| I.a.1184. | C₂H₅ | F | F | CF₃ | F |
| I.a.1185. | C₂H₅ | F | F | CF₃ | Cl |
| I.a.1186. | C₂H₅ | F | F | CF₃ | Br |
| I.a.1187. | C₂H₅ | F | F | CF₃ | CH₃ |
| I.a.1188. | C₂H₅ | F | F | CF₃ | OCH₃ |
| I.a.1189. | C₂H₅ | Cl | H | CF₃ | H |
| I.a.1190. | C₂H₅ | Cl | H | CF₃ | F |
| I.a.1191. | C₂H₅ | Cl | H | CF₃ | Cl |
| I.a.1192. | C₂H₅ | Cl | H | CF₃ | Br |
| I.a.1193. | C₂H₅ | Cl | H | CF₃ | CH₃ |
| I.a.1194. | C₂H₅ | Cl | H | CF₃ | OCH₃ |
| I.a.1195. | C₂H₅ | Cl | F | CF₃ | H |
| I.a.1196. | C₂H₅ | Cl | F | CF₃ | F |
| I.a.1197. | C₂H₅ | Cl | F | CF₃ | Cl |
| I.a.1198. | C₂H₅ | Cl | F | CF₃ | Br |
| I.a.1199. | C₂H₅ | Cl | F | CF₃ | CH₃ |
| I.a.1200. | C₂H₅ | Cl | F | CF₃ | OCH₃ |
| I.a.1201. | C₂H₅ | Br | H | CF₃ | H |
| I.a.1202. | C₂H₅ | Br | H | CF₃ | F |
| I.a.1203. | C₂H₅ | Br | H | CF₃ | Cl |
| I.a.1204. | C₂H₅ | Br | H | CF₃ | Br |
| I.a.1205. | C₂H₅ | Br | H | CF₃ | CH₃ |
| I.a.1206. | C₂H₅ | Br | H | CF₃ | OCH₃ |
| I.a.1207. | C₂H₅ | Br | F | CF₃ | H |
| I.a.1208. | C₂H₅ | Br | F | CF₃ | F |
| I.a.1209. | C₂H₅ | Br | F | CF₃ | Cl |
| I.a.1210. | C₂H₅ | Br | F | CF₃ | Br |
| I.a.1211. | C₂H₅ | Br | F | CF₃ | CH₃ |
| I.a.1212. | C₂H₅ | Br | F | CF₃ | OCH₃ |
| I.a.1213. | C₂H₅ | I | H | CF₃ | H |
| I.a.1214. | C₂H₅ | I | H | CF₃ | F |
| I.a.1215. | C₂H₅ | I | H | CF₃ | Cl |
| I.a.1216. | C₂H₅ | I | H | CF₃ | Br |
| I.a.1217. | C₂H₅ | I | H | CF₃ | CH₃ |
| I.a.1218. | C₂H₅ | I | H | CF₃ | OCH₃ |
| I.a.1219. | C₂H₅ | I | F | CF₃ | H |
| I.a.1220. | C₂H₅ | I | F | CF₃ | F |
| I.a.1221. | C₂H₅ | I | F | CF₃ | Cl |
| I.a.1222. | C₂H₅ | I | F | CF₃ | Br |
| I.a.1223. | C₂H₅ | I | F | CF₃ | CH₃ |
| I.a.1224. | C₂H₅ | I | F | CF₃ | OCH₃ |
| I.a.1225. | C₂H₅ | CH₃ | H | CF₃ | H |
| I.a.1226. | C₂H₅ | CH₃ | H | CF₃ | F |
| I.a.1227. | C₂H₅ | CH₃ | H | CF₃ | Cl |
| I.a.1228. | C₂H₅ | CH₃ | H | CF₃ | Br |
| I.a.1229. | C₂H₅ | CH₃ | H | CF₃ | CH₃ |
| I.a.1230. | C₂H₅ | CH₃ | H | CF₃ | OCH₃ |
| I.a.1231. | C₂H₅ | CH₃ | F | CF₃ | H |
| I.a.1232. | C₂H₅ | CH₃ | F | CF₃ | F |
| I.a.1233. | C₂H₅ | CH₃ | F | CF₃ | Cl |
| I.a.1234. | C₂H₅ | CH₃ | F | CF₃ | Br |
| I.a.1235. | C₂H₅ | CH₃ | F | CF₃ | CH₃ |
| I.a.1236. | C₂H₅ | CH₃ | F | CF₃ | OCH₃ |
| I.a.1237. | C₂H₅ | OCH₃ | H | CF₃ | H |
| I.a.1238. | C₂H₅ | OCH₃ | H | CF₃ | F |
| I.a.1239. | C₂H₅ | OCH₃ | H | CF₃ | Cl |
| I.a.1240. | C₂H₅ | OCH₃ | H | CF₃ | Br |
| I.a.1241. | C₂H₅ | OCH₃ | H | CF₃ | CH₃ |
| I.a.1242. | C₂H₅ | OCH₃ | H | CF₃ | OCH₃ |
| I.a.1243. | C₂H₅ | OCH₃ | F | CF₃ | H |
| I.a.1244. | C₂H₅ | OCH₃ | F | CF₃ | F |
| I.a.1245. | C₂H₅ | OCH₃ | F | CF₃ | Cl |
| I.a.1246. | C₂H₅ | OCH₃ | F | CF₃ | Br |
| I.a.1247. | C₂H₅ | OCH₃ | F | CF₃ | CH₃ |
| I.a.1248. | C₂H₅ | OCH₃ | F | CF₃ | OCH₃ |
| I.a.1249. | C₂H₅ | CF₃ | H | CF₃ | H |
| I.a.1250. | C₂H₅ | CF₃ | H | CF₃ | F |
| I.a.1251. | C₂H₅ | CF₃ | H | CF₃ | Cl |
| I.a.1252. | C₂H₅ | CF₃ | H | CF₃ | Br |
| I.a.1253. | C₂H₅ | CF₃ | H | CF₃ | CH₃ |
| I.a.1254. | C₂H₅ | CF₃ | H | CF₃ | OCH₃ |
| I.a.1255. | C₂H₅ | CF₃ | F | CF₃ | H |
| I.a.1256. | C₂H₅ | CF₃ | F | CF₃ | F |
| I.a.1257. | C₂H₅ | CF₃ | F | CF₃ | Cl |
| I.a.1258. | C₂H₅ | CF₃ | F | CF₃ | Br |
| I.a.1259. | C₂H₅ | CF₃ | F | CF₃ | CH₃ |
| I.a.1260. | C₂H₅ | CF₃ | F | CF₃ | OCH₃ |
| I.a.1261. | OCH₃ | F | H | CF₃ | H |
| I.a.1262. | OCH₃ | F | H | CF₃ | F |
| I.a.1263. | OCH₃ | F | H | CF₃ | Cl |
| I.a.1264. | OCH₃ | F | H | CF₃ | Br |
| I.a.1265. | OCH₃ | F | H | CF₃ | CH₃ |
| I.a.1266. | OCH₃ | F | H | CF₃ | OCH₃ |
| I.a.1267. | OCH₃ | F | F | CF₃ | H |
| I.a.1268. | OCH₃ | F | F | CF₃ | F |
| I.a.1269. | OCH₃ | F | F | CF₃ | Cl |
| I.a.1270. | OCH₃ | F | F | CF₃ | Br |
| I.a.1271. | OCH₃ | F | F | CF₃ | CH₃ |
| I.a.1272. | OCH₃ | F | F | CF₃ | OCH₃ |
| I.a.1273. | OCH₃ | Cl | H | CF₃ | H |
| I.a.1274. | OCH₃ | Cl | H | CF₃ | F |
| I.a.1275. | OCH₃ | Cl | H | CF₃ | Cl |
| I.a.1276. | OCH₃ | Cl | H | CF₃ | Br |
| I.a.1277. | OCH₃ | Cl | H | CF₃ | CH₃ |
| I.a.1278. | OCH₃ | Cl | H | CF₃ | OCH₃ |

TABLE (I)-continued

| No. | R¹ | R³ | R⁵ | R⁶ | R⁷ |
|---|---|---|---|---|---|
| I.a.1279. | OCH₃ | Cl | F | CF₃ | H |
| I.a.1280. | OCH₃ | Cl | F | CF₃ | F |
| I.a.1281. | OCH₃ | Cl | F | CF₃ | Cl |
| I.a.1282. | OCH₃ | Cl | F | CF₃ | Br |
| I.a.1283. | OCH₃ | Cl | F | CF₃ | CH₃ |
| I.a.1284. | OCH₃ | Cl | F | CF₃ | OCH₃ |
| I.a.1285. | OCH₃ | Br | H | CF₃ | H |
| I.a.1286. | OCH₃ | Br | H | CF₃ | F |
| I.a.1287. | OCH₃ | Br | H | CF₃ | Cl |
| I.a.1288. | OCH₃ | Br | H | CF₃ | Br |
| I.a.1289. | OCH₃ | Br | H | CF₃ | CH₃ |
| I.a.1290. | OCH₃ | Br | H | CF₃ | OCH₃ |
| I.a.1291. | OCH₃ | Br | F | CF₃ | H |
| I.a.1292. | OCH₃ | Br | F | CF₃ | F |
| I.a.1293. | OCH₃ | Br | F | CF₃ | Cl |
| I.a.1294. | OCH₃ | Br | F | CF₃ | Br |
| I.a.1295. | OCH₃ | Br | F | CF₃ | CH₃ |
| I.a.1296. | OCH₃ | Br | F | CF₃ | OCH₃ |
| I.a.1297. | OCH₃ | I | H | CF₃ | H |
| I.a.1298. | OCH₃ | I | H | CF₃ | F |
| I.a.1299. | OCH₃ | I | H | CF₃ | Cl |
| I.a.1300. | OCH₃ | I | H | CF₃ | Br |
| I.a.1301. | OCH₃ | I | H | CF₃ | CH₃ |
| I.a.1302. | OCH₃ | I | H | CF₃ | OCH₃ |
| I.a.1303. | OCH₃ | I | F | CF₃ | H |
| I.a.1304. | OCH₃ | I | F | CF₃ | F |
| I.a.1305. | OCH₃ | I | F | CF₃ | Cl |
| I.a.1306. | OCH₃ | I | F | CF₃ | Br |
| I.a.1307. | OCH₃ | I | F | CF₃ | CH₃ |
| I.a.1308. | OCH₃ | I | F | CF₃ | OCH₃ |
| I.a.1309. | OCH₃ | CH₃ | H | CF₃ | H |
| I.a.1310. | OCH₃ | CH₃ | H | CF₃ | F |
| I.a.1311. | OCH₃ | CH₃ | H | CF₃ | Cl |
| I.a.1312. | OCH₃ | CH₃ | H | CF₃ | Br |
| I.a.1313. | OCH₃ | CH₃ | H | CF₃ | CH₃ |
| I.a.1314. | OCH₃ | CH₃ | H | CF₃ | OCH₃ |
| I.a.1315. | OCH₃ | CH₃ | F | CF₃ | H |
| I.a.1316. | OCH₃ | CH₃ | F | CF₃ | F |
| I.a.1317. | OCH₃ | CH₃ | F | CF₃ | Cl |
| I.a.1318. | OCH₃ | CH₃ | F | CF₃ | Br |
| I.a.1319. | OCH₃ | CH₃ | F | CF₃ | CH₃ |
| I.a.1320. | OCH₃ | CH₃ | F | CF₃ | OCH₃ |
| I.a.1321. | OCH₃ | OCH₃ | H | CF₃ | H |
| I.a.1322. | OCH₃ | OCH₃ | H | CF₃ | F |
| I.a.1323. | OCH₃ | OCH₃ | H | CF₃ | Cl |
| I.a.1324. | OCH₃ | OCH₃ | H | CF₃ | Br |
| I.a.1325. | OCH₃ | OCH₃ | H | CF₃ | CH₃ |
| I.a.1326. | OCH₃ | OCH₃ | H | CF₃ | OCH₃ |
| I.a.1327. | OCH₃ | OCH₃ | F | CF₃ | H |
| I.a.1328. | OCH₃ | OCH₃ | F | CF₃ | F |
| I.a.1329. | OCH₃ | OCH₃ | F | CF₃ | Cl |
| I.a.1330. | OCH₃ | OCH₃ | F | CF₃ | Br |
| I.a.1331. | OCH₃ | OCH₃ | F | CF₃ | CH₃ |
| I.a.1332. | OCH₃ | OCH₃ | F | CF₃ | OCH₃ |
| I.a.1333. | OCH₃ | CF₃ | H | CF₃ | H |
| I.a.1334. | OCH₃ | CF₃ | H | CF₃ | F |
| I.a.1335. | OCH₃ | CF₃ | H | CF₃ | Cl |
| I.a.1336. | OCH₃ | CF₃ | H | CF₃ | Br |
| I.a.1337. | OCH₃ | CF₃ | H | CF₃ | CH₃ |
| I.a.1338. | OCH₃ | CF₃ | H | CF₃ | OCH₃ |
| I.a.1339. | OCH₃ | CF₃ | F | CF₃ | H |
| I.a.1340. | OCH₃ | CF₃ | F | CF₃ | F |
| I.a.1341. | OCH₃ | CF₃ | F | CF₃ | Cl |
| I.a.1342. | OCH₃ | CF₃ | F | CF₃ | Br |
| I.a.1343. | OCH₃ | CF₃ | F | CF₃ | CH₃ |
| I.a.1344. | OCH₃ | CF₃ | F | CF₃ | OCH₃ |

Also preferred are the compositions, which comprise as active component A at least one, preferably exactly one, phenylpyrimidine of formula (I.b), particularly preferred of the phenylpyrimidines of formulae (I.b.1) to (I.b.1344), which differ from the corresponding phenylpyrimidines of formula (I.a) as well as formulae (I.a.1) to (I.a.1344) only in that $R^2$ is $OCH_3$:

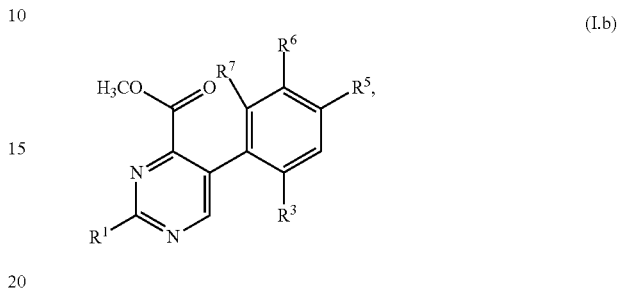

(I.b)

Also preferred are the compositions, which comprise as active component A at least one, preferably exactly one, phenylpyrimidine of formula (I.c), particularly preferred of the phenylpyrimidines of formulae (I.c.1) to (I.c.1344), which differ from the corresponding phenylpyrimidines of formula (I.a) as well as formulae (I.a.1) to (I.a.1344) only in that $R^2$ is $OC_2H_5$:

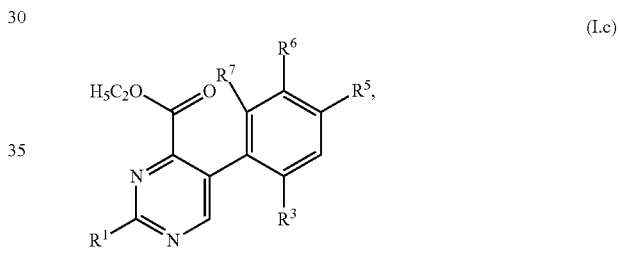

(I.c)

Also preferred are the compositions, which comprise as active component A at least one, preferably exactly one, phenylpyrimidine of formula (I.d), particularly preferred of the phenylpyrimidines of formulae (I.d.1) to (I.d.1344), which differ from the corresponding phenylpyrimidines of formula (I.a) as well as formulae (I.a.1) to (I.a.1344) only in that $R^2$ is $OCH_2C\equiv CH$:

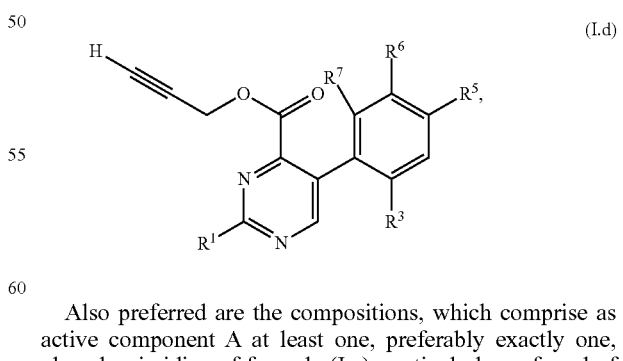

(I.d)

Also preferred are the compositions, which comprise as active component A at least one, preferably exactly one, phenylpyrimidine of formula (I.e), particularly preferred of the phenylpyrimidines of formulae (I.e.1) to (I.e.1344), which differ from the corresponding phenylpyrimidines of formula (I.a) as well as formulae (I.a.1) to (I.a.1344) only in that $R^2$ is $OCH_2CHF_2$:

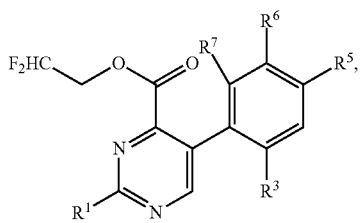

(I.e)

Particular preference is also given to the compositions, which comprise as active component A at least one, preferably exactly one, phenylpyrimidine of formula (I.I) (corresponds to phenylpyrimidines of formula (I) wherein $R^4$ is H and $R^1$, $R^2$, $R^3$ $R^5$, $R^6$ and $R^7$ are as defined below),

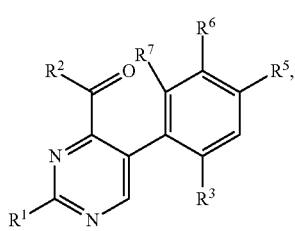

(I.1)

wherein $R^1$ is $C_3$-$C_6$-cycloalkyl, $C_1$-$C_6$-alkyl or $C_1$-$C_6$-alkoxy;
$R^2$ is OH, $C_1$-$C_6$-alkoxy, $C_3$-$C_6$-alkynyloxy or $C_1$-$C_6$-haloalkoxy;
$R^3$ is halogen, $C_1$-$C_6$-alkyl, $C_1$-$C_6$-haloalkyl or $C_1$-$C_6$-alkoxy;
$R^5$ is H, halogen or $C_1$-$C_6$-haloalkyl;
$R^6$ is H, halogen or $C_1$-$C_6$-haloalkyl; and
$R^7$ is H, halogen, $C_1$-$C_6$-alkyl or $C_1$-$C_6$-alkoxy.

Particular preference is also given to the compositions, which comprise as active component A at least one, preferably exactly one, phenylpyrimidine of formula (I.A) (corresponds to phenylpyrimidines of formula (I.1) wherein $R^2$ is OH; corresponds also to phenylpyrimidines of formula (I) wherein $R^2$ is OH, $R^4$ is H and $R^1$, $R^3$ $R^5$, $R^6$ and $R^7$ are as defined below),

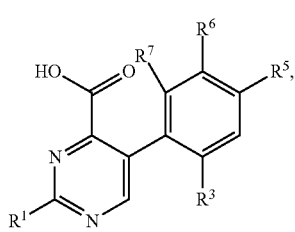

(I.A)

wherein $R^1$ is $C_3$-$C_6$-cycloalkyl, $C_1$-$C_6$-alkyl or $C_1$-$C_6$-alkoxy;
$R^3$ is halogen, $C_1$-$C_6$-alkyl, $C_1$-$C_6$-haloalkyl or $C_1$-$C_6$-alkoxy;
$R^5$ is H or halogen;
$R^6$ is H or halogen; and
$R^7$ is H, halogen, $C_1$-$C_6$-alkyl or $C_1$-$C_6$-alkoxy.

Also preferred are the compositions, which comprise as active component A at least one, preferably exactly one, phenylpyrimidine of formula (I.A.1) (corresponds to phenylpyrimidines of formula (I.A) wherein $R^1$ is $C_3$-$C_6$-cycloalkyl; corresponds also to phenylpyrimidines of formula (I.1) wherein $R^1$ is $C_3$-$C_6$-cycloalkyl and $R^2$ is OH; corresponds also to phenylpyrimidines of formula (I) wherein $R^1$ is $C_3$-$C_6$-cycloalkyl, $R^2$ is OH, $R^4$ is H and $R^1$, $R^3$ $R^5$, $R^6$ and $R^7$ are as defined below),

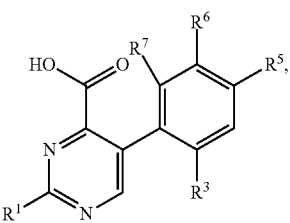

(I.A.1)

wherein $R^1$ is $C_3$-$C_6$-cycloalkyl;
$R^3$ is halogen, $C_1$-$C_6$-alkyl, $C_1$-$C_6$-haloalkyl or $C_1$-$C_6$-alkoxy;
$R^5$ is H, halogen or $C_1$-$C_6$-haloalkyl;
$R^6$ is H, halogen or $C_1$-$C_6$-haloalkyl; and
$R^7$ is H, halogen, $C_1$-$C_6$-alkyl or $C_1$-$C_6$-alkoxy;
particularly preferred the phenylpyrimidines of formulae (I.A.1.1) to (I.A.1.336), which correspond to the phenylpyrimidines of formulae (I.a.1) to (I.a.336) as defined above.

Particular preference is also given to the compositions, which comprise as active component A at least one, preferably exactly one, phenylpyrimidine of formula (I.B) (corresponds to phenylpyrimidines of formula (I.1) wherein $R^2$ is $C_1$-$C_6$-alkoxy, $C_3$-$C_6$-alkynyloxy or $C_1$-$C_6$-haloalkoxy; corresponds also to phenylpyrimidines of formula (I) wherein $R^2$ is $C_1$-$C_6$-alkoxy, $C_3$-$C_6$-alkynyloxy or $C_1$-$C_6$-haloalkoxy, $R^4$ is H and $R^1$, $R^3$ $R^5$, $R^6$ and $R^7$ are as defined below),

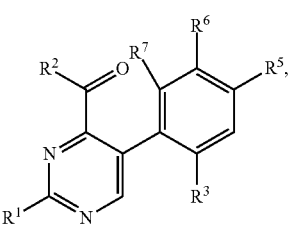

(I.B)

wherein $R^1$ is $C_3$-$C_6$-cycloalkyl, $C_1$-$C_6$-alkyl or $C_1$-$C_6$-alkoxy;
$R^2$ is $C_1$-$C_6$-alkoxy, $C_3$-$C_6$-alkynyloxy or $C_1$-$C_6$-haloalkoxy;
$R^3$ is halogen, $C_1$-$C_6$-alkyl, $C_1$-$C_6$-haloalkyl or $C_1$-$C_6$-alkoxy;
$R^5$ is H, halogen or $C_1$-$C_6$-haloalkyl;
$R^6$ is H, halogen or $C_1$-$C_6$-haloalkyl; and
$R^7$ is H, halogen, $C_1$-$C_6$-alkyl or $C_1$-$C_6$-alkoxy.

Also preferred are the compositions, which comprise as active component A at least one, preferably exactly one, phenylpyrimidine of formula (I.B.1) (corresponds to phenylpyrimidines of formula (I.B) wherein $R^2$ is $OCH_3$; corresponds also to phenylpyrimidines of formula (I.1) wherein $R^2$ is $OCH_3$; corresponds also to phenylpyrimidines of formula (I) wherein $R^2$ is $OCH_3$, $R^4$ is H and $R^1$, $R^3$ $R^5$, $R^6$ and $R^7$ are as defined below),

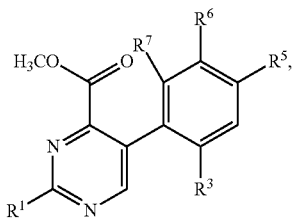

(I.B.1)

wherein R¹ is $C_3$-$C_6$-cycloalkyl, $C_1$-$C_6$-alkyl or $C_1$-$C_6$-alkoxy;

R³ is halogen, $C_1$-$C_6$-alkyl, $C_1$-$C_6$-haloalkyl or $C_1$-$C_6$-alkoxy;

R⁵ is H, halogen or $C_1$-$C_6$-haloalkyl;

R⁶ is H, halogen or $C_1$-$C_6$-haloalkyl; and

R⁷ is H, halogen, $C_1$-$C_6$-alkyl or $C_1$-$C_6$-alkoxy;

particularly preferred the phenylpyrimidines of formulae (I.B.1.1) to (I.B.1.1344), which correspond to the phenylpyrimidines of formulae (I.b.1) to (I.b.1344) as defined above.

Also preferred are the compositions, which comprise as active component A at least one, preferably exactly one, phenylpyrimidine of formula (I.B.2) (corresponds to phenylpyrimidines of formula (I.B) wherein R² is $OC_2H_5$, corresponds also to phenylpyrimidines of formula (I.1) wherein R² is $OC_2H_5$; corresponds also to phenylpyrimidines of formula (I) wherein R² is $OC_2H_5$, R⁴ is H and R¹, R³ R⁵, R⁶ and R⁷ are as defined below),

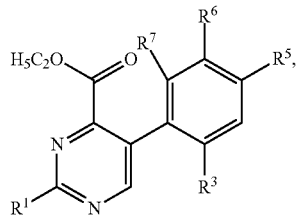

(I.B.2)

wherein R¹ is $C_3$-$C_6$-cycloalkyl, $C_1$-$C_6$-alkyl or $C_1$-$C_6$-alkoxy;

R³ is halogen, $C_1$-$C_6$-alkyl, $C_1$-$C_6$-haloalkyl or $C_1$-$C_6$-alkoxy;

R⁵ is H, halogen or $C_1$-$C_6$-haloalkyl;

R⁶ is H, halogen or $C_1$-$C_6$-haloalkyl; and

R⁷ is H, halogen, $C_1$-$C_6$-alkyl or $C_1$-$C_6$-alkoxy;

particularly preferred the phenylpyrimidines of formulae (I.B.2.1) to (I.B.2.1344), which correspond to the phenylpyrimidines of formulae (I.c.1) to (I.c.1344) as defined above.

Also preferred are the compositions, which comprise as active component A at least one, preferably exactly one, phenylpyrimidine of formula (I.B.3) (corresponds to phenylpyrimidines of formula (I.B) wherein R² is $OCH_2C\equiv CH$, corresponds also to phenylpyrimidines of formula (I.1) wherein R² is $OCH_2C\equiv CH$; corresponds also to phenylpyrimidines of formula (I) wherein R² is $OCH_2C\equiv CH$, R⁴ is H and R¹, R³ R⁵, R⁶ and R⁷ are as defined below),

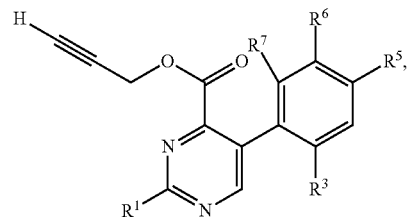

(I.B.3)

wherein R¹ is $C_3$-$C_6$-cycloalkyl, $C_1$-$C_6$-alkyl or $C_1$-$C_6$-alkoxy;

R³ is halogen, $C_1$-$C_6$-alkyl, $C_1$-$C_6$-haloalkyl or $C_1$-$C_6$-alkoxy;

R⁵ is H, halogen or $C_1$-$C_6$-haloalkyl;

R⁶ is H, halogen or $C_1$-$C_6$-haloalkyl; and

R⁷ is H, halogen, $C_1$-$C_6$-alkyl or $C_1$-$C_6$-alkoxy;

particularly preferred the phenylpyrimidines of formulae (I.B.3.1) to (I.B.3.1344), which correspond to the phenylpyrimidines of formulae (I.d.1) to (I.d.1344) as defined above.

Also preferred are the compositions, which comprise as active component A at least one, preferably exactly one, phenylpyrimidine of formula (I.B.4) (corresponds to phenylpyrimidines of formula (I.B) wherein R² is $OCH_2CHF_2$, corresponds also to phenylpyrimidines of formula (I.1) wherein R² is $OCH_2CHF_2$; corresponds also to phenylpyrimidines of formula (I) wherein R² is $OCH_2CHF_2$, R⁴ is H and R¹, R³ R⁵, R⁶ and R⁷ are as defined below),

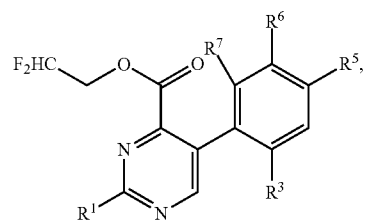

(I.B.4)

wherein R¹ is $C_3$-$C_6$-cycloalkyl, $C_1$-$C_6$-alkyl or $C_1$-$C_6$-alkoxy;

R³ is halogen, $C_1$-$C_6$-alkyl, $C_1$-$C_6$-haloalkyl or $C_1$-$C_6$-alkoxy;

R⁵ is H, halogen or $C_1$-$C_6$-haloalkyl;

R⁶ is H, halogen or $C_1$-$C_6$-haloalkyl; and

R⁷ is H, halogen, $C_1$-$C_6$-alkyl or $C_1$-$C_6$-alkoxy;

particularly preferred the phenylpyrimidines of formulae (I.B.4.1) to (I.B.4.1344), which correspond to the phenylpyrimidines of formulae (I.e.1) to (I.e.1344) as defined above.

In one embodiment of the present invention the compositions according to the present invention comprise at least one phenylpyrimidine of formula (I) and at least one further active compound B (herbicide B).

According to a first embodiment of the invention the compositions contain at least one inhibitor of the lipid biosynthesis (herbicide b1). These are compounds that inhibit lipid biosynthesis. Inhibition of the lipid biosynthesis can be affected either through inhibition of acetylCoA carboxylase (hereinafter termed ACC herbicides) or through a different mode of action (hereinafter termed non-ACC herbicides). The ACC herbicides belong to the group A of the HRAC classification system whereas the non-ACC herbicides belong to the group N of the HRAC classification.

According to a second embodiment of the invention the compositions contain at least one ALS inhibitor (herbicide b2). The herbicidal activity of these compounds is based on the inhibition of acetolactate synthase and thus on the inhibition of the branched chain amino acid biosynthesis. These inhibitors belong to the group B of the HRAC classification system.

According to a third embodiment of the invention the compositions contain at least one inhibitor of photosynthesis (herbicide b3). The herbicidal activity of these compounds is based either on the inhibition of the photosystem II in plants (so-called PSII inhibitors, groups C1, C2 and C3 of HRAC classification) or on diverting the electron transfer in photosystem I in plants (so-called PSI inhibitors, group D of HRAC classification) and thus on an inhibition of photosynthesis. Amongst these, PSII inhibitors are preferred.

According to a fourth embodiment of the invention the compositions contain at least one inhibitor of protoporphyrinogen-IX-oxidase (herbicide b4). The herbicidal activity of these compounds is based on the inhibition of the protoporphyrinogen-IX-oxidase. These inhibitors belong to the group E of the HRAC classification system.

According to a fifth embodiment of the invention the compositions contain at least one bleacher-herbicide (herbicide b5). The herbicidal activity of these compounds is based on the inhibition of the carotenoid biosynthesis. These include compounds which inhibit carotenoid biosynthesis by inhibition of phytoene desaturase (so-called PDS inhibitors, group F1 of HRAC classification), compounds that inhibit the 4-hydroxyphenylpyruvate-dioxygenase (HPPD inhibitors, group F2 of HRAC classification), compounds that inhibit DOXsynthase (group F4 of HRAC class) and compounds which inhibit carotenoid biosynthesis by an unknown mode of action (bleacher—unknown target, group F3 of HRAC classification).

According to a sixth embodiment of the invention the compositions contain at least one EPSP synthase inhibitor (herbicide b6). The herbicidal activity of these compounds is based on the inhibition of enolpyruvyl shikimate 3-phosphate synthase, and thus on the inhibition of the amino acid biosynthesis in plants. These inhibitors belong to the group G of the HRAC classification system.

According to a seventh embodiment of the invention the compositions contain at least one glutamine synthetase inhibitor (herbicide b7). The herbicidal activity of these compounds is based on the inhibition of glutamine synthetase, and thus on the inhibition of the aminoacid biosynthesis in plants. These inhibitors belong to the group H of the HRAC classification system.

According to an eighth embodiment of the invention the compositions contain at least one DHP synthase inhibitor (herbicide b8). The herbicidal activity of these compounds is based on the inhibition of 7,8-dihydropteroate synthase. These inhibitors belong to the group I of the HRAC classification system.

According to a ninth embodiment of the invention the compositions contain at least one mitosis inhibitor (herbicide b9). The herbicidal activity of these compounds is based on the disturbance or inhibition of microtubule formation or organization, and thus on the inhibition of mitosis. These inhibitors belong to the groups K1 and K2 of the HRAC classification system. Among these, compounds of the group K1, in particular dinitroanilines, are preferred.

According to a tenth embodiment of the invention the compositions contain at least one VLCFA inhibitor (herbicide b10). The herbicidal activity of these compounds is based on the inhibition of the synthesis of very long chain fatty acids and thus on the disturbance or inhibition of cell division in plants. These inhibitors belong to the group K3 of the H RAC classification system.

According to an eleventh embodiment of the invention the compositions contain at least one cellulose biosynthesis inhibitor (herbicide b11). The herbicidal activity of these compounds is based on the inhibition of the biosynthesis of cellulose and thus on the inhibition of the synthesis of cell walls in plants. These inhibitors belong to the group L of the HRAC classification system.

According to a twelfth embodiment of the invention the compositions contain at least one decoupler herbicide (herbicide b12). The herbicidal activity of these compounds is based on the disruption of the cell membrane. These inhibitors belong to the group M of the HRAC classification system.

According to a thirteenth embodiment of the invention the compositions contain at least one auxinic herbicide (herbicide b13). These include compounds that mimic auxins, i.e. plant hormones, and affect the growth of the plants. These compounds belong to the group O of the HRAC classification system.

According to a fourteenth embodiment of the invention the compositions contain at least one auxin transport inhibitor (herbicide b14). The herbicidal activity of these compounds is based on the inhibition of the auxin transport in plants. These compounds belong to the group P of the HRAC classification system.

As to the given mechanisms of action and classification of the active substances, see e.g. "HRAC, Classification of Herbicides According to Mode of Action", http://www-.plantprotection.org/hrac/MOA.html).

Preference is given to those compositions according to the present invention comprising at least one herbicide B selected from herbicides of class b1, b2, b3, b4, b5, b6, b9, b10, b13 and b14.

Specific preference is given to those compositions according to the present invention which comprise at least one herbicide B selected from the herbicides of class b1, b2, b3, b4, b5, b9, b10, b13, and b15.

also specific preference is given to those compositions according to the present invention which comprise at least one herbicide B selected from the herbicides of class b1, b2, b4, b5, b9, b10, b13 and b14.

Particular preference is given to those compositions according to the present invention which comprise at least one herbicide B selected from the herbicides of class b1, b2, b4, b5, b9, b10 and b13.

Examples of herbicides B which can be used in combination with the phenylpyrimidines of formula (I) according to the present invention are:

b1) from the group of the lipid biosynthesis inhibitors:

ACC-herbicides such as alloxydim, alloxydim-sodium, butroxydim, clethodim, clodinafop, clodinafop-propargyl, cycloxydim, cyhalofop, cyhalofop-butyl, diclofop, diclofop-methyl, fenoxaprop, fenoxaprop-ethyl, fenoxaprop-P, fenoxaprop-P-ethyl, fluazifop, fluazifop-butyl, fluazifop-P, fluazifop-P-butyl, haloxyfop, haloxyfop-methyl, haloxyfop-P, haloxyfop-P-methyl, metamifop, pinoxaden, profoxydim, propaquizafop, quizalofop, quizalofop-ethyl, quizalofop-tefuryl, quizalofop-P, quizalofop-P-ethyl, quizalofop-P-tefuryl, sethoxydim, tepraloxydim, tralkoxydim, 4-(4'-Chloro-4-cyclopropyl-2'-fluoro[, 1'-biphenyl]-3-yl)-5-hydroxy-2,2,6,6-tetramethyl-2H-pyran-3(6H)-one (CAS 1312337-72-6); 4-(2',4'-Dichloro-4-cyclopropyl[, 1'-biphenyl]-3-yl)-5-hydroxy-2,2,6,6-tetramethyl-2H-pyran-3(6H)-one (CAS 1312337-45-3); 4-(4'-Chloro-4-ethyl-2'-fluoro[1, 1'-biphenyl]-3-yl)-5-hydroxy-2,2,6,6-tetramethyl-2H-pyran-3(6H)-one (CAS 1033757-93-5); 4-(2',4'-Dichloro-4-ethyl[, 1'-biphenyl]-3-yl)-2,2,6,6-tetramethyl-2H-pyran-3,5 (4H,6H)-dione (CAS 1312340-84-3); 5-(Acetyloxy)-4-(4'-chloro-4-cyclopropyl-2'-fluoro[1,1'-biphenyl]-3-yl)-3,6-dihydro-2,2,6,6-tetramethyl-2H-pyran-3-one (CAS 1312337-48-6); 5-(Acetyloxy)-4-(2',4'-dichloro-4-cyclopropyl-[1,1'-biphenyl]-3-yl)-3,6-dihydro-2,2,6,6-tetramethyl-2H-pyran-3-one; 5-(Acetyloxy)-4-(4'-chloro-4-ethyl-2'-fluoro[1,1'-biphenyl]-3-yl)-3,6-dihydro-2,2,6,6-tetramethyl-2H-pyran-3-one (CAS 1312340-82-1); 5-(Acetyloxy)-4-(2',4'-dichloro-4-ethyl[1,1'-biphenyl]-3-yl)-3,6-dihydro-2,2,6,6-tetramethyl-2H-pyran-3-one (CAS 1033760-55-2); 4-(4'-Chloro-4-cyclopropyl-2'-fluoro[1,1'-biphenyl]-3-yl)-5,6-dihydro-2,2,6,6-tetramethyl-5-oxo-2H-pyran-3-yl carbonic acid methyl ester (CAS 1312337-51-1); 4-(2',4'-Dichloro-4-cyclopropyl-[1,1'-biphenyl]-3-yl)-5,6-dihydro-2,2,6,6-tetramethyl-5-oxo-2H-pyran-3-yl carbonic acid methyl ester; 4-(4'-Chloro-4-ethyl-2'-fluoro[1,1'-biphenyl]-3-yl)-5,6-dihydro-2,2,6,6-tetramethyl-5-oxo-2H-pyran-3-yl carbonic acid methyl ester (CAS 1312340-83-2); 4-(2',4'-Dichloro-4-ethyl[1,1'-biphenyl]-3-yl)-5,6-dihydro-2,2,6,6-tetramethyl-5-oxo-2H-pyran-3-yl carbonic acid methyl ester (CAS 1033760-58-5); and non ACC herbicides such as benfuresate, butylate, cycloate, dalapon, dimepiperate, EPTC, esprocarb, ethofumesate, flupropanate, molinate, orbencarb, pebulate, prosulfocarb, TCA, thiobencarb, tiocarbazil, triallate and vernolate;

b2) from the group of the ALS inhibitors:

sulfonylureas such as amidosulfuron, azimsulfuron, bensulfuron, bensulfuron-methyl, chlorimuron, chlorimuron-ethyl, chlorsulfuron, cinosulfuron, cyclosulfamuron, ethametsulfuron, ethametsulfuron-methyl, ethoxysulfuron, flazasulfuron, flucetosulfuron, flupyrsulfuron, flupyrsulfuron-methyl-sodium, foramsulfuron, halosulfuron, halosulfuron-methyl, imazosulfuron, iodosulfuron, iodosulfuron-methyl-sodium, iofensulfuron, iofensulfuron-sodium, mesosulfuron, metazosulfuron, metsulfuron, metsulfuron-methyl, nicosulfuron, orthosulfamuron, oxasulfuron, primisulfuron, primisulfuron-methyl, propyrisulfuron, prosulfuron, pyrazosulfuron, pyrazosulfuronethyl, rimsulfuron, sulfometuron, sulfometuron-methyl, sulfosulfuron, thifensulfuron, thifensulfuron-methyl, triasulfuron, tribenuron, tribenuron-methyl, trifloxysulfuron, triflusulfuron, triflusulfuron-methyl and tritosulfuron, imidazolinones such as imazamethabenz, imazamethabenz-methyl, imazamox, imazapic, imazapyr, imazaquin and imazethapyr, triazolopyrimidine herbicides and sulfonanilides such as cloransulam, cloransulam-methyl, diclosulam, flumetsulam, florasulam, metosulam, penoxsulam, pyrimisulfan and pyroxsulam, pyrimidinylbenzoates such as bispyribac, bispyribac-sodium, pyribenzoxim, pyriftalid, pyriminobac, pyriminobac-methyl, pyrithiobac, pyrithiobac-sodium, 4-[[[2-[(4,6-dimethoxy-2-pyrimidinyl)oxy]phenyl]methyl]amino]-benzoic acid-1-methylethyl ester (CAS 420138-41-6), 4-[[[2-[(4,6-dimethoxy-2-pyrimidinyl)oxy]phenyl]methyl]amino]-benzoic acid propyl ester (CAS 420138-40-5), N-(4-bromophenyl)-2-[(4,6-dimethoxy-2-pyrimidinyl)oxy]benzenemethanamine (CAS 420138-01-8), sulfonylaminocarbonyl-triazolinone herbicides such as flucarbazone, flucarbazone-sodium, propoxycarbazone, propoxycarbazone-sodium, thiencarbazone and thiencarbazone-methyl; and triafamone;

among these, a preferred embodiment of the invention relates to those compositions comprising at least one imidazolinone herbicide;

b3) from the group of the photosynthesis inhibitors:

amicarbazone, inhibitors of the photosystem II, e.g. 1-(6-tert-butylpyrimidin-4-yl)-2-hydroxy-4-methoxy-3-methyl-2H-pyrrol-5-one (CAS 1654744-66-7), 1-(5-tert-butylisoxazol-3-yl)-2-hydroxy-4-methoxy-3-methyl-2H-pyrrol-5-one (CAS 1637455-12-9), 1-(5-tert-butylisoxazol-3-yl)-4-chloro-2-hydroxy-3-methyl-2H-pyrrol-5-one (CAS 1637453-94-1), 1-(5-tert-butyl-1-methyl-pyrazol-3-yl)-4-chloro-2-hydroxy-3-methyl-2H-pyrrol-5-one (CAS 1654057-29-0), 1-(5-tert-butyl-1-methyl-pyrazol-3-yl)-3-chloro-2-hydroxy-4-methyl-2H-pyrrol-5-one (CAS 1654747-80-4), 4-hydroxy-1-methoxy-5-methyl-3-[4-(trifluoromethyl)-2-pyridyl]imidazolidin-2-one; (CAS 2023785-78-4), 4-hydroxy-1,5-dimethyl-3-[4-(trifluoromethyl)-2-pyridyl]imidazolidin-2-one (CAS 2023785-79-5), 5-ethoxy-4-hydroxy-1-methyl-3-[4-(trifluoromethyl)-2-pyridyl]imidazolidin-2-one (CAS 1701416-69-4), 4-hydroxy-1-methyl-3-[4-(trifluoromethyl)-2-pyridyl]imidazolidin-2-one (CAS 1708087-22-2), 4-hydroxy-1,5-dimethyl-3-[1-methyl-5-(trifluoromethyl)pyrazol-3-yl]imidazolidin-2-one (CAS 2023785-80-8), 1-(5-tert-butylisoxazol-3-yl)-4-ethoxy-5-hydroxy-3-methyl-imidazolidin-2-one (CAS 1844836-64-1), triazine herbicides, including of chlorotriazine, triazinones, triazindiones, methylthiotriazines and pyridazinones such as ametryn, atrazine, chloridazone, cyanazine, desmetryn, dimethametryn, hexazinone, metribuzin, prometon, prometryn, propazine, simazine, simetryn, terbumeton, terbuthylazin, terbutryn and trietazin, aryl urea such as chlorobromuron, saflufenacil, chloroxuron, dimefuron, diuron, fluometuron, isoproturon, isouron, linuron, metamitron, methabenzthiazuron, metobenzuron, metoxuron, monolinuron, neburon, siduron, tebuthiuron and thiadiazuron, phenyl carbamates such as desmedipham, karbutilat, phenmedipham, phenmedipham-ethyl, nitrile herbicides such as bromofenoxim, bromoxynil and its salts and esters, ioxynil and its salts and esters, uraciles such as bromacil, lenacil and terbacil, and bentazon and bentazon-sodium, pyridate, pyridafol, pentanochlor and propanil and inhibitors of the photosystem I such as diquat, diquat-dibromide, paraquat, paraquat-dichloride and paraquat-dimetilsulfate. Among these, a preferred embodiment of the invention relates to those compositions comprising at least one aryl urea herbicide. Among these, likewise a preferred embodiment of the invention relates to those compositions comprising at least one triazine herbicide. Among these, likewise a preferred embodiment of the invention relates to those compositions comprising at least one nitrile herbicide;

b4) from the group of the protoporphyrinogen-IX oxidase inhibitors:

acifluorfen, acifluorfen-sodium, azafenidin, bencarbazone, benzfendizone, bifenox, butafenacil, carfentrazone, carfentrazone-ethyl, chlomethoxyfen, chlorphthalim, cinidon-ethyl, fluazolate, flufenpyr, flufenpyr-ethyl, flumiclorac, flumiclorac-pentyl, flumioxazin, fluoroglycofen, fluoroglycofen-ethyl, fluthiacet, fluthiacet-methyl, fomesafen, halosafen, lactofen, oxadiargyl, oxadiazon, oxyfluorfen, pentoxazone, profluazol, pyraclonil, pyraflufen, pyraflufen-ethyl, saflufenacil, sulfentrazone, thidiazimin, tiafenacil, trifludimoxazin, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100), N-ethyl-3-(2,6-dichloro-4-trifluoromethyl phenoxy)-5-methyl-1H-pyrazole-1-carboxamide (CAS 452098-92-9), N-tetrahydrofurfuryl-3-(2,6-dichloro-4-trifluoromethylphenoxy)-5-methyl-1H-pyrazole-1-carboxamide (CAS 915396-43-9), N-ethyl-3-(2-chloro-6-fluoro-4-trifluoromethylphenoxy)-5-methyl-1H-pyrazole-1-carboxamide (CAS 452099-05-7), N-tetrahydrofurfuryl-3-(2-chloro-6-fluoro-4-trifluoromethylphenoxy)-5-methyl-1H-pyrazole-1-carboxamide (CAS 452100-03-7), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione (CAS 451484-50-7), 2-(2,2,7-trifluoro-3-oxo-4-prop-2-ynyl-3,4-dihydro-2H-benzo[1,4]oxazin-6-yl)-4,5,6,7-tetrahydro-isoindole-1,3-dione (CAS 1300118-96-0), 1-methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione (CAS 1304113-05-0), methyl (E)-4-[2-chloro-5-[4-chloro-5-(difluoromethoxy)-1H-methyl-pyrazol-3-yl]-4-fluoro-phenoxy]-3-methoxy-but-2-enoate (CAS 948893-00-3), and 3-[7-chloro-5-fluoro-2-(trifluoromethyl)-1H-benzimidazol-4-yl]-1-methyl-6-(trifluoromethyl)-1H-pyrimidine-2,4-dione (CAS 212754-02-4);

b5) from the group of the bleacher herbicides:

PDS inhibitors: beflubutamid, diflufenican, fluridone, flurochloridone, flurtamone, norflurazon, picolinafen, and 4-(3-trifluoromethylphenoxy)-2-(4-trifluoromethylphenyl)pyrimidine (CAS 180608-33-7), HPPD inhibitors: benzobicyclon, benzofenap, bicyclopyrone, clomazone, fenquinotrione, isoxaflutole, mesotrione, oxotrione (CAS 1486617-21-3), pyrasulfotole, pyrazolynate, pyrazoxyfen, sulcotrione, tefuryltrione, tembotrione, tolpyralate, topramezone, bleacher, unknown target: aclonifen, amitrole flumeturon, 2-chloro-3-methylsulfanyl-N-(1-methyltetrazol-5-yl)-4-(trifluoromethyl)benzamide (CAS 1361139-71-0), 2-(2,4-dichlorophenyl)methyl-4,4-dimethyl-3-isoxazolidone (CAS 81777-95-9) and 2-(2,5-dichlorophenyl)methyl-4,4-dimethyl-3-isoxazolidinone (CAS 81778-66-7);

b6) from the group of the EPSP synthase inhibitors: glyphosate, glyphosate-isopropylammonium, glyposate-potassium and glyphosate-trimesium (sulfosate);

b7) from the group of the glutamine synthase inhibitors: bilanaphos (bialaphos), bilanaphossodium, glufosinate, glufosinate-P and glufosinate-ammonium;

b8) from the group of the DHP synthase inhibitors: asulam;

b9) from the group of the mitosis inhibitors:

compounds of group K1: dinitroanilines such as benfluralin, butralin, dinitramine, ethalfluralin, fluchloralin, oryzalin, pendimethalin, prodiamine and trifluralin, phosphoramidates such as amiprophos, amiprophos-methyl, and butamiphos, benzoic acid herbicides such as chlorthal, chlorthal-dimethyl, pyridines such as dithiopyr and thiazopyr, benzamides such as propyzamide and tebutam; compounds of group K2: carbetamide, chlorpropham, flamprop, flamprop-isopropyl, flamprop-methyl, flamprop-M-isopropyl, flamprop-M-methyl and propham; among these, compounds of group K1, in particular dinitroanilines are preferred;

b10) from the group of the VLCFA inhibitors:

chloroacetamides such as acetochlor, alachlor, amidochlor, butachlor, dimethachlor, dimethenamid, dimethenamid-P, metazachlor, metolachlor, metolachlor-S, pethoxamid, pretilachlor, propachlor, propisochlor and thenylchlor, oxyacetanilides such as flufenacet and mefenacet, acetanilides such as diphenamid, naproanilide, napropamide and napropamide-M, tetrazolinones such fentrazamide, and other herbicides such as anilofos, cafenstrole, fenoxasulfone, ipfencarbazone, piperophos, pyroxasulfone and isoxazoline compounds of the formulae II.1, II.2, II.3, II.4, II.5, II.6, II.7, II.8 and II.9

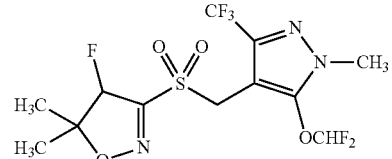

II.1

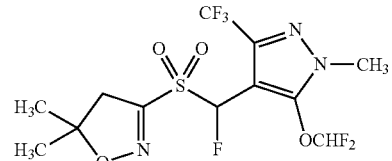

II.2

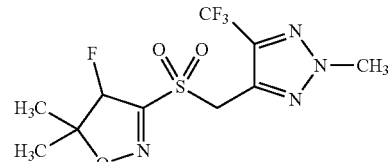

II.3

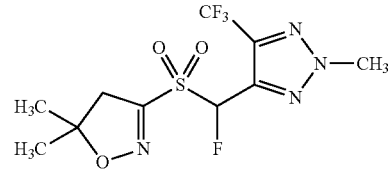

II.4

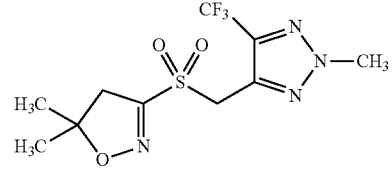

II.5

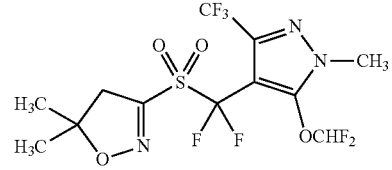

II.6

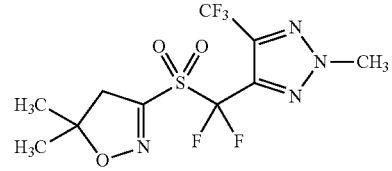

II.7

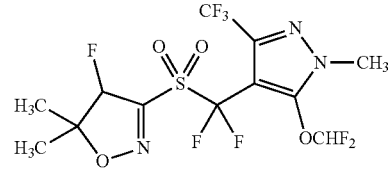

II.8

II.9

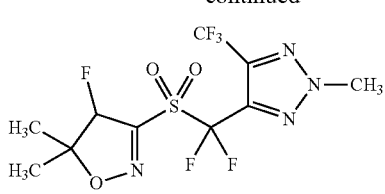

the isoxazoline compounds are known in the art, e.g. from WO 2006/024820, WO 2006/037945, WO 2007/071900 and WO 2007/096576;

among the VLCFA inhibitors, preference is given to chloroacetamides and oxyacetamides;

b11) from the group of the cellulose biosynthesis inhibitors: chlorthiamid, dichlobenil, flupoxam, indaziflam, isoxaben, triaziflam and 1-cyclohexyl-5-pentafluorphenyloxy-1$^4$-[1,2,4,6]thiatriazin-3-ylamine (CAS 175899-01-1);

b12) from the group of the decoupler herbicides: dinoseb, dinoterb and DNOC and its salts;

b13) from the group of the auxinic herbicides:

2,4-D and its salts and esters such as clacyfos, 2,4-DB and its salts and esters, aminocyclopyrachlor and its salts and esters, aminopyralid and its salts such as aminopyralid-dimethylammonium, aminopyralid-tris(2-hydroxypropyl) ammonium and its esters, benazolin, benazolin-ethyl, chloramben and its salts and esters, clomeprop, clopyralid and its salts and esters, dicamba and its salts and esters, dichlorprop and its salts and esters, dichlorprop-P and its salts and esters, flopyrauxifen, fluroxypyr, fluroxypyr-butometyl, fluroxypyr-meptyl, halauxifen and its salts and esters (CAS 943832-60-8); MCPA and its salts and esters, MCPA-thioethyl, MCPB and its salts and esters, mecoprop and its salts and esters, mecoprop-P and its salts and esters, picloram and its salts and esters, quinclorac, quinmerac, TBA (2,3,6) and its salts and esters, triclopyr and its salts and esters, florpyrauxifen, florpyrauxifen-benzyl (CAS 1390661-72-9) and 4-amino-3-chloro-5-fluoro-6-(7-fluoro-1H-indol-6-yl)picolinic acid (CAS 1629965-65-6);

b14) from the group of the auxin transport inhibitors: diflufenzopyr, diflufenzopyr-sodium, naptalam and naptalam-sodium;

b15) from the group of the other herbicides: bromobutide, chlorflurenol, chlorflurenol-methyl, cinmethylin, cumyluron, cyclopyrimorate (CAS 499223-49-3 and its salts and esters, dalapon, dazomet, difenzoquat, difenzoquat-metilsulfate, dimethipin, DSMA, dymron, endothal and its salts, etobenzanid, flurenol, flurenol-butyl, flurprimidol, fosamine, fosamine-ammonium, indanofan, maleic hydrazide, mefluidide, metam, methiozolin (CAS 403640-27-7), methyl azide, methyl bromide, methyl-dymron, methyl iodide, MSMA, oleic acid, oxaziclomefone, pelargonic acid, pyributicarb, quinoclamine and tridiphane.

Preferred herbicides B that can be used in combination with the pyrimidine compounds of the formula (I) according to the present invention are:

b1) from the group of the lipid biosynthesis inhibitors:

clethodim, clodinafop-propargyl, cycloxydim, cyhalofop-butyl, diclofop-methyl, fenoxaprop-P-ethyl, fluazifop-P-butyl, haloxyfop-P-methyl, metamifop, pinoxaden, profoxydim, propaquizafop, quizalofop-P-ethyl, quizalofop-P-tefuryl, sethoxydim, tepraloxydim, tralkoxydim, 4-(4'-Chloro-4-cyclopropyl-2'-fluoro[, 1'-biphenyl]-3-yl)-5-hydroxy-2,2,6,6-tetramethyl-2H-pyran-3(6H)-one (CAS 1312337-72-6); 4-(2',4'-Dichloro-4-cyclopropyl[, 1'-biphenyl]-3-yl)-5-hydroxy-2,2,6,6-tetramethyl-2H-pyran-3(6H)-one (CAS 1312337-45-3); 4-(4'-Chloro-4-ethyl-2'-fluoro[, 1'-biphenyl]-3-yl)-5-hydroxy-2,2,6,6-tetramethyl-2H-pyran-3(6H)-one (CAS 1033757-93-5); 4-(2',4'-Dichloro-4-ethyl[1,1'-biphenyl]-3-yl)-2,2,6,6-tetramethyl-2H-pyran-3,5 (4H,6H)-dione (CAS 1312340-84-3); 5-(Acetyloxy)-4-(4'-chloro-4-cyclopropyl-2'-fluoro[, 1'-biphenyl]-3-yl)-3,6-dihydro-2,2,6,6-tetramethyl-2H-pyran-3-one (CAS 1312337-48-6); 5-(Acetyloxy)-4-(2',4'-dichloro-4-cyclopropyl-[1,1'-biphenyl]-3-yl)-3,6-dihydro-2,2,6,6-tetramethyl-2H-pyran-3-one; 5-(Acetyloxy)-4-(4'-chloro-4-ethyl-2'-fluoro[1,1'-biphenyl]-3-yl)-3,6-dihydro-2,2,6,6-tetramethyl-2H-pyran-3-one (CAS 1312340-82-1); 5-(Acetyloxy)-4-(2',4'-dichloro-4-ethyl[, 1'-biphenyl]-3-yl)-3,6-dihydro-2,2,6,6-tetramethyl-2H-pyran-3-one (CAS 1033760-55-2); 4-(4'-Chloro-4-cyclopropyl-2'-fluoro[1,1'-biphenyl]-3-yl)-5,6-dihydro-2,2,6,6-tetramethyl-5-oxo-2H-pyran-3-yl carbonic acid methyl ester (CAS 1312337-51-1); 4-(2',4'-Dichloro-4-cyclopropyl-[1,1'-biphenyl]-3-yl)-5,6-dihydro-2,2,6,6-tetramethyl-5-oxo-2H-pyran-3-yl carbonic acid methyl ester; 4-(4'-Chloro-4-ethyl-2'-fluoro[1,1'-biphenyl]-3-yl)-5,6-dihydro-2,2,6,6-tetramethyl-5-oxo-2H-pyran-3-yl carbonic acid methyl ester (CAS 1312340-83-2); 4-(2',4'-Dichloro-4-ethyl[, 1'-biphenyl]-3-yl)-5,6-dihydro-2,2,6,6-tetramethyl-5-oxo-2H-pyran-3-yl carbonic acid methyl ester (CAS 1033760-58-5); benfuresate, dimepiperate, EPTC, esprocarb, ethofumesate, molinate, orbencarb, prosulfocarb, thiobencarb and triallate;

b2) from the group of the ALS inhibitors:

amidosulfuron, azimsulfuron, bensulfuron-methyl, bispyribac-sodium, chlorimuron-ethyl, chlorsulfuron, cloransulam-methyl, cyclosulfamuron, diclosulam, ethametsulfuron-methyl, ethoxysulfuron, flazasulfuron, florasulam, flucarbazone-sodium, flucetosulfuron, flumetsulam, flupyrsulfuron-methyl-sodium, foramsulfuron, halosulfuron-methyl, imazamethabenz-methyl, imazamox, imazapic, imazapyr, imazaquin, imazethapyr, imazosulfuron, iodosulfuron, iodosulfuron-methyl-sodium, iofensulfuron, iofensulfuron-sodium, mesosulfuron, metazosulfuron, metosulam, metsulfuron-methyl, nicosulfuron, orthosulfamuron, oxasulfuron, penoxsulam, primisulfuron-methyl, propoxycarbazon-sodium, propyrisulfuron, prosulfuron, pyrazosulfuron-ethyl, pyribenzoxim, pyrimisulfan, pyriftalid, pyriminobac-methyl, pyrithiobac-sodium, pyroxsulam, rimsulfuron, sulfometuron-methyl, sulfosulfuron, thiencarbazone-methyl, thifensulfuron-methyl, triasulfuron, tribenuron-methyl, trifloxysulfuron, triflusulfuron-methyl, tritosulfuron and triafamone;

b3) from the group of the photosynthesis inhibitors:

ametryn, amicarbazone, atrazine, bentazone, bentazone-sodium, bromoxynil and its salts and esters, chloridazone, saflufenacil, cyanazine, desmedipham, diquat-dibromide, diuron, fluometuron, hexazinone, ioxynil and its salts and esters, isoproturon, lenacil, linuron, metamitron, methabenzthiazuron, metribuzin, paraquat, paraquat-dichloride, phenmedipham, propanil, pyridate, simazine, terbutryn, terbuthylazine, thidiazuron, 1-(6-tert-butylpyrimidin-4-yl)-2-hydroxy-4-methoxy-3-methyl-2H-pyrrol-5-one (CAS 1654744-66-7), 1-(5-tert-butylisoxazol-3-yl)-2-hydroxy-4-methoxy-3-methyl-2H-pyrrol-5-one (CAS 1637455-12-9), 1-(5-tert-butylisoxazol-3-yl)-4-chloro-2-hydroxy-3-methyl-2H-pyrrol-5-one (CAS 1637453-94-1), 1-(5-tert-butyl-1-methyl-pyrazol-3-yl)-4-chloro-2-hydroxy-3-methyl-2H-pyrrol-5-one (CAS 1654057-29-0), 1-(5-tert-butyl-1-methyl-pyrazol-3-yl)-3-chloro-2-hydroxy-4-methyl-2H-pyrrol-5-one (CAS 1654747-80-4), 4-hydroxy-1-methoxy-5-methyl-3-[4-(trifluoromethyl)-2-pyridyl]imidazolidin-2-one; (CAS 2023785-78-4), 4-hydroxy-1,5-dimethyl-3-[4-

(trifluoromethyl)-2-pyridyl]imidazolidin-2-one (CAS 2023785-79-5), 5-ethoxy-4-hydroxy-1-methyl-3-[4-(trifluoromethyl)-2-pyridyl]imidazolidin-2-one (CAS 1701416-69-4), 4-hydroxy-1-methyl-3-[4-(trifluoromethyl)-2-pyridyl]imidazolidin-2-one (CAS 1708087-22-2), 4-hydroxy-1,5-dimethyl-3-[1-methyl-5-(trifluoromethyl)pyrazol-3-yl]imidazolidin-2-one (CAS 2023785-80-8) and 1-(5-tert-butylisoxazol-3-yl)-4-ethoxy-5-hydroxy-3-methyl-imidazolidin-2-one (CAS 1844836-64-1);

b4) from the group of the protoporphyrinogen-IX oxidase inhibitors:

acifluorfen-sodium, bencarbazone, benzfendizone, butafenacil, carfentrazone-ethyl, cinidon-ethyl, flufenpyr-ethyl, flumiclorac-pentyl, flumioxazin, fluoroglycofen-ethyl, fomesafen, lactofen, oxadiargyl, oxadiazon, oxyfluorfen, pentoxazone, pyraflufen, pyraflufen-ethyl, saflufenacil, sulfentrazone, tiafenacil, trifludimoxazin, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100), N-ethyl-3-(2,6-dichloro-4-trifluoromethyl phenoxy)-5-methyl-1H-pyrazole-1-carboxamide (CAS 452098-92-9), N-tetrahydrofurfuryl-3-(2,6-dichloro-4-trifluoromethylphenoxy)-5-methyl-1H-pyrazole-1-carboxamide (CAS 915396-43-9), N-ethyl-3-(2-chloro-6-fluoro-4-trifluoromethylphenoxy)-5-methyl-1H-pyrazole-1-carboxamide (CAS 452099-05-7), N-tetrahydrofurfuryl-3-(2-chloro-6-fluoro-4-trifluoromethylphenoxy)-5-methyl-1H-pyrazole-1-carboxamide (CAS 452100-03-7), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione (CAS 451484-50-7), 2-(2,2,7-trifluoro-3-oxo-4-prop-2-ynyl-3,4-dihydro-2H-benzo[1,4]oxazin-6-yl)-4,5,6,7-tetrahydro-isoindole-1,3-dione (CAS 1300118-96-0); 1-methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione (CAS 1304113-05-0), and 3-[7-chloro-5-fluoro-2-(trifluoromethyl)-1H-benzimidazol-4-yl]-1-methyl-6-(trifluoromethyl)-1H-pyrimidine-2,4-dione (CAS 212754-02-4);

b5) from the group of the bleacher herbicides:

aclonifen, amitrole, beflubutamid, benzobicyclon, bicyclopyrone, clomazone, diflufenican, fenquinotrione, flumeturon, flurochloridone, flurtamone, isoxaflutole, mesotrione, oxotrione (CAS 1486617-21-3), norflurazon, picolinafen, pyrasulfotole, pyrazolynate, sulcotrione, tefuryltrione, tembotrione, tolpyralate, topramezone, 4-(3-trifluoromethylphenoxy)-2-(4-trifluoromethylphenyl)-pyrimidine (CAS 180608-33-7), 2-chloro-3-methylsulfanyl-N-(1-methyltetrazol-5-yl)-4-(trifluoromethyl)benzamide (CAS 1361139-71-0, 2-(2,4-dichlorophenyl)methyl-4,4-dimethyl-3-isoxazolidone (CAS 81777-95-9) and 2-(2,5-dichlorophenyl)methyl-4,4-dimethyl-3-isoxazolidinone (CAS 81778-66-7);

b6) from the group of the EPSP synthase inhibitors:

glyphosate, glyphosate-isopropylammonium, glyphosate-potassium and glyphosate-trimesium (sulfosate);

b7) from the group of the glutamine synthase inhibitors:

glufosinate, glufosinate-P, glufosinate-ammonium;

b8) from the group of the DHP synthase inhibitors: asulam;

b9) from the group of the mitosis inhibitors:

benfluralin, dithiopyr, ethalfluralin, flamprop, flamprop-isopropyl, flamprop-methyl, flamprop-M-isopropyl, flamprop-M-methyl, oryzalin, pendimethalin, thiazopyr and trifluralin;

b10) from the group of the VLCFA inhibitors: acetochlor, alachlor, amidochlor, anilofos, butachlor, cafenstrole, dimethenamid, dimethenamid-P, fentrazamide, flufenacet, mefenacet, metazachlor, metolachlor, S-metolachlor, naproanilide, napropamide, napropamide-M, pretilachlor, fenoxasulfone, ipfencarbazone, pyroxasulfone thenylchlor and isoxazoline-compounds of the formulae II.1, II.2, II.3, II.4, II.5, II.6, II.7, II.8 and II.9 as mentioned above;

b11) from the group of the cellulose biosynthesis inhibitors: dichlobenil, flupoxam, indaziflam, isoxaben, triaziflam and 1-cyclohexyl-5-pentafluorphenyloxy-1$^4$-[1,2,4]thiatriazin-3-ylamine (CAS 175899-01-1);

b13) from the group of the auxinic herbicides:

2,4-D and its salts and esters, aminocyclopyrachlor and its salts and esters, aminopyralid and its salts such as aminopyralid-dimethylammonium, aminopyralid-tris(2-hydroxypropyl)ammonium and its esters, clopyralid and its salts and esters, dicamba and its salts and esters, dichlorprop-P and its salts and esters, flopyrauxifen, fluroxypyr-meptyl, halauxifen and its salts and esters (CAS 943832-60-8), MCPA and its salts and esters, MCPB and its salts and esters, mecoprop-P and its salts and esters, picloram and its salts and esters, quinclorac, quinmerac, triclopyr and its salts and esters, florpyrauxifen, florpyrauxifen-benzyl (CAS 1390661-72-9) and 4-amino-3-chloro-5-fluoro-6-(7-fluoro-1H-indol-6-yl)picolinic acid (CAS 1629965-65-6);

b14) from the group of the auxin transport inhibitors: diflufenzopyr and diflufenzopyr-sodium;

b15) from the group of the other herbicides: bromobutide, cinmethylin, cumyluron, cyclopyrimorate (CAS 499223-49-3) and its salts and esters, dalapon, difenzoquat, difenzoquatmetilsulfate, DSMA, dymron (=daimuron), indanofan, metam, methylbromide, MSMA, oxaziclomefone, pyributicarb and tridiphane.

Particularly preferred herbicides B that can be used in combination with the pyrimidine compounds of the formula (I) according to the present invention are:

b1) from the group of the lipid biosynthesis inhibitors: clodinafop-propargyl, cycloxydim, cyhalofop-butyl, fenoxaprop-P-ethyl, pinoxaden, profoxydim, tepraloxydim, tralkoxydim, 4-(4'-Chloro-4-cyclopropyl-2'-fluoro[, 1'-biphenyl]-3-yl)-5-hydroxy-2,2,6,6-tetramethyl-2H-pyran-3 (6H)-one (CAS 1312337-72-6); 4-(2',4'-Dichloro-4-cyclopropyl[, 1'-biphenyl]-3-yl)-5-hydroxy-2,2,6,6-tetramethyl-2H-pyran-3(6H)-one (CAS 1312337-45-3); 4-(4'-Chloro-4-ethyl-2'-fluoro[, 1'-biphenyl]-3-yl)-5-hydroxy-2,2,6,6-tetramethyl-2H-pyran-3(6H)-one (CAS 1033757-93-5); 4-(2',4'-Dichloro-4-ethyl[1,1'-biphenyl]-3-yl)-2,2,6,6-tetramethyl-2H-pyran-3,5(4H,6H)-dione (CAS 1312340-84-3); 5-(Acetyloxy)-4-(4'-chloro-4-cyclopropyl-2'-fluoro[, 1'-biphenyl]-3-yl)-3,6-dihydro-2,2,6,6-tetramethyl-2H-pyran-3-one (CAS 1312337-48-6); 5-(Acetyloxy)-4-(2',4'-dichloro-4-cyclopropyl-[1,1'-biphenyl]-3-yl)-3,6-dihydro-2,2,6,6-tetramethyl-2H-pyran-3-one; 5-(Acetyloxy)-4-(4'-chloro-4-ethyl-2'-fluoro[1,1'-biphenyl]-3-yl)-3,6-dihydro-2,2,6,6-tetramethyl-2H-pyran-3-one (CAS 1312340-82-1); 5-(Acetyloxy)-4-(2',4'-dichloro-4-ethyl[, 1'-biphenyl]-3-yl)-3,6-dihydro-2,2,6,6-tetramethyl-2H-pyran-3-one (CAS 1033760-55-2); 4-(4'-Chloro-4-cyclopropyl-2'-fluoro[1,1'-biphenyl]-3-yl)-5,6-dihydro-2,2,6,6-tetramethyl-5-oxo-2H-pyran-3-yl carbonic acid methyl ester (CAS 1312337-51-1); 4-(2',4'-Dichloro-4-cyclopropyl-[1,1'-biphenyl]-3-yl)-5,6-dihydro-2,2,6,6-tetramethyl-5-oxo-2H-pyran-3-yl carbonic acid methyl ester; 4-(4'-Chloro-4-ethyl-2'-fluoro[1,1'-biphenyl]-3-yl)-5,6-dihydro-2,2,6,6-tetramethyl-5-oxo-2H-pyran-3-yl carbonic acid methyl ester (CAS 1312340-83-2); 4-(2',4'-Dichloro-4-ethyl[, 1'-biphenyl]-3-yl)-5,6-dihydro-2, 2,6,6-tetramethyl-5-oxo-2H-pyran-3-yl carbonic acid methyl ester (CAS 1033760-58-5); esprocarb, prosulfocarb, thiobencarb and triallate;

b2) from the group of the ALS inhibitors: bensulfuron-methyl, bispyribac-sodium, cyclosulfamuron, diclosulam, flumetsulam, flupyrsulfuron-methyl-sodium, foramsulfuron, imazamox, imazapic, imazapyr, imazaquin, imazethapyr, imazosulfuron, iodosulfuron, iodosulfuron-methyl-sodium, iofensulfuron, iofensulfuron-sodium, mesosulfuron, metazosulfuron, nicosulfuron, penoxsulam, propoxycarbazon-sodium, propyrisulfuron, pyrazosulfuron-ethyl, pyroxsulam, rimsulfuron, sulfosulfuron, thiencarbazon-methyl, tritosulfuron and triafamone;

b3) from the group of the photosynthesis inhibitors: ametryn, atrazine, diuron, fluometuron, hexazinone, isoproturon, linuron, metribuzin, paraquat, paraquat-dichloride, propanil, terbutryn, terbuthylazine, 1-(5-tert-butylisoxazol-3-yl)-2-hydroxy-4-methoxy-3-methyl-2H-pyrrol-5-one (CAS 1637455-12-9), 1-(5-tert-butylisoxazol-3-yl)-4-chloro-2-hydroxy-3-methyl-2H-pyrrol-5-one (CAS 1637453-94-1), 1-(5-tert-butylisoxazol-3-yl)-4-ethoxy-5-hydroxy-3-methyl-imidazolidin-2-one (CAS 1844836-64-1);

b4) from the group of the protoporphyrinogen-IX oxidase inhibitors: flumioxazin, oxyfluorfen, pyraflufen, pyraflufen-ethyl, saflufenacil, sulfentrazone, trifludimoxazin, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100, 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione (CAS 451484-50-7), 2-(2,2,7-trifluoro-3-oxo-4-prop-2-ynyl-3,4-dihydro-2H-benzo[1,4]oxazin-6-yl)-4,5,6,7-tetrahydro-isoindole-1,3-dione (CAS 1300118-96-0), and 1-methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione (CAS 1304113-05-0);

b5) from the group of the bleacher herbicides: amitrole, bicyclopyrone, clomazone, diflufenican, fenquinotrione, flumeturon, flurochloridone, isoxaflutole, mesotrione, oxotrione (CAS 1486617-21-3), picolinafen, sulcotrione, tefuryltrione, tembotrione, tolpyralate, topramezone, 2-chloro-3-methylsulfanyl-N-(1-methyltetrazol-5-yl)-4-(trifluoromethyl)benzamide (CAS 1361139-71-0), 2-(2,4-dichlorophenyl)methyl-4,4-dimethyl-3-isoxazolidone (CAS 81777-95-9); and 2-(2,5-dichlorophenyl)methyl-4,4-dimethyl-3-isoxazolidinone (CAS 81778-66-7);

b6) from the group of the EPSP synthase inhibitors: glyphosate, glyphosate-isopropylammonium and glyphosate-trimesium (sulfosate);

b7) from the group of the glutamine synthase inhibitors: glufosinate, glufosinate-P and glufosinate-ammonium;

b9) from the group of the mitosis inhibitors: pendimethalin and trifluralin;

b10) from the group of the VLCFA inhibitors: acetochlor, cafenstrole, dimethenamid-P, fentrazamide, flufenacet, mefenacet, metazachlor, metolachlor, S-metolachlor, fenoxasulfone, ipfencarbazone and pyroxasulfone; likewise, preference is given to isoxazoline compounds of the formulae II.1, II.2, II.3, II.4, II.5, II.6, II.7, II.8 and II.9 as mentioned above;

b11) from the group of the cellulose biosynthesis inhibitors: indaziflam, isoxaben and triazflam;

b13) from the group of the auxinic herbicides: 2,4-D and its salts and esters such as clacyfos, and aminocyclopyrachlor and its salts and esters, aminopyralid and its salts and its esters, clopyralid and its salts and esters, dicamba and its salts and esters, flopyrauxifen, fluroxypyrmeptyl, halauxifen, halauxifen-methyl, quinclorac, quinmerac, florpyrauxifen, florpyrauxifen-benzyl (CAS 1390661-72-9) and 4-amino-3-chloro-5-fluoro-6-(7-fluoro-1H-indol-6-yl) picolinic acid (CAS 1629965-65-6);

b14) from the group of the auxin transport inhibitors: diflufenzopyr and diflufenzopyr-sodium, b15) from the group of the other herbicides: cinmethylin, dymon (=daimuron), indanofan, oxaziclomefone.

Particularly preferred herbicides B are the herbicides B as defined above; in particular, the herbicides B.1-B.202 listed below in table B:

TABLE B

| B | Herbicide B |
|---|---|
| B.1 | clethodim |
| B.2 | clodinafop-propargyl |
| B.3 | cycloxydim |
| B.4 | cyhalofop-butyl |
| B.5 | fenoxaprop-ethyl |
| B.6 | fenoxaprop-P-ethyl |
| B.7 | metamifop |
| B.8 | pinoxaden |
| B.9 | profoxydim |
| B.10 | sethoxydim |
| B.11 | tepraloxydim |
| B.12 | tralkoxydim |
| B.13 | esprocarb |
| B.14 | ethofumesate |
| B.15 | molinate |
| B.16 | prosulfocarb |
| B.17 | thiobencarb |
| B.18 | triallate |
| B.19 | bensulfuron-methyl |
| B.20 | bispyribac-sodium |
| B.21 | cloransulam-methyl |
| B.22 | chlorsulfuron |
| B.23 | clorimuron |
| B.24 | cyclosulfamuron |
| B.25 | diclosulam |
| B.26 | florasulam |
| B.27 | flumetsulam |
| B.28 | flupyrsulfuron-methyl-sodium |
| B.29 | foramsulfuron |
| B.30 | imazamox |
| B.31 | imazamox-ammonium |
| B.32 | imazapic |
| B.33 | imazapic-ammonium |
| B.34 | imazapic-isopropylammonium |
| B.35 | imazapyr |
| B.36 | imazapyr-ammonium |
| B.37 | imazapyr-isopropylammonium |
| B.38 | imazaquin |
| B.39 | imazaquin-ammonium |
| B.40 | imazethapyr |
| B.41 | imazethapyr-ammonium |
| B.42 | imazethapyr-isopropylammonium |
| B.43 | imazosulfuron |
| B.44 | iodosulfuron-methyl-sodium |
| B.45 | iofensulfuron |
| B.46 | iofensulfuron-sodium |
| B.47 | mesosulfuron-methyl |
| B.48 | metazosulfuron |
| B.49 | metsulfuron-methyl |
| B.50 | metosulam |
| B.51 | nicosulfuron |
| B.52 | penoxsulam |
| B.53 | propoxycarbazon-sodium |
| B.54 | pyrazosulfuron-ethyl |
| B.55 | pyribenzoxim |
| B.56 | pyriftalid |
| B.57 | pyroxsulam |
| B.58 | propyrisulfuron |
| B.59 | rimsulfuron |
| B.60 | sulfosulfuron |
| B.61 | thiencarbazone-methyl |
| B.62 | thifensulfuron-methyl |

TABLE B-continued

| B | Herbicide B |
|---|---|
| B.63 | tribenuron-methyl |
| B.64 | tritosulfuron |
| B.65 | triafamone |
| B.66 | ametryne |
| B.67 | atrazine |
| B.68 | bentazon |
| B.69 | bromoxynil |
| B.70 | bromoxynil-octanoate |
| B.71 | bromoxynil-heptanoate |
| B.72 | bromoxynil-potassium |
| B.73 | diuron |
| B.74 | fluometuron |
| B.75 | hexazinone |
| B.76 | isoproturon |
| B.77 | linuron |
| B.78 | metamitron |
| B.79 | metribuzin |
| B.80 | propanil |
| B.81 | simazin |
| B.82 | terbuthylazine |
| B.83 | terbutryn |
| B.84 | paraquat-dichloride |
| B.85 | acifluorfen |
| B.86 | butafenacil |
| B.87 | carfentrazone-ethyl |
| B.88 | flumioxazin |
| B.89 | fomesafen |
| B.90 | oxadiargyl |
| B.91 | oxyfluorfen |
| B.92 | pyraflufen |
| B.93 | pyraflufen-ethyl |
| B.94 | saflufenacil |
| B.95 | sulfentrazone |
| B.96 | trifludimoxazin |
| B.97 | ethyl [3-[2-chloro-4-fluoro-5-(1-methyl-6-trifluoromethyl-2,4-dioxo-1,2,3,4-tetrahydropyrimidin-3-yl)phenoxy]-2-pyridyl-oxy]acetate |
| B.98 | benzobicyclon |
| B.99 | bicyclopyrone |
| B.100 | clomazone |
| B.101 | diflufenican |
| B.102 | flurochloridone |
| B.103 | isoxaflutole |
| B.104 | mesotrione |
| B.105 | norflurazone |
| B.106 | picolinafen |
| B.107 | sulcotrione |
| B.108 | tefuryltrione |
| B.109 | tembotrione |
| B.110 | tolpyralate |
| B.111 | topramezone |
| B.112 | topramezone-sodium |
| B.113 | amitrole |
| B.114 | fluometuron |
| B.115 | fenquinotrione |
| B.116 | glyphosate |
| B.117 | glyphosate-ammonium |
| B.118 | glyphosate-dimethylammonium |
| B.119 | glyphosate-isopropylammonium |
| B.120 | glyphosate-trimesium (sulfosate) |
| B.121 | glyphosate-potassium |
| B.122 | glufosinate |
| B.123 | glufosinate-ammonium |
| B.124 | glufosinate-P |
| B.125 | glufosinate-P-ammonium |
| B.126 | pendimethalin |
| B.127 | trifluralin |
| B.128 | acetochlor |
| B.129 | butachlor |
| B.130 | cafenstrole |
| B.131 | dimethenamid-P |
| B.132 | fentrazamide |
| B.133 | flufenacet |
| B.134 | mefenacet |
| B.135 | metazachlor |
| B.136 | metolachlor |
| B.137 | S-metolachlor |
| B.138 | pretilachlor |
| B.139 | fenoxasulfone |
| B.140 | indaziflam |
| B.141 | isoxaben |
| B.142 | triaziflam |
| B.143 | ipfencarbazone |
| B.144 | pyroxasulfone |
| B.145 | 2,4-D |
| B.146 | 2,4-D-isobutyl |
| B.147 | 2,4-D-dimethylammonium |
| B.148 | 2,4-D-N,N,N-trimethylethanolammonium |
| B.149 | aminopyralid |
| B.150 | aminopyralid-methyl |
| B.151 | aminopyralid-dimethylammonium |
| B.152 | aminopyralid-tris(2-hydroxypropyl)ammonium |
| B.153 | clopyralid |
| B.154 | clopyralid-methyl |
| B.155 | clopyralid-olamine |
| B.156 | dicamba |
| B.157 | dicamba-butotyl |
| B.158 | dicamba-diglycolamine |
| B.159 | dicamba-dimethylammonium |
| B.160 | dicamba-diolamine |
| B.161 | dicamba-isopropylammonium |
| B.162 | dicamba-potassium |
| B.163 | dicamba-sodium |
| B.164 | dicamba-trolamine |
| B.165 | dicamba-N,N-bis-(3-aminopropyl)methylamine |
| B.166 | dicamba-diethylenetriamine |
| B.167 | fluroxypyr |
| B.168 | fluroxypyr-meptyl |
| B.169 | halauxifen |
| B.170 | halauxifen-methyl |
| B.171 | MCPA |
| B.172 | MCPA-2-ethylhexyl |
| B.173 | MCPA-dimethylammonium |
| B.174 | quinclorac |
| B.175 | quinclorac-dimethylammonium |
| B.176 | quinmerac |
| B.177 | quinmerac-dimethylammonium |
| B.178 | florpyrauxifen |
| B.179 | florpyrauxifen-benzyl |
| B.180 | aminocyclopyrachlor |
| B.181 | aminocyclopyrachlor-potassium |
| B.182 | aminocyclopyrachlor-methyl |
| B.183 | diflufenzopyr |
| B.184 | diflufenzopyr-sodium |
| B.185 | dymron |
| B.186 | indanofan |
| B.187 | oxaziclomefone |
| B.188 | II.1 |
| B.189 | II.2 |
| B.190 | II.3 |
| B.191 | II.4 |
| B.192 | II.5 |
| B.193 | II.6 |
| B.194 | II.7 |
| B.195 | II.8 |
| B.196 | II.9 |
| B.197 | 4-amino-3-chloro-5-fluoro-6-(7-fluoro-1H-indol-6-yl)picolinic acid |
| B.198 | flopyrauxifen |
| B.199 | oxotrione |
| B.200 | cinmethylin |
| B.201 | 2-chloro-3-methylsulfanyl-N-(1-methyltetrazol-5-yl)-4-(trifluoromethyl)benzamide |
| B.202 | 2-(2,4-dichlorophenyl)methyl-4,4-dimethyl-3-isoxazolidone |

In another embodiment the herbicide B excludes 1-(6-tert-butylpyrimidin-4-yl)-2-hydroxy-4-methoxy-3-methyl-2H-pyrrol-5-one, 1-(5-tert-butylisoxazol-3-yl)-2-hydroxy- 4-methoxy-3-methyl-2H-pyrrol-5-one, 1-(5-tert-butylisoxazol-3-yl)-4-chloro-2-hydroxy-3-methyl-2H-pyrrol-5-one (CAS 1637453-94-1), 1-(5-tert-butyl-1-methyl-pyrazol-3-yl)-4-chloro-2-hydroxy-3-methyl-2H-pyrrol-5-one (CAS 1654057-29-0), 1-(5-tert-butyl-1-methyl-pyrazol-3-yl)-3-chloro-2-hydroxy-4-methyl-2H-pyrrol-5-one (CAS 1654747-80-4), 4-hydroxy-1-methoxy-5-methyl-3-[4-(trifluoromethyl)-2-pyridyl]imidazolidin-2-one; (CAS 2023785-78-4), 4-hydroxy-1,5-dimethyl-3-[4-(trifluoromethyl)-2-pyridyl]imidazolidin-2-one (CAS 2023785-79-5), 5-ethoxy-4-hydroxy-1-methyl-3-[4-(trifluoromethyl)-2-pyridyl]imidazolidin-2-one (CAS 1701416-69-4), 4-hydroxy-1-methyl-3-[4-(trifluoromethyl)-2-pyridyl] imidazolidin-2-one (CAS 1708087-22-2), 4-hydroxy-1,5-dimethyl-3-[1-methyl-5-(trifluoromethyl)pyrazol-3-yl] imidazolidin-2-one (CAS 2023785-80-8), 1-(5-tert-butylisoxazol-3-yl)-4-ethoxy-5-hydroxy-3-methyl-imidazolidin-2-one (CAS 1844836-64-1), from group b3); chlorphthalim from group b4); 2-(2,4-dichlorophenyl) methyl-4,4-dimethyl-3-isoxazolidone (CAS 81777-95-9) and 2-(2,5-dichlorophenyl)methyl-4,4-dimethyl-3-isoxazolidinone (CAS 81778-66-7) from group b5).

more particularly preferred herbicides B are selected from cinmethylin, trifludimoxazin, bentazone, bromoxynil, saflufenacil, dicamba, diflufenican, flufenacet, flumioxazin, isoproturon, metazachlor, metribuzin, pendimethalin, picolinafen, pinoxaden, prosulfocarb, pyridate, pyroxasulfone, pyroxsulam, saflufenazil, sulfosulfuron, terbutylazin, dimethenamid (dmta), mesosulfuron, iodosulfuron, cycloxydim, clomazone, quinmerac, and topramezone.

In another embodiment of the present invention the compositions according to the present invention comprise at least one phenylpyrimidine of formula (I) and at least one safener C.

Safeners are chemical compounds which prevent or reduce damage on useful plants without having a major impact on the herbicidal action of the herbicidal active components of the present compositions towards unwanted plants. They can be applied either before sowings (e.g. on seed treatments, shoots or seedlings) or in the pre-emergence application or post-emergence application of the useful plant. The safeners and the phenylpyrimidines of formula (I) and/or the herbicides B can be applied simultaneously or in succession.

Suitable safeners are e.g. (quinolin-8-oxy)acetic acids, 1-phenyl-5-haloalkyl-1H-1,2,4-triazol-3-carboxylic acids, 1-phenyl-4,5-dihydro-5-alkyl-1H-pyrazol-3,5-dicarboxylic acids, 4,5-dihydro-5,5-diaryl-3-isoxazol carboxylic acids, dichloroacetamides, alpha-oximinophenylacetonitriles, acetophenonoximes, 4,6-dihalo-2-phenylpyrimidines, N-[[4-(aminocarbonyl)phenyl]sulfonyl]-2-benzoic amides, 1,8-naphthalic anhydride, 2-halo-4-(haloalkyl)-5-thiazol carboxylic acids, phosphorthiolates and N-alkyl-O-phenylcarbamates and their agriculturally acceptable salts and their agriculturally acceptable derivatives such amides, esters, and thioesters, provided they have an acid group.

Examples of preferred safeners C are benoxacor, cloquintocet, cyometrinil, cyprosulfamide, dichlormid, dicyclonon, dietholate, fenchlorazole, fenclorim, flurazole, fluxofenim, furilazole, isoxadifen, mefenpyr, mephenate, naphtalic anhydride, oxabetrinil, 4-(dichloroacetyl)-1-oxa-4-azaspiro [4.5]decane (MON4660, CAS 71526-07-3), 2,2,5-trimethyl-3-(dichloroacetyl)-1,3-oxazolidine (R-29148, CAS 52836-31-4) and N-(2-Methoxybenzoyl)-4-[(methylaminocarbonyl)amino]benzenesulfonamide (CAS 129531-12-0).

Especially preferred safeners C are benoxacor, cloquintocet, cyprosulfamide, dichlormid, fenchlorazole, fenclorim, flurazole, fluxofenim, furilazole, isoxadifen, mefenpyr, naphthalic anhydride, oxabetrinil, 4-(dichloroacetyl)-1-oxa-4-azaspiro[4.5]decane (MON4660, CAS 71526-07-3), 2,2,5-trimethyl-3-(dichloroacetyl)-1,3-oxazolidine (R-29148, CAS 52836-31-4) and N-(2-Methoxybenzoyl)-4-[(methylaminocarbonyl)amino]benzenesulfonamide (CAS 129531-12-0).

Particularly preferred safeners C are benoxacor, cloquintocet, cyprosulfamide, dichlormid, fenchlorazole, fenclorim, furilazole, isoxadifen, mefenpyr, naphtalic anhydride, 4-(dichloroacetyl)-1-oxa-4-azaspiro[4.5]decane (MON4660, CAS 71526-07-3), 2,2,5-trimethyl-3-(dichloroacetyl)-1,3-oxazolidine (R-29148, CAS 52836-31-4) and N-(2-Methoxybenzoyl)-4-[(methylaminocarbonyl)amino]benzenesulfonamide (CAS 129531-12-0).

Particularly preferred safeners C, which, as component C, are constituent of the composition according to the invention are the safeners C as defined above; in particular the safeners C.1-C.17 listed below in table C:

TABLE C

| | Safener C |
|---|---|
| C.1 | benoxacor |
| C.2 | cloquintocet |
| C.3 | cloquintocet-mexyl |
| C.4 | cyprosulfamide |
| C.5 | dichlormid |
| C.6 | fenchlorazole |
| C.7 | fenchlorazole-ethyl |
| C.8 | fenclorim |
| C.9 | furilazole |
| C.10 | isoxadifen |
| C.11 | isoxadifen-ethyl |
| C.12 | mefenpyr |
| C.13 | mefenpyr-diethyl |
| C.14 | naphtalic acid anhydride |
| C.15 | 4-(dichloroacetyl)-1-oxa-4-azaspiro[4.5]decane (MON4660, CAS 71526-07-3) |
| C.16 | 2,2,5-trimethyl-3-(dichloroacetyl)-1,3-oxazolidine (R-29148, CAS 52836-31-4) |
| C.17 | metcamifen |

The active compounds B of groups b1) to b15) and the active compounds C are known herbicides and safeners, see, for example, The Compendium of Pesticide Common Names (http://www.alanwood.net/pesticides/); Farm Chemicals Handbook 2000 volume 86, Meister Publishing Company, 2000; B. Hock, C. Fedtke, R. R. Schmidt, Herbizide [Herbicides], Georg Thieme Verlag, Stuttgart 1995; W. H. Ahrens, Herbicide Handbook, 7th edition, Weed Science Society of America, 1994; and K. K. Hatzios, Herbicide Handbook, Supplement for the 7th edition, Weed Science Society of America, 1998. 2,2,5-Trimethyl-3-(dichloroacetyl)-1,3-oxazolidine [CAS No. 52836-31-4] is also referred to as R-29148. 4-(Dichloroacetyl)-1-oxa-4-azaspiro [4.5]decane [CAS No. 71526-07-3] is also referred to as AD-67 and MON 4660.

The assignment of the active compounds to the respective mechanisms of action is based on current knowledge. If several mechanisms of action apply to one active compound, this substance was only assigned to one mechanism of action.

Active compounds B and C having a carboxyl group can be employed in the form of the acid, in the form of an agriculturally suitable salt as mentioned above or else in the form of an agriculturally acceptable derivative in the compositions according to the invention.

In the case of dicamba, suitable salts include those, where the counterion is an agriculturally acceptable cation. For example, suitable salts of dicamba are dicamba-sodium, dicamba-potassium, dicamba-methylammonium, dicamba-dimethylammonium, dicamba-isopropylammonium, dicamba-diglycolamine, dicamba-olamine, dicamba-diolamine, dicamba-trolamine, dicamba-N,N-bis-(3-aminopropyl)methylamine and dicamba-diethylenetriamine. Examples of a suitable ester are dicamba-methyl and dicamba-butotyl.

Suitable salts of 2,4-D are 2,4-D-ammonium, 2,4-D-dimethylammonium, 2,4-D-diethylammonium, 2,4-D-diethanolammonium (2,4-D-diolamine), 2,4-D-triethanolammonium, 2,4-D-isopropylammonium, 2,4-D-triisopropanolammonium, 2,4-D-heptylammonium, 2,4-D-dodecylammonium, 2,4-D-tetradecylammonium, 2,4-D-triethylammonium, 2,4-D-tris(2-hydroxypropyl)ammonium, 2,4-D-tris(isopropyl)ammonium, 2,4-D-trolamine, 2,4-D-lithium, 2,4-D-sodium. Examples of suitable esters of 2,4-D are 2,4-D-butotyl, 2,4-D-2-butoxypropyl, 2,4-D-3-butoxypropyl, 2,4-D-butyl, 2,4-D-ethyl, 2,4-D-ethylhexyl, 2,4-D-isobutyl, 2,4-D-isooctyl, 2,4-D-isopropyl, 2,4-D-meptyl, 2,4-D-methyl, 2,4-D-octyl, 2,4-D-pentyl, 2,4-D-propyl, 2,4-D-tefuryl and clacyfos.

Suitable salts of 2,4-DB are for example 2,4-DB-sodium, 2,4-DB-potassium and 2,4-DB-dimethylammonium. Suitable esters of 2,4-DB are for example 2,4-DB-butyl and 2,4-DB-isoctyl.

Suitable salts of dichlorprop are for example dichlorprop-sodium, dichlorprop-potassium and dichlorprop-dimethylammonium. Examples of suitable esters of dichlorprop are dichlorpropbutotyl and dichlorprop-isoctyl.

Suitable salts and esters of MCPA include MCPA-butotyl, MCPA-butyl, MCPA-dimethylammonium, MCPA-diolamine, MCPA-ethyl, MCPA-thioethyl, MCPA-2-ethylhexyl, MCPA-isobutyl, MCPA-isoctyl, MCPA-isopropyl, MCPA-isopropylammonium, MCPA-methyl, MCPA-olamine, MCPA-potassium, MCPA-sodium and MCPA-trolamine.

A suitable salt of MCPB is MCPB sodium. A suitable ester of MCPB is MCPB-ethyl.

Suitable salts of clopyralid are clopyralid-potassium, clopyralid-olamine and clopyralid-tris-(2-hydroxypropyl)ammonium. Example of suitable esters of clopyralid is clopyralid-methyl.

Examples of a suitable ester of fluroxypyr are fluroxypyr-meptyl and fluroxypyr-2-butoxy-1-methylethyl, wherein fluroxypyr-meptyl is preferred.

Suitable salts of picloram are picloram-dimethylammonium, picloram-potassium, picloram-triisopropanolammonium, picloram-triisopropylammonium and picloram-trolamine. A suitable ester of picloram is picloram-isoctyl.

A suitable salt of triclopyr is triclopyr-triethylammonium. Suitable esters of triclopyr are for example triclopyr-ethyl and triclopyr-butotyl.

Suitable salts and esters of chloramben include chloramben-ammonium, chloramben-diolamine, chloramben-methyl, chloramben-methylammonium and chloramben-sodium. Suitable salts and esters of 2,3,6-TBA include 2,3,6-TBA-dimethylammonium, 2,3,6-TBA-lithium, 2,3,6-TBA-potassium and 2,3,6-TBA-sodium.

Suitable salts and esters of aminopyralid include aminopyralid-potassium, aminopyralid-dimethylammonium, and aminopyralid-tris(2-hydroxypropyl)ammonium.

Suitable salts of glyphosate are for example glyphosate-ammonium, glyphosate-diammonium, glyphoste-dimethylammonium, glyphosate-isopropylammonium, glyphosate-potassium, glyphosate-sodium, glyphosate-trimesium as well as the ethanolamine and diethanolamine salts, preferably glyphosate-diammonium, glyphosate-isopropylammonium and glyphosate-trimesium (sulfosate).

A suitable salt of glufosinate is for example glufosinate-ammonium.

A suitable salt of glufosinate-P is for example glufosinate-P-ammonium.

Suitable salts and esters of bromoxynil are for example bromoxynil-butyrate, bromoxynil-heptanoate, bromoxynil-octanoate, bromoxynil-potassium and bromoxynil-sodium.

Suitable salts and esters of ioxonil are for example ioxonil-octanoate, ioxonil-potassium and ioxonil-sodium.

Suitable salts and esters of mecoprop include mecoprop-butotyl, mecoprop-dimethylammonium, mecoprop-diolamine, mecoprop-ethadyl, mecoprop-2-ethylhexyl, mecoprop-isoctyl, mecoprop-methyl, mecoprop-potassium, mecoprop-sodium and mecoprop-trolamine.

Suitable salts of mecoprop-P are for example mecoprop-P-butotyl, mecoprop-P-dimethylammonium, mecoprop-P-2-ethylhexyl, mecoprop-P-isobutyl, mecoprop-P-potassium and mecoprop-P-sodium.

A suitable salt of diflufenzopyr is for example diflufenzopyr-sodium.

A suitable salt of naptalam is for example naptalam-sodium.

Suitable salts and esters of aminocyclopyrachlor are for example aminocyclopyrachlor-dimethylammonium, aminocyclopyrachlor-methyl, aminocyclopyrachlor-triisopropanolammonium, aminocyclopyrachlor-sodium and aminocyclopyrachlor-potassium.

A suitable salt of quinclorac is for example quinclorac-dimethylammonium.

A suitable salt of quinmerac is for example quinmerac-dimethylammonium.

A suitable salt of imazamox is for example imazamox-ammonium.

Suitable salts of imazapic are for example imazapic-ammonium and imazapic-isopropylammonium.

Suitable salts of imazapyr are for example imazapyr-ammonium and imazapyr-isopropylammonium.

A suitable salt of imazaquin is for example imazaquin-ammonium.

Suitable salts of imazethapyr are for example imazethapyr-ammonium and imazethapyr-isopropylammonium.

A suitable salt of topramezone is for example topramezone-sodium.

According to a preferred embodiment of the invention, the composition comprises as herbicidal active compound B or component B at least one, preferably exactly one herbicide B.

According to another preferred embodiment of the invention, the composition comprises as herbicidal active compounds B or component B at least two, preferably exactly two herbicides B different from each other.

According to another preferred embodiment of the invention, the composition comprises as herbicidal active compounds B or component B at least three, preferably exactly three herbicides B different from each other.

According to another preferred embodiment of the invention, the composition comprises as safening compound C or component C at least one, preferably exactly one safener C.

According to another preferred embodiment of the invention, the composition comprises as component B at least one, preferably exactly one herbicide B, and as component C at least one, preferably exactly one, safener C.

According to another preferred embodiment of the invention, the composition comprises at least two, preferably exactly two, herbicides B different from each other, and as component C at least one, preferably exactly one, safener C.

According to another preferred embodiment of the invention, the composition comprises at least three, preferably exactly three, herbicides B different from each other, and as component C at least one, preferably exactly one, safener C.

According to another preferred embodiment of the invention, the composition comprises as component A at least one, preferably exactly one compound of formula (I), preferably of formula (I.1), especially preferred the compounds (I.a.1), (I.a.25), (I.a.31), (I.a.37), (I.a.49), (I.a.55), (I.a.61), (I.a.73), (I.a.685), (I.a.697), (I.a.1021) and (I.a.1033), and as component B at least one, preferably exactly one, herbicide B.

According to another preferred embodiment of the invention, the composition comprises as component A at least one, preferably exactly one compound of formula (I), preferably of formula (I.1), especially preferred the compounds (I.a.1), (I.a.25), (I.a.31), (I.a.37), (I.a.49), (I.a.55), (I.a.61), (I.a.73), (I.a.685), (I.a.697), (I.a.1021) and (I.a.1033), and at least two, preferably exactly two, herbicides B different from each other.

According to another preferred embodiment of the invention, the composition comprises as component A at least one, preferably exactly one compound of formula (I), preferably of formula (I.1), especially preferred the compounds (I.a.1), (I.a.25), (I.a.31), (I.a.37), (I.a.49), (I.a.55), (I.a.61), (I.a.73), (I.a.685), (I.a.697), (I.a.1021) and (I.a.1033), and at least three, preferably exactly three, herbicides B different from each other.

According to another preferred embodiment of the invention, the composition comprises as component A at least one, preferably exactly one one compound of formula (I), preferably of formula (I.1), especially preferred the compounds (I.a.1), (I.a.25), (I.a.31), (I.a.37), (I.a.49), (I.a.55), (I.a.61), (I.a.73), (I.a.685), (I.a.697), (I.a.1021) and (I.a.1033), and as component C at least one, preferably exactly one, safener C.

According to another preferred embodiment of the invention, the composition comprises as component A at least one, preferably exactly one compound of formula (I), preferably of formula (I.1), especially preferred the compounds (I.a.1), (I.a.25), (I.a.31), (I.a.37), (I.a.49), (I.a.55), (I.a.61), (I.a.73), (I.a.685), (I.a.697), (I.a.1021) and (I.a.1033), as component B at least one, preferably exactly one, herbicide B, and as component C at least one, preferably exactly one safener C.

According to another preferred embodiment of the invention, the composition comprises as component A at least one, preferably exactly one compound of formula (I), preferably of formula (I.1), especially preferred the compounds (I.a.1), (I.a.25), (I.a.31), (I.a.37), (I.a.49), (I.a.55), (I.a.61), (I.a.73), (I.a.685), (I.a.697), (I.a.1021) and (I.a.1033), at least two, preferably exactly two herbicides B different from each other, and as component C at least one, preferably exactly one, safener C.

According to another preferred embodiment of the invention, the composition comprises as component A at least one, preferably exactly one compound of formula (I), preferably of formula (I.1), especially preferred the compounds (I.a.1), (I.a.25), (I.a.31), (I.a.37), (I.a.49), (I.a.55), (I.a.61), (I.a.73), (I.a.685), (I.a.697), (I.a.1021) and (I.a.1033), at least three, preferably exactly three herbicides B different from each other, and as component C at least one, preferably exactly one, safener C.

According to another preferred embodiment of the invention, the composition comprises, in addition to a phenylpyrimidine of formula (I), especially an active compound from the group consisting of (I.a.1), (I.a.25), (I.a.31), (I.a.37), (I.a.49), (I.a.55), (I.a.61), (I.a.73), (I.a.685), (I.a.697), (I.a.1021) and (I.a.1033), at least one and especially exactly one herbicidally active compound from group b1), in particular selected from the group consisting of clethodim, clodinafop-propargyl, cycloxydim, cyhalofop-butyl, fenoxaprop-ethyl, fenoxaprop-P-ethyl, metamifop, pinoxaden, profoxydim, sethoxydim, tepraloxydim, tralkoxydim, esprocarb, ethofumesate, molinate, prosulfocarb, thiobencarb and triallate.

According to another preferred embodiment of the invention, the composition comprises, in addition to a phenylpyrimidine of formula (I), especially an active compound from the group consisting of (I.a.1), (I.a.25), (I.a.31), (I.a.37), (I.a.49), (I.a.55), (I.a.61), (I.a.73), (I.a.685), (I.a.697), (I.a.1021) and (I.a.1033), at least one and especially exactly one herbicidally active compound from group b2), in particular selected from the group consisting of bensulfuron-methyl, bispyribac-sodium, cloransulam-methyl, chlorsulfuron, clorimuron, cyclosulfamuron, diclosulam, florasulam, flumetsulam, flupyrsulfuron-methyl-sodium, foramsulfuron, imazamox, imazamox-ammonium, imazapic, imazapic-ammonium, imazapic-isopropylammonium, imazapyr, imazapyr-ammonium, imazethapyr-isopropylammonium, imazaquin, imazaquin-ammonium, imazethapyr, imazethapyr-ammonium, imazethapyr-isopropylammonium, imazosulfuron, iodosulfuron-methyl-sodium, iofensulfuron, iofensulfuron-sodium, mesosulfuron-methyl, metazosulfuron, metsulfuron-methyl, metosulam, nicosulfuron, penoxsulam, propoxycarbazon-sodium, pyrazosulfuron-ethyl, pyribenzoxim, pyriftalid, pyroxsulam, propyrisulfuron, rimsulfuron, sulfosulfuron, thiencarbazon-methyl, thifensulfuron-methyl, tribenuron-methyl, tritosulfuron and triafamone.

According to another preferred embodiment of the invention, the composition comprises, in addition to a phenylpyrimidine of formula (I), especially an active compound from the group consisting (I.a.1), (I.a.25), (I.a.31), (I.a.37), (I.a.49), (I.a.55), (I.a.61), (I.a.73), (I.a.685), (I.a.697), (I.a.1021) and (I.a.1033), at least one and especially exactly one herbicidally active compound from group b3), in particular selected from the group consisting of ametryn, atrazine, bentazon, bromoxynil, bromoxynil-octanoate, bromoxynil-heptanoate, bromoxynil-potassium, diuron, fluometuron, hexazinone, isoproturon, linuron, metamitron, metribuzin, paraquat-dichloride, propanil, simazin, terbutryn and terbuthylazine.

According to another preferred embodiment of the invention, the composition comprises, in addition to a phenylpyrimidine of formula (I), especially an active compound from the group consisting of (I.a.1), (I.a.25), (I.a.31), (I.a.37), (I.a.49), (I.a.55), (I.a.61), (I.a.73), (I.a.685), (I.a.697), (I.a.1021) and (I.a.1033), at least one and especially exactly one herbicidally active compound from group b4), in particular selected from the group consisting of acifluorfen, butafencil, carfenetrazone-ethyl, flumioxazin, fomesafen, oxadiargyl, oxyfluorfen, pyraflufen, pyraflufen-ethyl, saflufenacil, sulfentrazone, trifludimoxazin, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate.

According to another preferred embodiment of the invention, the composition comprises, in addition to a phenylpyrimidine of formula (I), especially an active compound from the group consisting of (I.a.1), (I.a.25), (I.a.31), (I.a.37), (I.a.49), (I.a.55), (I.a.61), (I.a.73), (I.a.685), (I.a.697), (I.a.1021) and (I.a.1033), at least one and especially exactly one herbicidally active compound from group b5), in particular selected from the group consisting of amitrole, benzobicyclon, bicyclopyrone, clomazone, diflufenican, fenquintrone, fluometuron, flurochloridone, isoxaflutole, mesotrione, norflurazon, oxotrione, picolinafen, sulcotrione, tefuryltrione, tembotrione, tolpyralate, topramezone, topramezone-sodium and 2-chloro-3-methylsulfanyl-N-(1-methyltetrazol-5-yl)-4-(trifluoromethyl)benzamide.

According to another preferred embodiment of the invention, the composition comprises, in addition to a phenylpyrimidine of formula (I), especially an active compound from the group consisting of (I.a.1), (I.a.25), (I.a.31), (I.a.37), (I.a.49), (I.a.55), (I.a.61), (I.a.73), (I.a.685), (I.a.697), (I.a.1021) and (I.a.1033), at least one and especially exactly one herbicidally active compound from group b6), in particular selected from the group consisting of glyphosate, glyphosate-ammonium, glyphosate-dimethylammonium, glyphosate-isopropylammonium and glyphosate-trimesium (sulfosate) and glyphosate-potassium.

According to another preferred embodiment of the invention, the composition comprises, in addition to a phenylpyrimidine of formula (I), especially an active compound from the group consisting of (I.a.1), (I.a.25), (I.a.31), (I.a.37), (I.a.49), (I.a.55), (I.a.61), (I.a.73), (I.a.685), (I.a.697), (I.a.1021) and (I.a.1033), at least one and especially exactly one herbicidally active compound from group b7), in particular selected from the group consisting of glufosinate, glufosinate-ammonium, glufosinate-P and glufosinate-P-ammonium.

According to another preferred embodiment of the invention, the composition comprises, in addition to a phenylpyrimidine of formula (I), especially an active compound from the group consisting of (I.a.1), (I.a.25), (I.a.31), (I.a.37), (I.a.49), (I.a.55), (I.a.61), (I.a.73), (I.a.685), (I.a.697), (I.a.1021) and (I.a.1033), at least one and especially exactly one herbicidally active compound from group b9), in particular selected from the group consisting of pendimethalin and trifluralin.

According to another preferred embodiment of the invention, the composition comprises, in addition to a phenylpyrimidine of formula (I), especially an active compound from the group consisting of (I.a.1), (I.a.25), (I.a.31), (I.a.37), (I.a.49), (I.a.55), (I.a.61), (I.a.73), (I.a.685), (I.a.697), (I.a.1021) and (I.a.1033), at least one and especially exactly one herbicidally active compound from group b10), in particular selected from the group consisting of acetochlor, butachlor, cafenstrole, dimethenamid-P, fentrazamide, flufenacet, mefenacet, metazachlor, metolachlor, S-metolachlor, fenoxasulfone, ipfencarbazone and pyroxasulfone. Likewise, preference is given to compositions comprising in addition to a phenylpyrimidine of formula (I), especially an active compound from the group consisting of (I.a.1), (I.a.25), (I.a.31), (I.a.37), (I.a.49), (I.a.55), (I.a.61), (I.a.73), (I.a.685), (I.a.697), (I.a.1021) and (I.a.1033), at least one and especially exactly one herbicidally active compound from group b10), in particular selected from the group consisting of isoxazoline compounds of the formulae II.1, II.2, II.3, II.4, II.5, II.6, II.7, II.8 and II.9, as defined above.

According to another preferred embodiment of the invention, the composition comprises, in addition to a phenylpyrimidine of formula (I), especially an active compound from the group consisting of (I.a.1), (I.a.25), (I.a.31), (I.a.37), (I.a.49), (I.a.55), (I.a.61), (I.a.73), (I.a.685), (I.a.697), (I.a.1021) and (I.a.1033), at least one and especially exactly one herbicidally active compound from group b11), in particular indaziflam, isoxaben and triaziflam.

According to another preferred embodiment of the invention, the composition comprises, in addition to a phenylpyrimidine of formula (I), especially an active compound from the group consisting of (I.a.1), (I.a.25), (I.a.31), (I.a.37), (I.a.49), (I.a.55), (I.a.61), (I.a.73), (I.a.685), (I.a.697), (I.a.1021) and (I.a.1033), at least one and especially exactly one herbicidally active compound from group b13), in particular selected from the group consisting of 2,4-D, 2,4-D-isobutyl, 2,4-D-dimethylammonium, 2,4-D-N,N,N-trimethylethanolammonium, aminocyclopyrachlor, aminocyclopyrachlor-potassium, aminocyclopyrachlor-methyl, aminopyralid, aminopyralid-methyl, aminopyralid-dimethylammonium, aminopyralid-tris(2-hydroxypropyl)ammonium, clopyralid, clopyralid-methyl, clopyralid-olamine, dicamba, dicamba-butotyl, dicamba-diglycolamine, dicamba-dimethylammonium, dicamba-diolamine, dicamba-isopropylammonium, dicamba-potassium, dicamba-sodium, dicamba-trolamine, dicamba-N,N-bis-(3-aminopropyl)methylamine, dicamba-diethylenetriamine, flopyrauxifen, fluroxypyr, fluroxypyr-meptyl, halauxifen, halauxifen-methyl, MCPA, MCPA-2-ethylhexyl, MCPA-dimethylammonium, quinclorac, quinclorac-dimethylammonium, quinmerac, quinmerac-dimethylammonium, florpyrauxifen, florpyrauxifen-benzyl, and 4-amino-3-chloro-5-fluoro-6-(7-fluoro-1H-indol-6-yl)picolinic acid.

According to another preferred embodiment of the invention, the composition comprises, in addition to a phenylpyrimidine of formula (I), especially an active compound from the group consisting of (I.a.1), (I.a.25), (I.a.31), (I.a.37), (I.a.49), (I.a.55), (I.a.61), (I.a.73), (I.a.685), (I.a.697), (I.a.1021) and (I.a.1033), at least one and especially exactly one herbicidally active compound from group b14), in particular selected from the group consisting of diflufenzopyr, diflufenzopyr-sodium, dymron, indanofan and diflufenzopyr-sodium.

According to another preferred embodiment of the invention, the composition comprises, in addition to a phenylpyrimidine of formula (I), especially an active compound from the group consisting of (I.a.1), (I.a.25), (I.a.31), (I.a.37), (I.a.49), (I.a.55), (I.a.61), (I.a.73), (I.a.685), (I.a.697), (I.a.1021) and (I.a.1033) at least one and especially exactly one herbicidally active compound from group b15), in particular selected from the group consisting of cinmethylin, dymron (=daimuron), indanofan and oxaziclomefone.

According to another preferred embodiment of the invention, the composition comprises, in addition to a phenylpyrimidine of formula (I), especially an active compound from the group consisting of (I.a.1), (I.a.25), (I.a.31), (I.a.37), (I.a.49), (I.a.55), (I.a.61), (I.a.73), (I.a.685), (I.a.697), (I.a.1021) and (I.a.1033), at least one and especially exactly one safener C, in particular selected from the group consisting of benoxacor, cloquintocet, cyprosulfamide, dichlormid, fenchlorazole, fenclorim, furilazole, isoxadifen, mefenpyr, 4-(dichloroacetyl)-1-oxa-4-azaspiro[4.5]decane (MON4660, CAS 71526-07-3) and 2,2,5-trimethyl-3-(dichloroacetyl)-1,3-oxazolidine (R-29148, CAS 52836-31-4).

Here and below, the term "binary compositions" includes compositions comprising one or more, for example 1, 2 or 3, phenylpyrimidines of formula (I) and either one or more, for example 1, 2 or 3, herbicides B or one or more safeners C.

Correspondingly, the term "ternary compositions" includes compositions comprising one or more, for example 1, 2 or 3, phenylpyrimidines of formula (I), one or more, for example 1, 2 or 3, herbicides B and one or more, for example 1, 2 or 3, safeners C.

In binary compositions comprising at least one phenylpyrimidine of formula (I) as component A and at least one herbicide B, the weight ratio of the active compounds A:B is generally in the range of from 1:1000 to 1000:1, preferably in the range of from 1:500 to 500:1, in particular in the range of from 1:250 to 250:1 and particularly preferably in the range of from 1:75 to 75:1.

In binary compositions comprising at least one phenylpyrimidine of formula (I) as component A and at least one safener C, the weight ratio of the active compounds A:C is generally in the range of from 1:1000 to 1000:1, preferably in the range of from 1:500 to 500:1, in particular in the range of from 1:250 to 250:1 and particularly preferably in the range of from 1:75 to 75:1.

In ternary compositions comprising at least one phenylpyrimidine of formula (I) as component A, at least one herbicide B and at least one safener C, the relative proportions by weight of the components A:B are generally in the range of from 1:1000 to 1000:1, preferably in the range of from 1:500 to 500:1, in particular in the range of from 1:250 to 250:1 and particularly preferably in the range of from 1:75 to 75:1 and more particularly preferably in the range of from 1:30 to 30:1, the weight ratio of the components A:C is generally in the range of from 1:1000 to 1000:1, preferably in the range of from 1:500 to 500:1, in particular in the range of from 1:250 to 250:1 and particularly preferably in the range of from 1:75 to 75:1 and more particularly preferably in the range of from 1:30 to 30:1, and the weight ratio of the components B:C is generally in the range of from 1:1000 to 1000:1, preferably in the range of from 1:500 to 500:1, in particular in the range of from 1:250 to 250:1 and particularly preferably in the range of from 1:75 to 75:1. The weight ratio of components A+B to component C is preferably in the range of from 1:500 to 500:1, in particular in the range of from 1:250 to 250:1 and particularly preferably in the range of from 1:75 to 75:1.

The weight ratios of the individual components in the preferred mixtures mentioned below are within the limits given above, in particular within the preferred limits.

Particularly preferred are the compositions mentioned below comprising the phenylpyrimidines of formula (I) as defined and the substance(s) as defined in the respective row of table 1;

especially preferred comprising as only herbicidal active compounds the phenylpyrimidines of formula (I) as defined and the substance(s) as defined in the respective row of table 1; most preferably comprising as only active compounds the phenylpyrimidines of formula (I) as defined and the substance(s) as defined in the respective row of table 1.

Particularly preferred are compositions 1.1 to 1.3653, comprising the phenylpyrimidine of formula (I.a.25) and the substance(s) as defined in the respective row of table 1:

TABLE 1

(compositions 1.1 to 1.3653):

| comp. no. | herbicide B | safener C |
|---|---|---|
| 1.1 | B.1 | — |
| 1.2 | B.2 | — |
| 1.3 | B.3 | — |
| 1.4 | B.4 | — |
| 1.5 | B.5 | — |
| 1.6 | B.6 | — |
| 1.7 | B.7 | — |
| 1.8 | B.8 | — |
| 1.9 | B.9 | — |
| 1.10 | B.10 | — |
| 1.11 | B.11 | — |
| 1.12 | B.12 | — |
| 1.13 | B.13 | — |
| 1.14 | B.14 | — |
| 1.15 | B.15 | — |
| 1.16 | B.16 | — |
| 1.17 | B.17 | — |
| 1.18 | B.18 | — |
| 1.19 | B.19 | — |
| 1.20 | B.20 | — |
| 1.21 | B.21 | — |
| 1.22 | B.22 | — |
| 1.23 | B.23 | — |
| 1.24 | B.24 | — |
| 1.25 | B.25 | — |
| 1.26 | B.26 | — |
| 1.27 | B.27 | — |
| 1.28 | B.28 | — |
| 1.29 | B.29 | — |
| 1.30 | B.30 | — |
| 1.31 | B.31 | — |
| 1.32 | B.32 | — |
| 1.33 | B.33 | — |
| 1.34 | B.34 | — |
| 1.35 | B.35 | — |
| 1.36 | B.36 | — |
| 1.37 | B.37 | — |
| 1.38 | B.38 | — |
| 1.39 | B.39 | — |
| 1.40 | B.40 | — |
| 1.41 | B.41 | — |
| 1.42 | B.42 | — |
| 1.43 | B.43 | — |
| 1.44 | B.44 | — |
| 1.45 | B.45 | — |
| 1.46 | B.46 | — |
| 1.47 | B.47 | — |
| 1.48 | B.48 | — |
| 1.49 | B.49 | — |
| 1.50 | B.50 | — |
| 1.51 | B.51 | — |
| 1.52 | B.52 | — |
| 1.53 | B.53 | — |
| 1.54 | B.54 | — |
| 1.55 | B.55 | — |
| 1.56 | B.56 | — |
| 1.57 | B.57 | — |
| 1.58 | B.58 | — |
| 1.59 | B.59 | — |
| 1.60 | B.60 | — |
| 1.61 | B.61 | — |
| 1.62 | B.62 | — |
| 1.63 | B.63 | — |
| 1.64 | B.64 | — |
| 1.65 | B.65 | — |
| 1.66 | B.66 | — |
| 1.67 | B.67 | — |
| 1.68 | B.68 | — |
| 1.69 | B.69 | — |
| 1.70 | B.70 | — |
| 1.71 | B.71 | — |
| 1.72 | B.72 | — |
| 1.73 | B.73 | — |
| 1.74 | B.74 | — |
| 1.75 | B.75 | — |
| 1.76 | B.76 | — |
| 1.77 | B.77 | — |
| 1.78 | B.78 | — |
| 1.79 | B.79 | — |

TABLE 1-continued (compositions 1.1 to 1.3653):

| comp. no. | herbicide B | safener C |
|---|---|---|
| 1.80 | B.80 | — |
| 1.81 | B.81 | — |
| 1.82 | B.82 | — |
| 1.83 | B.83 | — |
| 1.84 | B.84 | — |
| 1.85 | B.85 | — |
| 1.86 | B.86 | — |
| 1.87 | B.87 | — |
| 1.88 | B.88 | — |
| 1.89 | B.89 | — |
| 1.90 | B.90 | — |
| 1.91 | B.91 | — |
| 1.92 | B.92 | — |
| 1.93 | B.93 | — |
| 1.94 | B.94 | — |
| 1.95 | B.95 | — |
| 1.96 | B.96 | — |
| 1.97 | B.97 | — |
| 1.98 | B.98 | — |
| 1.99 | B.99 | — |
| 1.100 | B.100 | — |
| 1.101 | B.101 | — |
| 1.102 | B.102 | — |
| 1.103 | B.103 | — |
| 1.104 | B.104 | — |
| 1.105 | B.105 | — |
| 1.106 | B.106 | — |
| 1.107 | B.107 | — |
| 1.108 | B.108 | — |
| 1.109 | B.109 | — |
| 1.110 | B.110 | — |
| 1.111 | B.111 | — |
| 1.112 | B.112 | — |
| 1.113 | B.113 | — |
| 1.114 | B.114 | — |
| 1.115 | B.115 | — |
| 1.116 | B.116 | — |
| 1.117 | B.117 | — |
| 1.118 | B.118 | — |
| 1.119 | B.119 | — |
| 1.120 | B.120 | — |
| 1.121 | B.121 | — |
| 1.122 | B.122 | — |
| 1.123 | B.123 | — |
| 1.124 | B.124 | — |
| 1.125 | B.125 | — |
| 1.126 | B.126 | — |
| 1.127 | B.127 | — |
| 1.128 | B.128 | — |
| 1.129 | B.129 | — |
| 1.130 | B.130 | — |
| 1.131 | B.131 | — |
| 1.132 | B.132 | — |
| 1.133 | B.133 | — |
| 1.134 | B.134 | — |
| 1.135 | B.135 | — |
| 1.136 | B.136 | — |
| 1.137 | B.137 | — |
| 1.138 | B.138 | — |
| 1.139 | B.139 | — |
| 1.140 | B.140 | — |
| 1.141 | B.141 | — |
| 1.142 | B.142 | — |
| 1.143 | B.143 | — |
| 1.144 | B.144 | — |
| 1.145 | B.145 | — |
| 1.146 | B.146 | — |
| 1.147 | B.147 | — |
| 1.148 | B.148 | — |
| 1.149 | B.149 | — |
| 1.150 | B.150 | — |
| 1.151 | B.151 | — |
| 1.152 | B.152 | — |
| 1.153 | B.153 | — |
| 1.154 | B.154 | — |
| 1.155 | B.155 | — |
| 1.156 | B.156 | — |
| 1.157 | B.157 | — |
| 1.158 | B.158 | — |
| 1.159 | B.159 | — |
| 1.160 | B.160 | — |
| 1.161 | B.161 | — |
| 1.162 | B.162 | — |
| 1.163 | B.163 | — |
| 1.164 | B.164 | — |
| 1.165 | B.165 | — |
| 1.166 | B.166 | — |
| 1.167 | B.167 | — |
| 1.168 | B.168 | — |
| 1.169 | B.169 | — |
| 1.170 | B.170 | — |
| 1.171 | B.171 | — |
| 1.172 | B.172 | — |
| 1.173 | B.173 | — |
| 1.174 | B.174 | — |
| 1.175 | B.175 | — |
| 1.176 | B.176 | — |
| 1.177 | B.177 | — |
| 1.178 | B.178 | — |
| 1.179 | B.179 | — |
| 1.180 | B.180 | — |
| 1.181 | B.181 | — |
| 1.182 | B.182 | — |
| 1.183 | B.183 | — |
| 1.184 | B.184 | — |
| 1.185 | B.185 | — |
| 1.186 | B.186 | — |
| 1.187 | B.187 | — |
| 1.188 | B.188 | — |
| 1.189 | B.189 | — |
| 1.190 | B.190 | — |
| 1.191 | B.191 | — |
| 1.192 | B.192 | — |
| 1.193 | B.193 | — |
| 1.194 | B.194 | — |
| 1.195 | B.195 | — |
| 1.196 | B.196 | — |
| 1.197 | B.197 | — |
| 1.198 | B.198 | — |
| 1.199 | B.199 | — |
| 1.200 | B.200 | — |
| 1.201 | B.201 | — |
| 1.202 | B.202 | — |
| 1.203 | B.1 | C.1 |
| 1.204 | B.2 | C.1 |
| 1.205 | B.3 | C.1 |
| 1.206 | B.4 | C.1 |
| 1.207 | B.5 | C.1 |
| 1.208 | B.6 | C.1 |
| 1.209 | B.7 | C.1 |
| 1.210 | B.8 | C.1 |
| 1.211 | B.9 | C.1 |
| 1.212 | B.10 | C.1 |
| 1.213 | B.11 | C.1 |
| 1.214 | B.12 | C.1 |
| 1.215 | B.13 | C.1 |
| 1.216 | B.14 | C.1 |
| 1.217 | B.15 | C.1 |
| 1.218 | B.16 | C.1 |
| 1.219 | B.17 | C.1 |
| 1.220 | B.18 | C.1 |
| 1.221 | B.19 | C.1 |
| 1.222 | B.20 | C.1 |
| 1.223 | B.21 | C.1 |
| 1.224 | B.22 | C.1 |
| 1.225 | B.23 | C.1 |
| 1.226 | B.24 | C.1 |
| 1.227 | B.25 | C.1 |
| 1.228 | B.26 | C.1 |
| 1.229 | B.27 | C.1 |
| 1.230 | B.28 | C.1 |
| 1.231 | B.29 | C.1 |

TABLE 1-continued (compositions 1.1 to 1.3653):

| comp. no. | herbicide B | safener C |
|---|---|---|
| 1.232 | B.30 | C.1 |
| 1.233 | B.31 | C.1 |
| 1.234 | B.32 | C.1 |
| 1.235 | B.33 | C.1 |
| 1.236 | B.34 | C.1 |
| 1.237 | B.35 | C.1 |
| 1.238 | B.36 | C.1 |
| 1.239 | B.37 | C.1 |
| 1.240 | B.38 | C.1 |
| 1.241 | B.39 | C.1 |
| 1.242 | B.40 | C.1 |
| 1.243 | B.41 | C.1 |
| 1.244 | B.42 | C.1 |
| 1.245 | B.43 | C.1 |
| 1.246 | B.44 | C.1 |
| 1.247 | B.45 | C.1 |
| 1.248 | B.46 | C.1 |
| 1.249 | B.47 | C.1 |
| 1.250 | B.48 | C.1 |
| 1.251 | B.49 | C.1 |
| 1.252 | B.50 | C.1 |
| 1.253 | B.51 | C.1 |
| 1.254 | B.52 | C.1 |
| 1.255 | B.53 | C.1 |
| 1.256 | B.54 | C.1 |
| 1.257 | B.55 | C.1 |
| 1.258 | B.56 | C.1 |
| 1.259 | B.57 | C.1 |
| 1.260 | B.58 | C.1 |
| 1.261 | B.59 | C.1 |
| 1.262 | B.60 | C.1 |
| 1.263 | B.61 | C.1 |
| 1.264 | B.62 | C.1 |
| 1.265 | B.63 | C.1 |
| 1.266 | B.64 | C.1 |
| 1.267 | B.65 | C.1 |
| 1.268 | B.66 | C.1 |
| 1.269 | B.67 | C.1 |
| 1.270 | B.68 | C.1 |
| 1.271 | B.69 | C.1 |
| 1.272 | B.70 | C.1 |
| 1.273 | B.71 | C.1 |
| 1.274 | B.72 | C.1 |
| 1.275 | B.73 | C.1 |
| 1.276 | B.74 | C.1 |
| 1.277 | B.75 | C.1 |
| 1.278 | B.76 | C.1 |
| 1.279 | B.77 | C.1 |
| 1.280 | B.78 | C.1 |
| 1.281 | B.79 | C.1 |
| 1.282 | B.80 | C.1 |
| 1.283 | B.81 | C.1 |
| 1.284 | B.82 | C.1 |
| 1.285 | B.83 | C.1 |
| 1.286 | B.84 | C.1 |
| 1.287 | B.85 | C.1 |
| 1.288 | B.86 | C.1 |
| 1.289 | B.87 | C.1 |
| 1.290 | B.88 | C.1 |
| 1.291 | B.89 | C.1 |
| 1.292 | B.90 | C.1 |
| 1.293 | B.91 | C.1 |
| 1.294 | B.92 | C.1 |
| 1.295 | B.93 | C.1 |
| 1.296 | B.94 | C.1 |
| 1.297 | B.95 | C.1 |
| 1.298 | B.96 | C.1 |
| 1.299 | B.97 | C.1 |
| 1.300 | B.98 | C.1 |
| 1.301 | B.99 | C.1 |
| 1.302 | B.100 | C.1 |
| 1.303 | B.101 | C.1 |
| 1.304 | B.102 | C.1 |
| 1.305 | B.103 | C.1 |
| 1.306 | B.104 | C.1 |
| 1.307 | B.105 | C.1 |
| 1.308 | B.106 | C.1 |
| 1.309 | B.107 | C.1 |
| 1.310 | B.108 | C.1 |
| 1.311 | B.109 | C.1 |
| 1.312 | B.110 | C.1 |
| 1.313 | B.111 | C.1 |
| 1.314 | B.112 | C.1 |
| 1.315 | B.113 | C.1 |
| 1.316 | B.114 | C.1 |
| 1.317 | B.115 | C.1 |
| 1.318 | B.116 | C.1 |
| 1.319 | B.117 | C.1 |
| 1.320 | B.118 | C.1 |
| 1.321 | B.119 | C.1 |
| 1.322 | B.120 | C.1 |
| 1.323 | B.121 | C.1 |
| 1.324 | B.122 | C.1 |
| 1.325 | B.123 | C.1 |
| 1.326 | B.124 | C.1 |
| 1.327 | B.125 | C.1 |
| 1.328 | B.126 | C.1 |
| 1.329 | B.127 | C.1 |
| 1.330 | B.128 | C.1 |
| 1.331 | B.129 | C.1 |
| 1.332 | B.130 | C.1 |
| 1.333 | B.131 | C.1 |
| 1.334 | B.132 | C.1 |
| 1.335 | B.133 | C.1 |
| 1.336 | B.134 | C.1 |
| 1.337 | B.135 | C.1 |
| 1.338 | B.136 | C.1 |
| 1.339 | B.137 | C.1 |
| 1.340 | B.138 | C.1 |
| 1.341 | B.139 | C.1 |
| 1.342 | B.140 | C.1 |
| 1.343 | B.141 | C.1 |
| 1.344 | B.142 | C.1 |
| 1.345 | B.143 | C.1 |
| 1.346 | B.144 | C.1 |
| 1.347 | B.145 | C.1 |
| 1.348 | B.146 | C.1 |
| 1.349 | B.147 | C.1 |
| 1.350 | B.148 | C.1 |
| 1.351 | B.149 | C.1 |
| 1.352 | B.150 | C.1 |
| 1.353 | B.151 | C.1 |
| 1.354 | B.152 | C.1 |
| 1.355 | B.153 | C.1 |
| 1.356 | B.154 | C.1 |
| 1.357 | B.155 | C.1 |
| 1.358 | B.156 | C.1 |
| 1.359 | B.157 | C.1 |
| 1.360 | B.158 | C.1 |
| 1.361 | B.159 | C.1 |
| 1.362 | B.160 | C.1 |
| 1.363 | B.161 | C.1 |
| 1.364 | B.162 | C.1 |
| 1.365 | B.163 | C.1 |
| 1.366 | B.164 | C.1 |
| 1.367 | B.165 | C.1 |
| 1.368 | B.166 | C.1 |
| 1.369 | B.167 | C.1 |
| 1.370 | B.168 | C.1 |
| 1.371 | B.169 | C.1 |
| 1.372 | B.170 | C.1 |
| 1.373 | B.171 | C.1 |
| 1.374 | B.172 | C.1 |
| 1.375 | B.173 | C.1 |
| 1.376 | B.174 | C.1 |
| 1.377 | B.175 | C.1 |
| 1.378 | B.176 | C.1 |
| 1.379 | B.177 | C.1 |
| 1.380 | B.178 | C.1 |
| 1.381 | B.179 | C.1 |
| 1.382 | B.180 | C.1 |
| 1.383 | B.181 | C.1 |

TABLE 1-continued (compositions 1.1 to 1.3653):

| comp. no. | herbicide B | safener C |
|---|---|---|
| 1.384 | B.182 | C.1 |
| 1.385 | B.183 | C.1 |
| 1.386 | B.184 | C.1 |
| 1.387 | B.185 | C.1 |
| 1.388 | B.186 | C.1 |
| 1.389 | B.187 | C.1 |
| 1.390 | B.188 | C.1 |
| 1.391 | B.189 | C.1 |
| 1.392 | B.190 | C.1 |
| 1.393 | B.191 | C.1 |
| 1.394 | B.192 | C.1 |
| 1.395 | B.193 | C.1 |
| 1.396 | B.194 | C.1 |
| 1.397 | B.195 | C.1 |
| 1.398 | B.196 | C.1 |
| 1.399 | B.197 | C.1 |
| 1.400 | B.198 | C.1 |
| 1.401 | B.199 | C.1 |
| 1.402 | B.200 | C.1 |
| 1.403 | B.201 | C.1 |
| 1.404 | B.202 | C.1 |
| 1.405 | B.1 | C.2 |
| 1.406 | B.2 | C.2 |
| 1.407 | B.3 | C.2 |
| 1.408 | B.4 | C.2 |
| 1.409 | B.5 | C.2 |
| 1.410 | B.6 | C.2 |
| 1.411 | B.7 | C.2 |
| 1.412 | B.8 | C.2 |
| 1.413 | B.9 | C.2 |
| 1.414 | B.10 | C.2 |
| 1.415 | B.11 | C.2 |
| 1.416 | B.12 | C.2 |
| 1.417 | B.13 | C.2 |
| 1.418 | B.14 | C.2 |
| 1.419 | B.15 | C.2 |
| 1.420 | B.16 | C.2 |
| 1.421 | B.17 | C.2 |
| 1.422 | B.18 | C.2 |
| 1.423 | B.19 | C.2 |
| 1.424 | B.20 | C.2 |
| 1.425 | B.21 | C.2 |
| 1.426 | B.22 | C.2 |
| 1.427 | B.23 | C.2 |
| 1.428 | B.24 | C.2 |
| 1.429 | B.25 | C.2 |
| 1.430 | B.26 | C.2 |
| 1.431 | B.27 | C.2 |
| 1.432 | B.28 | C.2 |
| 1.433 | B.29 | C.2 |
| 1.434 | B.30 | C.2 |
| 1.435 | B.31 | C.2 |
| 1.436 | B.32 | C.2 |
| 1.437 | B.33 | C.2 |
| 1.438 | B.34 | C.2 |
| 1.439 | B.35 | C.2 |
| 1.440 | B.36 | C.2 |
| 1.441 | B.37 | C.2 |
| 1.442 | B.38 | C.2 |
| 1.443 | B.39 | C.2 |
| 1.444 | B.40 | C.2 |
| 1.445 | B.41 | C.2 |
| 1.446 | B.42 | C.2 |
| 1.447 | B.43 | C.2 |
| 1.448 | B.44 | C.2 |
| 1.449 | B.45 | C.2 |
| 1.450 | B.46 | C.2 |
| 1.451 | B.47 | C.2 |
| 1.452 | B.48 | C.2 |
| 1.453 | B.49 | C.2 |
| 1.454 | B.50 | C.2 |
| 1.455 | B.51 | C.2 |
| 1.456 | B.52 | C.2 |
| 1.457 | B.53 | C.2 |
| 1.458 | B.54 | C.2 |
| 1.459 | B.55 | C.2 |
| 1.460 | B.56 | C.2 |
| 1.461 | B.57 | C.2 |
| 1.462 | B.58 | C.2 |
| 1.463 | B.59 | C.2 |
| 1.464 | B.60 | C.2 |
| 1.465 | B.61 | C.2 |
| 1.466 | B.62 | C.2 |
| 1.467 | B.63 | C.2 |
| 1.468 | B.64 | C.2 |
| 1.469 | B.65 | C.2 |
| 1.470 | B.66 | C.2 |
| 1.471 | B.67 | C.2 |
| 1.472 | B.68 | C.2 |
| 1.473 | B.69 | C.2 |
| 1.474 | B.70 | C.2 |
| 1.475 | B.71 | C.2 |
| 1.476 | B.72 | C.2 |
| 1.477 | B.73 | C.2 |
| 1.478 | B.74 | C.2 |
| 1.479 | B.75 | C.2 |
| 1.480 | B.76 | C.2 |
| 1.481 | B.77 | C.2 |
| 1.482 | B.78 | C.2 |
| 1.483 | B.79 | C.2 |
| 1.484 | B.80 | C.2 |
| 1.485 | B.81 | C.2 |
| 1.486 | B.82 | C.2 |
| 1.487 | B.83 | C.2 |
| 1.488 | B.84 | C.2 |
| 1.489 | B.85 | C.2 |
| 1.490 | B.86 | C.2 |
| 1.491 | B.87 | C.2 |
| 1.492 | B.88 | C.2 |
| 1.493 | B.89 | C.2 |
| 1.494 | B.90 | C.2 |
| 1.495 | B.91 | C.2 |
| 1.496 | B.92 | C.2 |
| 1.497 | B.93 | C.2 |
| 1.498 | B.94 | C.2 |
| 1.499 | B.95 | C.2 |
| 1.500 | B.96 | C.2 |
| 1.501 | B.97 | C.2 |
| 1.502 | B.98 | C.2 |
| 1.503 | B.99 | C.2 |
| 1.504 | B.100 | C.2 |
| 1.505 | B.101 | C.2 |
| 1.506 | B.102 | C.2 |
| 1.507 | B.103 | C.2 |
| 1.508 | B.104 | C.2 |
| 1.509 | B.105 | C.2 |
| 1.510 | B.106 | C.2 |
| 1.511 | B.107 | C.2 |
| 1.512 | B.108 | C.2 |
| 1.513 | B.109 | C.2 |
| 1.514 | B.110 | C.2 |
| 1.515 | B.111 | C.2 |
| 1.516 | B.112 | C.2 |
| 1.517 | B.113 | C.2 |
| 1.518 | B.114 | C.2 |
| 1.519 | B.115 | C.2 |
| 1.520 | B.116 | C.2 |
| 1.521 | B.117 | C.2 |
| 1.522 | B.118 | C.2 |
| 1.523 | B.119 | C.2 |
| 1.524 | B.120 | C.2 |
| 1.525 | B.121 | C.2 |
| 1.526 | B.122 | C.2 |
| 1.527 | B.123 | C.2 |
| 1.528 | B.124 | C.2 |
| 1.529 | B.125 | C.2 |
| 1.530 | B.126 | C.2 |
| 1.531 | B.127 | C.2 |
| 1.532 | B.128 | C.2 |
| 1.533 | B.129 | C.2 |
| 1.534 | B.130 | C.2 |
| 1.535 | B.131 | C.2 |

TABLE 1-continued (compositions 1.1 to 1.3653):

| comp. no. | herbicide B | safener C |
|---|---|---|
| 1.536 | B.132 | C.2 |
| 1.537 | B.133 | C.2 |
| 1.538 | B.134 | C.2 |
| 1.539 | B.135 | C.2 |
| 1.540 | B.136 | C.2 |
| 1.541 | B.137 | C.2 |
| 1.542 | B.138 | C.2 |
| 1.543 | B.139 | C.2 |
| 1.544 | B.140 | C.2 |
| 1.545 | B.141 | C.2 |
| 1.546 | B.142 | C.2 |
| 1.547 | B.143 | C.2 |
| 1.548 | B.144 | C.2 |
| 1.549 | B.145 | C.2 |
| 1.550 | B.146 | C.2 |
| 1.551 | B.147 | C.2 |
| 1.552 | B.148 | C.2 |
| 1.553 | B.149 | C.2 |
| 1.554 | B.150 | C.2 |
| 1.555 | B.151 | C.2 |
| 1.556 | B.152 | C.2 |
| 1.557 | B.153 | C.2 |
| 1.558 | B.154 | C.2 |
| 1.559 | B.155 | C.2 |
| 1.560 | B.156 | C.2 |
| 1.561 | B.157 | C.2 |
| 1.562 | B.158 | C.2 |
| 1.563 | B.159 | C.2 |
| 1.564 | B.160 | C.2 |
| 1.565 | B.161 | C.2 |
| 1.566 | B.162 | C.2 |
| 1.567 | B.163 | C.2 |
| 1.568 | B.164 | C.2 |
| 1.569 | B.165 | C.2 |
| 1.570 | B.166 | C.2 |
| 1.571 | B.167 | C.2 |
| 1.572 | B.168 | C.2 |
| 1.573 | B.169 | C.2 |
| 1.574 | B.170 | C.2 |
| 1.575 | B.171 | C.2 |
| 1.576 | B.172 | C.2 |
| 1.577 | B.173 | C.2 |
| 1.578 | B.174 | C.2 |
| 1.579 | B.175 | C.2 |
| 1.580 | B.176 | C.2 |
| 1.581 | B.177 | C.2 |
| 1.582 | B.178 | C.2 |
| 1.583 | B.179 | C.2 |
| 1.584 | B.180 | C.2 |
| 1.585 | B.181 | C.2 |
| 1.586 | B.182 | C.2 |
| 1.587 | B.183 | C.2 |
| 1.588 | B.184 | C.2 |
| 1.589 | B.185 | C.2 |
| 1.590 | B.186 | C.2 |
| 1.591 | B.187 | C.2 |
| 1.592 | B.188 | C.2 |
| 1.593 | B.189 | C.2 |
| 1.594 | B.190 | C.2 |
| 1.595 | B.191 | C.2 |
| 1.596 | B.192 | C.2 |
| 1.597 | B.193 | C.2 |
| 1.598 | B.194 | C.2 |
| 1.599 | B.195 | C.2 |
| 1.600 | B.196 | C.2 |
| 1.601 | B.197 | C.2 |
| 1.602 | B.198 | C.2 |
| 1.603 | B.199 | C.2 |
| 1.604 | B.200 | C.2 |
| 1.605 | B.201 | C.2 |
| 1.606 | B.202 | C.2 |
| 1.607 | B.1 | C.3 |
| 1.608 | B.2 | C.3 |
| 1.609 | B.3 | C.3 |
| 1.610 | B.4 | C.3 |
| 1.611 | B.5 | C.3 |
| 1.612 | B.6 | C.3 |
| 1.613 | B.7 | C.3 |
| 1.614 | B.8 | C.3 |
| 1.615 | B.9 | C.3 |
| 1.616 | B.10 | C.3 |
| 1.617 | B.11 | C.3 |
| 1.618 | B.12 | C.3 |
| 1.619 | B.13 | C.3 |
| 1.620 | B.14 | C.3 |
| 1.621 | B.15 | C.3 |
| 1.622 | B.16 | C.3 |
| 1.623 | B.17 | C.3 |
| 1.624 | B.18 | C.3 |
| 1.625 | B.19 | C.3 |
| 1.626 | B.20 | C.3 |
| 1.627 | B.21 | C.3 |
| 1.628 | B.22 | C.3 |
| 1.629 | B.23 | C.3 |
| 1.630 | B.24 | C.3 |
| 1.631 | B.25 | C.3 |
| 1.632 | B.26 | C.3 |
| 1.633 | B.27 | C.3 |
| 1.634 | B.28 | C.3 |
| 1.635 | B.29 | C.3 |
| 1.636 | B.30 | C.3 |
| 1.637 | B.31 | C.3 |
| 1.638 | B.32 | C.3 |
| 1.639 | B.33 | C.3 |
| 1.640 | B.34 | C.3 |
| 1.641 | B.35 | C.3 |
| 1.642 | B.36 | C.3 |
| 1.643 | B.37 | C.3 |
| 1.644 | B.38 | C.3 |
| 1.645 | B.39 | C.3 |
| 1.646 | B.40 | C.3 |
| 1.647 | B.41 | C.3 |
| 1.648 | B.42 | C.3 |
| 1.649 | B.43 | C.3 |
| 1.650 | B.44 | C.3 |
| 1.651 | B.45 | C.3 |
| 1.652 | B.46 | C.3 |
| 1.653 | B.47 | C.3 |
| 1.654 | B.48 | C.3 |
| 1.655 | B.49 | C.3 |
| 1.656 | B.50 | C.3 |
| 1.657 | B.51 | C.3 |
| 1.658 | B.52 | C.3 |
| 1.659 | B.53 | C.3 |
| 1.660 | B.54 | C.3 |
| 1.661 | B.55 | C.3 |
| 1.662 | B.56 | C.3 |
| 1.663 | B.57 | C.3 |
| 1.664 | B.58 | C.3 |
| 1.665 | B.59 | C.3 |
| 1.666 | B.60 | C.3 |
| 1.667 | B.61 | C.3 |
| 1.668 | B.62 | C.3 |
| 1.669 | B.63 | C.3 |
| 1.670 | B.64 | C.3 |
| 1.671 | B.65 | C.3 |
| 1.672 | B.66 | C.3 |
| 1.673 | B.67 | C.3 |
| 1.674 | B.68 | C.3 |
| 1.675 | B.69 | C.3 |
| 1.676 | B.70 | C.3 |
| 1.677 | B.71 | C.3 |
| 1.678 | B.72 | C.3 |
| 1.679 | B.73 | C.3 |
| 1.680 | B.74 | C.3 |
| 1.681 | B.75 | C.3 |
| 1.682 | B.76 | C.3 |
| 1.683 | B.77 | C.3 |
| 1.684 | B.78 | C.3 |
| 1.685 | B.79 | C.3 |
| 1.686 | B.80 | C.3 |
| 1.687 | B.81 | C.3 |

TABLE 1-continued (compositions 1.1 to 1.3653):

| comp. no. | herbicide B | safener C |
|---|---|---|
| 1.688 | B.82 | C.3 |
| 1.689 | B.83 | C.3 |
| 1.690 | B.84 | C.3 |
| 1.691 | B.85 | C.3 |
| 1.692 | B.86 | C.3 |
| 1.693 | B.87 | C.3 |
| 1.694 | B.88 | C.3 |
| 1.695 | B.89 | C.3 |
| 1.696 | B.90 | C.3 |
| 1.697 | B.91 | C.3 |
| 1.698 | B.92 | C.3 |
| 1.699 | B.93 | C.3 |
| 1.700 | B.94 | C.3 |
| 1.701 | B.95 | C.3 |
| 1.702 | B.96 | C.3 |
| 1.703 | B.97 | C.3 |
| 1.704 | B.98 | C.3 |
| 1.705 | B.99 | C.3 |
| 1.706 | B.100 | C.3 |
| 1.707 | B.101 | C.3 |
| 1.708 | B.102 | C.3 |
| 1.709 | B.103 | C.3 |
| 1.710 | B.104 | C.3 |
| 1.711 | B.105 | C.3 |
| 1.712 | B.106 | C.3 |
| 1.713 | B.107 | C.3 |
| 1.714 | B.108 | C.3 |
| 1.715 | B.109 | C.3 |
| 1.716 | B.110 | C.3 |
| 1.717 | B.111 | C.3 |
| 1.718 | B.112 | C.3 |
| 1.719 | B.113 | C.3 |
| 1.720 | B.114 | C.3 |
| 1.721 | B.115 | C.3 |
| 1.722 | B.116 | C.3 |
| 1.723 | B.117 | C.3 |
| 1.724 | B.118 | C.3 |
| 1.725 | B.119 | C.3 |
| 1.726 | B.120 | C.3 |
| 1.727 | B.121 | C.3 |
| 1.728 | B.122 | C.3 |
| 1.729 | B.123 | C.3 |
| 1.730 | B.124 | C.3 |
| 1.731 | B.125 | C.3 |
| 1.732 | B.126 | C.3 |
| 1.733 | B.127 | C.3 |
| 1.734 | B.128 | C.3 |
| 1.735 | B.129 | C.3 |
| 1.736 | B.130 | C.3 |
| 1.737 | B.131 | C.3 |
| 1.738 | B.132 | C.3 |
| 1.739 | B.133 | C.3 |
| 1.740 | B.134 | C.3 |
| 1.741 | B.135 | C.3 |
| 1.742 | B.136 | C.3 |
| 1.743 | B.137 | C.3 |
| 1.744 | B.138 | C.3 |
| 1.745 | B.139 | C.3 |
| 1.746 | B.140 | C.3 |
| 1.747 | B.141 | C.3 |
| 1.748 | B.142 | C.3 |
| 1.749 | B.143 | C.3 |
| 1.750 | B.144 | C.3 |
| 1.751 | B.145 | C.3 |
| 1.752 | B.146 | C.3 |
| 1.753 | B.147 | C.3 |
| 1.754 | B.148 | C.3 |
| 1.755 | B.149 | C.3 |
| 1.756 | B.150 | C.3 |
| 1.757 | B.151 | C.3 |
| 1.758 | B.152 | C.3 |
| 1.759 | B.153 | C.3 |
| 1.760 | B.154 | C.3 |
| 1.761 | B.155 | C.3 |
| 1.762 | B.156 | C.3 |
| 1.763 | B.157 | C.3 |
| 1.764 | B.158 | C.3 |
| 1.765 | B.159 | C.3 |
| 1.766 | B.160 | C.3 |
| 1.767 | B.161 | C.3 |
| 1.768 | B.162 | C.3 |
| 1.769 | B.163 | C.3 |
| 1.770 | B.164 | C.3 |
| 1.771 | B.165 | C.3 |
| 1.772 | B.166 | C.3 |
| 1.773 | B.167 | C.3 |
| 1.774 | B.168 | C.3 |
| 1.775 | B.169 | C.3 |
| 1.776 | B.170 | C.3 |
| 1.777 | B.171 | C.3 |
| 1.778 | B.172 | C.3 |
| 1.779 | B.173 | C.3 |
| 1.780 | B.174 | C.3 |
| 1.781 | B.175 | C.3 |
| 1.782 | B.176 | C.3 |
| 1.783 | B.177 | C.3 |
| 1.784 | B.178 | C.3 |
| 1.785 | B.179 | C.3 |
| 1.786 | B.180 | C.3 |
| 1.787 | B.181 | C.3 |
| 1.788 | B.182 | C.3 |
| 1.789 | B.183 | C.3 |
| 1.790 | B.184 | C.3 |
| 1.791 | B.185 | C.3 |
| 1.792 | B.186 | C.3 |
| 1.793 | B.187 | C.3 |
| 1.794 | B.188 | C.3 |
| 1.795 | B.189 | C.3 |
| 1.796 | B.190 | C.3 |
| 1.797 | B.191 | C.3 |
| 1.798 | B.192 | C.3 |
| 1.799 | B.193 | C.3 |
| 1.800 | B.194 | C.3 |
| 1.801 | B.195 | C.3 |
| 1.802 | B.196 | C.3 |
| 1.803 | B.197 | C.3 |
| 1.804 | B.198 | C.3 |
| 1.805 | B.199 | C.3 |
| 1.806 | B.200 | C.3 |
| 1.807 | B.201 | C.3 |
| 1.808 | B.202 | C.3 |
| 1.809 | B.1 | C.4 |
| 1.810 | B.2 | C.4 |
| 1.811 | B.3 | C.4 |
| 1.812 | B.4 | C.4 |
| 1.813 | B.5 | C.4 |
| 1.814 | B.6 | C.4 |
| 1.815 | B.7 | C.4 |
| 1.816 | B.8 | C.4 |
| 1.817 | B.9 | C.4 |
| 1.818 | B.10 | C.4 |
| 1.819 | B.11 | C.4 |
| 1.820 | B.12 | C.4 |
| 1.821 | B.13 | C.4 |
| 1.822 | B.14 | C.4 |
| 1.823 | B.15 | C.4 |
| 1.824 | B.16 | C.4 |
| 1.825 | B.17 | C.4 |
| 1.826 | B.18 | C.4 |
| 1.827 | B.19 | C.4 |
| 1.828 | B.20 | C.4 |
| 1.829 | B.21 | C.4 |
| 1.830 | B.22 | C.4 |
| 1.831 | B.23 | C.4 |
| 1.832 | B.24 | C.4 |
| 1.833 | B.25 | C.4 |
| 1.834 | B.26 | C.4 |
| 1.835 | B.27 | C.4 |
| 1.836 | B.28 | C.4 |
| 1.837 | B.29 | C.4 |
| 1.838 | B.30 | C.4 |
| 1.839 | B.31 | C.4 |

TABLE 1-continued (compositions 1.1 to 1.3653):

| comp. no. | herbicide B | safener C |
|---|---|---|
| 1.840 | B.32 | C.4 |
| 1.841 | B.33 | C.4 |
| 1.842 | B.34 | C.4 |
| 1.843 | B.35 | C.4 |
| 1.844 | B.36 | C.4 |
| 1.845 | B.37 | C.4 |
| 1.846 | B.38 | C.4 |
| 1.847 | B.39 | C.4 |
| 1.848 | B.40 | C.4 |
| 1.849 | B.41 | C.4 |
| 1.850 | B.42 | C.4 |
| 1.851 | B.43 | C.4 |
| 1.852 | B.44 | C.4 |
| 1.853 | B.45 | C.4 |
| 1.854 | B.46 | C.4 |
| 1.855 | B.47 | C.4 |
| 1.856 | B.48 | C.4 |
| 1.857 | B.49 | C.4 |
| 1.858 | B.50 | C.4 |
| 1.859 | B.51 | C.4 |
| 1.860 | B.52 | C.4 |
| 1.861 | B.53 | C.4 |
| 1.862 | B.54 | C.4 |
| 1.863 | B.55 | C.4 |
| 1.864 | B.56 | C.4 |
| 1.865 | B.57 | C.4 |
| 1.866 | B.58 | C.4 |
| 1.867 | B.59 | C.4 |
| 1.868 | B.60 | C.4 |
| 1.869 | B.61 | C.4 |
| 1.870 | B.62 | C.4 |
| 1.871 | B.63 | C.4 |
| 1.872 | B.64 | C.4 |
| 1.873 | B.65 | C.4 |
| 1.874 | B.66 | C.4 |
| 1.875 | B.67 | C.4 |
| 1.876 | B.68 | C.4 |
| 1.877 | B.69 | C.4 |
| 1.878 | B.70 | C.4 |
| 1.879 | B.71 | C.4 |
| 1.880 | B.72 | C.4 |
| 1.881 | B.73 | C.4 |
| 1.882 | B.74 | C.4 |
| 1.883 | B.75 | C.4 |
| 1.884 | B.76 | C.4 |
| 1.885 | B.77 | C.4 |
| 1.886 | B.78 | C.4 |
| 1.887 | B.79 | C.4 |
| 1.888 | B.80 | C.4 |
| 1.889 | B.81 | C.4 |
| 1.890 | B.82 | C.4 |
| 1.891 | B.83 | C.4 |
| 1.892 | B.84 | C.4 |
| 1.893 | B.85 | C.4 |
| 1.894 | B.86 | C.4 |
| 1.895 | B.87 | C.4 |
| 1.896 | B.88 | C.4 |
| 1.897 | B.89 | C.4 |
| 1.898 | B.90 | C.4 |
| 1.899 | B.91 | C.4 |
| 1.900 | B.92 | C.4 |
| 1.901 | B.93 | C.4 |
| 1.902 | B.94 | C.4 |
| 1.903 | B.95 | C.4 |
| 1.904 | B.96 | C.4 |
| 1.905 | B.97 | C.4 |
| 1.906 | B.98 | C.4 |
| 1.907 | B.99 | C.4 |
| 1.908 | B.100 | C.4 |
| 1.909 | B.101 | C.4 |
| 1.910 | B.102 | C.4 |
| 1.911 | B.103 | C.4 |
| 1.912 | B.104 | C.4 |
| 1.913 | B.105 | C.4 |
| 1.914 | B.106 | C.4 |
| 1.915 | B.107 | C.4 |
| 1.916 | B.108 | C.4 |
| 1.917 | B.109 | C.4 |
| 1.918 | B.110 | C.4 |
| 1.919 | B.111 | C.4 |
| 1.920 | B.112 | C.4 |
| 1.921 | B.113 | C.4 |
| 1.922 | B.114 | C.4 |
| 1.923 | B.115 | C.4 |
| 1.924 | B.116 | C.4 |
| 1.925 | B.117 | C.4 |
| 1.926 | B.118 | C.4 |
| 1.927 | B.119 | C.4 |
| 1.928 | B.120 | C.4 |
| 1.929 | B.121 | C.4 |
| 1.930 | B.122 | C.4 |
| 1.931 | B.123 | C.4 |
| 1.932 | B.124 | C.4 |
| 1.933 | B.125 | C.4 |
| 1.934 | B.126 | C.4 |
| 1.935 | B.127 | C.4 |
| 1.936 | B.128 | C.4 |
| 1.937 | B.129 | C.4 |
| 1.938 | B.130 | C.4 |
| 1.939 | B.131 | C.4 |
| 1.940 | B.132 | C.4 |
| 1.941 | B.133 | C.4 |
| 1.942 | B.134 | C.4 |
| 1.943 | B.135 | C.4 |
| 1.944 | B.136 | C.4 |
| 1.945 | B.137 | C.4 |
| 1.946 | B.138 | C.4 |
| 1.947 | B.139 | C.4 |
| 1.948 | B.140 | C.4 |
| 1.949 | B.141 | C.4 |
| 1.950 | B.142 | C.4 |
| 1.951 | B.143 | C.4 |
| 1.952 | B.144 | C.4 |
| 1.953 | B.145 | C.4 |
| 1.954 | B.146 | C.4 |
| 1.955 | B.147 | C.4 |
| 1.956 | B.148 | C.4 |
| 1.957 | B.149 | C.4 |
| 1.958 | B.150 | C.4 |
| 1.959 | B.151 | C.4 |
| 1.960 | B.152 | C.4 |
| 1.961 | B.153 | C.4 |
| 1.962 | B.154 | C.4 |
| 1.963 | B.155 | C.4 |
| 1.964 | B.156 | C.4 |
| 1.965 | B.157 | C.4 |
| 1.966 | B.158 | C.4 |
| 1.967 | B.159 | C.4 |
| 1.968 | B.160 | C.4 |
| 1.969 | B.161 | C.4 |
| 1.970 | B.162 | C.4 |
| 1.971 | B.163 | C.4 |
| 1.972 | B.164 | C.4 |
| 1.973 | B.165 | C.4 |
| 1.974 | B.166 | C.4 |
| 1.975 | B.167 | C.4 |
| 1.976 | B.168 | C.4 |
| 1.977 | B.169 | C.4 |
| 1.978 | B.170 | C.4 |
| 1.979 | B.171 | C.4 |
| 1.980 | B.172 | C.4 |
| 1.981 | B.173 | C.4 |
| 1.982 | B.174 | C.4 |
| 1.983 | B.175 | C.4 |
| 1.984 | B.176 | C.4 |
| 1.985 | B.177 | C.4 |
| 1.986 | B.178 | C.4 |
| 1.987 | B.179 | C.4 |
| 1.988 | B.180 | C.4 |
| 1.989 | B.181 | C.4 |
| 1.990 | B.182 | C.4 |
| 1.991 | B.183 | C.4 |

TABLE 1-continued (compositions 1.1 to 1.3653):

| comp. no. | herbicide B | safener C |
|---|---|---|
| 1.992 | B.184 | C.4 |
| 1.993 | B.185 | C.4 |
| 1.994 | B.186 | C.4 |
| 1.995 | B.187 | C.4 |
| 1.996 | B.188 | C.4 |
| 1.997 | B.189 | C.4 |
| 1.998 | B.190 | C.4 |
| 1.999 | B.191 | C.4 |
| 1.1000 | B.192 | C.4 |
| 1.1001 | B.193 | C.4 |
| 1.1002 | B.194 | C.4 |
| 1.1003 | B.195 | C.4 |
| 1.1004 | B.196 | C.4 |
| 1.1005 | B.197 | C.4 |
| 1.1006 | B.198 | C.4 |
| 1.1007 | B.199 | C.4 |
| 1.1008 | B.200 | C.4 |
| 1.1009 | B.201 | C.4 |
| 1.1010 | B.202 | C.4 |
| 1.1011 | B.1 | C.5 |
| 1.1012 | B.2 | C.5 |
| 1.1013 | B.3 | C.5 |
| 1.1014 | B.4 | C.5 |
| 1.1015 | B.5 | C.5 |
| 1.1016 | B.6 | C.5 |
| 1.1017 | B.7 | C.5 |
| 1.1018 | B.8 | C.5 |
| 1.1019 | B.9 | C.5 |
| 1.1020 | B.10 | C.5 |
| 1.1021 | B.11 | C.5 |
| 1.1022 | B.12 | C.5 |
| 1.1023 | B.13 | C.5 |
| 1.1024 | B.14 | C.5 |
| 1.1025 | B.15 | C.5 |
| 1.1026 | B.16 | C.5 |
| 1.1027 | B.17 | C.5 |
| 1.1028 | B.18 | C.5 |
| 1.1029 | B.19 | C.5 |
| 1.1030 | B.20 | C.5 |
| 1.1031 | B.21 | C.5 |
| 1.1032 | B.22 | C.5 |
| 1.1033 | B.23 | C.5 |
| 1.1034 | B.24 | C.5 |
| 1.1035 | B.25 | C.5 |
| 1.1036 | B.26 | C.5 |
| 1.1037 | B.27 | C.5 |
| 1.1038 | B.28 | C.5 |
| 1.1039 | B.29 | C.5 |
| 1.1040 | B.30 | C.5 |
| 1.1041 | B.31 | C.5 |
| 1.1042 | B.32 | C.5 |
| 1.1043 | B.33 | C.5 |
| 1.1044 | B.34 | C.5 |
| 1.1045 | B.35 | C.5 |
| 1.1046 | B.36 | C.5 |
| 1.1047 | B.37 | C.5 |
| 1.1048 | B.38 | C.5 |
| 1.1049 | B.39 | C.5 |
| 1.1050 | B.40 | C.5 |
| 1.1051 | B.41 | C.5 |
| 1.1052 | B.42 | C.5 |
| 1.1053 | B.43 | C.5 |
| 1.1054 | B.44 | C.5 |
| 1.1055 | B.45 | C.5 |
| 1.1056 | B.46 | C.5 |
| 1.1057 | B.47 | C.5 |
| 1.1058 | B.48 | C.5 |
| 1.1059 | B.49 | C.5 |
| 1.1060 | B.50 | C.5 |
| 1.1061 | B.51 | C.5 |
| 1.1062 | B.52 | C.5 |
| 1.1063 | B.53 | C.5 |
| 1.1064 | B.54 | C.5 |
| 1.1065 | B.55 | C.5 |
| 1.1066 | B.56 | C.5 |
| 1.1067 | B.57 | C.5 |
| 1.1068 | B.58 | C.5 |
| 1.1069 | B.59 | C.5 |
| 1.1070 | B.60 | C.5 |
| 1.1071 | B.61 | C.5 |
| 1.1072 | B.62 | C.5 |
| 1.1073 | B.63 | C.5 |
| 1.1074 | B.64 | C.5 |
| 1.1075 | B.65 | C.5 |
| 1.1076 | B.66 | C.5 |
| 1.1077 | B.67 | C.5 |
| 1.1078 | B.68 | C.5 |
| 1.1079 | B.69 | C.5 |
| 1.1080 | B.70 | C.5 |
| 1.1081 | B.71 | C.5 |
| 1.1082 | B.72 | C.5 |
| 1.1083 | B.73 | C.5 |
| 1.1084 | B.74 | C.5 |
| 1.1085 | B.75 | C.5 |
| 1.1086 | B.76 | C.5 |
| 1.1087 | B.77 | C.5 |
| 1.1088 | B.78 | C.5 |
| 1.1089 | B.79 | C.5 |
| 1.1090 | B.80 | C.5 |
| 1.1091 | B.81 | C.5 |
| 1.1092 | B.82 | C.5 |
| 1.1093 | B.83 | C.5 |
| 1.1094 | B.84 | C.5 |
| 1.1095 | B.85 | C.5 |
| 1.1096 | B.86 | C.5 |
| 1.1097 | B.87 | C.5 |
| 1.1098 | B.88 | C.5 |
| 1.1099 | B.89 | C.5 |
| 1.1100 | B.90 | C.5 |
| 1.1101 | B.91 | C.5 |
| 1.1102 | B.92 | C.5 |
| 1.1103 | B.93 | C.5 |
| 1.1104 | B.94 | C.5 |
| 1.1105 | B.95 | C.5 |
| 1.1106 | B.96 | C.5 |
| 1.1107 | B.97 | C.5 |
| 1.1108 | B.98 | C.5 |
| 1.1109 | B.99 | C.5 |
| 1.1110 | B.100 | C.5 |
| 1.1111 | B.101 | C.5 |
| 1.1112 | B.102 | C.5 |
| 1.1113 | B.103 | C.5 |
| 1.1114 | B.104 | C.5 |
| 1.1115 | B.105 | C.5 |
| 1.1116 | B.106 | C.5 |
| 1.1117 | B.107 | C.5 |
| 1.1118 | B.108 | C.5 |
| 1.1119 | B.109 | C.5 |
| 1.1120 | B.110 | C.5 |
| 1.1121 | B.111 | C.5 |
| 1.1122 | B.112 | C.5 |
| 1.1123 | B.113 | C.5 |
| 1.1124 | B.114 | C.5 |
| 1.1125 | B.115 | C.5 |
| 1.1126 | B.116 | C.5 |
| 1.1127 | B.117 | C.5 |
| 1.1128 | B.118 | C.5 |
| 1.1129 | B.119 | C.5 |
| 1.1130 | B.120 | C.5 |
| 1.1131 | B.121 | C.5 |
| 1.1132 | B.122 | C.5 |
| 1.1133 | B.123 | C.5 |
| 1.1134 | B.124 | C.5 |
| 1.1135 | B.125 | C.5 |
| 1.1136 | B.126 | C.5 |
| 1.1137 | B.127 | C.5 |
| 1.1138 | B.128 | C.5 |
| 1.1139 | B.129 | C.5 |
| 1.1140 | B.130 | C.5 |
| 1.1141 | B.131 | C.5 |
| 1.1142 | B.132 | C.5 |
| 1.1143 | B.133 | C.5 |

TABLE 1-continued (compositions 1.1 to 1.3653):

| comp. no. | herbicide B | safener C |
|---|---|---|
| 1.1144 | B.134 | C.5 |
| 1.1145 | B.135 | C.5 |
| 1.1146 | B.136 | C.5 |
| 1.1147 | B.137 | C.5 |
| 1.1148 | B.138 | C.5 |
| 1.1149 | B.139 | C.5 |
| 1.1150 | B.140 | C.5 |
| 1.1151 | B.141 | C.5 |
| 1.1152 | B.142 | C.5 |
| 1.1153 | B.143 | C.5 |
| 1.1154 | B.144 | C.5 |
| 1.1155 | B.145 | C.5 |
| 1.1156 | B.146 | C.5 |
| 1.1157 | B.147 | C.5 |
| 1.1158 | B.148 | C.5 |
| 1.1159 | B.149 | C.5 |
| 1.1160 | B.150 | C.5 |
| 1.1161 | B.151 | C.5 |
| 1.1162 | B.152 | C.5 |
| 1.1163 | B.153 | C.5 |
| 1.1164 | B.154 | C.5 |
| 1.1165 | B.155 | C.5 |
| 1.1166 | B.156 | C.5 |
| 1.1167 | B.157 | C.5 |
| 1.1168 | B.158 | C.5 |
| 1.1169 | B.159 | C.5 |
| 1.1170 | B.160 | C.5 |
| 1.1171 | B.161 | C.5 |
| 1.1172 | B.162 | C.5 |
| 1.1173 | B.163 | C.5 |
| 1.1174 | B.164 | C.5 |
| 1.1175 | B.165 | C.5 |
| 1.1176 | B.166 | C.5 |
| 1.1177 | B.167 | C.5 |
| 1.1178 | B.168 | C.5 |
| 1.1179 | B.169 | C.5 |
| 1.1180 | B.170 | C.5 |
| 1.1181 | B.171 | C.5 |
| 1.1182 | B.172 | C.5 |
| 1.1183 | B.173 | C.5 |
| 1.1184 | B.174 | C.5 |
| 1.1185 | B.175 | C.5 |
| 1.1186 | B.176 | C.5 |
| 1.1187 | B.177 | C.5 |
| 1.1188 | B.178 | C.5 |
| 1.1189 | B.179 | C.5 |
| 1.1190 | B.180 | C.5 |
| 1.1191 | B.181 | C.5 |
| 1.1192 | B.182 | C.5 |
| 1.1193 | B.183 | C.5 |
| 1.1194 | B.184 | C.5 |
| 1.1195 | B.185 | C.5 |
| 1.1196 | B.186 | C.5 |
| 1.1197 | B.187 | C.5 |
| 1.1198 | B.188 | C.5 |
| 1.1199 | B.189 | C.5 |
| 1.1200 | B.190 | C.5 |
| 1.1201 | B.191 | C.5 |
| 1.1202 | B.192 | C.5 |
| 1.1203 | B.193 | C.5 |
| 1.1204 | B.194 | C.5 |
| 1.1205 | B.195 | C.5 |
| 1.1206 | B.196 | C.5 |
| 1.1207 | B.197 | C.5 |
| 1.1208 | B.198 | C.5 |
| 1.1209 | B.199 | C.5 |
| 1.1210 | B.200 | C.5 |
| 1.1211 | B.201 | C.5 |
| 1.1212 | B.202 | C.5 |
| 1.1213 | B.1 | C.6 |
| 1.1214 | B.2 | C.6 |
| 1.1215 | B.3 | C.6 |
| 1.1216 | B.4 | C.6 |
| 1.1217 | B.5 | C.6 |
| 1.1218 | B.6 | C.6 |
| 1.1219 | B.7 | C.6 |
| 1.1220 | B.8 | C.6 |
| 1.1221 | B.9 | C.6 |
| 1.1222 | B.10 | C.6 |
| 1.1223 | B.11 | C.6 |
| 1.1224 | B.12 | C.6 |
| 1.1225 | B.13 | C.6 |
| 1.1226 | B.14 | C.6 |
| 1.1227 | B.15 | C.6 |
| 1.1228 | B.16 | C.6 |
| 1.1229 | B.17 | C.6 |
| 1.1230 | B.18 | C.6 |
| 1.1231 | B.19 | C.6 |
| 1.1232 | B.20 | C.6 |
| 1.1233 | B.21 | C.6 |
| 1.1234 | B.22 | C.6 |
| 1.1235 | B.23 | C.6 |
| 1.1236 | B.24 | C.6 |
| 1.1237 | B.25 | C.6 |
| 1.1238 | B.26 | C.6 |
| 1.1239 | B.27 | C.6 |
| 1.1240 | B.28 | C.6 |
| 1.1241 | B.29 | C.6 |
| 1.1242 | B.30 | C.6 |
| 1.1243 | B.31 | C.6 |
| 1.1244 | B.32 | C.6 |
| 1.1245 | B.33 | C.6 |
| 1.1246 | B.34 | C.6 |
| 1.1247 | B.35 | C.6 |
| 1.1248 | B.36 | C.6 |
| 1.1249 | B.37 | C.6 |
| 1.1250 | B.38 | C.6 |
| 1.1251 | B.39 | C.6 |
| 1.1252 | B.40 | C.6 |
| 1.1253 | B.41 | C.6 |
| 1.1254 | B.42 | C.6 |
| 1.1255 | B.43 | C.6 |
| 1.1256 | B.44 | C.6 |
| 1.1257 | B.45 | C.6 |
| 1.1258 | B.46 | C.6 |
| 1.1259 | B.47 | C.6 |
| 1.1260 | B.48 | C.6 |
| 1.1261 | B.49 | C.6 |
| 1.1262 | B.50 | C.6 |
| 1.1263 | B.51 | C.6 |
| 1.1264 | B.52 | C.6 |
| 1.1265 | B.53 | C.6 |
| 1.1266 | B.54 | C.6 |
| 1.1267 | B.55 | C.6 |
| 1.1268 | B.56 | C.6 |
| 1.1269 | B.57 | C.6 |
| 1.1270 | B.58 | C.6 |
| 1.1271 | B.59 | C.6 |
| 1.1272 | B.60 | C.6 |
| 1.1273 | B.61 | C.6 |
| 1.1274 | B.62 | C.6 |
| 1.1275 | B.63 | C.6 |
| 1.1276 | B.64 | C.6 |
| 1.1277 | B.65 | C.6 |
| 1.1278 | B.66 | C.6 |
| 1.1279 | B.67 | C.6 |
| 1.1280 | B.68 | C.6 |
| 1.1281 | B.69 | C.6 |
| 1.1282 | B.70 | C.6 |
| 1.1283 | B.71 | C.6 |
| 1.1284 | B.72 | C.6 |
| 1.1285 | B.73 | C.6 |
| 1.1286 | B.74 | C.6 |
| 1.1287 | B.75 | C.6 |
| 1.1288 | B.76 | C.6 |
| 1.1289 | B.77 | C.6 |
| 1.1290 | B.78 | C.6 |
| 1.1291 | B.79 | C.6 |
| 1.1292 | B.80 | C.6 |
| 1.1293 | B.81 | C.6 |
| 1.1294 | B.82 | C.6 |
| 1.1295 | B.83 | C.6 |

TABLE 1-continued (compositions 1.1 to 1.3653):

| comp. no. | herbicide B | safener C |
|---|---|---|
| 1.1296 | B.84 | C.6 |
| 1.1297 | B.85 | C.6 |
| 1.1298 | B.86 | C.6 |
| 1.1299 | B.87 | C.6 |
| 1.1300 | B.88 | C.6 |
| 1.1301 | B.89 | C.6 |
| 1.1302 | B.90 | C.6 |
| 1.1303 | B.91 | C.6 |
| 1.1304 | B.92 | C.6 |
| 1.1305 | B.93 | C.6 |
| 1.1306 | B.94 | C.6 |
| 1.1307 | B.95 | C.6 |
| 1.1308 | B.96 | C.6 |
| 1.1309 | B.97 | C.6 |
| 1.1310 | B.98 | C.6 |
| 1.1311 | B.99 | C.6 |
| 1.1312 | B.100 | C.6 |
| 1.1313 | B.101 | C.6 |
| 1.1314 | B.102 | C.6 |
| 1.1315 | B.103 | C.6 |
| 1.1316 | B.104 | C.6 |
| 1.1317 | B.105 | C.6 |
| 1.1318 | B.106 | C.6 |
| 1.1319 | B.107 | C.6 |
| 1.1320 | B.108 | C.6 |
| 1.1321 | B.109 | C.6 |
| 1.1322 | B.110 | C.6 |
| 1.1323 | B.111 | C.6 |
| 1.1324 | B.112 | C.6 |
| 1.1325 | B.113 | C.6 |
| 1.1326 | B.114 | C.6 |
| 1.1327 | B.115 | C.6 |
| 1.1328 | B.116 | C.6 |
| 1.1329 | B.117 | C.6 |
| 1.1330 | B.118 | C.6 |
| 1.1331 | B.119 | C.6 |
| 1.1332 | B.120 | C.6 |
| 1.1333 | B.121 | C.6 |
| 1.1334 | B.122 | C.6 |
| 1.1335 | B.123 | C.6 |
| 1.1336 | B.124 | C.6 |
| 1.1337 | B.125 | C.6 |
| 1.1338 | B.126 | C.6 |
| 1.1339 | B.127 | C.6 |
| 1.1340 | B.128 | C.6 |
| 1.1341 | B.129 | C.6 |
| 1.1342 | B.130 | C.6 |
| 1.1343 | B.131 | C.6 |
| 1.1344 | B.132 | C.6 |
| 1.1345 | B.133 | C.6 |
| 1.1346 | B.134 | C.6 |
| 1.1347 | B.135 | C.6 |
| 1.1348 | B.136 | C.6 |
| 1.1349 | B.137 | C.6 |
| 1.1350 | B.138 | C.6 |
| 1.1351 | B.139 | C.6 |
| 1.1352 | B.140 | C.6 |
| 1.1353 | B.141 | C.6 |
| 1.1354 | B.142 | C.6 |
| 1.1355 | B.143 | C.6 |
| 1.1356 | B.144 | C.6 |
| 1.1357 | B.145 | C.6 |
| 1.1358 | B.146 | C.6 |
| 1.1359 | B.147 | C.6 |
| 1.1360 | B.148 | C.6 |
| 1.1361 | B.149 | C.6 |
| 1.1362 | B.150 | C.6 |
| 1.1363 | B.151 | C.6 |
| 1.1364 | B.152 | C.6 |
| 1.1365 | B.153 | C.6 |
| 1.1366 | B.154 | C.6 |
| 1.1367 | B.155 | C.6 |
| 1.1368 | B.156 | C.6 |
| 1.1369 | B.157 | C.6 |
| 1.1370 | B.158 | C.6 |
| 1.1371 | B.159 | C.6 |
| 1.1372 | B.160 | C.6 |
| 1.1373 | B.161 | C.6 |
| 1.1374 | B.162 | C.6 |
| 1.1375 | B.163 | C.6 |
| 1.1376 | B.164 | C.6 |
| 1.1377 | B.165 | C.6 |
| 1.1378 | B.166 | C.6 |
| 1.1379 | B.167 | C.6 |
| 1.1380 | B.168 | C.6 |
| 1.1381 | B.169 | C.6 |
| 1.1382 | B.170 | C.6 |
| 1.1383 | B.171 | C.6 |
| 1.1384 | B.172 | C.6 |
| 1.1385 | B.173 | C.6 |
| 1.1386 | B.174 | C.6 |
| 1.1387 | B.175 | C.6 |
| 1.1388 | B.176 | C.6 |
| 1.1389 | B.177 | C.6 |
| 1.1390 | B.178 | C.6 |
| 1.1391 | B.179 | C.6 |
| 1.1392 | B.180 | C.6 |
| 1.1393 | B.181 | C.6 |
| 1.1394 | B.182 | C.6 |
| 1.1395 | B.183 | C.6 |
| 1.1396 | B.184 | C.6 |
| 1.1397 | B.185 | C.6 |
| 1.1398 | B.186 | C.6 |
| 1.1399 | B.187 | C.6 |
| 1.1400 | B.188 | C.6 |
| 1.1401 | B.189 | C.6 |
| 1.1402 | B.190 | C.6 |
| 1.1403 | B.191 | C.6 |
| 1.1404 | B.192 | C.6 |
| 1.1405 | B.193 | C.6 |
| 1.1406 | B.194 | C.6 |
| 1.1407 | B.195 | C.6 |
| 1.1408 | B.196 | C.6 |
| 1.1409 | B.197 | C.6 |
| 1.1410 | B.198 | C.6 |
| 1.1411 | B.199 | C.6 |
| 1.1412 | B.200 | C.6 |
| 1.1413 | B.201 | C.6 |
| 1.1414 | B.202 | C.6 |
| 1.1415 | B.1 | C.7 |
| 1.1416 | B.2 | C.7 |
| 1.1417 | B.3 | C.7 |
| 1.1418 | B.4 | C.7 |
| 1.1419 | B.5 | C.7 |
| 1.1420 | B.6 | C.7 |
| 1.1421 | B.7 | C.7 |
| 1.1422 | B.8 | C.7 |
| 1.1423 | B.9 | C.7 |
| 1.1424 | B.10 | C.7 |
| 1.1425 | B.11 | C.7 |
| 1.1426 | B.12 | C.7 |
| 1.1427 | B.13 | C.7 |
| 1.1428 | B.14 | C.7 |
| 1.1429 | B.15 | C.7 |
| 1.1430 | B.16 | C.7 |
| 1.1431 | B.17 | C.7 |
| 1.1432 | B.18 | C.7 |
| 1.1433 | B.19 | C.7 |
| 1.1434 | B.20 | C.7 |
| 1.1435 | B.21 | C.7 |
| 1.1436 | B.22 | C.7 |
| 1.1437 | B.23 | C.7 |
| 1.1438 | B.24 | C.7 |
| 1.1439 | B.25 | C.7 |
| 1.1440 | B.26 | C.7 |
| 1.1441 | B.27 | C.7 |
| 1.1442 | B.28 | C.7 |
| 1.1443 | B.29 | C.7 |
| 1.1444 | B.30 | C.7 |
| 1.1445 | B.31 | C.7 |
| 1.1446 | B.32 | C.7 |
| 1.1447 | B.33 | C.7 |

TABLE 1-continued (compositions 1.1 to 1.3653):

| comp. no. | herbicide B | safener C |
|---|---|---|
| 1.1448 | B.34 | C.7 |
| 1.1449 | B.35 | C.7 |
| 1.1450 | B.36 | C.7 |
| 1.1451 | B.37 | C.7 |
| 1.1452 | B.38 | C.7 |
| 1.1453 | B.39 | C.7 |
| 1.1454 | B.40 | C.7 |
| 1.1455 | B.41 | C.7 |
| 1.1456 | B.42 | C.7 |
| 1.1457 | B.43 | C.7 |
| 1.1458 | B.44 | C.7 |
| 1.1459 | B.45 | C.7 |
| 1.1460 | B.46 | C.7 |
| 1.1461 | B.47 | C.7 |
| 1.1462 | B.48 | C.7 |
| 1.1463 | B.49 | C.7 |
| 1.1464 | B.50 | C.7 |
| 1.1465 | B.51 | C.7 |
| 1.1466 | B.52 | C.7 |
| 1.1467 | B.53 | C.7 |
| 1.1468 | B.54 | C.7 |
| 1.1469 | B.55 | C.7 |
| 1.1470 | B.56 | C.7 |
| 1.1471 | B.57 | C.7 |
| 1.1472 | B.58 | C.7 |
| 1.1473 | B.59 | C.7 |
| 1.1474 | B.60 | C.7 |
| 1.1475 | B.61 | C.7 |
| 1.1476 | B.62 | C.7 |
| 1.1477 | B.63 | C.7 |
| 1.1478 | B.64 | C.7 |
| 1.1479 | B.65 | C.7 |
| 1.1480 | B.66 | C.7 |
| 1.1481 | B.67 | C.7 |
| 1.1482 | B.68 | C.7 |
| 1.1483 | B.69 | C.7 |
| 1.1484 | B.70 | C.7 |
| 1.1485 | B.71 | C.7 |
| 1.1486 | B.72 | C.7 |
| 1.1487 | B.73 | C.7 |
| 1.1488 | B.74 | C.7 |
| 1.1489 | B.75 | C.7 |
| 1.1490 | B.76 | C.7 |
| 1.1491 | B.77 | C.7 |
| 1.1492 | B.78 | C.7 |
| 1.1493 | B.79 | C.7 |
| 1.1494 | B.80 | C.7 |
| 1.1495 | B.81 | C.7 |
| 1.1496 | B.82 | C.7 |
| 1.1497 | B.83 | C.7 |
| 1.1498 | B.84 | C.7 |
| 1.1499 | B.85 | C.7 |
| 1.1500 | B.86 | C.7 |
| 1.1501 | B.87 | C.7 |
| 1.1502 | B.88 | C.7 |
| 1.1503 | B.89 | C.7 |
| 1.1504 | B.90 | C.7 |
| 1.1505 | B.91 | C.7 |
| 1.1506 | B.92 | C.7 |
| 1.1507 | B.93 | C.7 |
| 1.1508 | B.94 | C.7 |
| 1.1509 | B.95 | C.7 |
| 1.1510 | B.96 | C.7 |
| 1.1511 | B.97 | C.7 |
| 1.1512 | B.98 | C.7 |
| 1.1513 | B.99 | C.7 |
| 1.1514 | B.100 | C.7 |
| 1.1515 | B.101 | C.7 |
| 1.1516 | B.102 | C.7 |
| 1.1517 | B.103 | C.7 |
| 1.1518 | B.104 | C.7 |
| 1.1519 | B.105 | C.7 |
| 1.1520 | B.106 | C.7 |
| 1.1521 | B.107 | C.7 |
| 1.1522 | B.108 | C.7 |
| 1.1523 | B.109 | C.7 |
| 1.1524 | B.110 | C.7 |
| 1.1525 | B.111 | C.7 |
| 1.1526 | B.112 | C.7 |
| 1.1527 | B.113 | C.7 |
| 1.1528 | B.114 | C.7 |
| 1.1529 | B.115 | C.7 |
| 1.1530 | B.116 | C.7 |
| 1.1531 | B.117 | C.7 |
| 1.1532 | B.118 | C.7 |
| 1.1533 | B.119 | C.7 |
| 1.1534 | B.120 | C.7 |
| 1.1535 | B.121 | C.7 |
| 1.1536 | B.122 | C.7 |
| 1.1537 | B.123 | C.7 |
| 1.1538 | B.124 | C.7 |
| 1.1539 | B.125 | C.7 |
| 1.1540 | B.126 | C.7 |
| 1.1541 | B.127 | C.7 |
| 1.1542 | B.128 | C.7 |
| 1.1543 | B.129 | C.7 |
| 1.1544 | B.130 | C.7 |
| 1.1545 | B.131 | C.7 |
| 1.1546 | B.132 | C.7 |
| 1.1547 | B.133 | C.7 |
| 1.1548 | B.134 | C.7 |
| 1.1549 | B.135 | C.7 |
| 1.1550 | B.136 | C.7 |
| 1.1551 | B.137 | C.7 |
| 1.1552 | B.138 | C.7 |
| 1.1553 | B.139 | C.7 |
| 1.1554 | B.140 | C.7 |
| 1.1555 | B.141 | C.7 |
| 1.1556 | B.142 | C.7 |
| 1.1557 | B.143 | C.7 |
| 1.1558 | B.144 | C.7 |
| 1.1559 | B.145 | C.7 |
| 1.1560 | B.146 | C.7 |
| 1.1561 | B.147 | C.7 |
| 1.1562 | B.148 | C.7 |
| 1.1563 | B.149 | C.7 |
| 1.1564 | B.150 | C.7 |
| 1.1565 | B.151 | C.7 |
| 1.1566 | B.152 | C.7 |
| 1.1567 | B.153 | C.7 |
| 1.1568 | B.154 | C.7 |
| 1.1569 | B.155 | C.7 |
| 1.1570 | B.156 | C.7 |
| 1.1571 | B.157 | C.7 |
| 1.1572 | B.158 | C.7 |
| 1.1573 | B.159 | C.7 |
| 1.1574 | B.160 | C.7 |
| 1.1575 | B.161 | C.7 |
| 1.1576 | B.162 | C.7 |
| 1.1577 | B.163 | C.7 |
| 1.1578 | B.164 | C.7 |
| 1.1579 | B.165 | C.7 |
| 1.1580 | B.166 | C.7 |
| 1.1581 | B.167 | C.7 |
| 1.1582 | B.168 | C.7 |
| 1.1583 | B.169 | C.7 |
| 1.1584 | B.170 | C.7 |
| 1.1585 | B.171 | C.7 |
| 1.1586 | B.172 | C.7 |
| 1.1587 | B.173 | C.7 |
| 1.1588 | B.174 | C.7 |
| 1.1589 | B.175 | C.7 |
| 1.1590 | B.176 | C.7 |
| 1.1591 | B.177 | C.7 |
| 1.1592 | B.178 | C.7 |
| 1.1593 | B.179 | C.7 |
| 1.1594 | B.180 | C.7 |
| 1.1595 | B.181 | C.7 |
| 1.1596 | B.182 | C.7 |
| 1.1597 | B.183 | C.7 |
| 1.1598 | B.184 | C.7 |
| 1.1599 | B.185 | C.7 |

TABLE 1-continued (compositions 1.1 to 1.3653):

| comp. no. | herbicide B | safener C |
|---|---|---|
| 1.1600 | B.186 | C.7 |
| 1.1601 | B.187 | C.7 |
| 1.1602 | B.188 | C.7 |
| 1.1603 | B.189 | C.7 |
| 1.1604 | B.190 | C.7 |
| 1.1605 | B.191 | C.7 |
| 1.1606 | B.192 | C.7 |
| 1.1607 | B.193 | C.7 |
| 1.1608 | B.194 | C.7 |
| 1.1609 | B.195 | C.7 |
| 1.1610 | B.196 | C.7 |
| 1.1611 | B.197 | C.7 |
| 1.1612 | B.198 | C.7 |
| 1.1613 | B.199 | C.7 |
| 1.1614 | B.200 | C.7 |
| 1.1615 | B.201 | C.7 |
| 1.1616 | B.202 | C.7 |
| 1.1617 | B.1 | C.8 |
| 1.1618 | B.2 | C.8 |
| 1.1619 | B.3 | C.8 |
| 1.1620 | B.4 | C.8 |
| 1.1621 | B.5 | C.8 |
| 1.1622 | B.6 | C.8 |
| 1.1623 | B.7 | C.8 |
| 1.1624 | B.8 | C.8 |
| 1.1625 | B.9 | C.8 |
| 1.1626 | B.10 | C.8 |
| 1.1627 | B.11 | C.8 |
| 1.1628 | B.12 | C.8 |
| 1.1629 | B.13 | C.8 |
| 1.1630 | B.14 | C.8 |
| 1.1631 | B.15 | C.8 |
| 1.1632 | B.16 | C.8 |
| 1.1633 | B.17 | C.8 |
| 1.1634 | B.18 | C.8 |
| 1.1635 | B.19 | C.8 |
| 1.1636 | B.20 | C.8 |
| 1.1637 | B.21 | C.8 |
| 1.1638 | B.22 | C.8 |
| 1.1639 | B.23 | C.8 |
| 1.1640 | B.24 | C.8 |
| 1.1641 | B.25 | C.8 |
| 1.1642 | B.26 | C.8 |
| 1.1643 | B.27 | C.8 |
| 1.1644 | B.28 | C.8 |
| 1.1645 | B.29 | C.8 |
| 1.1646 | B.30 | C.8 |
| 1.1647 | B.31 | C.8 |
| 1.1648 | B.32 | C.8 |
| 1.1649 | B.33 | C.8 |
| 1.1650 | B.34 | C.8 |
| 1.1651 | B.35 | C.8 |
| 1.1652 | B.36 | C.8 |
| 1.1653 | B.37 | C.8 |
| 1.1654 | B.38 | C.8 |
| 1.1655 | B.39 | C.8 |
| 1.1656 | B.40 | C.8 |
| 1.1657 | B.41 | C.8 |
| 1.1658 | B.42 | C.8 |
| 1.1659 | B.43 | C.8 |
| 1.1660 | B.44 | C.8 |
| 1.1661 | B.45 | C.8 |
| 1.1662 | B.46 | C.8 |
| 1.1663 | B.47 | C.8 |
| 1.1664 | B.48 | C.8 |
| 1.1665 | B.49 | C.8 |
| 1.1666 | B.50 | C.8 |
| 1.1667 | B.51 | C.8 |
| 1.1668 | B.52 | C.8 |
| 1.1669 | B.53 | C.8 |
| 1.1670 | B.54 | C.8 |
| 1.1671 | B.55 | C.8 |
| 1.1672 | B.56 | C.8 |
| 1.1673 | B.57 | C.8 |
| 1.1674 | B.58 | C.8 |
| 1.1675 | B.59 | C.8 |
| 1.1676 | B.60 | C.8 |
| 1.1677 | B.61 | C.8 |
| 1.1678 | B.62 | C.8 |
| 1.1679 | B.63 | C.8 |
| 1.1680 | B.64 | C.8 |
| 1.1681 | B.65 | C.8 |
| 1.1682 | B.66 | C.8 |
| 1.1683 | B.67 | C.8 |
| 1.1684 | B.68 | C.8 |
| 1.1685 | B.69 | C.8 |
| 1.1686 | B.70 | C.8 |
| 1.1687 | B.71 | C.8 |
| 1.1688 | B.72 | C.8 |
| 1.1689 | B.73 | C.8 |
| 1.1690 | B.74 | C.8 |
| 1.1691 | B.75 | C.8 |
| 1.1692 | B.76 | C.8 |
| 1.1693 | B.77 | C.8 |
| 1.1694 | B.78 | C.8 |
| 1.1695 | B.79 | C.8 |
| 1.1696 | B.80 | C.8 |
| 1.1697 | B.81 | C.8 |
| 1.1698 | B.82 | C.8 |
| 1.1699 | B.83 | C.8 |
| 1.1700 | B.84 | C.8 |
| 1.1701 | B.85 | C.8 |
| 1.1702 | B.86 | C.8 |
| 1.1703 | B.87 | C.8 |
| 1.1704 | B.88 | C.8 |
| 1.1705 | B.89 | C.8 |
| 1.1706 | B.90 | C.8 |
| 1.1707 | B.91 | C.8 |
| 1.1708 | B.92 | C.8 |
| 1.1709 | B.93 | C.8 |
| 1.1710 | B.94 | C.8 |
| 1.1711 | B.95 | C.8 |
| 1.1712 | B.96 | C.8 |
| 1.1713 | B.97 | C.8 |
| 1.1714 | B.98 | C.8 |
| 1.1715 | B.99 | C.8 |
| 1.1716 | B.100 | C.8 |
| 1.1717 | B.101 | C.8 |
| 1.1718 | B.102 | C.8 |
| 1.1719 | B.103 | C.8 |
| 1.1720 | B.104 | C.8 |
| 1.1721 | B.105 | C.8 |
| 1.1722 | B.106 | C.8 |
| 1.1723 | B.107 | C.8 |
| 1.1724 | B.108 | C.8 |
| 1.1725 | B.109 | C.8 |
| 1.1726 | B.110 | C.8 |
| 1.1727 | B.111 | C.8 |
| 1.1728 | B.112 | C.8 |
| 1.1729 | B.113 | C.8 |
| 1.1730 | B.114 | C.8 |
| 1.1731 | B.115 | C.8 |
| 1.1732 | B.116 | C.8 |
| 1.1733 | B.117 | C.8 |
| 1.1734 | B.118 | C.8 |
| 1.1735 | B.119 | C.8 |
| 1.1736 | B.120 | C.8 |
| 1.1737 | B.121 | C.8 |
| 1.1738 | B.122 | C.8 |
| 1.1739 | B.123 | C.8 |
| 1.1740 | B.124 | C.8 |
| 1.1741 | B.125 | C.8 |
| 1.1742 | B.126 | C.8 |
| 1.1743 | B.127 | C.8 |
| 1.1744 | B.128 | C.8 |
| 1.1745 | B.129 | C.8 |
| 1.1746 | B.130 | C.8 |
| 1.1747 | B.131 | C.8 |
| 1.1748 | B.132 | C.8 |
| 1.1749 | B.133 | C.8 |
| 1.1750 | B.134 | C.8 |
| 1.1751 | B.135 | C.8 |

TABLE 1-continued (compositions 1.1 to 1.3653):

| comp. no. | herbicide B | safener C |
|---|---|---|
| 1.1752 | B.136 | C.8 |
| 1.1753 | B.137 | C.8 |
| 1.1754 | B.138 | C.8 |
| 1.1755 | B.139 | C.8 |
| 1.1756 | B.140 | C.8 |
| 1.1757 | B.141 | C.8 |
| 1.1758 | B.142 | C.8 |
| 1.1759 | B.143 | C.8 |
| 1.1760 | B.144 | C.8 |
| 1.1761 | B.145 | C.8 |
| 1.1762 | B.146 | C.8 |
| 1.1763 | B.147 | C.8 |
| 1.1764 | B.148 | C.8 |
| 1.1765 | B.149 | C.8 |
| 1.1766 | B.150 | C.8 |
| 1.1767 | B.151 | C.8 |
| 1.1768 | B.152 | C.8 |
| 1.1769 | B.153 | C.8 |
| 1.1770 | B.154 | C.8 |
| 1.1771 | B.155 | C.8 |
| 1.1772 | B.156 | C.8 |
| 1.1773 | B.157 | C.8 |
| 1.1774 | B.158 | C.8 |
| 1.1775 | B.159 | C.8 |
| 1.1776 | B.160 | C.8 |
| 1.1777 | B.161 | C.8 |
| 1.1778 | B.162 | C.8 |
| 1.1779 | B.163 | C.8 |
| 1.1780 | B.164 | C.8 |
| 1.1781 | B.165 | C.8 |
| 1.1782 | B.166 | C.8 |
| 1.1783 | B.167 | C.8 |
| 1.1784 | B.168 | C.8 |
| 1.1785 | B.169 | C.8 |
| 1.1786 | B.170 | C.8 |
| 1.1787 | B.171 | C.8 |
| 1.1788 | B.172 | C.8 |
| 1.1789 | B.173 | C.8 |
| 1.1790 | B.174 | C.8 |
| 1.1791 | B.175 | C.8 |
| 1.1792 | B.176 | C.8 |
| 1.1793 | B.177 | C.8 |
| 1.1794 | B.178 | C.8 |
| 1.1795 | B.179 | C.8 |
| 1.1796 | B.180 | C.8 |
| 1.1797 | B.181 | C.8 |
| 1.1798 | B.182 | C.8 |
| 1.1799 | B.183 | C.8 |
| 1.1800 | B.184 | C.8 |
| 1.1801 | B.185 | C.8 |
| 1.1802 | B.186 | C.8 |
| 1.1803 | B.187 | C.8 |
| 1.1804 | B.188 | C.8 |
| 1.1805 | B.189 | C.8 |
| 1.1806 | B.190 | C.8 |
| 1.1807 | B.191 | C.8 |
| 1.1808 | B.192 | C.8 |
| 1.1809 | B.193 | C.8 |
| 1.1810 | B.194 | C.8 |
| 1.1811 | B.195 | C.8 |
| 1.1812 | B.196 | C.8 |
| 1.1813 | B.197 | C.8 |
| 1.1814 | B.198 | C.8 |
| 1.1815 | B.199 | C.8 |
| 1.1816 | B.200 | C.8 |
| 1.1817 | B.201 | C.8 |
| 1.1818 | B.202 | C.8 |
| 1.1819 | B.1 | C.9 |
| 1.1820 | B.2 | C.9 |
| 1.1821 | B.3 | C.9 |
| 1.1822 | B.4 | C.9 |
| 1.1823 | B.5 | C.9 |
| 1.1824 | B.6 | C.9 |
| 1.1825 | B.7 | C.9 |
| 1.1826 | B.8 | C.9 |
| 1.1827 | B.9 | C.9 |
| 1.1828 | B.10 | C.9 |
| 1.1829 | B.11 | C.9 |
| 1.1830 | B.12 | C.9 |
| 1.1831 | B.13 | C.9 |
| 1.1832 | B.14 | C.9 |
| 1.1833 | B.15 | C.9 |
| 1.1834 | B.16 | C.9 |
| 1.1835 | B.17 | C.9 |
| 1.1836 | B.18 | C.9 |
| 1.1837 | B.19 | C.9 |
| 1.1838 | B.20 | C.9 |
| 1.1839 | B.21 | C.9 |
| 1.1840 | B.22 | C.9 |
| 1.1841 | B.23 | C.9 |
| 1.1842 | B.24 | C.9 |
| 1.1843 | B.25 | C.9 |
| 1.1844 | B.26 | C.9 |
| 1.1845 | B.27 | C.9 |
| 1.1846 | B.28 | C.9 |
| 1.1847 | B.29 | C.9 |
| 1.1848 | B.30 | C.9 |
| 1.1849 | B.31 | C.9 |
| 1.1850 | B.32 | C.9 |
| 1.1851 | B.33 | C.9 |
| 1.1852 | B.34 | C.9 |
| 1.1853 | B.35 | C.9 |
| 1.1854 | B.36 | C.9 |
| 1.1855 | B.37 | C.9 |
| 1.1856 | B.38 | C.9 |
| 1.1857 | B.39 | C.9 |
| 1.1858 | B.40 | C.9 |
| 1.1859 | B.41 | C.9 |
| 1.1860 | B.42 | C.9 |
| 1.1861 | B.43 | C.9 |
| 1.1862 | B.44 | C.9 |
| 1.1863 | B.45 | C.9 |
| 1.1864 | B.46 | C.9 |
| 1.1865 | B.47 | C.9 |
| 1.1866 | B.48 | C.9 |
| 1.1867 | B.49 | C.9 |
| 1.1868 | B.50 | C.9 |
| 1.1869 | B.51 | C.9 |
| 1.1870 | B.52 | C.9 |
| 1.1871 | B.53 | C.9 |
| 1.1872 | B.54 | C.9 |
| 1.1873 | B.55 | C.9 |
| 1.1874 | B.56 | C.9 |
| 1.1875 | B.57 | C.9 |
| 1.1876 | B.58 | C.9 |
| 1.1877 | B.59 | C.9 |
| 1.1878 | B.60 | C.9 |
| 1.1879 | B.61 | C.9 |
| 1.1880 | B.62 | C.9 |
| 1.1881 | B.63 | C.9 |
| 1.1882 | B.64 | C.9 |
| 1.1883 | B.65 | C.9 |
| 1.1884 | B.66 | C.9 |
| 1.1885 | B.67 | C.9 |
| 1.1886 | B.68 | C.9 |
| 1.1887 | B.69 | C.9 |
| 1.1888 | B.70 | C.9 |
| 1.1889 | B.71 | C.9 |
| 1.1890 | B.72 | C.9 |
| 1.1891 | B.73 | C.9 |
| 1.1892 | B.74 | C.9 |
| 1.1893 | B.75 | C.9 |
| 1.1894 | B.76 | C.9 |
| 1.1895 | B.77 | C.9 |
| 1.1896 | B.78 | C.9 |
| 1.1897 | B.79 | C.9 |
| 1.1898 | B.80 | C.9 |
| 1.1899 | B.81 | C.9 |
| 1.1900 | B.82 | C.9 |
| 1.1901 | B.83 | C.9 |
| 1.1902 | B.84 | C.9 |
| 1.1903 | B.85 | C.9 |

TABLE 1-continued (compositions 1.1 to 1.3653):

| comp. no. | herbicide B | safener C |
|---|---|---|
| 1.1904 | B.86 | C.9 |
| 1.1905 | B.87 | C.9 |
| 1.1906 | B.88 | C.9 |
| 1.1907 | B.89 | C.9 |
| 1.1908 | B.90 | C.9 |
| 1.1909 | B.91 | C.9 |
| 1.1910 | B.92 | C.9 |
| 1.1911 | B.93 | C.9 |
| 1.1912 | B.94 | C.9 |
| 1.1913 | B.95 | C.9 |
| 1.1914 | B.96 | C.9 |
| 1.1915 | B.97 | C.9 |
| 1.1916 | B.98 | C.9 |
| 1.1917 | B.99 | C.9 |
| 1.1918 | B.100 | C.9 |
| 1.1919 | B.101 | C.9 |
| 1.1920 | B.102 | C.9 |
| 1.1921 | B.103 | C.9 |
| 1.1922 | B.104 | C.9 |
| 1.1923 | B.105 | C.9 |
| 1.1924 | B.106 | C.9 |
| 1.1925 | B.107 | C.9 |
| 1.1926 | B.108 | C.9 |
| 1.1927 | B.109 | C.9 |
| 1.1928 | B.110 | C.9 |
| 1.1929 | B.111 | C.9 |
| 1.1930 | B.112 | C.9 |
| 1.1931 | B.113 | C.9 |
| 1.1932 | B.114 | C.9 |
| 1.1933 | B.115 | C.9 |
| 1.1934 | B.116 | C.9 |
| 1.1935 | B.117 | C.9 |
| 1.1936 | B.118 | C.9 |
| 1.1937 | B.119 | C.9 |
| 1.1938 | B.120 | C.9 |
| 1.1939 | B.121 | C.9 |
| 1.1940 | B.122 | C.9 |
| 1.1941 | B.123 | C.9 |
| 1.1942 | B.124 | C.9 |
| 1.1943 | B.125 | C.9 |
| 1.1944 | B.126 | C.9 |
| 1.1945 | B.127 | C.9 |
| 1.1946 | B.128 | C.9 |
| 1.1947 | B.129 | C.9 |
| 1.1948 | B.130 | C.9 |
| 1.1949 | B.131 | C.9 |
| 1.1950 | B.132 | C.9 |
| 1.1951 | B.133 | C.9 |
| 1.1952 | B.134 | C.9 |
| 1.1953 | B.135 | C.9 |
| 1.1954 | B.136 | C.9 |
| 1.1955 | B.137 | C.9 |
| 1.1956 | B.138 | C.9 |
| 1.1957 | B.139 | C.9 |
| 1.1958 | B.140 | C.9 |
| 1.1959 | B.141 | C.9 |
| 1.1960 | B.142 | C.9 |
| 1.1961 | B.143 | C.9 |
| 1.1962 | B.144 | C.9 |
| 1.1963 | B.145 | C.9 |
| 1.1964 | B.146 | C.9 |
| 1.1965 | B.147 | C.9 |
| 1.1966 | B.148 | C.9 |
| 1.1967 | B.149 | C.9 |
| 1.1968 | B.150 | C.9 |
| 1.1969 | B.151 | C.9 |
| 1.1970 | B.152 | C.9 |
| 1.1971 | B.153 | C.9 |
| 1.1972 | B.154 | C.9 |
| 1.1973 | B.155 | C.9 |
| 1.1974 | B.156 | C.9 |
| 1.1975 | B.157 | C.9 |
| 1.1976 | B.158 | C.9 |
| 1.1977 | B.159 | C.9 |
| 1.1978 | B.160 | C.9 |
| 1.1979 | B.161 | C.9 |
| 1.1980 | B.162 | C.9 |
| 1.1981 | B.163 | C.9 |
| 1.1982 | B.164 | C.9 |
| 1.1983 | B.165 | C.9 |
| 1.1984 | B.166 | C.9 |
| 1.1985 | B.167 | C.9 |
| 1.1986 | B.168 | C.9 |
| 1.1987 | B.169 | C.9 |
| 1.1988 | B.170 | C.9 |
| 1.1989 | B.171 | C.9 |
| 1.1990 | B.172 | C.9 |
| 1.1991 | B.173 | C.9 |
| 1.1992 | B.174 | C.9 |
| 1.1993 | B.175 | C.9 |
| 1.1994 | B.176 | C.9 |
| 1.1995 | B.177 | C.9 |
| 1.1996 | B.178 | C.9 |
| 1.1997 | B.179 | C.9 |
| 1.1998 | B.180 | C.9 |
| 1.1999 | B.181 | C.9 |
| 1.2000 | B.182 | C.9 |
| 1.2001 | B.183 | C.9 |
| 1.2002 | B.184 | C.9 |
| 1.2003 | B.185 | C.9 |
| 1.2004 | B.186 | C.9 |
| 1.2005 | B.187 | C.9 |
| 1.2006 | B.188 | C.9 |
| 1.2007 | B.189 | C.9 |
| 1.2008 | B.190 | C.9 |
| 1.2009 | B.191 | C.9 |
| 1.2010 | B.192 | C.9 |
| 1.2011 | B.193 | C.9 |
| 1.2012 | B.194 | C.9 |
| 1.2013 | B.195 | C.9 |
| 1.2014 | B.196 | C.9 |
| 1.2015 | B.197 | C.9 |
| 1.2016 | B.198 | C.9 |
| 1.2017 | B.199 | C.9 |
| 1.2018 | B.200 | C.9 |
| 1.2019 | B.201 | C.9 |
| 1.2020 | B.202 | C.9 |
| 1.2021 | B.1 | C.10 |
| 1.2022 | B.2 | C.10 |
| 1.2023 | B.3 | C.10 |
| 1.2024 | B.4 | C.10 |
| 1.2025 | B.5 | C.10 |
| 1.2026 | B.6 | C.10 |
| 1.2027 | B.7 | C.10 |
| 1.2028 | B.8 | C.10 |
| 1.2029 | B.9 | C.10 |
| 1.2030 | B.10 | C.10 |
| 1.2031 | B.11 | C.10 |
| 1.2032 | B.12 | C.10 |
| 1.2033 | B.13 | C.10 |
| 1.2034 | B.14 | C.10 |
| 1.2035 | B.15 | C.10 |
| 1.2036 | B.16 | C.10 |
| 1.2037 | B.17 | C.10 |
| 1.2038 | B.18 | C.10 |
| 1.2039 | B.19 | C.10 |
| 1.2040 | B.20 | C.10 |
| 1.2041 | B.21 | C.10 |
| 1.2042 | B.22 | C.10 |
| 1.2043 | B.23 | C.10 |
| 1.2044 | B.24 | C.10 |
| 1.2045 | B.25 | C.10 |
| 1.2046 | B.26 | C.10 |
| 1.2047 | B.27 | C.10 |
| 1.2048 | B.28 | C.10 |
| 1.2049 | B.29 | C.10 |
| 1.2050 | B.30 | C.10 |
| 1.2051 | B.31 | C.10 |
| 1.2052 | B.32 | C.10 |
| 1.2053 | B.33 | C.10 |
| 1.2054 | B.34 | C.10 |
| 1.2055 | B.35 | C.10 |

TABLE 1-continued (compositions 1.1 to 1.3653):

| comp. no. | herbicide B | safener C |
|---|---|---|
| 1.2056 | B.36 | C.10 |
| 1.2057 | B.37 | C.10 |
| 1.2058 | B.38 | C.10 |
| 1.2059 | B.39 | C.10 |
| 1.2060 | B.40 | C.10 |
| 1.2061 | B.41 | C.10 |
| 1.2062 | B.42 | C.10 |
| 1.2063 | B.43 | C.10 |
| 1.2064 | B.44 | C.10 |
| 1.2065 | B.45 | C.10 |
| 1.2066 | B.46 | C.10 |
| 1.2067 | B.47 | C.10 |
| 1.2068 | B.48 | C.10 |
| 1.2069 | B.49 | C.10 |
| 1.2070 | B.50 | C.10 |
| 1.2071 | B.51 | C.10 |
| 1.2072 | B.52 | C.10 |
| 1.2073 | B.53 | C.10 |
| 1.2074 | B.54 | C.10 |
| 1.2075 | B.55 | C.10 |
| 1.2076 | B.56 | C.10 |
| 1.2077 | B.57 | C.10 |
| 1.2078 | B.58 | C.10 |
| 1.2079 | B.59 | C.10 |
| 1.2080 | B.60 | C.10 |
| 1.2081 | B.61 | C.10 |
| 1.2082 | B.62 | C.10 |
| 1.2083 | B.63 | C.10 |
| 1.2084 | B.64 | C.10 |
| 1.2085 | B.65 | C.10 |
| 1.2086 | B.66 | C.10 |
| 1.2087 | B.67 | C.10 |
| 1.2088 | B.68 | C.10 |
| 1.2089 | B.69 | C.10 |
| 1.2090 | B.70 | C.10 |
| 1.2091 | B.71 | C.10 |
| 1.2092 | B.72 | C.10 |
| 1.2093 | B.73 | C.10 |
| 1.2094 | B.74 | C.10 |
| 1.2095 | B.75 | C.10 |
| 1.2096 | B.76 | C.10 |
| 1.2097 | B.77 | C.10 |
| 1.2098 | B.78 | C.10 |
| 1.2099 | B.79 | C.10 |
| 1.2100 | B.80 | C.10 |
| 1.2101 | B.81 | C.10 |
| 1.2102 | B.82 | C.10 |
| 1.2103 | B.83 | C.10 |
| 1.2104 | B.84 | C.10 |
| 1.2105 | B.85 | C.10 |
| 1.2106 | B.86 | C.10 |
| 1.2107 | B.87 | C.10 |
| 1.2108 | B.88 | C.10 |
| 1.2109 | B.89 | C.10 |
| 1.2110 | B.90 | C.10 |
| 1.2111 | B.91 | C.10 |
| 1.2112 | B.92 | C.10 |
| 1.2113 | B.93 | C.10 |
| 1.2114 | B.94 | C.10 |
| 1.2115 | B.95 | C.10 |
| 1.2116 | B.96 | C.10 |
| 1.2117 | B.97 | C.10 |
| 1.2118 | B.98 | C.10 |
| 1.2119 | B.99 | C.10 |
| 1.2120 | B.100 | C.10 |
| 1.2121 | B.101 | C.10 |
| 1.2122 | B.102 | C.10 |
| 1.2123 | B.103 | C.10 |
| 1.2124 | B.104 | C.10 |
| 1.2125 | B.105 | C.10 |
| 1.2126 | B.106 | C.10 |
| 1.2127 | B.107 | C.10 |
| 1.2128 | B.108 | C.10 |
| 1.2129 | B.109 | C.10 |
| 1.2130 | B.110 | C.10 |
| 1.2131 | B.111 | C.10 |
| 1.2132 | B.112 | C.10 |
| 1.2133 | B.113 | C.10 |
| 1.2134 | B.114 | C.10 |
| 1.2135 | B.115 | C.10 |
| 1.2136 | B.116 | C.10 |
| 1.2137 | B.117 | C.10 |
| 1.2138 | B.118 | C.10 |
| 1.2139 | B.119 | C.10 |
| 1.2140 | B.120 | C.10 |
| 1.2141 | B.121 | C.10 |
| 1.2142 | B.122 | C.10 |
| 1.2143 | B.123 | C.10 |
| 1.2144 | B.124 | C.10 |
| 1.2145 | B.125 | C.10 |
| 1.2146 | B.126 | C.10 |
| 1.2147 | B.127 | C.10 |
| 1.2148 | B.128 | C.10 |
| 1.2149 | B.129 | C.10 |
| 1.2150 | B.130 | C.10 |
| 1.2151 | B.131 | C.10 |
| 1.2152 | B.132 | C.10 |
| 1.2153 | B.133 | C.10 |
| 1.2154 | B.134 | C.10 |
| 1.2155 | B.135 | C.10 |
| 1.2156 | B.136 | C.10 |
| 1.2157 | B.137 | C.10 |
| 1.2158 | B.138 | C.10 |
| 1.2159 | B.139 | C.10 |
| 1.2160 | B.140 | C.10 |
| 1.2161 | B.141 | C.10 |
| 1.2162 | B.142 | C.10 |
| 1.2163 | B.143 | C.10 |
| 1.2164 | B.144 | C.10 |
| 1.2165 | B.145 | C.10 |
| 1.2166 | B.146 | C.10 |
| 1.2167 | B.147 | C.10 |
| 1.2168 | B.148 | C.10 |
| 1.2169 | B.149 | C.10 |
| 1.2170 | B.150 | C.10 |
| 1.2171 | B.151 | C.10 |
| 1.2172 | B.152 | C.10 |
| 1.2173 | B.153 | C.10 |
| 1.2174 | B.154 | C.10 |
| 1.2175 | B.155 | C.10 |
| 1.2176 | B.156 | C.10 |
| 1.2177 | B.157 | C.10 |
| 1.2178 | B.158 | C.10 |
| 1.2179 | B.159 | C.10 |
| 1.2180 | B.160 | C.10 |
| 1.2181 | B.161 | C.10 |
| 1.2182 | B.162 | C.10 |
| 1.2183 | B.163 | C.10 |
| 1.2184 | B.164 | C.10 |
| 1.2185 | B.165 | C.10 |
| 1.2186 | B.166 | C.10 |
| 1.2187 | B.167 | C.10 |
| 1.2188 | B.168 | C.10 |
| 1.2189 | B.169 | C.10 |
| 1.2190 | B.170 | C.10 |
| 1.2191 | B.171 | C.10 |
| 1.2192 | B.172 | C.10 |
| 1.2193 | B.173 | C.10 |
| 1.2194 | B.174 | C.10 |
| 1.2195 | B.175 | C.10 |
| 1.2196 | B.176 | C.10 |
| 1.2197 | B.177 | C.10 |
| 1.2198 | B.178 | C.10 |
| 1.2199 | B.179 | C.10 |
| 1.2200 | B.180 | C.10 |
| 1.2201 | B.181 | C.10 |
| 1.2202 | B.182 | C.10 |
| 1.2203 | B.183 | C.10 |
| 1.2204 | B.184 | C.10 |
| 1.2205 | B.185 | C.10 |
| 1.2206 | B.186 | C.10 |
| 1.2207 | B.187 | C.10 |

TABLE 1-continued (compositions 1.1 to 1.3653):

| comp. no. | herbicide B | safener C |
|---|---|---|
| 1.2208 | B.188 | C.10 |
| 1.2209 | B.189 | C.10 |
| 1.2210 | B.190 | C.10 |
| 1.2211 | B.191 | C.10 |
| 1.2212 | B.192 | C.10 |
| 1.2213 | B.193 | C.10 |
| 1.2214 | B.194 | C.10 |
| 1.2215 | B.195 | C.10 |
| 1.2216 | B.196 | C.10 |
| 1.2217 | B.197 | C.10 |
| 1.2218 | B.198 | C.10 |
| 1.2219 | B.199 | C.10 |
| 1.2220 | B.200 | C.10 |
| 1.2221 | B.201 | C.10 |
| 1.2222 | B.202 | C.10 |
| 1.2223 | B.1 | C.11 |
| 1.2224 | B.2 | C.11 |
| 1.2225 | B.3 | C.11 |
| 1.2226 | B.4 | C.11 |
| 1.2227 | B.5 | C.11 |
| 1.2228 | B.6 | C.11 |
| 1.2229 | B.7 | C.11 |
| 1.2230 | B.8 | C.11 |
| 1.2231 | B.9 | C.11 |
| 1.2232 | B.10 | C.11 |
| 1.2233 | B.11 | C.11 |
| 1.2234 | B.12 | C.11 |
| 1.2235 | B.13 | C.11 |
| 1.2236 | B.14 | C.11 |
| 1.2237 | B.15 | C.11 |
| 1.2238 | B.16 | C.11 |
| 1.2239 | B.17 | C.11 |
| 1.2240 | B.18 | C.11 |
| 1.2241 | B.19 | C.11 |
| 1.2242 | B.20 | C.11 |
| 1.2243 | B.21 | C.11 |
| 1.2244 | B.22 | C.11 |
| 1.2245 | B.23 | C.11 |
| 1.2246 | B.24 | C.11 |
| 1.2247 | B.25 | C.11 |
| 1.2248 | B.26 | C.11 |
| 1.2249 | B.27 | C.11 |
| 1.2250 | B.28 | C.11 |
| 1.2251 | B.29 | C.11 |
| 1.2252 | B.30 | C.11 |
| 1.2253 | B.31 | C.11 |
| 1.2254 | B.32 | C.11 |
| 1.2255 | B.33 | C.11 |
| 1.2256 | B.34 | C.11 |
| 1.2257 | B.35 | C.11 |
| 1.2258 | B.36 | C.11 |
| 1.2259 | B.37 | C.11 |
| 1.2260 | B.38 | C.11 |
| 1.2261 | B.39 | C.11 |
| 1.2262 | B.40 | C.11 |
| 1.2263 | B.41 | C.11 |
| 1.2264 | B.42 | C.11 |
| 1.2265 | B.43 | C.11 |
| 1.2266 | B.44 | C.11 |
| 1.2267 | B.45 | C.11 |
| 1.2268 | B.46 | C.11 |
| 1.2269 | B.47 | C.11 |
| 1.2270 | B.48 | C.11 |
| 1.2271 | B.49 | C.11 |
| 1.2272 | B.50 | C.11 |
| 1.2273 | B.51 | C.11 |
| 1.2274 | B.52 | C.11 |
| 1.2275 | B.53 | C.11 |
| 1.2276 | B.54 | C.11 |
| 1.2277 | B.55 | C.11 |
| 1.2278 | B.56 | C.11 |
| 1.2279 | B.57 | C.11 |
| 1.2280 | B.58 | C.11 |
| 1.2281 | B.59 | C.11 |
| 1.2282 | B.60 | C.11 |
| 1.2283 | B.61 | C.11 |
| 1.2284 | B.62 | C.11 |
| 1.2285 | B.63 | C.11 |
| 1.2286 | B.64 | C.11 |
| 1.2287 | B.65 | C.11 |
| 1.2288 | B.66 | C.11 |
| 1.2289 | B.67 | C.11 |
| 1.2290 | B.68 | C.11 |
| 1.2291 | B.69 | C.11 |
| 1.2292 | B.70 | C.11 |
| 1.2293 | B.71 | C.11 |
| 1.2294 | B.72 | C.11 |
| 1.2295 | B.73 | C.11 |
| 1.2296 | B.74 | C.11 |
| 1.2297 | B.75 | C.11 |
| 1.2298 | B.76 | C.11 |
| 1.2299 | B.77 | C.11 |
| 1.2300 | B.78 | C.11 |
| 1.2301 | B.79 | C.11 |
| 1.2302 | B.80 | C.11 |
| 1.2303 | B.81 | C.11 |
| 1.2304 | B.82 | C.11 |
| 1.2305 | B.83 | C.11 |
| 1.2306 | B.84 | C.11 |
| 1.2307 | B.85 | C.11 |
| 1.2308 | B.86 | C.11 |
| 1.2309 | B.87 | C.11 |
| 1.2310 | B.88 | C.11 |
| 1.2311 | B.89 | C.11 |
| 1.2312 | B.90 | C.11 |
| 1.2313 | B.91 | C.11 |
| 1.2314 | B.92 | C.11 |
| 1.2315 | B.93 | C.11 |
| 1.2316 | B.94 | C.11 |
| 1.2317 | B.95 | C.11 |
| 1.2318 | B.96 | C.11 |
| 1.2319 | B.97 | C.11 |
| 1.2320 | B.98 | C.11 |
| 1.2321 | B.99 | C.11 |
| 1.2322 | B.100 | C.11 |
| 1.2323 | B.101 | C.11 |
| 1.2324 | B.102 | C.11 |
| 1.2325 | B.103 | C.11 |
| 1.2326 | B.104 | C.11 |
| 1.2327 | B.105 | C.11 |
| 1.2328 | B.106 | C.11 |
| 1.2329 | B.107 | C.11 |
| 1.2330 | B.108 | C.11 |
| 1.2331 | B.109 | C.11 |
| 1.2332 | B.110 | C.11 |
| 1.2333 | B.111 | C.11 |
| 1.2334 | B.112 | C.11 |
| 1.2335 | B.113 | C.11 |
| 1.2336 | B.114 | C.11 |
| 1.2337 | B.115 | C.11 |
| 1.2338 | B.116 | C.11 |
| 1.2339 | B.117 | C.11 |
| 1.2340 | B.118 | C.11 |
| 1.2341 | B.119 | C.11 |
| 1.2342 | B.120 | C.11 |
| 1.2343 | B.121 | C.11 |
| 1.2344 | B.122 | C.11 |
| 1.2345 | B.123 | C.11 |
| 1.2346 | B.124 | C.11 |
| 1.2347 | B.125 | C.11 |
| 1.2348 | B.126 | C.11 |
| 1.2349 | B.127 | C.11 |
| 1.2350 | B.128 | C.11 |
| 1.2351 | B.129 | C.11 |
| 1.2352 | B.130 | C.11 |
| 1.2353 | B.131 | C.11 |
| 1.2354 | B.132 | C.11 |
| 1.2355 | B.133 | C.11 |
| 1.2356 | B.134 | C.11 |
| 1.2357 | B.135 | C.11 |
| 1.2358 | B.136 | C.11 |
| 1.2359 | B.137 | C.11 |

TABLE 1-continued (compositions 1.1 to 1.3653):

| comp. no. | herbicide B | safener C |
|---|---|---|
| 1.2360 | B.138 | C.11 |
| 1.2361 | B.139 | C.11 |
| 1.2362 | B.140 | C.11 |
| 1.2363 | B.141 | C.11 |
| 1.2364 | B.142 | C.11 |
| 1.2365 | B.143 | C.11 |
| 1.2366 | B.144 | C.11 |
| 1.2367 | B.145 | C.11 |
| 1.2368 | B.146 | C.11 |
| 1.2369 | B.147 | C.11 |
| 1.2370 | B.148 | C.11 |
| 1.2371 | B.149 | C.11 |
| 1.2372 | B.150 | C.11 |
| 1.2373 | B.151 | C.11 |
| 1.2374 | B.152 | C.11 |
| 1.2375 | B.153 | C.11 |
| 1.2376 | B.154 | C.11 |
| 1.2377 | B.155 | C.11 |
| 1.2378 | B.156 | C.11 |
| 1.2379 | B.157 | C.11 |
| 1.2380 | B.158 | C.11 |
| 1.2381 | B.159 | C.11 |
| 1.2382 | B.160 | C.11 |
| 1.2383 | B.161 | C.11 |
| 1.2384 | B.162 | C.11 |
| 1.2385 | B.163 | C.11 |
| 1.2386 | B.164 | C.11 |
| 1.2387 | B.165 | C.11 |
| 1.2388 | B.166 | C.11 |
| 1.2389 | B.167 | C.11 |
| 1.2390 | B.168 | C.11 |
| 1.2391 | B.169 | C.11 |
| 1.2392 | B.170 | C.11 |
| 1.2393 | B.171 | C.11 |
| 1.2394 | B.172 | C.11 |
| 1.2395 | B.173 | C.11 |
| 1.2396 | B.174 | C.11 |
| 1.2397 | B.175 | C.11 |
| 1.2398 | B.176 | C.11 |
| 1.2399 | B.177 | C.11 |
| 1.2400 | B.178 | C.11 |
| 1.2401 | B.179 | C.11 |
| 1.2402 | B.180 | C.11 |
| 1.2403 | B.181 | C.11 |
| 1.2404 | B.182 | C.11 |
| 1.2405 | B.183 | C.11 |
| 1.2406 | B.184 | C.11 |
| 1.2407 | B.185 | C.11 |
| 1.2408 | B.186 | C.11 |
| 1.2409 | B.187 | C.11 |
| 1.2410 | B.188 | C.11 |
| 1.2411 | B.189 | C.11 |
| 1.2412 | B.190 | C.11 |
| 1.2413 | B.191 | C.11 |
| 1.2414 | B.192 | C.11 |
| 1.2415 | B.193 | C.11 |
| 1.2416 | B.194 | C.11 |
| 1.2417 | B.195 | C.11 |
| 1.2418 | B.196 | C.11 |
| 1.2419 | B.197 | C.11 |
| 1.2420 | B.198 | C.11 |
| 1.2421 | B.199 | C.11 |
| 1.2422 | B.200 | C.11 |
| 1.2423 | B.201 | C.11 |
| 1.2424 | B.202 | C.11 |
| 1.2425 | B.1 | C.12 |
| 1.2426 | B.2 | C.12 |
| 1.2427 | B.3 | C.12 |
| 1.2428 | B.4 | C.12 |
| 1.2429 | B.5 | C.12 |
| 1.2430 | B.6 | C.12 |
| 1.2431 | B.7 | C.12 |
| 1.2432 | B.8 | C.12 |
| 1.2433 | B.9 | C.12 |
| 1.2434 | B.10 | C.12 |
| 1.2435 | B.11 | C.12 |
| 1.2436 | B.12 | C.12 |
| 1.2437 | B.13 | C.12 |
| 1.2438 | B.14 | C.12 |
| 1.2439 | B.15 | C.12 |
| 1.2440 | B.16 | C.12 |
| 1.2441 | B.17 | C.12 |
| 1.2442 | B.18 | C.12 |
| 1.2443 | B.19 | C.12 |
| 1.2444 | B.20 | C.12 |
| 1.2445 | B.21 | C.12 |
| 1.2446 | B.22 | C.12 |
| 1.2447 | B.23 | C.12 |
| 1.2448 | B.24 | C.12 |
| 1.2449 | B.25 | C.12 |
| 1.2450 | B.26 | C.12 |
| 1.2451 | B.27 | C.12 |
| 1.2452 | B.28 | C.12 |
| 1.2453 | B.29 | C.12 |
| 1.2454 | B.30 | C.12 |
| 1.2455 | B.31 | C.12 |
| 1.2456 | B.32 | C.12 |
| 1.2457 | B.33 | C.12 |
| 1.2458 | B.34 | C.12 |
| 1.2459 | B.35 | C.12 |
| 1.2460 | B.36 | C.12 |
| 1.2461 | B.37 | C.12 |
| 1.2462 | B.38 | C.12 |
| 1.2463 | B.39 | C.12 |
| 1.2464 | B.40 | C.12 |
| 1.2465 | B.41 | C.12 |
| 1.2466 | B.42 | C.12 |
| 1.2467 | B.43 | C.12 |
| 1.2468 | B.44 | C.12 |
| 1.2469 | B.45 | C.12 |
| 1.2470 | B.46 | C.12 |
| 1.2471 | B.47 | C.12 |
| 1.2472 | B.48 | C.12 |
| 1.2473 | B.49 | C.12 |
| 1.2474 | B.50 | C.12 |
| 1.2475 | B.51 | C.12 |
| 1.2476 | B.52 | C.12 |
| 1.2477 | B.53 | C.12 |
| 1.2478 | B.54 | C.12 |
| 1.2479 | B.55 | C.12 |
| 1.2480 | B.56 | C.12 |
| 1.2481 | B.57 | C.12 |
| 1.2482 | B.58 | C.12 |
| 1.2483 | B.59 | C.12 |
| 1.2484 | B.60 | C.12 |
| 1.2485 | B.61 | C.12 |
| 1.2486 | B.62 | C.12 |
| 1.2487 | B.63 | C.12 |
| 1.2488 | B.64 | C.12 |
| 1.2489 | B.65 | C.12 |
| 1.2490 | B.66 | C.12 |
| 1.2491 | B.67 | C.12 |
| 1.2492 | B.68 | C.12 |
| 1.2493 | B.69 | C.12 |
| 1.2494 | B.70 | C.12 |
| 1.2495 | B.71 | C.12 |
| 1.2496 | B.72 | C.12 |
| 1.2497 | B.73 | C.12 |
| 1.2498 | B.74 | C.12 |
| 1.2499 | B.75 | C.12 |
| 1.2500 | B.76 | C.12 |
| 1.2501 | B.77 | C.12 |
| 1.2502 | B.78 | C.12 |
| 1.2503 | B.79 | C.12 |
| 1.2504 | B.80 | C.12 |
| 1.2505 | B.81 | C.12 |
| 1.2506 | B.82 | C.12 |
| 1.2507 | B.83 | C.12 |
| 1.2508 | B.84 | C.12 |
| 1.2509 | B.85 | C.12 |
| 1.2510 | B.86 | C.12 |
| 1.2511 | B.87 | C.12 |

TABLE 1-continued (compositions 1.1 to 1.3653):

| comp. no. | herbicide B | safener C |
|---|---|---|
| 1.2512 | B.88 | C.12 |
| 1.2513 | B.89 | C.12 |
| 1.2514 | B.90 | C.12 |
| 1.2515 | B.91 | C.12 |
| 1.2516 | B.92 | C.12 |
| 1.2517 | B.93 | C.12 |
| 1.2518 | B.94 | C.12 |
| 1.2519 | B.95 | C.12 |
| 1.2520 | B.96 | C.12 |
| 1.2521 | B.97 | C.12 |
| 1.2522 | B.98 | C.12 |
| 1.2523 | B.99 | C.12 |
| 1.2524 | B.100 | C.12 |
| 1.2525 | B.101 | C.12 |
| 1.2526 | B.102 | C.12 |
| 1.2527 | B.103 | C.12 |
| 1.2528 | B.104 | C.12 |
| 1.2529 | B.105 | C.12 |
| 1.2530 | B.106 | C.12 |
| 1.2531 | B.107 | C.12 |
| 1.2532 | B.108 | C.12 |
| 1.2533 | B.109 | C.12 |
| 1.2534 | B.110 | C.12 |
| 1.2535 | B.111 | C.12 |
| 1.2536 | B.112 | C.12 |
| 1.2537 | B.113 | C.12 |
| 1.2538 | B.114 | C.12 |
| 1.2539 | B.115 | C.12 |
| 1.2540 | B.116 | C.12 |
| 1.2541 | B.117 | C.12 |
| 1.2542 | B.118 | C.12 |
| 1.2543 | B.119 | C.12 |
| 1.2544 | B.120 | C.12 |
| 1.2545 | B.121 | C.12 |
| 1.2546 | B.122 | C.12 |
| 1.2547 | B.123 | C.12 |
| 1.2548 | B.124 | C.12 |
| 1.2549 | B.125 | C.12 |
| 1.2550 | B.126 | C.12 |
| 1.2551 | B.127 | C.12 |
| 1.2552 | B.128 | C.12 |
| 1.2553 | B.129 | C.12 |
| 1.2554 | B.130 | C.12 |
| 1.2555 | B.131 | C.12 |
| 1.2556 | B.132 | C.12 |
| 1.2557 | B.133 | C.12 |
| 1.2558 | B.134 | C.12 |
| 1.2559 | B.135 | C.12 |
| 1.2560 | B.136 | C.12 |
| 1.2561 | B.137 | C.12 |
| 1.2562 | B.138 | C.12 |
| 1.2563 | B.139 | C.12 |
| 1.2564 | B.140 | C.12 |
| 1.2565 | B.141 | C.12 |
| 1.2566 | B.142 | C.12 |
| 1.2567 | B.143 | C.12 |
| 1.2568 | B.144 | C.12 |
| 1.2569 | B.145 | C.12 |
| 1.2570 | B.146 | C.12 |
| 1.2571 | B.147 | C.12 |
| 1.2572 | B.148 | C.12 |
| 1.2573 | B.149 | C.12 |
| 1.2574 | B.150 | C.12 |
| 1.2575 | B.151 | C.12 |
| 1.2576 | B.152 | C.12 |
| 1.2577 | B.153 | C.12 |
| 1.2578 | B.154 | C.12 |
| 1.2579 | B.155 | C.12 |
| 1.2580 | B.156 | C.12 |
| 1.2581 | B.157 | C.12 |
| 1.2582 | B.158 | C.12 |
| 1.2583 | B.159 | C.12 |
| 1.2584 | B.160 | C.12 |
| 1.2585 | B.161 | C.12 |
| 1.2586 | B.162 | C.12 |
| 1.2587 | B.163 | C.12 |
| 1.2588 | B.164 | C.12 |
| 1.2589 | B.165 | C.12 |
| 1.2590 | B.166 | C.12 |
| 1.2591 | B.167 | C.12 |
| 1.2592 | B.168 | C.12 |
| 1.2593 | B.169 | C.12 |
| 1.2594 | B.170 | C.12 |
| 1.2595 | B.171 | C.12 |
| 1.2596 | B.172 | C.12 |
| 1.2597 | B.173 | C.12 |
| 1.2598 | B.174 | C.12 |
| 1.2599 | B.175 | C.12 |
| 1.2600 | B.176 | C.12 |
| 1.2601 | B.177 | C.12 |
| 1.2602 | B.178 | C.12 |
| 1.2603 | B.179 | C.12 |
| 1.2604 | B.180 | C.12 |
| 1.2605 | B.181 | C.12 |
| 1.2606 | B.182 | C.12 |
| 1.2607 | B.183 | C.12 |
| 1.2608 | B.184 | C.12 |
| 1.2609 | B.185 | C.12 |
| 1.2610 | B.186 | C.12 |
| 1.2611 | B.187 | C.12 |
| 1.2612 | B.188 | C.12 |
| 1.2613 | B.189 | C.12 |
| 1.2614 | B.190 | C.12 |
| 1.2615 | B.191 | C.12 |
| 1.2616 | B.192 | C.12 |
| 1.2617 | B.193 | C.12 |
| 1.2618 | B.194 | C.12 |
| 1.2619 | B.195 | C.12 |
| 1.2620 | B.196 | C.12 |
| 1.2621 | B.197 | C.12 |
| 1.2622 | B.198 | C.12 |
| 1.2623 | B.199 | C.12 |
| 1.2624 | B.200 | C.12 |
| 1.2625 | B.201 | C.12 |
| 1.2626 | B.202 | C.12 |
| 1.2627 | B.1 | C.13 |
| 1.2628 | B.2 | C.13 |
| 1.2629 | B.3 | C.13 |
| 1.2630 | B.4 | C.13 |
| 1.2631 | B.5 | C.13 |
| 1.2632 | B.6 | C.13 |
| 1.2633 | B.7 | C.13 |
| 1.2634 | B.8 | C.13 |
| 1.2635 | B.9 | C.13 |
| 1.2636 | B.10 | C.13 |
| 1.2637 | B.11 | C.13 |
| 1.2638 | B.12 | C.13 |
| 1.2639 | B.13 | C.13 |
| 1.2640 | B.14 | C.13 |
| 1.2641 | B.15 | C.13 |
| 1.2642 | B.16 | C.13 |
| 1.2643 | B.17 | C.13 |
| 1.2644 | B.18 | C.13 |
| 1.2645 | B.19 | C.13 |
| 1.2646 | B.20 | C.13 |
| 1.2647 | B.21 | C.13 |
| 1.2648 | B.22 | C.13 |
| 1.2649 | B.23 | C.13 |
| 1.2650 | B.24 | C.13 |
| 1.2651 | B.25 | C.13 |
| 1.2652 | B.26 | C.13 |
| 1.2653 | B.27 | C.13 |
| 1.2654 | B.28 | C.13 |
| 1.2655 | B.29 | C.13 |
| 1.2656 | B.30 | C.13 |
| 1.2657 | B.31 | C.13 |
| 1.2658 | B.32 | C.13 |
| 1.2659 | B.33 | C.13 |
| 1.2660 | B.34 | C.13 |
| 1.2661 | B.35 | C.13 |
| 1.2662 | B.36 | C.13 |
| 1.2663 | B.37 | C.13 |

TABLE 1-continued (compositions 1.1 to 1.3653):

| comp. no. | herbicide B | safener C |
|---|---|---|
| 1.2664 | B.38 | C.13 |
| 1.2665 | B.39 | C.13 |
| 1.2666 | B.40 | C.13 |
| 1.2667 | B.41 | C.13 |
| 1.2668 | B.42 | C.13 |
| 1.2669 | B.43 | C.13 |
| 1.2670 | B.44 | C.13 |
| 1.2671 | B.45 | C.13 |
| 1.2672 | B.46 | C.13 |
| 1.2673 | B.47 | C.13 |
| 1.2674 | B.48 | C.13 |
| 1.2675 | B.49 | C.13 |
| 1.2676 | B.50 | C.13 |
| 1.2677 | B.51 | C.13 |
| 1.2678 | B.52 | C.13 |
| 1.2679 | B.53 | C.13 |
| 1.2680 | B.54 | C.13 |
| 1.2681 | B.55 | C.13 |
| 1.2682 | B.56 | C.13 |
| 1.2683 | B.57 | C.13 |
| 1.2684 | B.58 | C.13 |
| 1.2685 | B.59 | C.13 |
| 1.2686 | B.60 | C.13 |
| 1.2687 | B.61 | C.13 |
| 1.2688 | B.62 | C.13 |
| 1.2689 | B.63 | C.13 |
| 1.2690 | B.64 | C.13 |
| 1.2691 | B.65 | C.13 |
| 1.2692 | B.66 | C.13 |
| 1.2693 | B.67 | C.13 |
| 1.2694 | B.68 | C.13 |
| 1.2695 | B.69 | C.13 |
| 1.2696 | B.70 | C.13 |
| 1.2697 | B.71 | C.13 |
| 1.2698 | B.72 | C.13 |
| 1.2699 | B.73 | C.13 |
| 1.2700 | B.74 | C.13 |
| 1.2701 | B.75 | C.13 |
| 1.2702 | B.76 | C.13 |
| 1.2703 | B.77 | C.13 |
| 1.2704 | B.78 | C.13 |
| 1.2705 | B.79 | C.13 |
| 1.2706 | B.80 | C.13 |
| 1.2707 | B.81 | C.13 |
| 1.2708 | B.82 | C.13 |
| 1.2709 | B.83 | C.13 |
| 1.2710 | B.84 | C.13 |
| 1.2711 | B.85 | C.13 |
| 1.2712 | B.86 | C.13 |
| 1.2713 | B.87 | C.13 |
| 1.2714 | B.88 | C.13 |
| 1.2715 | B.89 | C.13 |
| 1.2716 | B.90 | C.13 |
| 1.2717 | B.91 | C.13 |
| 1.2718 | B.92 | C.13 |
| 1.2719 | B.93 | C.13 |
| 1.2720 | B.94 | C.13 |
| 1.2721 | B.95 | C.13 |
| 1.2722 | B.96 | C.13 |
| 1.2723 | B.97 | C.13 |
| 1.2724 | B.98 | C.13 |
| 1.2725 | B.99 | C.13 |
| 1.2726 | B.100 | C.13 |
| 1.2727 | B.101 | C.13 |
| 1.2728 | B.102 | C.13 |
| 1.2729 | B.103 | C.13 |
| 1.2730 | B.104 | C.13 |
| 1.2731 | B.105 | C.13 |
| 1.2732 | B.106 | C.13 |
| 1.2733 | B.107 | C.13 |
| 1.2734 | B.108 | C.13 |
| 1.2735 | B.109 | C.13 |
| 1.2736 | B.110 | C.13 |
| 1.2737 | B.111 | C.13 |
| 1.2738 | B.112 | C.13 |
| 1.2739 | B.113 | C.13 |
| 1.2740 | B.114 | C.13 |
| 1.2741 | B.115 | C.13 |
| 1.2742 | B.116 | C.13 |
| 1.2743 | B.117 | C.13 |
| 1.2744 | B.118 | C.13 |
| 1.2745 | B.119 | C.13 |
| 1.2746 | B.120 | C.13 |
| 1.2747 | B.121 | C.13 |
| 1.2748 | B.122 | C.13 |
| 1.2749 | B.123 | C.13 |
| 1.2750 | B.124 | C.13 |
| 1.2751 | B.125 | C.13 |
| 1.2752 | B.126 | C.13 |
| 1.2753 | B.127 | C.13 |
| 1.2754 | B.128 | C.13 |
| 1.2755 | B.129 | C.13 |
| 1.2756 | B.130 | C.13 |
| 1.2757 | B.131 | C.13 |
| 1.2758 | B.132 | C.13 |
| 1.2759 | B.133 | C.13 |
| 1.2760 | B.134 | C.13 |
| 1.2761 | B.135 | C.13 |
| 1.2762 | B.136 | C.13 |
| 1.2763 | B.137 | C.13 |
| 1.2764 | B.138 | C.13 |
| 1.2765 | B.139 | C.13 |
| 1.2766 | B.140 | C.13 |
| 1.2767 | B.141 | C.13 |
| 1.2768 | B.142 | C.13 |
| 1.2769 | B.143 | C.13 |
| 1.2770 | B.144 | C.13 |
| 1.2771 | B.145 | C.13 |
| 1.2772 | B.146 | C.13 |
| 1.2773 | B.147 | C.13 |
| 1.2774 | B.148 | C.13 |
| 1.2775 | B.149 | C.13 |
| 1.2776 | B.150 | C.13 |
| 1.2777 | B.151 | C.13 |
| 1.2778 | B.152 | C.13 |
| 1.2779 | B.153 | C.13 |
| 1.2780 | B.154 | C.13 |
| 1.2781 | B.155 | C.13 |
| 1.2782 | B.156 | C.13 |
| 1.2783 | B.157 | C.13 |
| 1.2784 | B.158 | C.13 |
| 1.2785 | B.159 | C.13 |
| 1.2786 | B.160 | C.13 |
| 1.2787 | B.161 | C.13 |
| 1.2788 | B.162 | C.13 |
| 1.2789 | B.163 | C.13 |
| 1.2790 | B.164 | C.13 |
| 1.2791 | B.165 | C.13 |
| 1.2792 | B.166 | C.13 |
| 1.2793 | B.167 | C.13 |
| 1.2794 | B.168 | C.13 |
| 1.2795 | B.169 | C.13 |
| 1.2796 | B.170 | C.13 |
| 1.2797 | B.171 | C.13 |
| 1.2798 | B.172 | C.13 |
| 1.2799 | B.173 | C.13 |
| 1.2800 | B.174 | C.13 |
| 1.2801 | B.175 | C.13 |
| 1.2802 | B.176 | C.13 |
| 1.2803 | B.177 | C.13 |
| 1.2804 | B.178 | C.13 |
| 1.2805 | B.179 | C.13 |
| 1.2806 | B.180 | C.13 |
| 1.2807 | B.181 | C.13 |
| 1.2808 | B.182 | C.13 |
| 1.2809 | B.183 | C.13 |
| 1.2810 | B.184 | C.13 |
| 1.2811 | B.185 | C.13 |
| 1.2812 | B.186 | C.13 |
| 1.2813 | B.187 | C.13 |
| 1.2814 | B.188 | C.13 |
| 1.2815 | B.189 | C.13 |

TABLE 1-continued (compositions 1.1 to 1.3653):

| comp. no. | herbicide B | safener C |
|---|---|---|
| 1.2816 | B.190 | C.13 |
| 1.2817 | B.191 | C.13 |
| 1.2818 | B.192 | C.13 |
| 1.2819 | B.193 | C.13 |
| 1.2820 | B.194 | C.13 |
| 1.2821 | B.195 | C.13 |
| 1.2822 | B.196 | C.13 |
| 1.2823 | B.197 | C.13 |
| 1.2824 | B.198 | C.13 |
| 1.2825 | B.199 | C.13 |
| 1.2826 | B.200 | C.13 |
| 1.2827 | B.201 | C.13 |
| 1.2828 | B.202 | C.13 |
| 1.2829 | B.1 | C.14 |
| 1.2830 | B.2 | C.14 |
| 1.2831 | B.3 | C.14 |
| 1.2832 | B.4 | C.14 |
| 1.2833 | B.5 | C.14 |
| 1.2834 | B.6 | C.14 |
| 1.2835 | B.7 | C.14 |
| 1.2836 | B.8 | C.14 |
| 1.2837 | B.9 | C.14 |
| 1.2838 | B.10 | C.14 |
| 1.2839 | B.11 | C.14 |
| 1.2840 | B.12 | C.14 |
| 1.2841 | B.13 | C.14 |
| 1.2842 | B.14 | C.14 |
| 1.2843 | B.15 | C.14 |
| 1.2844 | B.16 | C.14 |
| 1.2845 | B.17 | C.14 |
| 1.2846 | B.18 | C.14 |
| 1.2847 | B.19 | C.14 |
| 1.2848 | B.20 | C.14 |
| 1.2849 | B.21 | C.14 |
| 1.2850 | B.22 | C.14 |
| 1.2851 | B.23 | C.14 |
| 1.2852 | B.24 | C.14 |
| 1.2853 | B.25 | C.14 |
| 1.2854 | B.26 | C.14 |
| 1.2855 | B.27 | C.14 |
| 1.2856 | B.28 | C.14 |
| 1.2857 | B.29 | C.14 |
| 1.2858 | B.30 | C.14 |
| 1.2859 | B.31 | C.14 |
| 1.2860 | B.32 | C.14 |
| 1.2861 | B.33 | C.14 |
| 1.2862 | B.34 | C.14 |
| 1.2863 | B.35 | C.14 |
| 1.2864 | B.36 | C.14 |
| 1.2865 | B.37 | C.14 |
| 1.2866 | B.38 | C.14 |
| 1.2867 | B.39 | C.14 |
| 1.2868 | B.40 | C.14 |
| 1.2869 | B.41 | C.14 |
| 1.2870 | B.42 | C.14 |
| 1.2871 | B.43 | C.14 |
| 1.2872 | B.44 | C.14 |
| 1.2873 | B.45 | C.14 |
| 1.2874 | B.46 | C.14 |
| 1.2875 | B.47 | C.14 |
| 1.2876 | B.48 | C.14 |
| 1.2877 | B.49 | C.14 |
| 1.2878 | B.50 | C.14 |
| 1.2879 | B.51 | C.14 |
| 1.2880 | B.52 | C.14 |
| 1.2881 | B.53 | C.14 |
| 1.2882 | B.54 | C.14 |
| 1.2883 | B.55 | C.14 |
| 1.2884 | B.56 | C.14 |
| 1.2885 | B.57 | C.14 |
| 1.2886 | B.58 | C.14 |
| 1.2887 | B.59 | C.14 |
| 1.2888 | B.60 | C.14 |
| 1.2889 | B.61 | C.14 |
| 1.2890 | B.62 | C.14 |
| 1.2891 | B.63 | C.14 |
| 1.2892 | B.64 | C.14 |
| 1.2893 | B.65 | C.14 |
| 1.2894 | B.66 | C.14 |
| 1.2895 | B.67 | C.14 |
| 1.2896 | B.68 | C.14 |
| 1.2897 | B.69 | C.14 |
| 1.2898 | B.70 | C.14 |
| 1.2899 | B.71 | C.14 |
| 1.2900 | B.72 | C.14 |
| 1.2901 | B.73 | C.14 |
| 1.2902 | B.74 | C.14 |
| 1.2903 | B.75 | C.14 |
| 1.2904 | B.76 | C.14 |
| 1.2905 | B.77 | C.14 |
| 1.2906 | B.78 | C.14 |
| 1.2907 | B.79 | C.14 |
| 1.2908 | B.80 | C.14 |
| 1.2909 | B.81 | C.14 |
| 1.2910 | B.82 | C.14 |
| 1.2911 | B.83 | C.14 |
| 1.2912 | B.84 | C.14 |
| 1.2913 | B.85 | C.14 |
| 1.2914 | B.86 | C.14 |
| 1.2915 | B.87 | C.14 |
| 1.2916 | B.88 | C.14 |
| 1.2917 | B.89 | C.14 |
| 1.2918 | B.90 | C.14 |
| 1.2919 | B.91 | C.14 |
| 1.2920 | B.92 | C.14 |
| 1.2921 | B.93 | C.14 |
| 1.2922 | B.94 | C.14 |
| 1.2923 | B.95 | C.14 |
| 1.2924 | B.96 | C.14 |
| 1.2925 | B.97 | C.14 |
| 1.2926 | B.98 | C.14 |
| 1.2927 | B.99 | C.14 |
| 1.2928 | B.100 | C.14 |
| 1.2929 | B.101 | C.14 |
| 1.2930 | B.102 | C.14 |
| 1.2931 | B.103 | C.14 |
| 1.2932 | B.104 | C.14 |
| 1.2933 | B.105 | C.14 |
| 1.2934 | B.106 | C.14 |
| 1.2935 | B.107 | C.14 |
| 1.2936 | B.108 | C.14 |
| 1.2937 | B.109 | C.14 |
| 1.2938 | B.110 | C.14 |
| 1.2939 | B.111 | C.14 |
| 1.2940 | B.112 | C.14 |
| 1.2941 | B.113 | C.14 |
| 1.2942 | B.114 | C.14 |
| 1.2943 | B.115 | C.14 |
| 1.2944 | B.116 | C.14 |
| 1.2945 | B.117 | C.14 |
| 1.2946 | B.118 | C.14 |
| 1.2947 | B.119 | C.14 |
| 1.2948 | B.120 | C.14 |
| 1.2949 | B.121 | C.14 |
| 1.2950 | B.122 | C.14 |
| 1.2951 | B.123 | C.14 |
| 1.2952 | B.124 | C.14 |
| 1.2953 | B.125 | C.14 |
| 1.2954 | B.126 | C.14 |
| 1.2955 | B.127 | C.14 |
| 1.2956 | B.128 | C.14 |
| 1.2957 | B.129 | C.14 |
| 1.2958 | B.130 | C.14 |
| 1.2959 | B.131 | C.14 |
| 1.2960 | B.132 | C.14 |
| 1.2961 | B.133 | C.14 |
| 1.2962 | B.134 | C.14 |
| 1.2963 | B.135 | C.14 |
| 1.2964 | B.136 | C.14 |
| 1.2965 | B.137 | C.14 |
| 1.2966 | B.138 | C.14 |
| 1.2967 | B.139 | C.14 |

TABLE 1-continued (compositions 1.1 to 1.3653):

| comp. no. | herbicide B | safener C |
|---|---|---|
| 1.2968 | B.140 | C.14 |
| 1.2969 | B.141 | C.14 |
| 1.2970 | B.142 | C.14 |
| 1.2971 | B.143 | C.14 |
| 1.2972 | B.144 | C.14 |
| 1.2973 | B.145 | C.14 |
| 1.2974 | B.146 | C.14 |
| 1.2975 | B.147 | C.14 |
| 1.2976 | B.148 | C.14 |
| 1.2977 | B.149 | C.14 |
| 1.2978 | B.150 | C.14 |
| 1.2979 | B.151 | C.14 |
| 1.2980 | B.152 | C.14 |
| 1.2981 | B.153 | C.14 |
| 1.2982 | B.154 | C.14 |
| 1.2983 | B.155 | C.14 |
| 1.2984 | B.156 | C.14 |
| 1.2985 | B.157 | C.14 |
| 1.2986 | B.158 | C.14 |
| 1.2987 | B.159 | C.14 |
| 1.2988 | B.160 | C.14 |
| 1.2989 | B.161 | C.14 |
| 1.2990 | B.162 | C.14 |
| 1.2991 | B.163 | C.14 |
| 1.2992 | B.164 | C.14 |
| 1.2993 | B.165 | C.14 |
| 1.2994 | B.166 | C.14 |
| 1.2995 | B.167 | C.14 |
| 1.2996 | B.168 | C.14 |
| 1.2997 | B.169 | C.14 |
| 1.2998 | B.170 | C.14 |
| 1.2999 | B.171 | C.14 |
| 1.3000 | B.172 | C.14 |
| 1.3001 | B.173 | C.14 |
| 1.3002 | B.174 | C.14 |
| 1.3003 | B.175 | C.14 |
| 1.3004 | B.176 | C.14 |
| 1.3005 | B.177 | C.14 |
| 1.3006 | B.178 | C.14 |
| 1.3007 | B.179 | C.14 |
| 1.3008 | B.180 | C.14 |
| 1.3009 | B.181 | C.14 |
| 1.3010 | B.182 | C.14 |
| 1.3011 | B.183 | C.14 |
| 1.3012 | B.184 | C.14 |
| 1.3013 | B.185 | C.14 |
| 1.3014 | B.186 | C.14 |
| 1.3015 | B.187 | C.14 |
| 1.3016 | B.188 | C.14 |
| 1.3017 | B.189 | C.14 |
| 1.3018 | B.190 | C.14 |
| 1.3019 | B.191 | C.14 |
| 1.3020 | B.192 | C.14 |
| 1.3021 | B.193 | C.14 |
| 1.3022 | B.194 | C.14 |
| 1.3023 | B.195 | C.14 |
| 1.3024 | B.196 | C.14 |
| 1.3025 | B.197 | C.14 |
| 1.3026 | B.198 | C.14 |
| 1.3027 | B.199 | C.14 |
| 1.3028 | B.200 | C.14 |
| 1.3029 | B.201 | C.14 |
| 1.3030 | B.202 | C.14 |
| 1.3031 | B.1 | C.15 |
| 1.3032 | B.2 | C.15 |
| 1.3033 | B.3 | C.15 |
| 1.3034 | B.4 | C.15 |
| 1.3035 | B.5 | C.15 |
| 1.3036 | B.6 | C.15 |
| 1.3037 | B.7 | C.15 |
| 1.3038 | B.8 | C.15 |
| 1.3039 | B.9 | C.15 |
| 1.3040 | B.10 | C.15 |
| 1.3041 | B.11 | C.15 |
| 1.3042 | B.12 | C.15 |
| 1.3043 | B.13 | C.15 |
| 1.3044 | B.14 | C.15 |
| 1.3045 | B.15 | C.15 |
| 1.3046 | B.16 | C.15 |
| 1.3047 | B.17 | C.15 |
| 1.3048 | B.18 | C.15 |
| 1.3049 | B.19 | C.15 |
| 1.3050 | B.20 | C.15 |
| 1.3051 | B.21 | C.15 |
| 1.3052 | B.22 | C.15 |
| 1.3053 | B.23 | C.15 |
| 1.3054 | B.24 | C.15 |
| 1.3055 | B.25 | C.15 |
| 1.3056 | B.26 | C.15 |
| 1.3057 | B.27 | C.15 |
| 1.3058 | B.28 | C.15 |
| 1.3059 | B.29 | C.15 |
| 1.3060 | B.30 | C.15 |
| 1.3061 | B.31 | C.15 |
| 1.3062 | B.32 | C.15 |
| 1.3063 | B.33 | C.15 |
| 1.3064 | B.34 | C.15 |
| 1.3065 | B.35 | C.15 |
| 1.3066 | B.36 | C.15 |
| 1.3067 | B.37 | C.15 |
| 1.3068 | B.38 | C.15 |
| 1.3069 | B.39 | C.15 |
| 1.3070 | B.40 | C.15 |
| 1.3071 | B.41 | C.15 |
| 1.3072 | B.42 | C.15 |
| 1.3073 | B.43 | C.15 |
| 1.3074 | B.44 | C.15 |
| 1.3075 | B.45 | C.15 |
| 1.3076 | B.46 | C.15 |
| 1.3077 | B.47 | C.15 |
| 1.3078 | B.48 | C.15 |
| 1.3079 | B.49 | C.15 |
| 1.3080 | B.50 | C.15 |
| 1.3081 | B.51 | C.15 |
| 1.3082 | B.52 | C.15 |
| 1.3083 | B.53 | C.15 |
| 1.3084 | B.54 | C.15 |
| 1.3085 | B.55 | C.15 |
| 1.3086 | B.56 | C.15 |
| 1.3087 | B.57 | C.15 |
| 1.3088 | B.58 | C.15 |
| 1.3089 | B.59 | C.15 |
| 1.3090 | B.60 | C.15 |
| 1.3091 | B.61 | C.15 |
| 1.3092 | B.62 | C.15 |
| 1.3093 | B.63 | C.15 |
| 1.3094 | B.64 | C.15 |
| 1.3095 | B.65 | C.15 |
| 1.3096 | B.66 | C.15 |
| 1.3097 | B.67 | C.15 |
| 1.3098 | B.68 | C.15 |
| 1.3099 | B.69 | C.15 |
| 1.3100 | B.70 | C.15 |
| 1.3101 | B.71 | C.15 |
| 1.3102 | B.72 | C.15 |
| 1.3103 | B.73 | C.15 |
| 1.3104 | B.74 | C.15 |
| 1.3105 | B.75 | C.15 |
| 1.3106 | B.76 | C.15 |
| 1.3107 | B.77 | C.15 |
| 1.3108 | B.78 | C.15 |
| 1.3109 | B.79 | C.15 |
| 1.3110 | B.80 | C.15 |
| 1.3111 | B.81 | C.15 |
| 1.3112 | B.82 | C.15 |
| 1.3113 | B.83 | C.15 |
| 1.3114 | B.84 | C.15 |
| 1.3115 | B.85 | C.15 |
| 1.3116 | B.86 | C.15 |
| 1.3117 | B.87 | C.15 |
| 1.3118 | B.88 | C.15 |
| 1.3119 | B.89 | C.15 |

TABLE 1-continued (compositions 1.1 to 1.3653):

| comp. no. | herbicide B | safener C |
|---|---|---|
| 1.3120 | B.90 | C.15 |
| 1.3121 | B.91 | C.15 |
| 1.3122 | B.92 | C.15 |
| 1.3123 | B.93 | C.15 |
| 1.3124 | B.94 | C.15 |
| 1.3125 | B.95 | C.15 |
| 1.3126 | B.96 | C.15 |
| 1.3127 | B.97 | C.15 |
| 1.3128 | B.98 | C.15 |
| 1.3129 | B.99 | C.15 |
| 1.3130 | B.100 | C.15 |
| 1.3131 | B.101 | C.15 |
| 1.3132 | B.102 | C.15 |
| 1.3133 | B.103 | C.15 |
| 1.3134 | B.104 | C.15 |
| 1.3135 | B.105 | C.15 |
| 1.3136 | B.106 | C.15 |
| 1.3137 | B.107 | C.15 |
| 1.3138 | B.108 | C.15 |
| 1.3139 | B.109 | C.15 |
| 1.3140 | B.110 | C.15 |
| 1.3141 | B.111 | C.15 |
| 1.3142 | B.112 | C.15 |
| 1.3143 | B.113 | C.15 |
| 1.3144 | B.114 | C.15 |
| 1.3145 | B.115 | C.15 |
| 1.3146 | B.116 | C.15 |
| 1.3147 | B.117 | C.15 |
| 1.3148 | B.118 | C.15 |
| 1.3149 | B.119 | C.15 |
| 1.3150 | B.120 | C.15 |
| 1.3151 | B.121 | C.15 |
| 1.3152 | B.122 | C.15 |
| 1.3153 | B.123 | C.15 |
| 1.3154 | B.124 | C.15 |
| 1.3155 | B.125 | C.15 |
| 1.3156 | B.126 | C.15 |
| 1.3157 | B.127 | C.15 |
| 1.3158 | B.128 | C.15 |
| 1.3159 | B.129 | C.15 |
| 1.3160 | B.130 | C.15 |
| 1.3161 | B.131 | C.15 |
| 1.3162 | B.132 | C.15 |
| 1.3163 | B.133 | C.15 |
| 1.3164 | B.134 | C.15 |
| 1.3165 | B.135 | C.15 |
| 1.3166 | B.136 | C.15 |
| 1.3167 | B.137 | C.15 |
| 1.3168 | B.138 | C.15 |
| 1.3169 | B.139 | C.15 |
| 1.3170 | B.140 | C.15 |
| 1.3171 | B.141 | C.15 |
| 1.3172 | B.142 | C.15 |
| 1.3173 | B.143 | C.15 |
| 1.3174 | B.144 | C.15 |
| 1.3175 | B.145 | C.15 |
| 1.3176 | B.146 | C.15 |
| 1.3177 | B.147 | C.15 |
| 1.3178 | B.148 | C.15 |
| 1.3179 | B.149 | C.15 |
| 1.3180 | B.150 | C.15 |
| 1.3181 | B.151 | C.15 |
| 1.3182 | B.152 | C.15 |
| 1.3183 | B.153 | C.15 |
| 1.3184 | B.154 | C.15 |
| 1.3185 | B.155 | C.15 |
| 1.3186 | B.156 | C.15 |
| 1.3187 | B.157 | C.15 |
| 1.3188 | B.158 | C.15 |
| 1.3189 | B.159 | C.15 |
| 1.3190 | B.160 | C.15 |
| 1.3191 | B.161 | C.15 |
| 1.3192 | B.162 | C.15 |
| 1.3193 | B.163 | C.15 |
| 1.3194 | B.164 | C.15 |
| 1.3195 | B.165 | C.15 |
| 1.3196 | B.166 | C.15 |
| 1.3197 | B.167 | C.15 |
| 1.3198 | B.168 | C.15 |
| 1.3199 | B.169 | C.15 |
| 1.3200 | B.170 | C.15 |
| 1.3201 | B.171 | C.15 |
| 1.3202 | B.172 | C.15 |
| 1.3203 | B.173 | C.15 |
| 1.3204 | B.174 | C.15 |
| 1.3205 | B.175 | C.15 |
| 1.3206 | B.176 | C.15 |
| 1.3207 | B.177 | C.15 |
| 1.3208 | B.178 | C.15 |
| 1.3209 | B.179 | C.15 |
| 1.3210 | B.180 | C.15 |
| 1.3211 | B.181 | C.15 |
| 1.3212 | B.182 | C.15 |
| 1.3213 | B.183 | C.15 |
| 1.3214 | B.184 | C.15 |
| 1.3215 | B.185 | C.15 |
| 1.3216 | B.186 | C.15 |
| 1.3217 | B.187 | C.15 |
| 1.3218 | B.188 | C.15 |
| 1.3219 | B.189 | C.15 |
| 1.3220 | B.190 | C.15 |
| 1.3221 | B.191 | C.15 |
| 1.3222 | B.192 | C.15 |
| 1.3223 | B.193 | C.15 |
| 1.3224 | B.194 | C.15 |
| 1.3225 | B.195 | C.15 |
| 1.3226 | B.196 | C.15 |
| 1.3227 | B.197 | C.15 |
| 1.3228 | B.198 | C.15 |
| 1.3229 | B.199 | C.15 |
| 1.3230 | B.200 | C.15 |
| 1.3231 | B.201 | C.15 |
| 1.3232 | B.202 | C.15 |
| 1.3233 | B.1 | C.16 |
| 1.3234 | B.2 | C.16 |
| 1.3235 | B.3 | C.16 |
| 1.3236 | B.4 | C.16 |
| 1.3237 | B.5 | C.16 |
| 1.3238 | B.6 | C.16 |
| 1.3239 | B.7 | C.16 |
| 1.3240 | B.8 | C.16 |
| 1.3241 | B.9 | C.16 |
| 1.3242 | B.10 | C.16 |
| 1.3243 | B.11 | C.16 |
| 1.3244 | B.12 | C.16 |
| 1.3245 | B.13 | C.16 |
| 1.3246 | B.14 | C.16 |
| 1.3247 | B.15 | C.16 |
| 1.3248 | B.16 | C.16 |
| 1.3249 | B.17 | C.16 |
| 1.3250 | B.18 | C.16 |
| 1.3251 | B.19 | C.16 |
| 1.3252 | B.20 | C.16 |
| 1.3253 | B.21 | C.16 |
| 1.3254 | B.22 | C.16 |
| 1.3255 | B.23 | C.16 |
| 1.3256 | B.24 | C.16 |
| 1.3257 | B.25 | C.16 |
| 1.3258 | B.26 | C.16 |
| 1.3259 | B.27 | C.16 |
| 1.3260 | B.28 | C.16 |
| 1.3261 | B.29 | C.16 |
| 1.3262 | B.30 | C.16 |
| 1.3263 | B.31 | C.16 |
| 1.3264 | B.32 | C.16 |
| 1.3265 | B.33 | C.16 |
| 1.3266 | B.34 | C.16 |
| 1.3267 | B.35 | C.16 |
| 1.3268 | B.36 | C.16 |
| 1.3269 | B.37 | C.16 |
| 1.3270 | B.38 | C.16 |
| 1.3271 | B.39 | C.16 |

TABLE 1-continued (compositions 1.1 to 1.3653):

| comp. no. | herbicide B | safener C |
|---|---|---|
| 1.3272 | B.40 | C.16 |
| 1.3273 | B.41 | C.16 |
| 1.3274 | B.42 | C.16 |
| 1.3275 | B.43 | C.16 |
| 1.3276 | B.44 | C.16 |
| 1.3277 | B.45 | C.16 |
| 1.3278 | B.46 | C.16 |
| 1.3279 | B.47 | C.16 |
| 1.3280 | B.48 | C.16 |
| 1.3281 | B.49 | C.16 |
| 1.3282 | B.50 | C.16 |
| 1.3283 | B.51 | C.16 |
| 1.3284 | B.52 | C.16 |
| 1.3285 | B.53 | C.16 |
| 1.3286 | B.54 | C.16 |
| 1.3287 | B.55 | C.16 |
| 1.3288 | B.56 | C.16 |
| 1.3289 | B.57 | C.16 |
| 1.3290 | B.58 | C.16 |
| 1.3291 | B.59 | C.16 |
| 1.3292 | B.60 | C.16 |
| 1.3293 | B.61 | C.16 |
| 1.3294 | B.62 | C.16 |
| 1.3295 | B.63 | C.16 |
| 1.3296 | B.64 | C.16 |
| 1.3297 | B.65 | C.16 |
| 1.3298 | B.66 | C.16 |
| 1.3299 | B.67 | C.16 |
| 1.3300 | B.68 | C.16 |
| 1.3301 | B.69 | C.16 |
| 1.3302 | B.70 | C.16 |
| 1.3303 | B.71 | C.16 |
| 1.3304 | B.72 | C.16 |
| 1.3305 | B.73 | C.16 |
| 1.3306 | B.74 | C.16 |
| 1.3307 | B.75 | C.16 |
| 1.3308 | B.76 | C.16 |
| 1.3309 | B.77 | C.16 |
| 1.3310 | B.78 | C.16 |
| 1.3311 | B.79 | C.16 |
| 1.3312 | B.80 | C.16 |
| 1.3313 | B.81 | C.16 |
| 1.3314 | B.82 | C.16 |
| 1.3315 | B.83 | C.16 |
| 1.3316 | B.84 | C.16 |
| 1.3317 | B.85 | C.16 |
| 1.3318 | B.86 | C.16 |
| 1.3319 | B.87 | C.16 |
| 1.3320 | B.88 | C.16 |
| 1.3321 | B.89 | C.16 |
| 1.3322 | B.90 | C.16 |
| 1.3323 | B.91 | C.16 |
| 1.3324 | B.92 | C.16 |
| 1.3325 | B.93 | C.16 |
| 1.3326 | B.94 | C.16 |
| 1.3327 | B.95 | C.16 |
| 1.3328 | B.96 | C.16 |
| 1.3329 | B.97 | C.16 |
| 1.3330 | B.98 | C.16 |
| 1.3331 | B.99 | C.16 |
| 1.3332 | B.100 | C.16 |
| 1.3333 | B.101 | C.16 |
| 1.3334 | B.102 | C.16 |
| 1.3335 | B.103 | C.16 |
| 1.3336 | B.104 | C.16 |
| 1.3337 | B.105 | C.16 |
| 1.3338 | B.106 | C.16 |
| 1.3339 | B.107 | C.16 |
| 1.3340 | B.108 | C.16 |
| 1.3341 | B.109 | C.16 |
| 1.3342 | B.110 | C.16 |
| 1.3343 | B.111 | C.16 |
| 1.3344 | B.112 | C.16 |
| 1.3345 | B.113 | C.16 |
| 1.3346 | B.114 | C.16 |
| 1.3347 | B.115 | C.16 |
| 1.3348 | B.116 | C.16 |
| 1.3349 | B.117 | C.16 |
| 1.3350 | B.118 | C.16 |
| 1.3351 | B.119 | C.16 |
| 1.3352 | B.120 | C.16 |
| 1.3353 | B.121 | C.16 |
| 1.3354 | B.122 | C.16 |
| 1.3355 | B.123 | C.16 |
| 1.3356 | B.124 | C.16 |
| 1.3357 | B.125 | C.16 |
| 1.3358 | B.126 | C.16 |
| 1.3359 | B.127 | C.16 |
| 1.3360 | B.128 | C.16 |
| 1.3361 | B.129 | C.16 |
| 1.3362 | B.130 | C.16 |
| 1.3363 | B.131 | C.16 |
| 1.3364 | B.132 | C.16 |
| 1.3365 | B.133 | C.16 |
| 1.3366 | B.134 | C.16 |
| 1.3367 | B.135 | C.16 |
| 1.3368 | B.136 | C.16 |
| 1.3369 | B.137 | C.16 |
| 1.3370 | B.138 | C.16 |
| 1.3371 | B.139 | C.16 |
| 1.3372 | B.140 | C.16 |
| 1.3373 | B.141 | C.16 |
| 1.3374 | B.142 | C.16 |
| 1.3375 | B.143 | C.16 |
| 1.3376 | B.144 | C.16 |
| 1.3377 | B.145 | C.16 |
| 1.3378 | B.146 | C.16 |
| 1.3379 | B.147 | C.16 |
| 1.3380 | B.148 | C.16 |
| 1.3381 | B.149 | C.16 |
| 1.3382 | B.150 | C.16 |
| 1.3383 | B.151 | C.16 |
| 1.3384 | B.152 | C.16 |
| 1.3385 | B.153 | C.16 |
| 1.3386 | B.154 | C.16 |
| 1.3387 | B.155 | C.16 |
| 1.3388 | B.156 | C.16 |
| 1.3389 | B.157 | C.16 |
| 1.3390 | B.158 | C.16 |
| 1.3391 | B.159 | C.16 |
| 1.3392 | B.160 | C.16 |
| 1.3393 | B.161 | C.16 |
| 1.3394 | B.162 | C.16 |
| 1.3395 | B.163 | C.16 |
| 1.3396 | B.164 | C.16 |
| 1.3397 | B.165 | C.16 |
| 1.3398 | B.166 | C.16 |
| 1.3399 | B.167 | C.16 |
| 1.3400 | B.168 | C.16 |
| 1.3401 | B.169 | C.16 |
| 1.3402 | B.170 | C.16 |
| 1.3403 | B.171 | C.16 |
| 1.3404 | B.172 | C.16 |
| 1.3405 | B.173 | C.16 |
| 1.3406 | B.174 | C.16 |
| 1.3407 | B.175 | C.16 |
| 1.3408 | B.176 | C.16 |
| 1.3409 | B.177 | C.16 |
| 1.3410 | B.178 | C.16 |
| 1.3411 | B.179 | C.16 |
| 1.3412 | B.180 | C.16 |
| 1.3413 | B.181 | C.16 |
| 1.3414 | B.182 | C.16 |
| 1.3415 | B.183 | C.16 |
| 1.3416 | B.184 | C.16 |
| 1.3417 | B.185 | C.16 |
| 1.3418 | B.186 | C.16 |
| 1.3419 | B.187 | C.16 |
| 1.3420 | B.188 | C.16 |
| 1.3421 | B.189 | C.16 |
| 1.3422 | B.190 | C.16 |
| 1.3423 | B.191 | C.16 |

TABLE 1-continued (compositions 1.1 to 1.3653):

| comp. no. | herbicide B | safener C |
|---|---|---|
| 1.3424 | B.192 | C.16 |
| 1.3425 | B.193 | C.16 |
| 1.3426 | B.194 | C.16 |
| 1.3427 | B.195 | C.16 |
| 1.3428 | B.196 | C.16 |
| 1.3429 | B.197 | C.16 |
| 1.3430 | B.198 | C.16 |
| 1.3431 | B.199 | C.16 |
| 1.3432 | B.200 | C.16 |
| 1.3433 | B.201 | C.16 |
| 1.3434 | B.202 | C.16 |
| 1.3435 | B.1 | C.17 |
| 1.3436 | B.2 | C.17 |
| 1.3437 | B.3 | C.17 |
| 1.3438 | B.4 | C.17 |
| 1.3439 | B.5 | C.17 |
| 1.3440 | B.6 | C.17 |
| 1.3441 | B.7 | C.17 |
| 1.3442 | B.8 | C.17 |
| 1.3443 | B.9 | C.17 |
| 1.3444 | B.10 | C.17 |
| 1.3445 | B.11 | C.17 |
| 1.3446 | B.12 | C.17 |
| 1.3447 | B.13 | C.17 |
| 1.3448 | B.14 | C.17 |
| 1.3449 | B.15 | C.17 |
| 1.3450 | B.16 | C.17 |
| 1.3451 | B.17 | C.17 |
| 1.3452 | B.18 | C.17 |
| 1.3453 | B.19 | C.17 |
| 1.3454 | B.20 | C.17 |
| 1.3455 | B.21 | C.17 |
| 1.3456 | B.22 | C.17 |
| 1.3457 | B.23 | C.17 |
| 1.3458 | B.24 | C.17 |
| 1.3459 | B.25 | C.17 |
| 1.3460 | B.26 | C.17 |
| 1.3461 | B.27 | C.17 |
| 1.3462 | B.28 | C.17 |
| 1.3463 | B.29 | C.17 |
| 1.3464 | B.30 | C.17 |
| 1.3465 | B.31 | C.17 |
| 1.3466 | B.32 | C.17 |
| 1.3467 | B.33 | C.17 |
| 1.3468 | B.34 | C.17 |
| 1.3469 | B.35 | C.17 |
| 1.3470 | B.36 | C.17 |
| 1.3471 | B.37 | C.17 |
| 1.3472 | B.38 | C.17 |
| 1.3473 | B.39 | C.17 |
| 1.3474 | B.40 | C.17 |
| 1.3475 | B.41 | C.17 |
| 1.3476 | B.42 | C.17 |
| 1.3477 | B.43 | C.17 |
| 1.3478 | B.44 | C.17 |
| 1.3479 | B.45 | C.17 |
| 1.3480 | B.46 | C.17 |
| 1.3481 | B.47 | C.17 |
| 1.3482 | B.48 | C.17 |
| 1.3483 | B.49 | C.17 |
| 1.3484 | B.50 | C.17 |
| 1.3485 | B.51 | C.17 |
| 1.3486 | B.52 | C.17 |
| 1.3487 | B.53 | C.17 |
| 1.3488 | B.54 | C.17 |
| 1.3489 | B.55 | C.17 |
| 1.3490 | B.56 | C.17 |
| 1.3491 | B.57 | C.17 |
| 1.3492 | B.58 | C.17 |
| 1.3493 | B.59 | C.17 |
| 1.3494 | B.60 | C.17 |
| 1.3495 | B.61 | C.17 |
| 1.3496 | B.62 | C.17 |
| 1.3497 | B.63 | C.17 |
| 1.3498 | B.64 | C.17 |
| 1.3499 | B.65 | C.17 |
| 1.3500 | B.66 | C.17 |
| 1.3501 | B.67 | C.17 |
| 1.3502 | B.68 | C.17 |
| 1.3503 | B.69 | C.17 |
| 1.3504 | B.70 | C.17 |
| 1.3505 | B.71 | C.17 |
| 1.3506 | B.72 | C.17 |
| 1.3507 | B.73 | C.17 |
| 1.3508 | B.74 | C.17 |
| 1.3509 | B.75 | C.17 |
| 1.3510 | B.76 | C.17 |
| 1.3511 | B.77 | C.17 |
| 1.3512 | B.78 | C.17 |
| 1.3513 | B.79 | C.17 |
| 1.3514 | B.80 | C.17 |
| 1.3515 | B.81 | C.17 |
| 1.3516 | B.82 | C.17 |
| 1.3517 | B.83 | C.17 |
| 1.3518 | B.84 | C.17 |
| 1.3519 | B.85 | C.17 |
| 1.3520 | B.86 | C.17 |
| 1.3521 | B.87 | C.17 |
| 1.3522 | B.88 | C.17 |
| 1.3523 | B.89 | C.17 |
| 1.3524 | B.90 | C.17 |
| 1.3525 | B.91 | C.17 |
| 1.3526 | B.92 | C.17 |
| 1.3527 | B.93 | C.17 |
| 1.3528 | B.94 | C.17 |
| 1.3529 | B.95 | C.17 |
| 1.3530 | B.96 | C.17 |
| 1.3531 | B.97 | C.17 |
| 1.3532 | B.98 | C.17 |
| 1.3533 | B.99 | C.17 |
| 1.3534 | B.100 | C.17 |
| 1.3535 | B.101 | C.17 |
| 1.3536 | B.102 | C.17 |
| 1.3537 | B.103 | C.17 |
| 1.3538 | B.104 | C.17 |
| 1.3539 | B.105 | C.17 |
| 1.3540 | B.106 | C.17 |
| 1.3541 | B.107 | C.17 |
| 1.3542 | B.108 | C.17 |
| 1.3543 | B.109 | C.17 |
| 1.3544 | B.110 | C.17 |
| 1.3545 | B.111 | C.17 |
| 1.3546 | B.112 | C.17 |
| 1.3547 | B.113 | C.17 |
| 1.3548 | B.114 | C.17 |
| 1.3549 | B.115 | C.17 |
| 1.3550 | B.116 | C.17 |
| 1.3551 | B.117 | C.17 |
| 1.3552 | B.118 | C.17 |
| 1.3553 | B.119 | C.17 |
| 1.3554 | B.120 | C.17 |
| 1.3555 | B.121 | C.17 |
| 1.3556 | B.122 | C.17 |
| 1.3557 | B.123 | C.17 |
| 1.3558 | B.124 | C.17 |
| 1.3559 | B.125 | C.17 |
| 1.3560 | B.126 | C.17 |
| 1.3561 | B.127 | C.17 |
| 1.3562 | B.128 | C.17 |
| 1.3563 | B.129 | C.17 |
| 1.3564 | B.130 | C.17 |
| 1.3565 | B.131 | C.17 |
| 1.3566 | B.132 | C.17 |
| 1.3567 | B.133 | C.17 |
| 1.3568 | B.134 | C.17 |
| 1.3569 | B.135 | C.17 |
| 1.3570 | B.136 | C.17 |
| 1.3571 | B.137 | C.17 |
| 1.3572 | B.138 | C.17 |
| 1.3573 | B.139 | C.17 |
| 1.3574 | B.140 | C.17 |
| 1.3575 | B.141 | C.17 |

TABLE 1-continued (compositions 1.1 to 1.3653):

| comp. no. | herbicide B | safener C |
|---|---|---|
| 1.3576 | B.142 | C.17 |
| 1.3577 | B.143 | C.17 |
| 1.3578 | B.144 | C.17 |
| 1.3579 | B.145 | C.17 |
| 1.3580 | B.146 | C.17 |
| 1.3581 | B.147 | C.17 |
| 1.3582 | B.148 | C.17 |
| 1.3583 | B.149 | C.17 |
| 1.3584 | B.150 | C.17 |
| 1.3585 | B.151 | C.17 |
| 1.3586 | B.152 | C.17 |
| 1.3587 | B.153 | C.17 |
| 1.3588 | B.154 | C.17 |
| 1.3589 | B.155 | C.17 |
| 1.3590 | B.156 | C.17 |
| 1.3591 | B.157 | C.17 |
| 1.3592 | B.158 | C.17 |
| 1.3593 | B.159 | C.17 |
| 1.3594 | B.160 | C.17 |
| 1.3595 | B.161 | C.17 |
| 1.3596 | B.162 | C.17 |
| 1.3597 | B.163 | C.17 |
| 1.3598 | B.164 | C.17 |
| 1.3599 | B.165 | C.17 |
| 1.3600 | B.166 | C.17 |
| 1.3601 | B.167 | C.17 |
| 1.3602 | B.168 | C.17 |
| 1.3603 | B.169 | C.17 |
| 1.3604 | B.170 | C.17 |
| 1.3605 | B.171 | C.17 |
| 1.3606 | B.172 | C.17 |
| 1.3607 | B.173 | C.17 |
| 1.3608 | B.174 | C.17 |
| 1.3609 | B.175 | C.17 |
| 1.3610 | B.176 | C.17 |
| 1.3611 | B.177 | C.17 |
| 1.3612 | B.178 | C.17 |
| 1.3613 | B.179 | C.17 |
| 1.3614 | B.180 | C.17 |
| 1.3615 | B.181 | C.17 |
| 1.3616 | B.182 | C.17 |
| 1.3617 | B.183 | C.17 |
| 1.3618 | B.184 | C.17 |
| 1.3619 | B.185 | C.17 |
| 1.3620 | B.186 | C.17 |
| 1.3621 | B.187 | C.17 |
| 1.3622 | B.188 | C.17 |
| 1.3623 | B.189 | C.17 |
| 1.3624 | B.190 | C.17 |
| 1.3625 | B.191 | C.17 |
| 1.3626 | B.192 | C.17 |
| 1.3627 | B.193 | C.17 |
| 1.3628 | B.194 | C.17 |
| 1.3629 | B.195 | C.17 |
| 1.3630 | B.196 | C.17 |
| 1.3631 | B.197 | C.17 |
| 1.3632 | B.198 | C.17 |
| 1.3633 | B.199 | C.17 |
| 1.3634 | B.200 | C.17 |
| 1.3635 | B.201 | C.17 |
| 1.3636 | B.202 | C.17 |
| 1.3637 | — | C.1 |
| 1.3638 | — | C.2 |
| 1.3639 | — | C.3 |
| 1.3640 | — | C.4 |
| 1.3641 | — | C.5 |
| 1.3642 | — | C.6 |
| 1.3643 | — | C.7 |
| 1.3644 | — | C.8 |
| 1.3645 | — | C.9 |
| 1.3646 | — | C.10 |
| 1.3647 | — | C.11 |
| 1.3648 | — | C.12 |
| 1.3649 | — | C.13 |
| 1.3650 | — | C.14 |
| 1.3651 | — | C.15 |
| 1.3652 | — | C.16 |
| 1.3653 | — | C.17 |

The specific number for each single composition is deductible as follows:

Composition 1.203 e.g. comprises the compound I.a.25, clethodim (B.1) and benoxacor (C.1) (see table B, entry B.1 and table C, entry C.1).

Composition 2. 203 e.g. comprises the compound I.a.1, clethodim (B.1) and benoxacor (C.1) (see table B, entry B.1 and table C, entry C.1).

Composition 7.203 for example comprises imazapyr (B.35) (see the definition for compositions 7.1 to 7.3635 below), and the compound I.a.25, clethodim (B.1) and benoxacor (C.1) (see table B, entry B.1 and table C, entry C.1).

Also especially preferred are compositions 2.1. to 2.3653 which differ from the corresponding compositions 1.1 to 1.3653 only in that they comprise as the active compound A the phenylpyrimidine of formula (I.a.1).

Also especially preferred are compositions 3.1. to 3.3653 which differ from the corresponding compositions 1.1 to 1.3653 only in that they additionally comprise B.2 as further herbicide B.

Also especially preferred are compositions 4.1. to 4.3653 which differ from the corresponding compositions 1.1 to 1.3653 only in that they additionally comprise B.8 as further herbicide B.

Also especially preferred are compositions 5.1. to 5.3653 which differ from the corresponding compositions 1.1 to 1.3653 only in that they additionally comprise B.30 as further herbicide B.

Also especially preferred are compositions 6.1. to 6.3653 which differ from the corresponding compositions 1.1 to 1.3653 only in that they additionally comprise B.32 as further herbicide B.

Also especially preferred are compositions 7.1. to 7.3653 which differ from the corresponding compositions 1.1 to 1.3653 only in that they additionally comprise B.35 as further herbicide B.

Also especially preferred are compositions 8.1. to 8.3653 which differ from the corresponding compositions 1.1 to 1.3653 only in that they additionally comprise B.38 as further herbicide B.

Also especially preferred are compositions 9.1. to 9.3653 which differ from the corresponding compositions 1.1 to 1.3653 only in that they additionally comprise B.40/as further herbicide B.

Also especially preferred are compositions 10.1. to 10.3653 which differ from the corresponding compositions 1.1 to 1.3653 only in that they additionally comprise B.51 as further herbicide B.

Also especially preferred are compositions 11.1. to 11.3653 which differ from the corresponding compositions 1.1 to 1.3653 only in that they additionally comprise B.55 as further herbicide B.

Also especially preferred are compositions 12.1. to 12.3653 which differ from the corresponding compositions 1.1 to 1.3653 only in that they additionally comprise B.56 as further herbicide B.

Also especially preferred are compositions 13.1. to 13.3653 which differ from the corresponding compositions 1.1 to 1.3653 only in that they additionally comprise B.64 as further herbicide B.

Also especially preferred are compositions 14.1. to 14.3653 which differ from the corresponding compositions 1.1 to 1.3653 only in that they additionally comprise B.66 as further herbicide B.

Also especially preferred are compositions 15.1. to 15.3653 which differ from the corresponding compositions 1.1 to 1.3653 only in that they additionally comprise B.67 as further herbicide B.

Also especially preferred are compositions 16.1. to 16.3653 which differ from the corresponding compositions 1.1 to 1.3653 only in that they additionally comprise B.68 as further herbicide B.

Also especially preferred are compositions 17.1. to 17.3653 which differ from the corresponding compositions 1.1 to 1.3653 only in that they additionally comprise B.69 as further herbicide B.

Also especially preferred are compositions 18.1. to 18.3653 which differ from the corresponding compositions 1.1 to 1.3653 only in that they additionally comprise B.73 as further herbicide B.

Also especially preferred are compositions 19.1. to 19.3653 which differ from the corresponding compositions 1.1 to 1.3653 only in that they additionally comprise B.76 as further herbicide B.

Also especially preferred are compositions 20.1. to 20.3653 which differ from the corresponding compositions 1.1 to 1.3653 only in that they additionally comprise B.81 as further herbicide B.

Also especially preferred are compositions 21.1. to 21.3653 which differ from the corresponding compositions 1.1 to 1.3653 only in that they additionally comprise B.82 as further herbicide B.

Also especially preferred are compositions 22.1. to 22.3653 which differ from the corresponding compositions 1.1 to 1.3653 only in that they additionally comprise B.85 as further herbicide B.

Also especially preferred are compositions 23.1. to 23.3653 which differ from the corresponding compositions 1.1 to 1.3653 only in that they additionally comprise B.88 as further herbicide B.

Also especially preferred are compositions 24.1. to 24.3653 which differ from the corresponding compositions 1.1 to 1.3653 only in that they additionally comprise B.89 as further herbicide B.

Also especially preferred are compositions 25.1. to 25.3653 which differ from the corresponding compositions 1.1 to 1.3653 only in that they additionally comprise B.94 as further herbicide B.

Also especially preferred are compositions 26.1. to 26.3653 which differ from the corresponding compositions 1.1 to 1.3653 only in that they additionally comprise B.95 as further herbicide B.

Also especially preferred are compositions 27.1. to 27.3653 which differ from the corresponding compositions 1.1 to 1.3653 only in that they additionally comprise B.98 as further herbicide B.

Also especially preferred are compositions 28.1. to 28.3653 which differ from the corresponding compositions 1.1 to 1.3653 only in that they additionally comprise B.100 as further herbicide B.

Also especially preferred are compositions 29.1. to 29.3653 which differ from the corresponding compositions 1.1 to 1.3653 only in that they additionally comprise B.103 as further herbicide B.

Also especially preferred are compositions 30.1. to 30.3653 which differ from the corresponding compositions 1.1 to 1.3653 only in that they additionally comprise B.103 and B.67 as further herbicides B.

Also especially preferred are compositions 31.1. to 31.3653 which differ from the corresponding compositions 1.1 to 1.3653 only in that they additionally comprise B.103 and B.76 as further herbicides B.

Also especially preferred are compositions 32.1. to 32.3653 which differ from the corresponding compositions 1.1 to 1.3653 only in that they additionally comprise B.103 and B.82 as further herbicides B.

Also especially preferred are compositions 33.1. to 33.3653 which differ from the corresponding compositions 1.1 to 1.3653 only in that they additionally comprise B.104 as further herbicide B.

Also especially preferred are compositions 34.1. to 34.3653 which differ from the corresponding compositions 1.1 to 1.3653 only in that they additionally comprise B.104 and B.67 as further herbicides B.

Also especially preferred are compositions 35.1. to 35.3653 which differ from the corresponding compositions 1.1 to 1.3653 only in that they additionally comprise B.104 and B.76 as further herbicides B.

Also especially preferred are compositions 36.1. to 36.3653 which differ from the corresponding compositions 1.1 to 1.3653 only in that they additionally comprise B.104 and B.82 as further herbicides B.

Also especially preferred are compositions 37.1. to 37.3653 which differ from the corresponding compositions 1.1 to 1.3653 only in that they additionally comprise B.106 as further herbicide B.

Also especially preferred are compositions 38.1. to 38.3653 which differ from the corresponding compositions 1.1 to 1.3653 only in that they additionally comprise B.107 as further herbicide B.

Also especially preferred are compositions 39.1. to 39.3653 which differ from the corresponding compositions 1.1 to 1.3653 only in that they additionally comprise B. 107 and B.67 as further herbicides B.

Also especially preferred are compositions 40.1. to 40.3653 which differ from the corresponding compositions 1.1 to 1.3653 only in that they additionally comprise B. 107 and B.76/as further herbicides B.

Also especially preferred are compositions 41.1. to 41.3653 which differ from the corresponding compositions 1.1 to 1.3653 only in that they additionally comprise B. 107 and B.82 as further herbicides B.

Also especially preferred are compositions 42.1. to 42.3653 which differ from the corresponding compositions 1.1 to 1.3653 only in that they additionally comprise B.109 as further herbicide B.

Also especially preferred are compositions 43.1. to 43.3653 which differ from the corresponding compositions 1.1 to 1.3653 only in that they additionally comprise B.111 as further herbicide B.

Also especially preferred are compositions 44.1. to 44.3653 which differ from the corresponding compositions 1.1 to 1.3653 only in that they additionally comprise B.111 and B.67 as further herbicides B.

Also especially preferred are compositions 45.1. to 45.3653 which differ from the corresponding compositions 1.1 to 1.3653 only in that they additionally comprise B.111 and B.76 as further herbicides B.

Also especially preferred are compositions 46.1. to 46.3653 which differ from the corresponding compositions 1.1 to 1.3653 only in that they additionally comprise B.111 and B.82 as further herbicides B.

Also especially preferred are compositions 47.1. to 47.3653 which differ from the corresponding compositions 1.1 to 1.3653 only in that they additionally comprise B. 116 as further herbicide B.

Also especially preferred are compositions 48.1. to 48.3653 which differ from the corresponding compositions 1.1 to 1.3653 only in that they additionally comprise B.116 and B.67 as further herbicides B.

Also especially preferred are compositions 49.1. to 49.3653 which differ from the corresponding compositions 1.1 to 1.3653 only in that they additionally comprise B.116 and B.94 as further herbicides B.

Also especially preferred are compositions 50.1. to 50.3653 which differ from the corresponding compositions 1.1 to 1.3653 only in that they additionally comprise B.116 and B.103 as further herbicides B.

Also especially preferred are compositions 51.1. to 51.3653 which differ from the corresponding compositions 1.1 to 1.3653 only in that they additionally comprise B.116 and B.128 as further herbicides B.

Also especially preferred are compositions 52.1. to 52.3653 which differ from the corresponding compositions 1.1 to 1.3653 only in that they additionally comprise B.116 and B.104 as further herbicides B.

Also especially preferred are compositions 53.1. to 53.3653 which differ from the corresponding compositions 1.1 to 1.3653 only in that they additionally comprise B.116 and B.107 as further herbicides B.

Also especially preferred are compositions 54.1. to 54.3653 which differ from the corresponding compositions 1.1 to 1.3653 only in that they additionally comprise B.116 and B.111 as further herbicides B.

Also especially preferred are compositions 55.1. to 55.3653 which differ from the corresponding compositions 1.1 to 1.3653 only in that they additionally comprise B.122 as further herbicide B.

Also especially preferred are compositions 56.1. to 56.3653 which differ from the corresponding compositions 1.1 to 1.3653 only in that they additionally comprise B.126 as further herbicide B.

Also especially preferred are compositions 57.1. to 57.3653 which differ from the corresponding compositions 1.1 to 1.3653 only in that they additionally comprise B.128 as further herbicide B.

Also especially preferred are compositions 58.1. to 58.3653 which differ from the corresponding compositions 1.1 to 1.3653 only in that they additionally comprise B.131 s further herbicide B.

Also especially preferred are compositions 59.1. to 59.3653 which differ from the corresponding compositions 1.1 to 1.3653 only in that they additionally comprise B.132 as further herbicide B.

Also especially preferred are compositions 60.1. to 60.3653 which differ from the corresponding compositions 1.1 to 1.3653 only in that they additionally comprise B.133 as further herbicide B.

Also especially preferred are compositions 61.1. to 61.3653 which differ from the corresponding compositions 1.1 to 1.3653 only in that they additionally comprise B.135 as further herbicide B.

Also especially preferred are compositions 62.1. to 62.3653 which differ from the corresponding compositions 1.1 to 1.3653 only in that they additionally comprise B.137 as further herbicide B.

Also especially preferred are compositions 63.1. to 63.3653 which differ from the corresponding compositions 11.1 to 1.3653 only in that they additionally comprise B.138 as further herbicide B.

Also especially preferred are compositions 64.1. to 64.3653 which differ from the corresponding compositions 1.1 to 1.3653 only in that they additionally comprise B.140 is further herbicide B.

Also especially preferred are compositions 65.1. to 65.3653 which differ from the corresponding compositions 1.1 to 1.3653 only in that they additionally comprise B.145 as further herbicide B.

Also especially preferred are compositions 66.1. to 66.3653 which differ from the corresponding compositions 1.1 to 1.3653 only in that they additionally comprise B.153 as further herbicide B.

Also especially preferred are compositions 67.1. to 67.3653 which differ from the corresponding compositions 1.1 to 1.3653 only in that they additionally comprise B.156 as further herbicide B.

Also especially preferred are compositions 68.1. to 68.3653 which differ from the corresponding compositions 1.1 to 1.3653 only in that they additionally comprise B.171 as further herbicide B.

Also especially preferred are compositions 69.1. to 69.3653 which differ from the corresponding compositions 1.1 to 1.3653 only in that they additionally comprise B.174 as further herbicide B.

Also especially preferred are compositions 70.1. to 70.3653 which differ from the corresponding compositions 1.1 to 1.3653 only in that they comprise as the active compound A the phenylpyrimidine of formula (I.a.31).

Also especially preferred are compositions 71.1. to 71.3653 which differ from the corresponding compositions 1.1 to 1.3653 only in that they comprise as the active compound A the phenylpyrimidine of formula (I.a.37).

Also especially preferred are compositions 72.1. to 72.3653 which differ from the corresponding compositions 1.1 to 1.3653 only in that they comprise as the active compound A the phenylpyrimidine of formula (I.a.49).

Also especially preferred are compositions 73.1. to 73.3653 which differ from the corresponding compositions 1.1 to 1.3653 only in that they comprise as the active compound A the phenylpyrimidine of formula (I.a.55).

Also especially preferred are compositions 74.1. to 74.3653 which differ from the corresponding compositions 1.1 to 1.3653 only in that they comprise as the active compound A the phenylpyrimidine of formula (I.a.61).

Also especially preferred are compositions 75.1. to 75.3653 which differ from the corresponding compositions 1.1 to 1.3653 only in that they comprise as the active compound A the phenylpyrimidine of formula (I.a.73).

Also especially preferred are compositions 76.1. to 76.3653 which differ from the corresponding compositions 1.1 to 1.3653 only in that they comprise as the active compound A the phenylpyrimidine of formula (I.a.685).

Also especially preferred are compositions 77.1. to 77.3653 which differ from the corresponding compositions 1.1 to 1.3653 only in that they comprise as the active compound A the phenylpyrimidine of formula (I.a.697).

Also especially preferred are compositions 78.1. to 78.3653 which differ from the corresponding compositions 1.1 to 1.3653 only in that they comprise as the active compound A the phenylpyrimidine of formula (I.a.1021).

Also especially preferred are compositions 79.1. to 79.3653 which differ from the corresponding compositions 1.1 to 1.3653 only in that they comprise as the active compound A the phenylpyrimidine of formula (I.a.1033).

Also especially preferred are compositions 80.1. to 80.3653 which differ from the corresponding compositions 1.1 to 1.3653 only in that they comprise as the active compound A the phenylpyrimidine of formula (I.b.31).

The invention also relates to agrochemical compositions comprising an auxiliary and at least one composition according to the invention.

An agrochemical composition comprises a pesticidally effective amount of at least one composition according to the invention. The term "effective amount" denotes an amount of the active ingredients, which is sufficient for controlling unwanted plants, especially for controlling unwanted plants in cultivated plants and which does not result in a substantial damage to the treated plants. Such an amount can vary in a broad range and is dependent on various factors, such as the plants to be controlled, the treated cultivated plant or material, the climatic conditions and the specific composition according to the invention used.

The compounds A and optionally B and/or C, their N-oxides, salts or derivatives can be converted into customary types of agrochemical compositions, e.g. solutions, emulsions, suspensions, dusts, powders, pastes, granules, pressings, capsules, and mixtures thereof. Examples for agrochemical composition types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further agrochemical compositions types are defined in the "Catalogue of pesticide formulation types and international coding system", Technical Monograph No. 2, 6$^{th}$ Ed. May 2008, CropLife International.

The agrochemical compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e.g. toluene, paraffin, tetrahydronaphthalene, alkylated naphthalenes; alcohols, e.g. ethanol, propanol, butanol, benzylalcohol, cyclohexanol; glycols; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharides, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emulsifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are home- or copolymers of vinylpyrrolidone, vinylalcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds, which have a neglectable or even no pesticidal activity themselves, and which improve the biological performance of the compound I on the target. Examples are surfactants, mineral or vegetable oils, and other auxiliaries. Further examples are listed by Knowles, Adjuvants and additives, Agrow Reports DS256, T&F Informa UK, 2006, chapter 5.

Suitable thickeners are polysaccharides (e.g. xanthan gum, carboxymethylcellulose), inorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants).

Suitable tackifiers or binders are polyvinylpyrrolidons, polyvinylacetates, polyvinyl alcohols, polyacrylates, biological or synthetic waxes, and cellulose ethers.

Examples for agrochemical composition types and their preparation are:

i) Water-soluble concentrates (SL, LS)

10-60 wt % of a composition according to the invention and 5-15 wt % wetting agent (e.g. alcohol alkoxylates) are dissolved in water and/or in a water-soluble solvent (e.g. alcohols) ad 100 wt %. The active substance dissolves upon dilution with water.

ii) Dispersible concentrates (DC)

5-25 wt % of a composition according to the invention and 1-10 wt % dispersant (e.g. polyvinylpyrrolidone) are dissolved in organic solvent (e.g. cyclohexanone) ad 100 wt %. Dilution with water gives a dispersion.

iii) Emulsifiable concentrates (EC)

15-70 wt % of a composition according to the invention and 5-10 wt % emulsifiers (e.g. calcium dodecylbenzenesulfonate and castor oil ethoxylate) are dissolved in water-insoluble organic solvent (e.g. aromatic hydrocarbon) ad 100 wt %. Dilution with water gives an emulsion.

iv) Emulsions (EW, EO, ES)

5-40 wt % of a composition according to the invention and 1-10 wt % emulsifiers (e.g. calcium dodecylbenzenesulfonate and castor oil ethoxylate) are dissolved in 20-40 wt % water-insoluble organic solvent (e.g. aromatic hydrocarbon). This mixture is introduced into water ad 100 wt % by means of an emulsifying machine and made into a homogeneous emulsion. Dilution with water gives an emulsion.

v) Suspensions (SC, OD, FS)

In an agitated ball mill, 20-60 wt % of a composition according to the invention are comminuted with addition of 2-10 wt % dispersants and wetting agents (e.g. sodium lignosulfonate and alcohol ethoxylate), 0.1-2 wt % thickener (e.g. xanthan gum) and water ad 100 wt % to give a fine active substance suspension. Dilution with water gives a stable suspension of the active substance. For FS type composition up to 40 wt % binder (e.g. polyvinylalcohol) is added.

vi) Water-dispersible granules and water-soluble granules (WG, SG)

50-80 wt % of a composition according to the invention are ground finely with addition of dispersants and wetting agents (e.g. sodium lignosulfonate and alcohol ethoxylate) ad 100 wt % and prepared as water-dispersible or water-soluble granules by means of technical appliances (e.g. extrusion, spray tower, fluidized bed). Dilution with water gives a stable dispersion or solution of the active substance.

vii) Water-dispersible powders and water-soluble powders (WP, SP, WS) 50-80 wt % of a composition according to the invention are ground in a rotor-stator mill with addition of 1-5 wt % dispersants (e.g. sodium lignosulfonate), 1-3 wt % wetting agents (e.g. alcohol ethoxylate) and solid carrier (e.g. silica gel) ad 100 wt %. Dilution with water gives a stable dispersion or solution of the active substance.

viii) Gel (GW, GF)

In an agitated ball mill, 5-25 wt % of a composition according to the invention are comminuted with addition of 3-10 wt % dispersants (e.g. sodium lignosulfonate), 1-5 wt % thickener (e.g. carboxymethylcellulose) and water ad 100 wt % to give a fine suspension of the active substance. Dilution with water gives a stable suspension of the active substance.

iv) Microemulsion (ME)

5-20 wt % of a composition according to the invention are added to 5-30 wt % organic solvent blend (e.g. fatty acid dimethylamide and cyclohexanone), 10-25 wt % surfactant blend (e.g. alcohol ethoxylate and arylphenol ethoxylate), and water ad 100%. This mixture is stirred for 1 h to produce spontaneously a thermodynamically stable microemulsion.

iv) Microcapsules (CS)

An oil phase comprising 5-50 wt % of a composition according to the invention, 0-40 wt % water insoluble organic solvent (e.g. aromatic hydrocarbon), 2-15 wt % acrylic monomers (e.g. methylmethacrylate, methacrylic acid and a di- or triacrylate) are dispersed into an aqueous solution of a protective colloid (e.g. polyvinyl alcohol). Radical polymerization initiated by a radical initiator results in the formation of poly(meth)acrylate microcapsules. Alternatively, an oil phase comprising 5-50 wt % of a compound I according to the invention, 0-40 wt % water insoluble organic solvent (e.g. aromatic hydrocarbon), and an isocyanate monomer (e.g. diphenylmethene-4,4'-diisocyanate) are dispersed into an aqueous solution of a protective colloid (e.g. polyvinyl alcohol). The addition of a polyamine (e.g. hexamethylenediamine) results in the formation of polyurea microcapsules. The monomers amount to 1-10 wt %. The wt % relate to the total CS composition.

ix) Dustable powders (DP, DS)

1-10 wt % of a composition according to the invention are ground finely and mixed intimately with solid carrier (e.g. finely divided kaolin) ad 100 wt %.

x) Granules (GR, FG)

0.5-30 wt % of a composition according to the invention is ground finely and associated with solid carrier (e.g. silicate) ad 100 wt %. Granulation is achieved by extrusion, spray-drying or the fluidized bed.

xi) Ultra-low volume liquids (UL)

1-50 wt % of a composition according to the invention are dissolved in organic solvent (e.g. aromatic hydrocarbon) ad 100 wt %.

The agrochemical compositions types i) to xi) may optionally comprise further auxiliaries, such as 0.1-1 wt % bactericides, 5-15 wt % anti-freezing agents, 0.1-1 wt % anti-foaming agents, and 0.1-1 wt % colorants.

The agrochemical compositions generally comprise between 0.01 and 95%, preferably between 0.1 and 90%, and in particular between 0.5 and 75%, by weight of active substance. The active substances are employed in a purity of from 90% to 100%, preferably from 95% to 100% (according to NMR spectrum).

Solutions for seed treatment (LS), suspoemulsions (SE), flowable concentrates (FS), powders for dry treatment (DS), water-dispersible powders for slurry treatment (WS), water-soluble powders (SS), emulsions (ES), emulsifiable concentrates (EC) and gels (GF) are usually employed for the purposes of treatment of plant propagation materials, particularly seeds. The compositions in question give, after two-to-tenfold dilution, active substance concentrations of from 0.01 to 60% by weight, preferably from 0.1 to 40% by weight, in the ready-to-use preparations. Application can be carried out before or during sowing.

Methods for applying phenylpyrimidines of formula (I) and compositions thereof, respectively, on to plant propagation material, especially seeds include dressing, coating, pelleting, dusting, soaking and in-furrow application methods of the propagation material. Preferably, phenylpyrimidines of formula (I) or the compositions thereof, respectively, are applied on to the plant propagation material by a method such that germination is not induced, e.g. by seed dressing, pelleting, coating and dusting.

Various types of oils, wetters, adjuvants, fertilizer, or micronutrients, and further pesticides (e.g. herbicides, insecticides, fungicides, growth regulators, safeners) may be added to the active substances or the compositions comprising them as premix or, if appropriate not until immediately prior to use (tank mix). These agents can be admixed with the compositions according to the invention in a weight ratio of 1:100 to 100:1, preferably 1:10 to 10:1.

The user applies the agrochemical composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, either individual components of the agrochemical composition according to the invention or partially premixed components, e.g. agrochemical components comprising at least one phenylpyrimidine of formula (I) and/or active substances from the groups B and/or C may be mixed by the user in a spray tank and further auxiliaries and additives may be added, if appropriate.

In a further embodiment, individual components of the agrochemical composition according to the invention such as parts of a kit or parts of a binary or ternary mixture may be mixed by the user himself in a spray tank and further auxiliaries may be added, if appropriate.

In a further embodiment, either individual components of the agrochemical composition according to the invention or partially premixed components, e.g. components comprising at least one phenylpyrimidine of formula (I) and active substances from the groups B and/or C, can be applied jointly (e.g. after tank mix) or consecutively.

Accordingly, a first embodiment of the invention relates to compositions in the form of a agrochemical composition formulated as a 1-component composition comprising the at least one active phenylpyrimidine of formula (I) (active compound A) and at least one further active compound selected from the herbicides B and the safeners C and also a solid or liquid carrier and, if appropriate, one or more surfactants.

Accordingly, a second embodiment of the invention relates to compositions in the form of a agrochemical composition formulated as a 2-component composition comprising a first formulation (component) comprising the at least one active compound A, a solid or liquid carrier and, if appropriate, one or more surfactants, and a second component comprising at least one further active compound selected from the herbicides B and safeners C, a solid or liquid carrier and, if appropriate, one or more surfactants.

The active compound A and the at least one further active compound B and/or C can be formulated and applied jointly or separately, simultaneously or in succession, before, during or after the emergence of the plants. In case of separate application, the order of the application of the active compounds A, B and/or C is of minor importance. The only thing that is important is that the at least one active compound A and the at least one further active compound B and/or C are present simultaneously at the site of action, i.e. are at the same time in contact with or taken up by the plant to be controlled/safened.

The compositions according to the invention are suitable as herbicides. They are suitable as such or as an appropriately formulated composition (agrochemical composition).

The compositions according to the invention control vegetation on non-crop areas very efficiently, especially at high rates of application. They act against broad-leafed weeds and grass weeds in crops such as wheat, rice, corn, soybeans and cotton without causing any significant damage to the crop plants. This effect is mainly observed at low rates of application.

The compositions according to the invention are applied to the plants mainly by spraying the leaves. Here, the application can be carried out using, for example, water as carrier by customary spraying techniques using spray liquor amounts of from about 100 to 1000 l/ha (for example from 300 to 400 l/ha). The herbicidal compositions may also be applied by the low-volume or the ultra-low-volume method, or in the form of microgranules.

Application of the herbicidal compositions according to the present invention can be done before, during and/or after, preferably during and/or after, the emergence of the undesirable plants.

The herbicidal compositions according to the present invention can be applied pre- or post-emergence or together with the seed of a crop plant. It is also possible to apply the compounds and compositions by applying seed, pretreated with a composition of the invention, of a crop plant. If the active compounds A and B and, if appropriate C, are less well tolerated by certain crop plants, application techniques may be used in which the herbicidal compositions are sprayed, with the aid of the spraying equipment, in such a way that as far as possible they do not come into contact with the leaves of the sensitive crop plants, while the active compounds reach the leaves of undesirable plants growing underneath, or the bare soil surface (post-directed, lay-by).

In a further embodiment, the composition according to the invention can be applied by treating seed. The treatment of seed comprises essentially all procedures familiar to the person skilled in the art (seed dressing, seed coating, seed dusting, seed soaking, seed film coating, seed multilayer coating, seed encrusting, seed dripping and seed pelleting) based on the compounds of the formula (I) according to the invention or the compositions prepared therefrom. Here, the herbicidal compositions can be applied diluted or undiluted.

The term "seed" comprises seed of all types, such as, for example, corns, seeds, fruits, tubers, seedlings and similar forms. Here, preferably, the term seed describes corns and seeds. The seed used can be seed of the useful plants mentioned above, but also the seed of transgenic plants or plants obtained by customary breeding methods.

Moreover, it may be advantageous to apply the compositions of the present invention on their own or jointly in combination with other crop protection agents, for example with agents for controlling pests or phytopathogenic fungi or bacteria or with groups of active compounds which regulate growth. Also of interest is the miscibility with mineral salt solutions which are employed for treating nutritional and trace element deficiencies. Non-phytotoxic oils and oil concentrates can also be added.

When employed in plant protection, the amounts of active substances applied, i.e. A and B and, if appropriate, C without formulation auxiliaries, are, depending on the kind of effect desired, from 0.001 to 2 kg per ha, preferably from 0.005 to 2 kg per ha, more preferably from 0.05 to 0.9 kg per ha and in particular from 0.1 to 0.75 kg per ha.

In another embodiment of the invention, the application rate of A and B and, if appropriate, C, is from 0.001 to 3 kg/ha, preferably from 0.005 to 2.5 kg/ha and in particular from 0.01 to 2 kg/ha of active substance (a.s.).

In another preferred embodiment of the invention, the rates of application of the phenylpyrimidine of formula (I) according to the present invention (total amount of phenylpyrimidine of formula (I)) are from 0.1 g/ha to 3000 g/ha, preferably 50 g/ha to 750 g/ha, depending on the control target, the season, the target plants and the growth stage.

In another preferred embodiment of the invention, the application rates of the phenylpyrimidine of formula (I) are in the range from 0.1 g/ha to 5000 g/ha and preferably in the range from 5 g/ha to 2000 g/ha or from 50 g/ha to 1000 g/ha.

In another preferred embodiment of the invention, the application rate of the phenylpyrimidine of formula (I) is 0.1 to 1000 g/ha, preferably 1 to 750 g/ha, more preferably 5 to 500 g/ha.

The required application rates of herbicidal compounds B are generally in the range of from 0.0005 kg/ha to 2.5 kg/ha and preferably in the range of from 0.005 kg/ha to 2 kg/ha or 0.01 kg/ha to 1.5 kg/h of a.s.

The required application rates of safeners C are generally in the range of from 0.0005 kg/ha to 2.5 kg/ha and preferably in the range of from 0.005 kg/ha to 2 kg/ha or 0.01 kg/ha to 1.5 kg/h of a.s.

In treatment of plant propagation materials such as seeds, e.g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seeds) are generally required.

In another embodiment of the invention, to treat the seed, the amounts of active substances applied, i.e. A and B and, if appropriate, C are generally employed in amounts of from 0.001 to 10 kg per 100 kg of seed.

When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

In the methods of the present invention it is immaterial whether the herbicide compound A of formula (I), and the further herbicide component B and/or the herbicide safener compound C are formulated and applied jointly or separately.

In the case of separate application it is of minor importance, in which order the application takes place. It is only necessary, that the herbicide compound A and the herbicide compound B and/or the herbicide safener compound C are applied in a time frame that allows simultaneous action of the active ingredients on the plants, preferably within a time-frame of at most 14 days, in particular at most 7 days.

Depending on the application method in question, the compositions according to the invention can additionally be employed in a further number of crop plants for eliminating undesirable plants. Examples of suitable crops are the following:

*Allium cepa, Ananas comosus, Arachis hypogaea, Asparagus officinalis, Avena sativa, Beta vulgaris* spec. *altissima, Beta vulgaris* spec. *rapa, Brassica napus* var. *napus, Brassica napus* var. *napobrassica, Brassica rapa* var. *silvestris, Brassica oleracea, Brassica nigra, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec., *Manihot esculenta, Medicago sativa, Musa* spec., *Nicotiana tabacum* (*N.rustica*), *Olea europaea, Oryza sativa, Phaseolus lunatus, Phaseolus vulgaris, Picea abies, Pinus* spec., *Pistacia vera, Pisum sativum, Prunus avium, Prunus persica, Pyrus communis, Prunus armeniaca, Prunus cerasus, Prunus dulcis* and *prunus domestica, Ribes sylvestre, Ricinus communis, Saccharum officinarum, Secale cereale, Sinapis alba, Solanum tuberosum, Sorghum bicolor* (s. *vulgare*), *Theobroma cacao, Trifolium pratense, Triticum aestivum, Triticale, Triticum durum, Vicia faba, Vitis vinifera, Zea mays.*

Preferred crops are *Arachis hypogaea, Beta vulgaris* spec. *altissima, Brassica napus* var. *napus, Brassica oleracea, Citrus limon, Citrus sinensis, Coffea arabica* (*Coffea canephora, Coffea liberica*), *Cynodon dactylon, Glycine max, Gossypium hirsutum,* (*Gossypium arboreum, Gossypium herbaceum, Gossypium vitifolium*), *Helianthus annuus, Hordeum vulgare, Juglans regia, Lens culinaris, Linum usitatissimum, Lycopersicon lycopersicum, Malus* spec., *Medicago sativa, Nicotiana tabacum* (*N.rustica*), *Olea europaea, Oryza sativa, Phaseolus lunatus, Phaseolus vulgaris, Pistacia vera, Pisum sativum, Prunus dulcis, Saccharum officinarum, Secale cereale, Solanum tuberosum, Sorghum bicolor* (s. *vulgare*), *Triticale, Triticum aestivum, Triticum durum, Vicia faba, Vitis vinifera* and *Zea mays.*

Especially preferred crops are crops of canola, cereals, corn, soybeans, rice, oilseed rape, cotton, potatoes, peanuts or permanent crops.

The compositions according to the invention can also be used in genetically modified plants. The term "genetically modified plants" is to be understood as plants whose genetic material has been modified by the use of recombinant DNA techniques to include an inserted sequence of DNA that is not native to that plant species' genome or to exhibit a deletion of DNA that was native to that species' genome, wherein the modification(s) cannot readily be obtained by cross breeding, mutagenesis or natural recombination alone. Often, a particular genetically modified plant will be one that has obtained its genetic modification(s) by inheritance through a natural breeding or propagation process from an ancestral plant whose genome was the one directly treated by use of a recombinant DNA technique. Typically, one or more genes have been integrated into the genetic material of a genetically modified plant in order to improve certain properties of the plant. Such genetic modifications also include but are not limited to targeted posttranslational modification of protein(s), oligo- or polypeptides. e.g., by inclusion therein of amino acid mutation(s) that permit, decrease, or promote glycosylation or polymer additions such as prenylation, acetylation farnesylation, or PEG moiety attachment.

Plants that have been modified by breeding, mutagenesis or genetic engineering, e.g. have been rendered tolerant to applications of specific classes of herbicides, such as auxinic herbicides such as dicamba or 2,4-D; bleacher herbicides such as 4-hydroxyphenylpyruvate dioxygenase (HPPD) inhibitors or phytoene desaturase (PDS) inhibitors; acetolactate synthase (ALS) inhibitors such as sulfonylureas or imidazolinones; enolpyruvyl shikimate 3-phosphate synthase (EPSP) inhibitors such as glyphosate; glutamine synthetase (GS) inhibitors such as glufosinate; protoporphyrinogen-IX oxidase inhibitors; lipid biosynthesis inhibitors such as acetylCoA carboxylase (ACCase) inhibitors; or oxynil (i.e. bromoxynil or ioxynil) herbicides as a result of conventional methods of breeding or genetic engineering; furthermore, plants have been made resistant to multiple classes of herbicides through multiple genetic modifications, such as resistance to both glyphosate and glufosinate or to both glyphosate and a herbicide from another class such as ALS inhibitors, HPPD inhibitors, auxinic herbicides, or ACCase inhibitors. These herbicide resistance technologies are, for example, described in Pest Management Science 61, 2005, 246; 61, 2005, 258; 61, 2005, 277; 61, 2005, 269; 61, 2005, 286; 64, 2008, 326; 64, 2008, 332; Weed Science 57, 2009, 108; Australian Journal of Agricultural Research 58, 2007, 708; Science 316, 2007, 1185; and references quoted therein. Several cultivated plants have been rendered tolerant to herbicides by mutagenesis and conventional methods of breeding, e.g., Clearfield® summer rape (Canola, BASF SE, Germany) being tolerant to imidazolinones, e.g., imazamox, or ExpressSun® sunflowers (DuPont, USA) being tolerant to sulfonyl ureas, e.g., tribenuron. Genetic engineering methods have been used to render cultivated plants such as soybean, cotton, corn, beets and rape, tolerant to herbicides such as glyphosate, imidazolinones and glufosinate, some of which are under development or commercially available under the brands or trade names RoundupReady® (glyphosate tolerant, Monsanto, USA), Cultivance® (imidazolinone tolerant, BASF SE, Germany) and LibertyLink® (glufosinate tolerant, Bayer CropScience, Germany).

Furthermore, plants are also covered that are by the use of recombinant DNA techniques capable to synthesize one or more insecticidal proteins, especially those known from the bacterial genus Bacillus, particularly from Bacillus thuringiensis, such as delta-endotoxins, e.g., CryIA(b), CryIA(c), CryIF, CryIF(a2), CryIIA(b), CryIIIA, CryIIIB(b1) or Cry9c; vegetative insecticidal proteins (VIP), e.g., VIP1, VIP2, VIP3 or VIP3A; insecticidal proteins of bacteria colonizing nematodes, e.g., Photorhabdus spp. or Xenorhabdus spp.; toxins produced by animals, such as scorpion toxins, arachnid toxins, wasp toxins, or other insect-specific neurotoxins; toxins produced by fungi, such as Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxy-steroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilbene synthase, bibenzyl synthase, chitinases or glucanases. In the context of the present invention these insecticidal proteins or toxins are to be understood expressly also as including pre-toxins, hybrid proteins, truncated or otherwise modified proteins. Hybrid proteins are characterized by a new combination of protein domains, (see, e.g., WO 02/015701). Further examples of such toxins or genetically modified plants capable of synthesizing such toxins are disclosed, e.g., in EP-A 374 753, WO 93/007278, WO 95/34656, EP-A 427 529, EP-A 451 878, WO 03/18810 und WO 03/52073. The methods for producing such genetically modified plants are generally known to the person skilled in the art and are described, e.g., in the publications mentioned above. These insecticidal proteins contained in the genetically modified plants impart to the plants producing these proteins tolerance to harmful pests from all taxonomic groups of arthropods, especially to beetles (Coleoptera), two-winged insects (Diptera), and moths (Lepidoptera) and to nematodes (Nematoda). Genetically modified plants capable to synthesize one or more insecticidal proteins are, e.g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme Phosphinothricin-N-Acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); New-Leaf® (potato cultivars producing the Cry3A toxin); Bt-Xtra®, NatureGard®, Knock-Out®, BiteGard®, Protecta®, Bt11 (e.g., Agrisure® CB) and Bt176 from Syngenta Seeds SAS, France, (corn cultivars producing the Cry1Ab toxin and PAT enzyme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the Cry1F toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e.g., EP-A 392 225), plant disease resistance genes (e.g., potato culti-vars, which express resistance genes acting against Phytophthora infestans derived from the Mexican wild potato, Solanum bulbocastanum) or T4-lyso-zym (e.g., potato cultivars capable of synthesizing these proteins with increased resistance against bacteria such as Erwinia amylovora). The methods for producing such genetically modified plants are generally known to the person skilled in the art and are described, e.g., in the publications mentioned above.

Furthermore, plants are also covered that are by the use of recombinant DNA techniques capable to synthesize one or more proteins to increase the productivity (e.g., bio-mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of ingredients or new ingredients, specifically to improve human or animal nutrition, e.g., oil crops that produce health-promoting long-chain omega-3 fatty acids or unsaturated omega-9 fatty acids (e.g., Nexera® rape, Dow AgroSciences, Canada).

Furthermore, plants are also covered that contain by the use of recombinant DNA techniques a modified amount of ingredients or new ingredients, specifically to improve raw material production, e.g., potatoes that produce increased amounts of amylopectin (e.g. Amflora® potato, BASF SE, Germany).

Furthermore, it has been found that the the compositions according to the invention are also suitable for the defoliation and/or desiccation of plant parts, for which crop plants such as cotton, potato, oilseed rape, sunflower, soybean or field beans, in particular cotton, are suitable. In this regard compositions have been found for the desiccation and/or defoliation of plants, processes for preparing these compositions, and methods for desiccating and/or defoliating plants using the compositions according to the invention.

As desiccants, the compositions according to the invention are suitable in particular for desiccating the above-ground parts of crop plants such as potato, oilseed rape, sunflower and soybean, but also cereals. This makes possible the fully mechanical harvesting of these important crop plants.

Also of economic interest is the facilitation of harvesting, which is made possible by concentrating within a certain period of time the dehiscence, or reduction of adhesion to the tree, in citrus fruit, olives and other species and varieties of pomaceous fruit, stone fruit and nuts. The same mechanism, i.e. the promotion of the development of abscission tissue between fruit part or leaf part and shoot part of the plants is also essential for the controlled defoliation of useful plants, in particular cotton.

Moreover, a shortening of the time interval in which the individual cotton plants mature leads to an increased fiber quality after harvesting.

The examples of compounds of formula (I) Ex.1 to Ex.26 listed below in table 2 are known from WO2016120355,

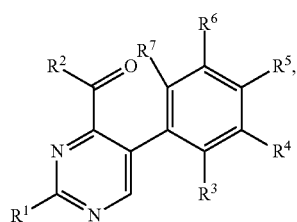

(I)

TABLE 2

| Example No. | $R^1$ | $R^2$ | $R^3$ | $R^4$ | $R^5$ | $R^6$ | $R^7$ |
|---|---|---|---|---|---|---|---|
| Ex. 1 | c-$C_4H_7$ | $OCH_3$ | Cl | H | H | H | H |
| Ex. 2 | c-$C_4H_7$ | OH | Cl | H | H | H | H |
| Ex. 3 | c-$C_3H_5$ | $SCH_2(CO)OCH_3$ | Cl | H | H | H | H |
| Ex. 4 | c-$C_3H_5$ | OH | F | H | H | H | H |
| Ex. 5 | c-$C_3H_5$ | OH | Cl | H | H | H | H |
| Ex. 6 | c-$C_3H_5$ | OH | Cl | H | H | F | H |
| Ex. 7 | c-$C_3H_5$ | OH | Cl | F | H | H | H |
| Ex. 8 | c-$C_3H_5$ | OH | Br | H | H | H | H |
| Ex. 9 | c-$C_3H_5$ | OH | I | H | H | H | H |
| Ex. 10 | c-$C_3H_5$ | OH | Cl | H | $CF_3$ | H | H |

TABLE 2-continued

| Example No. | $R^1$ | $R^2$ | $R^3$ | $R^4$ | $R^5$ | $R^6$ | $R^7$ |
|---|---|---|---|---|---|---|---|
| Ex. 11 | c-$C_3H_5$ | $OCH_3$ | Cl | H | $CF_3$ | H | H |
| Ex. 12 | c-$C_3H_5$ | OH | Cl | H | H | $CF_3$ | H |
| Ex. 13 | c-$C_3H_5$ | $OCH_3$ | Cl | H | H | $CF_3$ | H |
| Ex. 14 | 2-but-3-ynoxy | OH | Cl | H | H | H | H |
| Ex. 15 | c-$C_3H_5$ | OH | Cl | H | H | H | F |
| Ex. 16 | c-$C_3H_5$ | $OCH_3$ | Cl | H | H | H | F |
| Ex. 17 | c-$C_3H_5$ | $NHOCH_3$ | Cl | H | H | H | H |
| Ex. 18 | c-$C_3H_5$ | $NCH_3OCH_3$ | Cl | H | H | H | H |
| Ex. 19 | c-$C_3H_5$ | $NCH_3OH$ | Cl | H | H | H | H |
| Ex. 20 | c-$C_3H_3Cl_2$ | OH | Cl | H | H | H | H |
| Ex. 21 | c-$C_3H_3Cl_2$ | $OCH_3$ | Cl | H | H | H | H |
| Ex. 22 | c-$C_3H_3F_2$ | OH | Cl | H | H | H | H |
| Ex. 23 | c-$C_3H_5$ | $CF_3$ | Cl | H | H | H | H |
| Ex. 24 | c-$C_3H_5$ | 2-furyl | Cl | H | H | H | H |
| Ex. 25 | c-$C_3H_5$ | 2-thiophene | Cl | H | H | H | H |
| Ex. 26 | c-$C_3H_5$ | $OCH_3$ | Cl | H | F | H | H |

B USE EXAMPLES

The herbicidal action of the compounds and compositions according to the invention was demonstrated by the following greenhouse experiments:

The culture containers used were plastic pots containing loamy sand with approximately 3.0% of humus as substrate. The seeds of the test plants were sown separately for each species.

For the pre-emergence treatment, the active compounds, suspended or emulsified in water, were applied directly after sowing by means of finely distributing nozzles. The containers were irrigated gently to promote germination and growth and subsequently covered with transparent plastic hoods until the plants had rooted. This cover caused uniform germination of the test plants unless this was adversely affected by the active compounds.

For the post-emergence treatment, the test plants were grown to a plant height of from 3 to 15 cm, depending on the plant habit, and only then treated with the active compounds which had been suspended or emulsified in water. To this end, the test plants were either sown directly, and grown in the same containers, or they were first grown separately as seedlings and transplanted into the test containers a few days prior to treatment.

Depending on the species, the plants were kept at 10-25° C. and 20-35° C., respectively.

The test period extended over 2 to 4 weeks. During this time, the plants were tended and their response to the individual treatments was evaluated.

Evaluation was carried out using a scale from 0 to 100. 100 means no emergence of the plants, or complete destruction of at least the above-ground parts, and 0 means no damage or normal course of growth. A good herbicidal activity is given at values of at least 70, and very good herbicidal activity is given at values of at least 85.

The respective stated components A and B, and if appropriate, C were formulated as a 10% by weight strength emulsion concentrate and, with addition of the amount of solvent system, introduced into the spray liquor used for applying the active compound. In the examples, the solvent used was water.

The plants used in the greenhouse experiments belonged to the following species:

| EPPO Code | Scientific name |
|---|---|
| POAAN | *Poa annua* |
| ALOMY | *Alopecurus myosuroides* |
| PAPRH | *Papaver rhoeas* |
| AVEFA | *Avena fatua* |
| MATCH | *Matricaria chamomilla* |
| HELAN | *Helianthus annuus* |
| LOLMU | *Lolium multiflorum* |
| POLCO | *Polygonum convolvulus* |
| SETVI | *Setaria viridis* |
| GALAP | *Galium aparine* |
| STEME | *Stellaria media* |
| ECHCG | *Echinocloa crus-galli* |
| DIGSA | *Digitaria sanguinalis* |
| BROST | *Bromus sterilis* |
| BRADC | *Brachiaria decumbens* |
| APESV | *Apera spica-venti* |
| AMBEL | *Ambrosia elatior* |
| POLAV | *Polygonum aviculare* |
| LOLPE | *Lolium perenne* |
| LOLRI | *Lolium rigidum* |

In the examples below, using the method of S. R. Colby (1967) "Calculating synergistic and antagonistic responses of herbicide combinations", Weeds 15, p. 22ff., the value E, which is expected if the activity of the individual active compounds is only additive, was calculated.

$$E = X + Y - (X \cdot Y / 100)$$

where X=effect in percent using herbicide A at an application rate a;
Y=effect in percent using herbicide B at application rate b;
E=expected effect (in %) of herbicide A+herbicide B at application rates a+b.

If the value found experimentally is higher than the value E calculated according to Colby, a synergistic effect is present.

Each of Table X1 to X71 below relates to the herbicidal activity, in greenhouse trials, of the individual activities and the combinations of an Example from table 2 and a herbicide B applied at different rates and ratios.

TABLE X1

Ex. 5 and cinmethylin, in pre-emergence application at 20 days after treatment (DAT), wherein cinmethylin was used as EC formulation having an active ingredient concentration of 750 g/l.

| | solo application | | | | combination | | |
|---|---|---|---|---|---|---|---|
| | Ex. 5 | | cinmethylin | | Ex. 5 + cinmethylin | | COLBY |
| weed | use rate (gai/ha) | % activity | use rate (gai/ha) | % activity | use rate (gai/ha) | % activity | expected % activity |
| AMBEL | 250 | 98 | 125 | 0 | 250 + 125 | 100 | 98 |
| AMBEL | 62.5 | 45 | 125 | 0 | 62.5 + 125 | 80 | 45 |
| AMBEL | 62.5 | 45 | 62.5 | 0 | 62.5 + 62.5 | 85 | 45 |
| AMBEL | 31.25 | 30 | 125 | 0 | 31.25 + 125 | 50 | 30 |
| AVEFA | 250 | 90 | 62.5 | 10 | 250 + 62.5 | 95 | 91 |
| BROST | 125 | 80 | 250 | 75 | 125 + 250 | 100 | 95 |
| BROST | 62.5 | 65 | 62.5 | 55 | 62.5 + 62.5 | 95 | 84 |
| GALAP | 62.5 | 0 | 125 | 20 | 62.5 + 125 | 30 | 20 |
| GALAP | 62.5 | 0 | 62.5 | 0 | 62.5 + 62.5 | 20 | 0 |
| HELAN | 62.5 | 35 | 125 | 10 | 62.5 + 125 | 65 | 42 |
| POLCO | 125 | 80 | 250 | 0 | 125 + 250 | 90 | 80 |
| POLCO | 125 | 80 | 125 | 0 | 125 + 125 | 98 | 80 |
| POLCO | 125 | 80 | 62.5 | 0 | 125 + 62.5 | 95 | 80 |
| POLCO | 125 | 80 | 31.25 | 0 | 125 + 31.25 | 90 | 80 |
| POLCO | 62.5 | 60 | 125 | 0 | 62.5 + 125 | 75 | 60 |
| SETVI | 250 | 65 | 31.25 | 85 | 250 + 31.25 | 100 | 95 |
| SETVI | 125 | 45 | 31.25 | 85 | 125 + 31.25 | 100 | 92 |

TABLE X2

Ex. 5 and trifludimoxazin, in pre-emergence application at 20 DAT, wherein trifludimoxazin was used as SC formulation having an active ingredient concentration of 500 g/l.

| | solo application | | | | combination | | |
|---|---|---|---|---|---|---|---|
| | Ex. 5 | | trifludimoxazin | | Ex. 5 + trifludimoxazin | | COLBY |
| weed | use rate (gai/ha) | % activity | use rate (gai/ha) | % activity | use rate (gai/ha) | % activity | expected % activity |
| AMBEL | 62.5 | 0 | 9 | 50 | 62.5 + 9 | 95 | 50 |
| AMBEL | 62.5 | 0 | 4.5 | 0 | 62.5 + 4.5 | 40 | 0 |
| BRADC | 62.5 | 80 | 9 | 45 | 62.5 + 9 | 95 | 88 |

TABLE X2-continued

Ex. 5 and trifludimoxazin, in pre-emergence application at 20 DAT, wherein trifludimoxazin was used as SC formulation having an active ingredient concentration of 500 g/l.

| | solo application | | | | combination | | |
|---|---|---|---|---|---|---|---|
| | | | | | Ex. 5 + trifludimoxazin | | |
| | Ex. 5 | | trifludimoxazin | | | | COLBY |
| weed | use rate (gai/ha) | % activity | use rate (gai/ha) | % activity | use rate (gai/ha) | % activity | expected % activity |
| DIGSA | 62.5 | 65 | 4.5 | 50 | 62.5 + 4.5 | 90 | 83 |
| GALAP | 125 | 40 | 36 | 40 | 125 + 36 | 98 | 64 |
| GALAP | 125 | 40 | 9 | 0 | 125 + 9 | 55 | 40 |
| GALAP | 125 | 40 | 4.5 | 0 | 125 + 4.5 | 85 | 0 |
| GALAP | 62.5 | 0 | 36 | 40 | 62.5 + 36 | 90 | 40 |
| GALAP | 62.5 | 0 | 18 | 0 | 62.5 + 18 | 30 | 0 |
| GALAP | 62.5 | 0 | 9 | 0 | 62.5 + 9 | 65 | 0 |
| GALAP | 62.5 | 0 | 4.5 | 0 | 62.5 + 4.5 | 30 | 0 |
| HELAN | 125 | 40 | 18 | 0 | 125 + 18 | 60 | 40 |
| SETVI | 125 | 60 | 4.5 | 75 | 125 + 4.5 | 95 | 90 |

TABLE X3

Ex. 5 and bentazon, in post-emergence application at 20 DAT, wherein bentazone was used as SL formulation having an active ingredient concentration of 480 g/l.

| | solo application | | | | combination | | |
|---|---|---|---|---|---|---|---|
| | | | | | Ex. 5 + bentazon | | |
| | Ex. 5 | | bentazon | | | | COLBY |
| weed | use rate (gai/ha) | % activity | use rate (gai/ha) | % activity | use rate (gai/ha) | % activity | expected % activity |
| ALOMY | 62.5 | 75 | 240 | 0 | 62.5 + 240 | 85 | 75 |
| ALOMY | 62.5 | 75 | 120 | 0 | 62.5 + 120 | 80 | 75 |
| BRADC | 250 | 60 | 120 | 0 | 250 + 120 | 65 | 60 |
| BRADC | 250 | 60 | 60 | 0 | 250 + 60 | 65 | 60 |
| BRADC | 250 | 60 | 30 | 0 | 250 + 30 | 65 | 60 |
| BROST | 250 | 80 | 60 | 0 | 250 + 60 | 85 | 80 |
| DIGSA | 62.5 | 30 | 60 | 0 | 62.5 + 60 | 40 | 30 |
| DIGSA | 62.5 | 30 | 30 | 0 | 62.5 + 30 | 40 | 30 |
| ECHCG | 62.5 | 65 | 240 | 20 | 62.5 + 240 | 75 | 72 |
| ECHCG | 62.5 | 65 | 120 | 0 | 62.5 + 120 | 70 | 65 |
| ECHCG | 62.5 | 65 | 60 | 0 | 62.5 + 60 | 70 | 65 |
| MATCH | 250 | 70 | 60 | 30 | 250 + 60 | 100 | 79 |
| MATCH | 250 | 70 | 30 | 20 | 250 + 30 | 100 | 76 |
| MATCH | 125 | 30 | 60 | 30 | 125 + 60 | 100 | 51 |
| MATCH | 125 | 30 | 30 | 20 | 125 + 30 | 50 | 44 |
| MATCH | 62.5 | 30 | 60 | 30 | 62.5 + 60 | 100 | 51 |
| MATCH | 62.5 | 30 | 30 | 20 | 62.5 + 30 | 60 | 44 |
| PAPRH | 125 | 75 | 120 | 0 | 125 + 120 | 100 | 75 |
| PAPRH | 62.5 | 20 | 120 | 0 | 62.5 + 120 | 70 | 20 |
| SETVI | 250 | 60 | 60 | 0 | 250 + 60 | 65 | 60 |
| SETVI | 62.5 | 35 | 240 | 30 | 62.5 + 240 | 65 | 55 |
| SETVI | 62.5 | 35 | 60 | 0 | 62.5 + 60 | 50 | 35 |

TABLE X4

Ex. 5 and bromoxynil, in post-emergence application at 20 DAT, wherein bromoxynil was used as EC formulation having an active ingredient concentration of 235 g/l.

| | solo application | | | | combination | | |
|---|---|---|---|---|---|---|---|
| | | | | | Ex. 5 + bromoxynil | | COLBY |
| | Ex. 5 | | Bromoxynil | | | | |
| weed | use rate (gai/ha) | % activity | use rate (gai/ha) | % activity | use rate (gai/ha) | % activity | expected % activity |
| AVEFA | 125 | 75 | 125 | 0 | 125 + 125 | 80 | 75 |
| AVEFA | 125 | 75 | 31.25 | 0 | 125 + 31.25 | 80 | 75 |
| DIGSA | 250 | 70 | 250 | 0 | 250 + 250 | 80 | 70 |
| DIGSA | 250 | 70 | 125 | 0 | 250 + 125 | 80 | 70 |
| DIGSA | 250 | 70 | 62.5 | 0 | 250 + 62.5 | 80 | 70 |
| DIGSA | 125 | 50 | 250 | 0 | 125 + 250 | 75 | 50 |
| DIGSA | 125 | 50 | 125 | 0 | 125 + 125 | 65 | 50 |
| DIGSA | 125 | 50 | 62.5 | 0 | 125 + 62.5 | 60 | 50 |
| DIGSA | 125 | 50 | 31.25 | 0 | 125 + 31.25 | 65 | 50 |
| GALAP | 250 | 30 | 125 | 80 | 250 + 125 | 100 | 86 |
| GALAP | 250 | 30 | 62.5 | 65 | 250 + 62.5 | 95 | 76 |
| GALAP | 125 | 0 | 125 | 80 | 125 + 125 | 100 | 80 |
| GALAP | 125 | 0 | 62.5 | 65 | 125 + 62.5 | 90 | 65 |
| LOLMU | 250 | 80 | 250 | 0 | 250 + 250 | 90 | 80 |
| LOLMU | 250 | 80 | 125 | 0 | 250 + 125 | 90 | 80 |
| LOLMU | 250 | 80 | 62.5 | 0 | 250 + 62.5 | 85 | 80 |
| LOLMU | 250 | 80 | 31.25 | 0 | 250 + 31.25 | 85 | 80 |
| LOLMU | 125 | 80 | 250 | 0 | 125 + 250 | 90 | 80 |
| LOLMU | 125 | 80 | 125 | 0 | 125 + 125 | 90 | 80 |
| LOLMU | 125 | 80 | 62.5 | 0 | 125 + 62.5 | 85 | 80 |
| LOLMU | 125 | 80 | 31.25 | 0 | 125 + 31.25 | 85 | 80 |
| MATCH | 250 | 40 | 31.25 | 55 | 250 + 31.25 | 100 | 73 |
| MATCH | 125 | 40 | 31.25 | 55 | 125 + 31.25 | 100 | 73 |
| PAPRH | 125 | 5 | 31.25 | 40 | 125 + 31.25 | 50 | 43 |
| POLAV | 250 | 95 | 125 | 65 | 250 + 125 | 100 | 98 |
| POLAV | 250 | 95 | 62.5 | 65 | 250 + 62.5 | 100 | 98 |
| POLAV | 250 | 95 | 31.25 | 65 | 250 + 31.25 | 100 | 98 |
| POLAV | 125 | 95 | 125 | 65 | 125 + 125 | 100 | 98 |
| POLAV | 125 | 95 | 62.5 | 65 | 125 + 62.5 | 100 | 98 |
| SETVI | 250 | 50 | 250 | 0 | 250 + 250 | 65 | 50 |
| SETVI | 250 | 50 | 31.25 | 0 | 250 + 31.25 | 55 | 50 |

TABLE X5

Ex. 5 and chlorotoluron, in post-emergence application at 20 DAT, wherein chlorotoluron was used as SC formulation having an active ingredient concentration of 700 g/l.

| | solo application | | | | combination | | |
|---|---|---|---|---|---|---|---|
| | | | | | Ex. 5 + chlorotoluron | | COLBY |
| | Ex. 5 | | chlortolurom | | | | |
| weed | use rate (gai/ha) | % activity | use rate (gai/ha) | % activity | use rate (gai/ha) | % activity | expected % activity |
| ALOMY | 250 | 85 | 500 | 65 | 250 + 500 | 95 | 85 |
| AMBEL | 125 | 80 | 62.5 | 62 | 125 + 62.5 | 100 | 93 |
| AVEFA | 250 | 75 | 250 | 40 | 250 + 250 | 90 | 85 |
| AVEFA | 250 | 75 | 125 | 0 | 250 + 125 | 90 | 75 |
| AVEFA | 250 | 75 | 62.5 | 0 | 250 + 62.5 | 85 | 75 |
| AVEFA | 125 | 70 | 250 | 40 | 125 + 250 | 90 | 82 |
| AVEFA | 125 | 70 | 125 | 0 | 125 + 125 | 90 | 70 |
| AVEFA | 125 | 70 | 62.5 | 0 | 125 + 62.5 | 85 | 70 |
| BRADC | 125 | 50 | 500 | 70 | 125 + 500 | 98 | 85 |
| BRADC | 125 | 50 | 62.5 | 20 | 125 + 62.5 | 65 | 60 |
| DIGSA | 250 | 70 | 62.5 | 0 | 250 + 62.5 | 75 | 70 |
| DIGSA | 125 | 65 | 62.5 | 0 | 125 + 62.5 | 70 | 65 |
| GALAP | 250 | 0 | 500 | 70 | 250 + 500 | 85 | 70 |
| GALAP | 125 | 0 | 500 | 70 | 125 + 500 | 75 | 70 |
| MATCH | 250 | 10 | 125 | 50 | 250 + 125 | 100 | 55 |
| MATCH | 250 | 10 | 62.5 | 30 | 250 + 62.5 | 100 | 37 |
| MATCH | 125 | 10 | 125 | 50 | 125 + 125 | 90 | 55 |

TABLE X5-continued

Ex. 5 and chlorotoluron, in post-emergence application at 20 DAT, wherein chlorotoluron was used as SC formulation having an active ingredient concentration of 700 g/l.

| | solo application | | | | combination | | |
|---|---|---|---|---|---|---|---|
| | Ex. 5 | | chlortolurom | | Ex. 5 + chlorotoluron | | COLBY |
| weed | use rate (gai/ha) | % activity | use rate (gai/ha) | % activity | use rate (gai/ha) | % activity | expected % activity |
| MATCH | 125 | 10 | 62.5 | 30 | 125 + 62.5 | 50 | 37 |
| LOLMU | 125 | 80 | 250 | 70 | 125 + 250 | 100 | 94 |
| LOLMU | 125 | 80 | 125 | 65 | 125 + 125 | 95 | 93 |
| PAPRH | 125 | 30 | 500 | 25 | 125 + 500 | 90 | 48 |
| PAPRH | 125 | 30 | 250 | 50 | 125 + 250 | 75 | 44 |
| PAPRH | 125 | 30 | 125 | 0 | 125 + 125 | 65 | 30 |
| PAPRH | 125 | 30 | 62.5 | 0 | 125 + 62.5 | 65 | 30 |

TABLE X6

Ex. 5 and chlorotoluron, in pre-emergence application at 20 DAT, wherein chlorotoluron was used as SC formulation having an active ingredient concentration of 700 g/l.

| | solo application | | | | combination | | |
|---|---|---|---|---|---|---|---|
| | Ex. 5 | | chlorotoluron | | Ex. 5 + chlorotoluron | | COLBY |
| weed | use rate (gai/ha) | % activity | use rate (gai/ha) | % activity | use rate (gai/ha) | % activity | expected % activity |
| AMBEL | 62.5 | 0 | 500 | 40 | 62.5 + 500 | 85 | 40 |
| AMBEL | 62.5 | 0 | 250 | 0 | 62.5 + 250 | 30 | 0 |
| AMBEL | 62.5 | 0 | 62.5 | 0 | 62.5 + 62.5 | 40 | 0 |
| BRADC | 125 | 95 | 62.5 | 0 | 125 + 62.5 | 100 | 95 |
| BROST | 125 | 65 | 500 | 0 | 125 + 500 | 70 | 65 |
| DIGSA | 62.5 | 65 | 125 | 0 | 62.5 + 125 | 70 | 65 |
| GALAP | 62.5 | 0 | 500 | 30 | 62.5 + 500 | 40 | 30 |
| GALAP | 62.5 | 0 | 250 | 0 | 62.5 + 250 | 30 | 0 |
| HELAN | 125 | 40 | 500 | 10 | 125 + 500 | 50 | 46 |
| HELAN | 125 | 40 | 250 | 0 | 125 + 250 | 50 | 40 |
| HELAN | 31.25 | 0 | 500 | 10 | 31.25 + 500 | 30 | 10 |
| HELAN | 31.25 | 0 | 250 | 0 | 31.25 + 250 | 20 | 0 |
| HELAN | 31.25 | 0 | 125 | 0 | 31.25 + 125 | 20 | 0 |
| PAPRH | 125 | 85 | 62.5 | 0 | 125 + 62.5 | 95 | 85 |
| PAPRH | 31.25 | 20 | 62.5 | 0 | 31.25 + 62.5 | 30 | 20 |
| SETVI | 125 | 60 | 125 | 0 | 125 + 125 | 65 | 60 |
| SETVI | 125 | 60 | 62.5 | 0 | 125 + 62.5 | 65 | 60 |
| SETVI | 31.25 | 0 | 125 | 0 | 31.25 + 125 | 40 | 0 |

TABLE X7

Ex. 5 and dicamba, in post-emergence application at 20 DAT, wherein dicamba was used as SL formulation having an active ingredient concentration of 480 g/l.

| | solo application | | | | combination | | |
|---|---|---|---|---|---|---|---|
| | Ex. 5 | | Dicamba | | Ex. 5 + Dicamba | | COLBY |
| weed | use rate (gai/ha) | % activity | use rate (gai/ha) | % activity | use rate (gai/ha) | % activity | expected % activity |
| ALOMY | 125 | 80 | 35 | 0 | 125 + 35 | 85 | 80 |
| BRADC | 125 | 65 | 35 | 0 | 125 + 35 | 70 | 65 |
| MATCH | 125 | 30 | 70 | 0 | 125 + 70 | 35 | 30 |

TABLE X7-continued

Ex. 5 and dicamba, in post-emergence application at 20 DAT, wherein dicamba was used as SL formulation having an active ingredient concentration of 480 g/l.

| | solo application | | | | combination | | |
|---|---|---|---|---|---|---|---|
| | Ex. 5 | | Dicamba | | Ex. 5 + Dicamba | | COLBY |
| weed | use rate (gai/ha) | % activity | use rate (gai/ha) | % activity | use rate (gai/ha) | % activity | expected % activity |
| SETVI | 250 | 60 | 35 | 0 | 250 + 35 | 65 | 60 |
| ALOMY | 250 | 75 | 280 | 5 | 250 + 280 | 78 | 76 |
| ALOMY | 250 | 75 | 140 | 0 | 250 + 140 | 78 | 75 |
| ALOMY | 250 | 75 | 70 | 0 | 250 + 70 | 80 | 75 |
| ALOMY | 250 | 75 | 35 | 0 | 250 + 35 | 80 | 75 |

TABLE X8

Ex. 5 and diflufenican, in post-emergence application at 20 DAT, wherein diflufenican was used as SC formulation having an active ingredient concentration of 500g/l. LIM/H/A 2016-230-08;

| | solo application | | | | combination | | |
|---|---|---|---|---|---|---|---|
| | Ex. 5 | | diflufenican | | Ex. 5 + diflufenican | | COLBY |
| weed | use rate (gai/ha) | % activity | use rate (gai/ha) | % activity | use rate (gai/ha) | % activity | expected % activity |
| DIGSA | 250 | 65 | 30 | 5 | 250 + 30 | 70 | 67 |
| GALAP | 250 | 20 | 60 | 75 | 250 + 60 | 98 | 80 |
| GALAP | 250 | 20 | 30 | 70 | 250 + 30 | 80 | 76 |
| LOLMU | 125 | 85 | 120 | 10 | 125 + 120 | 90 | 87 |
| LOLMU | 125 | 85 | 60 | 10 | 125 + 60 | 90 | 87 |
| POAAN | 250 | 90 | 60 | 50 | 250 + 60 | 100 | 95 |
| POAAN | 125 | 90 | 60 | 50 | 125 + 60 | 100 | 95 |
| SETVI | 250 | 30 | 120 | 55 | 250 + 120 | 85 | 69 |
| SETVI | 250 | 30 | 60 | 30 | 250 + 60 | 60 | 51 |
| SETVI | 250 | 30 | 15 | 10 | 250 + 15 | 75 | 37 |
| SETVI | 125 | 30 | 120 | 55 | 125 + 120 | 80 | 69 |

TABLE X9

Ex. 5 and diflufenican, in pre-emergence application at 21 DAT, wherein diflufenican was used as SC formulation having an active ingredient concentration of 500 g/l.

| | solo application | | | | combination | | |
|---|---|---|---|---|---|---|---|
| | Ex. 5 | | diflufenican | | Ex. 5 + diflufenican | | COLBY |
| weed | use rate (gai/ha) | % activity | use rate (gai/ha) | % activity | use rate (gai/ha) | % activity | expected % activity |
| AVEFA | 250 | 90 | 60 | 0 | 250 + 60 | 95 | 90 |
| AVEFA | 250 | 90 | 15 | 0 | 250 + 15 | 95 | 90 |
| BRAPL | 125 | 90 | 120 | 20 | 125 + 120 | 100 | 92 |
| BRAPL | 125 | 90 | 30 | 0 | 125 + 30 | 98 | 90 |
| BRAPL | 125 | 90 | 15 | 0 | 125 + 15 | 98 | 90 |
| DIGSA | 125 | 90 | 60 | 45 | 125 + 60 | 100 | 95 |
| GALAP | 250 | 0 | 60 | 0 | 250 + 60 | 20 | 0 |
| GALAP | 125 | 0 | 60 | 0 | 125 + 60 | 10 | 0 |
| SETVI | 125 | 50 | 60 | 70 | 125 + 60 | 100 | 85 |

TABLE X10

Ex. 5 and flufenacet, in pre-emergence application at 20 DAT, wherein flufenacet was used as SC formulation having an active ingredient concentration of 500 g/l.

| | solo application | | | | combination | | |
|---|---|---|---|---|---|---|---|
| | | | | | Ex. 5 + flufenacet | | |
| | Ex. 5 | | flufenacet | | | | COLBY |
| weed | use rate (gai/ha) | % activity | use rate (gai/ha) | % activity | use rate (gai/ha) | % activity | expected % activity |
| AMBEL | 62.5 | 45 | 62.5 | 0 | 62.5 + 62.5 | 85 | 45 |
| AMBEL | 62.5 | 45 | 31.25 | 0 | 62.5 + 31.25 | 85 | 45 |
| AMBEL | 31.25 | 30 | 62.5 | 0 | 31.25 + 62.5 | 50 | 30 |
| GALAP | 250 | 35 | 31.25 | 0 | 250 + 31.25 | 70 | 35 |
| GALAP | 125 | 20 | 31.25 | 0 | 125 + 31.25 | 40 | 20 |
| GALAP | 62.5 | 0 | 62.5 | 0 | 62.5 + 62.5 | 10 | 0 |
| GALAP | 62.5 | 0 | 31.25 | 0 | 62.5 + 31.25 | 10 | 0 |
| POLCO | 125 | 80 | 125 | 0 | 125 + 125 | 98 | 80 |
| POLCO | 125 | 80 | 62.5 | 0 | 125 + 62.5 | 95 | 80 |
| POLCO | 125 | 80 | 31.25 | 0 | 125 + 31.25 | 95 | 80 |
| POLCO | 125 | 80 | 15.6 | 0 | 125 + 15.6 | 95 | 80 |
| POLCO | 31.25 | 60 | 62.5 | 0 | 31.25 + 62.5 | 80 | 60 |

TABLE X11

Ex. 5 and flumioxazin, in pre-emergence application at 20 DAT, wherein flumioxazin was used as WG formulation having an active ingredient concentration of 51%.

| | solo application | | | | combination | | |
|---|---|---|---|---|---|---|---|
| | | | | | Ex. 5 + saflufenacil | | |
| | Ex. 5 | | saflufenacil | | | | COLBY |
| weed | use rate (gai/ha) | % activity | use rate (gai/ha) | % activity | use rate (gai/ha) | % activity | expected % activity |
| AMBEL | 62.5 | 45 | 3.75 | 0 | 62.5 + 3.75 | 65 | 45 |
| GALAP | 125 | 0 | 30 | 65 | 125 + 30 | 70 | 65 |
| GALAP | 62.5 | 0 | 30 | 65 | 62.5 + 30 | 70 | 65 |

TABLE X12

Ex. 5 and isoproturon, in post-emergence application at 20 DAT, wherein isoproturon was used as SC formulation having an active ingredient concentration of 500 g/l.

| | solo application | | | | combination | | |
|---|---|---|---|---|---|---|---|
| | | | | | Ex. 5 + isoproturon | | |
| | Ex. 5 | | isoproturon | | | | COLBY |
| weed | use rate (gai/ha) | % activity | use rate (gai/ha) | % activity | use rate (gai/ha) | % activity | expected % activity |
| ALOMY | 125 | 80 | 125 | 70 | 125 + 125 | 100 | 94 |
| ALOMY | 62.5 | 70 | 125 | 70 | 62.5 + 125 | 100 | 91 |
| AVEFA | 62.5 | 75 | 125 | 65 | 62.5 + 125 | 98 | 91 |
| ECHCG | 125 | 65 | 125 | 40 | 125 + 125 | 85 | 79 |
| GALAP | 125 | 0 | 500 | 30 | 125 + 500 | 50 | 30 |
| GALAP | 125 | 0 | 250 | 0 | 125 + 250 | 60 | 0 |
| GALAP | 62.5 | 0 | 500 | 30 | 62.5 + 500 | 50 | 30 |
| GALAP | 62.5 | 0 | 250 | 0 | 62.5 + 250 | 50 | 0 |
| ALOMY | 31.25 | 70 | 125 | 55 | 31.25 + 125 | 100 | 87 |
| AVEFA | 250 | 90 | 250 | 45 | 250 + 250 | 98 | 95 |
| AVEFA | 250 | 90 | 125 | 25 | 250 + 125 | 95 | 93 |
| AVEFA | 125 | 85 | 250 | 45 | 125 + 250 | 98 | 92 |
| AVEFA | 62.5 | 80 | 250 | 45 | 62.5 + 250 | 100 | 89 |

TABLE X12-continued

Ex. 5 and isoproturon, in post-emergence application at 20 DAT, wherein isoproturon was used as SC formulation having an active ingredient concentration of 500 g/l.

| | solo application | | | | combination | | |
|---|---|---|---|---|---|---|---|
| | | | | | Ex. 5 + isoproturon | | |
| | Ex. 5 | | isoproturon | | | | COLBY |
| weed | use rate (gai/ha) | % activity | use rate (gai/ha) | % activity | use rate (gai/ha) | % activity | expected % activity |
| AVEFA | 31.25 | 70 | 250 | 45 | 31.25 + 250 | 95 | 84 |
| LOLMU | 125 | 85 | 125 | 60 | 125 + 125 | 100 | 94 |

TABLE X13

Ex. 5 and isoproturon, in pre-emergence application at 20 DAT, wherein isoproturon was used as SC formulation having an active ingredient concentration of 500 g/l.
LIM/H/A 2016-351-04

| | solo application | | | | combination | | |
|---|---|---|---|---|---|---|---|
| | | | | | Ex. 5 + isoproturon | | |
| | Ex. 5 | | isoproturon | | | | COLBY |
| weed | use rate (gai/ha) | % activity | use rate (gai/ha) | % activity | use rate (gai/ha) | % activity | expected % activity |
| ALOMY | 31.25 | 90 | 125 | 0 | 31.25 + 125 | 98 | 90 |
| AVEFA | 125 | 85 | 125 | 25 | 125 + 125 | 95 | 89 |
| AVEFA | 62.5 | 80 | 250 | 0 | 62.5 + 250 | 95 | 90 |
| AVEFA | 31.25 | 65 | 500 | 60 | 31.25 + 500 | 95 | 86 |
| BRADC | 31.25 | 85 | 500 | 30 | 31.25 + 500 | 95 | 90 |
| DIGSA | 125 | 90 | 125 | 25 | 125 + 125 | 100 | 93 |
| GALAP | 125 | 35 | 125 | 30 | 125 + 125 | 70 | 55 |
| GALAP | 62.5 | 20 | 250 | 0 | 62.5 + 250 | 30 | 20 |
| POLCO | 250 | 90 | 500 | 0 | 250 + 500 | 95 | 90 |
| POLCO | 250 | 90 | 250 | 0 | 250 + 250 | 95 | 90 |
| POLCO | 62.5 | 75 | 500 | 0 | 62.5 + 500 | 80 | 75 |
| POLCO | 31.25 | 60 | 250 | 0 | 31.25 + 250 | 65 | 60 |
| SETVI | 62.5 | 35 | 500 | 75 | 62.5 + 500 | 95 | 84 |
| SETVI | 62.5 | 35 | 125 | 0 | 62.5 + 125 | 50 | 35 |
| SETVI | 31.25 | 20 | 500 | 75 | 31.25 + 500 | 85 | 80 |
| SETVI | 31.25 | 20 | 125 | 0 | 31.25 + 125 | 50 | 20 |

TABLE X14

Ex. 5 and metazachlor, in pre-emergence application at 20 DAT, wherein metazachlor was used as SC formulation having an active ingredient concentration of 500 g/l.

| | solo application | | | | combination | | |
|---|---|---|---|---|---|---|---|
| | | | | | Ex. 5 + metazachlor | | |
| | Ex. 5 | | metazachlor | | | | COLBY |
| weed | use rate (gai/ha) | % activity | use rate (gai/ha) | % activity | use rate (gai/ha) | % activity | expected % activity |
| POLCO | 31.25 | 60 | 150 | 80 | 31.25 + 150 | 98 | 92 |

TABLE X15

Ex. 5 and metribuzin, in post-emergence application at 20 DAT, wherein metribuzin was used as WG formulation having an active ingredient concentration of 70%.

| | solo application | | | | combination | | |
|---|---|---|---|---|---|---|---|
| | | | | | Ex. 5 + metribuzin | | |
| | Ex. 5 | | metribuzin | | | | COLBY |
| weed | use rate (gai/ha) | % activity | use rate (gai/ha) | % activity | use rate (gai/ha) | % activity | expected % activity |
|---|---|---|---|---|---|---|---|
| ALOMY | 250 | 80 | 35 | 10 | 250 + 35 | 90 | 82 |
| ALOMY | 250 | 80 | 17.5 | 0 | 250 + 17.5 | 95 | 80 |
| ALOMY | 125 | 80 | 35 | 10 | 125 + 35 | 98 | 82 |
| ALOMY | 62.5 | 75 | 35 | 10 | 62.5 + 35 | 95 | 78 |
| ALOMY | 62.5 | 75 | 17.5 | 0 | 62.5 + 17.5 | 85 | 75 |
| AMBEL | 62.5 | 85 | 70 | 0 | 62.5 + 125 | 98 | 85 |
| AMBEL | 62.5 | 85 | 35 | 0 | 62.5 + 35 | 100 | 85 |
| AMBEL | 62.5 | 85 | 17.5 | 0 | 62.5 + 17.5 | 98 | 85 |
| APESV | 250 | 85 | 17.5 | 10 | 250 + 17.5 | 95 | 87 |
| APESV | 125 | 80 | 70 | 90 | 125 + 70 | 100 | 98 |
| APESV | 125 | 80 | 35 | 55 | 125 + 35 | 100 | 91 |
| APESV | 125 | 80 | 17.5 | 10 | 125 + 17.5 | 90 | 82 |
| APESV | 62.5 | 70 | 35 | 55 | 62.5 + 35 | 98 | 87 |
| APESV | 62.5 | 70 | 17.5 | 10 | 62.5 + 17.5 | 95 | 73 |
| AVEFA | 250 | 80 | 70 | 40 | 250 + 70 | 95 | 88 |
| AVEFA | 250 | 80 | 17.5 | 5 | 250 + 17.5 | 85 | 81 |
| AVEFA | 125 | 75 | 70 | 40 | 125 + 70 | 95 | 85 |
| AVEFA | 62.5 | 70 | 35 | 10 | 62.5 + 35 | 85 | 73 |
| AVEFA | 62.5 | 70 | 17.5 | 5 | 62.5 + 17.5 | 75 | 72 |
| BROST | 250 | 70 | 35 | 55 | 250 + 35 | 95 | 87 |
| BROST | 125 | 65 | 35 | 55 | 125 + 35 | 90 | 84 |
| BROST | 62.5 | 55 | 35 | 55 | 62.5 + 35 | 90 | 80 |
| BROST | 62.5 | 55 | 17.5 | 25 | 62.5 + 17.5 | 70 | 66 |
| DIGSA | 125 | 50 | 17.5 | 0 | 125 + 17.5 | 70 | 50 |
| DIGSA | 62.5 | 35 | 140 | 85 | 62.5 + 140 | 98 | 90 |
| DIGSA | 62.5 | 35 | 35 | 35 | 62.5 + 35 | 65 | 58 |
| DIGSA | 62.5 | 35 | 17.5 | 0 | 62.5 + 17.5 | 40 | 35 |
| GALAP | 250 | 30 | 140 | 0 | 250 + 140 | 70 | 30 |
| GALAP | 125 | 0 | 140 | 0 | 125 + 140 | 30 | 0 |
| GALAP | 62.5 | 0 | 70 | 0 | 62.5 + 70 | 40 | 0 |
| GALAP | 62.5 | 0 | 35 | 0 | 62.5 + 35 | 60 | 0 |
| LOLMU | 250 | 80 | 35 | 60 | 250 + 35 | 98 | 92 |
| LOLMU | 250 | 80 | 17.5 | 20 | 250 + 17.5 | 98 | 84 |
| LOLMU | 125 | 80 | 17.5 | 20 | 125 + 17.5 | 90 | 84 |
| LOLMU | 62.5 | 75 | 70 | 65 | 62.5 + 70 | 98 | 91 |
| LOLMU | 62.5 | 75 | 17.5 | 20 | 62.5 + 17.5 | 85 | 80 |
| MATCH | 250 | 40 | 35 | 25 | 250 + 35 | 100 | 55 |
| MATCH | 250 | 40 | 17.5 | 0 | 250 + 17.5 | 100 | 40 |
| MATCH | 125 | 40 | 35 | 25 | 125 + 35 | 70 | 55 |
| MATCH | 125 | 40 | 17.5 | 0 | 125 + 17.5 | 50 | 40 |
| MATCH | 62.5 | 20 | 35 | 25 | 62.5 + 35 | 65 | 40 |
| MATCH | 62.5 | 20 | 17.5 | 0 | 62.5 + 17.5 | 30 | 20 |
| PAPRH | 250 | 70 | 17.5 | 60 | 250 + 17.5 | 100 | 88 |
| PAPRH | 125 | 5 | 17.5 | 60 | 125 + 17.5 | 65 | 62 |
| PAPRH | 62.5 | 5 | 17.5 | 60 | 62.5 + 17.5 | 100 | 62 |
| POAAN | 125 | 85 | 17.5 | 60 | 125 + 17.5 | 100 | 94 |
| POAAN | 62.5 | 85 | 17.5 | 60 | 62.5 + 17.5 | 100 | 94 |
| SETVI | 250 | 50 | 17.5 | 30 | 250 + 17.5 | 70 | 65 |
| SETVI | 62.5 | 20 | 17.5 | 30 | 62.5 + 17.5 | 70 | 44 |

TABLE X16

Ex. 5 and metribuzin, in pre-emergence application at 20 DAT, wherein metribuzin was used as WG formulation having an active ingredient concentration of 70%.

| | solo application | | | | combination | | |
|---|---|---|---|---|---|---|---|
| | | | | | Ex. 5 + metribuzin | | |
| | Ex. 5 | | metribuzin | | | | COLBY |
| weed | use rate (gai/ha) | % activity | use rate (gai/ha) | % activity | use rate (gai/ha) | % activity | expected % activity |
| APESV | 125 | 80 | 62.5 | 50 | 125 + 62.5 | 98 | 90 |
| APESV | 125 | 80 | 31.25 | 30 | 125 + 31.25 | 95 | 86 |
| AMBEL | 62.5 | 70 | 125 | 70 | 62.5 + 125 | 98 | 91 |
| AMBEL | 62.5 | 70 | 62.5 | 40 | 62.5 + 62.5 | 98 | 82 |
| AMBEL | 62.5 | 70 | 31.25 | 40 | 62.5 + 31.25 | 95 | 82 |
| APESV | 31.25 | 75 | 62.5 | 50 | 31.25 + 62.5 | 95 | 88 |
| BRADC | 62.5 | 85 | 62.5 | 0 | 62.5 + 62.5 | 90 | 85 |
| BRADC | 31.25 | 55 | 62.5 | 0 | 31.25 + 62.5 | 60 | 55 |
| BROST | 62.5 | 45 | 62.5 | 10 | 62.5 + 62.5 | 70 | 51 |
| DIGSA | 31.25 | 65 | 31.25 | 40 | 31.25 + 31.25 | 85 | 79 |
| ECHCG | 125 | 95 | 62.5 | 30 | 125 + 62.5 | 100 | 97 |
| ECHCG | 125 | 95 | 31.25 | 0 | 125 + 31.25 | 100 | 95 |
| ECHCG | 31.25 | 95 | 31.25 | 0 | 31.25 + 31.25 | 100 | 95 |
| GALAP | 125 | 0 | 250 | 0 | 125 + 250 | 30 | 0 |
| GALAP | 31.25 | 0 | 250 | 0 | 31.25 + 250 | 20 | 0 |
| HELAN | 125 | 0 | 62.5 | 0 | 125 + 62.5 | 55 | 0 |
| HELAN | 125 | 0 | 31.25 | 0 | 125 + 31.25 | 40 | 0 |
| HELAN | 62.5 | 0 | 62.5 | 0 | 62.5 + 62.5 | 20 | 0 |
| HELAN | 31.25 | 0 | 250 | 50 | 31.25 + 250 | 55 | 50 |
| HELAN | 31.25 | 0 | 62.5 | 0 | 31.25 + 62.5 | 20 | 0 |
| HELAN | 31.25 | 0 | 31.25 | 0 | 31.25 + 31.25 | 30 | 0 |
| PAPRH | 62.5 | 70 | 31.25 | 80 | 62.5 + 31.25 | 98 | 94 |
| POLCO | 31.25 | 35 | 125 | 0 | 31.25 + 125 | 40 | 35 |
| POLCO | 31.25 | 35 | 62.5 | 0 | 31.25 + 62.5 | 40 | 35 |
| SETVI | 125 | 45 | 31.25 | 0 | 125 + 31.25 | 50 | 45 |
| SETVI | 31.25 | 10 | 31.25 | 0 | 31.25 + 31.25 | 40 | 10 |

TABLE X17

Ex. 5 and pendimethalin, in post-emergence application at 20 DAT, wherein pendimethalin was used as SC formulation having an active ingredient concentration of 400 g/l.

| | solo application | | | | combination | | |
|---|---|---|---|---|---|---|---|
| | | | | | Ex. 5 + pendimethalin | | |
| | Ex. 5 | | pendimethalin | | | | COLBY |
| weed | use rate (gai/ha) | % activity | use rate (gai/ha) | % activity | use rate (gai/ha) | % activity | expected % activity |
| AVEFA | 125 | 80 | 1000 | 0 | 125 + 1000 | 85 | 80 |
| AVEFA | 125 | 80 | 250 | 0 | 125 + 250 | 85 | 80 |
| APESV | 250 | 90 | 250 | 0 | 250 + 250 | 95 | 90 |
| BRADC | 250 | 60 | 1000 | 55 | 250 + 1000 | 85 | 82 |
| BRADC | 250 | 60 | 500 | 45 | 250 + 500 | 85 | 78 |
| BROST | 125 | 65 | 1000 | 0 | 125 + 1000 | 75 | 65 |
| BROST | 125 | 65 | 250 | 0 | 125 + 250 | 75 | 65 |
| LOLMU | 125 | 50 | 125 | 10 | 125 + 125 | 85 | 82 |
| MATCH | 250 | 45 | 250 | 0 | 250 + 250 | 65 | 45 |
| MATCH | 125 | 20 | 1000 | 0 | 125 + 1000 | 40 | 20 |
| MATCH | 125 | 20 | 250 | 0 | 125 + 250 | 40 | 20 |

TABLE X18

Ex. 5 and pendimethalin, in pre-emergence application at 21 DAT wherein pendimethalin was used as SC formulation having an active ingredient concentration of 400 g/l.

| | solo application | | | | combination | | |
| --- | --- | --- | --- | --- | --- | --- | --- |
| | | | | | Ex. 5 + pendimethalin | | |
| | Ex. 5 | | pendimethalin | | | | COLBY |
| weed | use rate (gai/ha) | % activity | use rate (gai/ha) | % activity | use rate (gai/ha) | % activity | expected % activity |
| GALAP | 250 | 25 | 1000 | 0 | 250 + 1000 | 30 | 25 |
| GALAP | 250 | 25 | 500 | 0 | 250 + 500 | 45 | 25 |
| GALAP | 250 | 25 | 250 | 0 | 250 + 250 | 45 | 25 |
| HELAN | 250 | 80 | 1000 | 10 | 250 + 1000 | 90 | 82 |
| HELAN | 250 | 80 | 250 | 0 | 250 + 250 | 85 | 80 |
| HELAN | 125 | 50 | 1000 | 10 | 125 + 1000 | 75 | 55 |
| HELAN | 125 | 50 | 500 | 10 | 125 + 500 | 75 | 55 |
| HELAN | 125 | 50 | 250 | 0 | 125 + 250 | 60 | 50 |
| HELAN | 125 | 50 | 125 | 0 | 125 + 125 | 60 | 50 |

TABLE X19

Ex. 5 and picolinafen, in post-emergence application at 20 DAT, wherein picolinafen was used as WG formulation having an active ingredient concentration of 75%.

| | solo application | | | | combination | | |
| --- | --- | --- | --- | --- | --- | --- | --- |
| | | | | | Ex. 5 + picolinafen | | |
| | Ex. 5 | | picolinafen | | | | COLBY |
| weed | use rate (gai/ha) | % activity | use rate (gai/ha) | % activity | use rate (gai/ha) | % activity | expected % activity |
| ALOMY | 62.5 | 75 | 50 | 10 | 62.5 + 50 | 80 | 78 |
| BRADC | 250 | 60 | 50 | 50 | 250 + 50 | 85 | 80 |
| BRADC | 250 | 60 | 25 | 35 | 250 + 25 | 80 | 74 |
| BRADC | 62.5 | 45 | 50 | 50 | 62.5 + 50 | 75 | 73 |
| BRADC | 62.5 | 45 | 25 | 35 | 62.5 + 25 | 75 | 64 |
| BROST | 250 | 80 | 100 | 20 | 250 + 100 | 90 | 84 |
| BROST | 62.5 | 10 | 100 | 20 | 62.5 + 100 | 40 | 28 |
| BROST | 62.5 | 10 | 50 | 10 | 62.5 + 50 | 35 | 19 |
| BROST | 62.5 | 10 | 25 | 0 | 62.5 + 25 | 35 | 10 |
| BROST | 62.5 | 10 | 12.5 | 0 | 62.5 + 12.5 | 25 | 10 |
| DIGSA | 62.5 | 35 | 100 | 75 | 62.5 + 100 | 90 | 84 |
| MATCH | 250 | 45 | 25 | 20 | 250 + 25 | 65 | 56 |
| MATCH | 250 | 45 | 12.5 | 0 | 250 + 12.5 | 50 | 45 |
| MATCH | 125 | 20 | 25 | 20 | 125 + 25 | 55 | 36 |
| MATCH | 125 | 20 | 12.5 | 0 | 125 + 12.5 | 25 | 20 |
| MATCH | 62.5 | 20 | 50 | 20 | 62.5 + 50 | 45 | 36 |
| MATCH | 62.5 | 20 | 25 | 20 | 62.5 + 25 | 50 | 36 |
| MATCH | 62.5 | 20 | 12.5 | 0 | 62.5 + 12.5 | 65 | 20 |
| PAPRH | 250 | 75 | 50 | 55 | 250 + 50 | 100 | 89 |
| PAPRH | 250 | 75 | 25 | 40 | 250 + 25 | 100 | 85 |
| PAPRH | 250 | 75 | 12.5 | 35 | 250 + 12.5 | 100 | 84 |
| PAPRH | 125 | 55 | 100 | 80 | 125 + 100 | 100 | 91 |
| PAPRH | 125 | 55 | 50 | 55 | 125 + 50 | 85 | 80 |
| PAPRH | 125 | 55 | 25 | 40 | 125 + 25 | 80 | 73 |
| PAPRH | 125 | 55 | 12.5 | 35 | 125 + 12.5 | 100 | 71 |
| PAPRH | 62.5 | 45 | 50 | 55 | 62.5 + 50 | 80 | 75 |
| PAPRH | 62.5 | 45 | 25 | 40 | 62.5 + 25 | 75 | 67 |
| PAPRH | 62.5 | 45 | 12.5 | 35 | 62.5 + 12.5 | 70 | 64 |
| POAAN | 250 | 85 | 12.5 | 40 | 250 + 12.5 | 98 | 91 |
| POAAN | 125 | 85 | 12.5 | 40 | 125 + 12.5 | 98 | 91 |
| SETVI | 250 | 50 | 50 | 80 | 250 + 50 | 95 | 88 |
| SETVI | 125 | 40 | 50 | 80 | 125 + 50 | 98 | 88 |
| SETVI | 62.5 | 35 | 50 | 80 | 62.5 + 50 | 95 | 87 |
| SETVI | 62.5 | 35 | 12.5 | 30 | 62.5 + 12.5 | 80 | 55 |

TABLE X20

Ex. 5 and picolinafen, in pre-emergence application at 21 DAT, wherein picolinafen was used as WG formulation having an active ingredient concentration of 75%.

| | solo application | | | | combination | | |
|---|---|---|---|---|---|---|---|
| | | | | | Ex. 5 + picolinafen | | |
| | Ex. 5 | | picolinafen | | | | COLBY |
| weed | use rate (gai/ha) | % activity | use rate (gai/ha) | % activity | use rate (gai/ha) | % activity | expected % activity |
| AMBEL | 125 | 70 | 50 | 0 | 125 + 50 | 90 | 70 |
| AMBEL | 125 | 70 | 25 | 0 | 125 + 25 | 95 | 70 |
| AMBEL | 125 | 70 | 12.5 | 0 | 125 + 12.5 | 85 | 70 |
| BROST | 125 | 75 | 50 | 20 | 125 + 50 | 90 | 80 |
| DIGSA | 250 | 65 | 50 | 60 | 250 + 50 | 95 | 86 |
| DIGSA | 250 | 65 | 25 | 30 | 250 + 25 | 98 | 76 |
| DIGSA | 125 | 60 | 50 | 60 | 125 + 50 | 90 | 84 |
| GALAP | 250 | 25 | 25 | 0 | 250 + 25 | 40 | 25 |
| GALAP | 250 | 25 | 12.5 | 0 | 250 + 12.5 | 40 | 25 |
| HELAN | 125 | 50 | 50 | 15 | 125 + 50 | 85 | 58 |
| HELAN | 125 | 50 | 25 | 20 | 125 + 25 | 65 | 60 |
| HELAN | 125 | 50 | 12.5 | 10 | 125 + 12.5 | 65 | 55 |
| POLCO | 125 | 85 | 50 | 20 | 125 + 50 | 100 | 88 |
| POLCO | 62.5 | 70 | 50 | 20 | 62.5 + 50 | 85 | 76 |
| SETVI | 250 | 65 | 50 | 80 | 250 + 50 | 100 | 93 |
| SETVI | 250 | 65 | 12.5 | 45 | 250 + 12.5 | 90 | 81 |
| SETVI | 125 | 60 | 50 | 80 | 125 + 50 | 98 | 92 |
| SETVI | 62.5 | 45 | 50 | 80 | 62.5 + 50 | 95 | 89 |

TABLE X21

Ex. 5 and pinoxaden, in post-emergence application at 20 DAT, wherein pinoxaden was used as EC formulation having an active ingredient concentration of 50 g/l.

| | solo application | | | | combination | | |
|---|---|---|---|---|---|---|---|
| | | | | | Ex. 5 + pinoxaden | | |
| | Ex. 5 | | pinoxaden | | | | COLBY |
| weed | use rate (gai/ha) | % activity | use rate (gai/ha) | % activity | use rate (gai/ha) | % activity | expected % activity |
| ALOMY | 125 | 75 | 7.5 | 48 | 125 + 7.5 | 93 | 87 |
| AVEFA | 125 | 60 | 7.5 | 33 | 125 + 7.5 | 90 | 73 |
| AVEFA | 62.5 | 55 | 7.5 | 33 | 62.5 + 7.5 | 83 | 70 |

TABLE X22

Ex. 5 and prosulfocarb, in pre-emergence application at 20 DAT, wherein prosulfocarb was used as EC formulation having an active ingredient concentration of 800 g/l.

| | solo application | | | | combination | | |
|---|---|---|---|---|---|---|---|
| | | | | | Ex. 5 + prosulfocarb | | |
| | Ex. 5 | | prosulfocarb | | | | COLBY |
| weed | use rate (gai/ha) | % activity | use rate (gai/ha) | % activity | use rate (gai/ha) | % activity | expected % activity |
| GALAP | 125 | 0 | 500 | 30 | 125 + 500 | 65 | 30 |
| GALAP | 62.5 | 0 | 500 | 30 | 62.5 + 500 | 45 | 30 |
| PAPRH | 62.5 | 70 | 1000 | 70 | 62.5 + 100 | 100 | 91 |
| SETVI | 125 | 45 | 125 | 10 | 125 + 125 | 60 | 51 |

TABLE X23

Ex. 5 and pyridate, in post-emergence application at 20 DAT, wherein pyridate was used as WP formulation having an active ingredient concentration of 45%.

| | solo application | | | | combination | | |
|---|---|---|---|---|---|---|---|
| | | | | | Ex. 5 + pyridate | | |
| | Ex. 5 | | pyridate | | | | COLBY |
| weed | use rate (gai/ha) | % activity | use rate (gai/ha) | % activity | use rate (gai/ha) | % activity | expected % activity |
| ALOMY | 62.5 | 70 | 900 | 20 | 62.5 + 900 | 80 | 76 |
| AMBEL | 125 | 80 | 225 | 10 | 125 + 225 | 98 | 82 |
| AMBEL | 125 | 80 | 112.5 | 0 | 125 + 112.5 | 100 | 80 |
| AMBEL | 62.5 | 80 | 225 | 10 | 125 + 225 | 100 | 82 |
| AMBEL | 62.5 | 80 | 112.5 | 0 | 125 + 112.5 | 98 | 80 |
| APESV | 62.5 | 75 | 450 | 0 | 62.5 + 450 | 80 | 75 |
| AVEFA | 250 | 75 | 450 | 10 | 250 + 450 | 85 | 78 |
| AVEFA | 250 | 75 | 225 | 0 | 250 + 225 | 85 | 75 |
| AVEFA | 125 | 70 | 900 | 30 | 125 + 900 | 85 | 79 |
| AVEFA | 125 | 70 | 450 | 10 | 125 + 450 | 80 | 73 |
| AVEFA | 125 | 70 | 225 | 0 | 125 + 225 | 75 | 70 |
| AVEFA | 125 | 70 | 112.5 | 0 | 125 + 112.5 | 75 | 70 |
| BRADC | 250 | 60 | 900 | 50 | 250 + 900 | 85 | 80 |
| BRADC | 250 | 60 | 450 | 20 | 250 + 450 | 85 | 68 |
| BRADC | 250 | 60 | 225 | 20 | 250 + 225 | 70 | 68 |
| BRADC | 250 | 60 | 112.5 | 0 | 250 + 112.5 | 65 | 60 |
| BRADC | 125 | 50 | 450 | 20 | 125 + 450 | 75 | 60 |
| BRADC | 125 | 50 | 225 | 20 | 125 + 225 | 65 | 60 |
| BRADC | 125 | 50 | 112.5 | 0 | 125 + 112.5 | 60 | 50 |
| BRADC | 62.5 | 30 | 900 | 50 | 62.5 + 900 | 80 | 65 |
| BRADC | 62.5 | 30 | 450 | 20 | 62.5 + 450 | 70 | 44 |
| BRADC | 62.5 | 30 | 225 | 20 | 62.5 + 225 | 50 | 44 |
| BRADC | 62.5 | 30 | 112.5 | 0 | 62.5 + 112.5 | 40 | 30 |
| BROST | 250 | 70 | 225 | 0 | 250 + 225 | 80 | 70 |
| BROST | 125 | 65 | 112.5 | 0 | 125 + 112.5 | 70 | 65 |
| BROST | 62.5 | 30 | 900 | 0 | 62.5 + 900 | 50 | 30 |
| GALAP | 250 | 0 | 112.5 | 40 | 250 + 112.5 | 50 | 40 |
| GALAP | 62.5 | 0 | 225 | 85 | 62.5 + 225 | 90 | 85 |
| GALAP | 62.5 | 0 | 112.5 | 40 | 62.5 + 112.5 | 80 | 40 |
| LOLMU | 250 | 85 | 225 | 20 | 250 + 225 | 95 | 88 |
| LOLMU | 125 | 80 | 112.5 | 0 | 125 + 112.5 | 85 | 80 |
| LOLMU | 62.5 | 80 | 225 | 20 | 62.5 + 225 | 85 | 80 |
| MATCH | 250 | 10 | 450 | 40 | 250 + 450 | 100 | 46 |
| MATCH | 250 | 10 | 225 | 0 | 250 + 225 | 100 | 10 |
| MATCH | 250 | 10 | 112.5 | 0 | 250 + 112.5 | 65 | 10 |
| MATCH | 125 | 10 | 450 | 40 | 125 + 450 | 100 | 46 |
| MATCH | 125 | 10 | 225 | 0 | 125 + 225 | 65 | 10 |
| MATCH | 62.5 | 10 | 450 | 40 | 62.5 + 450 | 100 | 46 |
| MATCH | 62.5 | 10 | 225 | 0 | 62.5 + 225 | 65 | 10 |
| MATCH | 62.5 | 10 | 112.5 | 0 | 62.5 + 112.5 | 60 | 10 |
| PAPRH | 125 | 30 | 900 | 70 | 125 + 900 | 100 | 79 |
| PAPRH | 125 | 30 | 450 | 50 | 125 + 450 | 80 | 65 |
| PAPRH | 125 | 30 | 225 | 10 | 125 + 225 | 65 | 37 |
| PAPRH | 125 | 30 | 112.5 | 0 | 125 + 112.5 | 55 | 30 |
| PAPRH | 62.5 | 0 | 900 | 70 | 62.5 + 900 | 100 | 70 |
| PAPRH | 62.5 | 0 | 450 | 50 | 62.5 + 445 | 100 | 50 |
| PAPRH | 62.5 | 0 | 225 | 10 | 62.5 + 225 | 50 | 10 |
| PAPRH | 62.5 | 0 | 112.5 | 0 | 62.5 + 112.5 | 50 | 0 |
| POAAN | 125 | 80 | 450 | 0 | 125 + 450 | 95 | 80 |
| POAAN | 125 | 80 | 225 | 0 | 125 + 225 | 90 | 80 |
| POAAN | 125 | 80 | 112.5 | 0 | 125 + 112.5 | 90 | 80 |
| POAAN | 62.5 | 80 | 450 | 0 | 62.5 + 450 | 90 | 80 |
| POAAN | 62.5 | 80 | 225 | 0 | 62.5 + 225 | 85 | 80 |
| POAAN | 62.5 | 80 | 112.5 | 0 | 62.5 + 112.5 | 85 | 80 |
| SETVI | 62.5 | 35 | 450 | 65 | 62.5 + 455 | 80 | 77 |
| SETVI | 62.5 | 35 | 225 | 25 | 62.5 + 225 | 65 | 51 |
| SETVI | 62.5 | 35 | 112.5 | 15 | 62.5 + 112.5 | 55 | 45 |

TABLE X24

Ex. 5 and pyroxasulfone, in post-emergence application at 21 DAT, wherein pyroxasulfone was used as WG formulation having an active ingredient concentration of 85%.

| | solo application | | | | combination | | |
|---|---|---|---|---|---|---|---|
| | Ex. 5 | | pyroxasulfone | | Ex. 5 + pyroxasulfone | | COLBY |
| weed | use rate (gai/ha) | % activity | use rate (gai/ha) | % activity | use rate (gai/ha) | % activity | expected % activity |
| DIGSA | 250 | 65 | 15 | 0 | 250 + 15 | 75 | 65 |
| DIGSA | 125 | 45 | 15 | 0 | 125 + 15 | 50 | 45 |
| DIGSA | 125 | 45 | 7.5 | 0 | 125 + 7.5 | 60 | 45 |
| GALAP | 125 | 0 | 15 | 70 | 125 + 15 | 75 | 70 |
| MATCH | 250 | 30 | 15 | 0 | 250 + 15 | 50 | 30 |
| PAPRH | 250 | 65 | 15 | 0 | 250 + 15 | 70 | 65 |
| PAPRH | 250 | 65 | 7.5 | 0 | 250 + 7.5 | 70 | 65 |
| PAPRH | 125 | 10 | 15 | 0 | 125 + 15 | 50 | 10 |
| PAPRH | 62.5 | 0 | 60 | 60 | 62.5 + 60 | 70 | 60 |
| PAPRH | 62.5 | 0 | 30 | 30 | 62.5 + 30 | 75 | 30 |
| POLCO | 62.5 | 90 | 60 | 30 | 62.5 + 60 | 100 | 93 |
| POLCO | 62.5 | 90 | 30 | 30 | 62.5 + 30 | 100 | 93 |
| POLCO | 62.5 | 90 | 15 | 30 | 62.5 + 15 | 100 | 93 |
| POLCO | 62.5 | 90 | 7.5 | 30 | 62.5 + 7.5 | 100 | 93 |
| SETVI | 62.5 | 35 | 15 | 40 | 62.5 + 15 | 65 | 61 |

TABLE X25

Ex. 5 and pyroxsulam, in post-emergence application at 20 DAT, wherein pyroxsulam was used as SC formulation having an active ingredient concentration of 30 g/l.

| | solo application | | | | combination | | |
|---|---|---|---|---|---|---|---|
| | Ex. 5 | | pyroxsulam | | Ex. 5 + pyroxsulam | | COLBY |
| weed | use rate (gai/ha) | % activity | use rate (gai/ha) | % activity | use rate (gai/ha) | % activity | expected % activity |
| BRADC | 62.5 | 45 | 1.875 | 20 | 62.5 + 1.875 | 70 | 56 |
| BROST | 62.5 | 30 | 1.875 | 60 | 62.5 + 1.875 | 75 | 72 |
| DIGSA | 62.5 | 35 | 7.5 | 80 | 62.5 + 7.5 | 90 | 87 |
| GALAP | 250 | 30 | 7.5 | 75 | 250 + 7.5 | 98 | 83 |
| GALAP | 125 | 0 | 7.5 | 75 | 125 + 7.5 | 95 | 75 |
| GALAP | 125 | 0 | 3.75 | 65 | 125 + 3.75 | 80 | 65 |
| GALAP | 125 | 0 | 1.875 | 60 | 125 + 1.875 | 65 | 60 |
| GALAP | 62.5 | 0 | 7.5 | 75 | 62.5 + 7.5 | 98 | 75 |
| GALAP | 62.5 | 0 | 3.75 | 65 | 62.5 + 3.75 | 90 | 65 |
| GALAP | 62.5 | 0 | 1.875 | 60 | 62.5 + 1.875 | 80 | 60 |
| MATCH | 250 | 30 | 15 | 80 | 250 + 15 | 95 | 86 |
| MATCH | 250 | 30 | 3.75 | 60 | 250 + 3.75 | 85 | 72 |
| MATCH | 250 | 30 | 1.875 | 30 | 250 + 1.875 | 80 | 51 |
| MATCH | 125 | 30 | 15 | 80 | 125 + 15 | 98 | 86 |
| MATCH | 125 | 30 | 1.875 | 30 | 125 + 1.875 | 65 | 51 |
| MATCH | 62.5 | 0 | 15 | 80 | 62.5 + 15 | 95 | 80 |
| MATCH | 62.5 | 0 | 3.75 | 60 | 62.5 + 3.75 | 90 | 60 |
| MATCH | 62.5 | 0 | 1.875 | 30 | 62.5 + 1.875 | 98 | 30 |
| PAPRH | 250 | 65 | 7.5 | 30 | 250 + 7.5 | 95 | 76 |
| PAPRH | 250 | 65 | 3.75 | 0 | 250 + 3.75 | 75 | 65 |
| PAPRH | 250 | 65 | 1.875 | 0 | 250 + 1.875 | 75 | 65 |
| PAPRH | 125 | 0 | 15 | 70 | 125 + 15 | 90 | 70 |
| PAPRH | 125 | 0 | 7.5 | 30 | 125 + 7.5 | 70 | 30 |
| PAPRH | 125 | 0 | 3.75 | 0 | 125 + 3.75 | 75 | 0 |
| PAPRH | 125 | 0 | 1.875 | 0 | 125 + 1.875 | 70 | 0 |
| PAPRH | 62.5 | 0 | 15 | 70 | 62.5 + 15 | 90 | 70 |
| SETVI | 62.5 | 30 | 1.875 | 75 | 62. + 1.875 | 90 | 83 |

TABLE X26

Ex. 5 and saflufenacil, in pre-emergence application at 20 DAT, wherein saflufenacil was used as SC formulation having an active ingredient concentration of 342 g/l.

| | solo application | | | | combination | | |
|---|---|---|---|---|---|---|---|
| | | | | | Ex. 5 + saflufenacil | | |
| | Ex. 5 | | saflufenacil | | | | COLBY |
| weed | use rate (gai/ha) | % activity | use rate (gai/ha) | % activity | use rate (gai/ha) | % activity | expected % activity |
| ALOMY | 62.5 | 90 | 25 | 0 | 62.5 + 25 | 95 | 90 |
| ALOMY | 62.5 | 90 | 12.5 | 0 | 62.5 + 12.5 | 95 | 90 |
| ALOMY | 62.5 | 90 | 6.25 | 0 | 62.5 + 6.25 | 95 | 90 |
| ALOMY | 31.25 | 90 | 25 | 0 | 31.25 + 25 | 95 | 90 |
| AVEFA | 125 | 90 | 12.5 | 0 | 125 + 12.5 | 95 | 90 |
| GALAP | 125 | 0 | 12.5 | 80 | 125 + 12.5 | 90 | 80 |
| GALAP | 62.5 | 0 | 12.5 | 80 | 62.5 + 12.5 | 98 | 80 |
| GALAP | 31.25 | 0 | 12.5 | 80 | 31.25 + 12.5 | 90 | 80 |
| SETVI | 125 | 45 | 6.25 | 25 | 125 + 6.25 | 60 | 56 |
| SETVI | 31.25 | 35 | 25 | 65 | 31.25 + 25 | 85 | 77 |

TABLE X27

Ex. 5 and sulfosulfuron, in post-emergence application at 20 DAT, wherein sulfosulfuron was used as WG formulation having an active ingredient concentration of 80%.

| | solo application | | | | combination | | |
|---|---|---|---|---|---|---|---|
| | | | | | Ex. 5 + sulfosulfuron | | |
| | Ex. 5 | | sulfosulfuron | | | | COLBY |
| weed | use rate (gai/ha) | % activity | use rate (gai/ha) | % activity | use rate (gai/ha) | % activity | expected % activity |
| GALAP | 250 | 30 | 3 | 85 | 250 + 3 | 95 | 90 |
| GALAP | 250 | 30 | 1.5 | 65 | 250 + 1.5 | 80 | 76 |
| GALAP | 125 | 0 | 1.5 | 65 | 125 + 1.5 | 80 | 65 |
| PAPRH | 250 | 65 | 1.5 | 25 | 250 + 1.5 | 90 | 74 |
| PAPRH | 125 | 0 | 1.5 | 25 | 125 + 1.5 | 70 | 25 |

TABLE X28

Ex. 5 and terbuthylazin, in post-emergence application at 20 DAT, wherein terbuthylazin was used as SC formulation having an active ingredient concentration of 500 g/l.

| | solo application | | | | combination | | |
|---|---|---|---|---|---|---|---|
| | | | | | Ex. 5 + terbuthylazin | | |
| | Ex. 5 | | terbuthylazin | | | | COLBY |
| weed | use rate (gai/ha) | % activity | use rate (gai/ha) | % activity | use rate (gai/ha) | % activity | expected % activity |
| ALOMY | 500 | 78 | 125 | 5 | 500 + 125 | 98 | 79 |
| ALOMY | 500 | 78 | 62.5 | 0 | 500 + 62.5 | 98 | 78 |
| ALOMY | 500 | 78 | 31.25 | 0 | 500 + 31.25 | 85 | 78 |
| ALOMY | 250 | 73 | 125 | 5 | 250 + 125 | 98 | 74 |
| ALOMY | 250 | 73 | 62.5 | 0 | 250 + 62.5 | 98 | 73 |
| ALOMY | 250 | 73 | 31.25 | 0 | 250 + 31.25 | 83 | 73 |
| ALOMY | 125 | 70 | 125 | 5 | 125 + 125 | 98 | 72 |
| ALOMY | 125 | 70 | 62.5 | 0 | 125 + 62.5 | 98 | 70 |
| ALOMY | 125 | 70 | 31.25 | 0 | 125 + 31.25 | 70 | 78 |
| ALOMY | 62.5 | 68 | 125 | 5 | 62.5 + 125 | 97 | 69 |
| ALOMY | 62.5 | 68 | 62.5 | 0 | 62.5 + 62.5 | 92 | 68 |
| AVEFA | 500 | 75 | 125 | 0 | 500 + 125 | 97 | 75 |
| AVEFA | 500 | 75 | 62.5 | 0 | 500 + 62.5 | 93 | 75 |
| AVEFA | 500 | 75 | 31.25 | 0 | 500 + 31.25 | 80 | 75 |
| AVEFA | 250 | 70 | 125 | 0 | 250 + 125 | 95 | 70 |

TABLE X28-continued

Ex. 5 and terbuthylazin, in post-emergence application at 20 DAT, wherein terbuthylazin was used as SC formulation having an active ingredient concentration of 500 g/l.

| | solo application | | | | combination | | |
|---|---|---|---|---|---|---|---|
| | | | | | Ex. 5 + terbuthylazin | | COLBY |
| | Ex. 5 | | terbuthylazin | | | | |
| weed | use rate (gai/ha) | % activity | use rate (gai/ha) | % activity | use rate (gai/ha) | % activity | expected % activity |
| AVEFA | 250 | 70 | 62.5 | 0 | 250 + 62.5 | 90 | 70 |
| AVEFA | 250 | 70 | 31.25 | 0 | 250 + 31.25 | 75 | 70 |
| AVEFA | 125 | 70 | 125 | 0 | 125 + 125 | 97 | 70 |
| AVEFA | 125 | 70 | 62.5 | 0 | 125 + 62.5 | 83 | 70 |
| AVEFA | 125 | 70 | 31.25 | 0 | 125 + 31.25 | 78 | 70 |
| AVEFA | 62.5 | 68 | 125 | 0 | 62.5 + 125 | 92 | 68 |
| AVEFA | 62.5 | 68 | 62.5 | 0 | 62.5 + 62.5 | 78 | 68 |
| BROST | 500 | 90 | 125 | 0 | 500 + 125 | 97 | 90 |
| BROST | 500 | 90 | 62.5 | 0 | 500 + 62.5 | 97 | 90 |
| BROST | 250 | 85 | 125 | 0 | 250 + 125 | 93 | 85 |
| BROST | 250 | 85 | 62.5 | 0 | 250 + 62.5 | 97 | 85 |
| BROST | 125 | 73 | 125 | 0 | 125 + 125 | 90 | 73 |
| BROST | 125 | 73 | 62.5 | 0 | 125 + 62.5 | 85 | 73 |
| BROST | 62.5 | 53 | 125 | 0 | 62.5 + 125 | 75 | 53 |
| BROST | 62.5 | 53 | 62.5 | 0 | 62.5 + 62.5 | 75 | 53 |
| BROST | 62.5 | 53 | 31.25 | 0 | 62.5 + 31.25 | 65 | 53 |
| LOLMU | 500 | 85 | 125 | 0 | 500 + 125 | 97 | 85 |
| LOLMU | 500 | 85 | 62.5 | 0 | 500 + 62.5 | 95 | 85 |
| LOLMU | 250 | 85 | 125 | 0 | 250 + 125 | 95 | 85 |
| LOLMU | 250 | 85 | 62.5 | 0 | 250 + 62.5 | 93 | 85 |
| LOLMU | 125 | 83 | 125 | 0 | 125 + 125 | 95 | 83 |
| LOLMU | 125 | 83 | 62.5 | 0 | 125 + 62.5 | 90 | 83 |
| LOLMU | 62.5 | 80 | 125 | 0 | 62.5 + 125 | 95 | 80 |
| LOLMU | 62.5 | 80 | 62.5 | 0 | 62.5 + 62.5 | 88 | 80 |
| SETVI | 500 | 73 | 125 | 13 | 500 + 125 | 85 | 76 |
| SETVI | 500 | 73 | 62.5 | 0 | 500 + 62.5 | 80 | 73 |
| SETVI | 62.5 | 48 | 125 | 13 | 62.5 + 125 | 63 | 54 |
| ALOMY | 500 | 80 | 125 | 40 | 500 + 125 | 98 | 88 |
| ALOMY | 250 | 80 | 125 | 40 | 250 + 125 | 100 | 88 |
| ALOMY | 15 | 80 | 125 | 40 | 125 + 125 | 100 | 88 |
| ALOMY | 62.5 | 70 | 125 | 40 | 62.5 + 125 | 100 | 82 |
| AVEFA | 62.5 | 75 | 125 | 30 | 62.5 + 125 | 100 | 83 |
| DIGSA | 500 | 75 | 125 | 0 | 500 + 125 | 85 | 75 |
| LOLMU | 500 | 85 | 125 | 45 | 500 + 125 | 100 | 92 |
| LOLMU | 250 | 85 | 125 | 45 | 250 + 125 | 100 | 92 |
| LOLMU | 15 | 85 | 125 | 45 | 125 + 125 | 100 | 92 |
| LOLMU | 62.5 | 80 | 125 | 45 | 62.5 + 125 | 98 | 89 |
| LOLPE | 500 | 85 | 125 | 35 | 500 + 125 | 95 | 90 |
| LOLPE | 250 | 85 | 125 | 35 | 250 + 125 | 95 | 90 |
| LOLPE | 15 | 85 | 125 | 35 | 125 + 125 | 95 | 90 |
| LOLPE | 62.5 | 80 | 125 | 35 | 62.5 + 125 | 95 | 87 |
| SETVI | 500 | 70 | 125 | 40 | 500 + 125 | 90 | 82 |
| SETVI | 250 | 65 | 125 | 40 | 250 + 125 | 85 | 79 |

TABLE X29

Ex. 5 and topramezone, in post-emergence application at 21 DAT, wherein topramezone was used as SC formulation having an active ingredient concentration of 336 g/l.

| | solo application | | | | combination | | |
|---|---|---|---|---|---|---|---|
| | | | | | Ex. 5 + topramezone | | COLBY |
| | Ex. 5 | | topramezone | | | | |
| weed | use rate (gai/ha) | % activity | use rate (gai/ha) | % activity | use rate (gai/ha) | % activity | expected % activity |
| ALOMY | 250 | 80 | 12 | 0 | 250 + 12 | 85 | 80 |
| ALOMY | 250 | 80 | 6 | 0 | 250 + 6 | 85 | 80 |
| ALOMY | 250 | 80 | 3 | 0 | 250 + 3 | 85 | 80 |
| ECHCG | 250 | 65 | 3 | 70 | 250 + 3 | 98 | 90 |
| ECHCG | 125 | 65 | 24 | 98 | 125 + 24 | 100 | 99 |

TABLE X29-continued

Ex. 5 and topramezone, in post-emergence application at 21 DAT, wherein topramezone was used as SC formulation having an active ingredient concentration of 336 g/l.

| | solo application | | | | combination | | |
| --- | --- | --- | --- | --- | --- | --- | --- |
| | | | | | Ex. 5 + topramezone | | |
| | Ex. 5 | | topramezone | | | | COLBY |
| weed | use rate (gai/ha) | % activity | use rate (gai/ha) | % activity | use rate (gai/ha) | % activity | expected % activity |
| ECHCG | 125 | 65 | 12 | 98 | 125 + 12 | 100 | 99 |
| ECHCG | 125 | 65 | 3 | 70 | 125 + 3 | 95 | 90 |
| LOLMU | 250 | 80 | 6 | 0 | 250 + 6 | 85 | 80 |
| PAPRH | 125 | 10 | 6 | 0 | 125 + 6 | 35 | 10 |
| PAPRH | 125 | 10 | 3 | 0 | 125 + 3 | 30 | 10 |
| POAAN | 250 | 85 | 24 | 0 | 250 + 24 | 95 | 85 |
| POAAN | 250 | 85 | 12 | 0 | 250 + 12 | 90 | 85 |
| POAAN | 250 | 85 | 3 | 0 | 250 + 3 | 90 | 85 |
| POAAN | 125 | 85 | 24 | 0 | 125 + 24 | 90 | 85 |
| POAAN | 125 | 85 | 12 | 0 | 125 + 12 | 90 | 85 |
| POAAN | 125 | 85 | 6 | 0 | 125 + 6 | 90 | 85 |
| POAAN | 125 | 85 | 3 | 0 | 125 + 3 | 90 | 85 |

TABLE X30

Ex. 26 and cinmethylin, in pre-emergence application at 20 DAT, wherein cinmethylin was used as EC formulation having an active ingredient concentration of 750 g/l.

| | solo application | | | | combination | | |
| --- | --- | --- | --- | --- | --- | --- | --- |
| | | | | | Ex. 26 + BAS 684 | | |
| | Ex. 26 | | BAS 684 | | | | COLBY |
| weed | use rate (gai/ha) | % activity | use rate (gai/ha) | % activity | use rate (gai/ha) | % activity | expected % activity |
| AVEFA | 250 | 75 | 31.25 | 0 | 250 + 31.25 | 80 | 75 |
| AVEFA | 125 | 65 | 31.25 | 0 | 125 + 31.25 | 70 | 65 |
| BRADC | 250 | 65 | 31.25 | 60 | 250 + 31.25 | 95 | 86 |
| BRADC | 125 | 20 | 31.25 | 60 | 125 + 31.25 | 80 | 68 |
| GALAP | 250 | 0 | 62.5 | 0 | 250 + 62.5 | 20 | 0 |
| GALAP | 250 | 0 | 31.25 | 0 | 250 + 31.25 | 10 | 0 |
| GALAP | 125 | 0 | 31.25 | 0 | 125 + 31.25 | 10 | 0 |
| HELAN | 62.5 | 0 | 125 | 10 | 62.5 + 125 | 25 | 10 |
| POLCO | 250 | 30 | 250 | 0 | 250 + 250 | 50 | 30 |
| POLCO | 125 | 0 | 250 | 0 | 125 + 250 | 20 | 0 |
| SETVI | 250 | 35 | 31.25 | 85 | 250 + 31.25 | 100 | 90 |
| SETVI | 125 | 10 | 31.25 | 85 | 125 + 31.25 | 100 | 87 |
| STEME | 125 | 20 | 250 | 80 | 125 + 250 | 90 | 84 |
| STEME | 125 | 20 | 125 | 60 | 125 + 125 | 75 | 68 |
| STEME | 125 | 20 | 62.5 | 10 | 125 + 62.5 | 40 | 28 |
| STEME | 125 | 20 | 31.25 | 0 | 125 + 31.25 | 30 | 20 |
| STEME | 31.25 | 0 | 62.5 | 10 | 31.25 + 62.5 | 25 | 10 |

TABLE X31

Ex. 26 and trifludimoxazin, in pre-emergence application at 20 DAT, wherein trifludimoxazin was used as SC formulation having an active ingredient concentration of 500 g/l.

| | solo application | | | | combination | | |
| | Ex. 26 | | trifludimoxazin | | Ex. 26 + trifludimoxazin | | COLBY |
| weed | use rate (gai/ha) | % activity | use rate (gai/ha) | % activity | use rate (gai/ha) | % activity | expected % activity |
|---|---|---|---|---|---|---|---|
| AVEFA | 62.5 | 40 | 36 | 50 | 62.5 + 36 | 80 | 73 |
| BRADC | 125 | 30 | 18 | 50 | 125 + 18 | 70 | 65 |
| BRADC | 62.5 | 0 | 36 | 80 | 62.5 + 36 | 95 | 80 |
| BRADC | 62.5 | 0 | 18 | 50 | 62.5 + 18 | 60 | 50 |
| GALAP | 125 | 0 | 36 | 40 | 125 + 36 | 80 | 40 |
| GALAP | 125 | 0 | 18 | 0 | 125 + 18 | 25 | 0 |
| GALAP | 125 | 0 | 9 | 0 | 125 + 9 | 30 | 0 |
| GALAP | 125 | 0 | 4.5 | 0 | 125 + 4.5 | 30 | 0 |
| GALAP | 62.5 | 0 | 36 | 40 | 62.5 + 36 | 90 | 40 |
| GALAP | 62.5 | 0 | 9 | 0 | 62.5 + 9 | 30 | 0 |
| GALAP | 62.5 | 0 | 4.5 | 0 | 62.5 + 4.5 | 25 | 0 |
| HELAN | 125 | 0 | 36 | 30 | 125 + 36 | 55 | 30 |
| HELAN | 62.5 | 0 | 18 | 0 | 62.5 + 18 | 20 | 0 |
| LOLMU | 62.5 | 0 | 36 | 75 | 62.5 + 36 | 85 | 75 |

TABLE X32

Ex. 26 and bentazone, in post-emergence application at 20 DAT, wherein bentazon was used as SL formulation having an active ingredient concentration of 480 g/l.

| | solo application | | | | combination | | |
| | Ex. 26 | | bentazon | | Ex. 26 + bentazon | | COLBY |
| weed | use rate (gai/ha) | % activity | use rate (gai/ha) | % activity | use rate (gai/ha) | % activity | expected % activity |
|---|---|---|---|---|---|---|---|
| ALOMY | 125 | 75 | 240 | 0 | 125 + 240 | 80 | 75 |
| ALOMY | 125 | 75 | 60 | 0 | 125 + 60 | 80 | 75 |
| AMBEL | 250 | 60 | 60 | 60 | 250 + 60 | 100 | 84 |
| AMBEL | 125 | 0 | 60 | 60 | 125 + 60 | 100 | 60 |
| AMBEL | 125 | 0 | 30 | 60 | 125 + 30 | 65 | 60 |
| AMBEL | 62.5 | 0 | 60 | 60 | 62.5 + 60 | 80 | 60 |
| BRADC | 125 | 30 | 240 | 20 | 125 + 240 | 60 | 44 |
| BRADC | 125 | 30 | 60 | 0 | 125 + 60 | 50 | 30 |
| BRADC | 125 | 30 | 30 | 0 | 125 + 30 | 40 | 30 |
| BROST | 250 | 65 | 240 | 0 | 250 + 240 | 75 | 65 |
| BROST | 250 | 65 | 120 | 0 | 250 + 120 | 75 | 65 |
| BROST | 250 | 65 | 60 | 0 | 250 + 60 | 70 | 65 |
| BROST | 250 | 65 | 30 | 0 | 250 + 30 | 75 | 65 |
| BROST | 125 | 60 | 240 | 0 | 125 + 240 | 65 | 60 |
| BROST | 125 | 60 | 120 | 0 | 125 + 120 | 65 | 60 |
| BROST | 125 | 60 | 60 | 0 | 125 + 60 | 65 | 60 |
| BROST | 125 | 60 | 30 | 0 | 125 + 30 | 65 | 60 |
| DIGSA | 250 | 30 | 240 | 30 | 250 + 240 | 65 | 51 |
| DIGSA | 250 | 30 | 120 | 0 | 250 + 120 | 35 | 30 |
| DIGSA | 250 | 30 | 60 | 0 | 250 + 60 | 65 | 30 |
| DIGSA | 250 | 30 | 30 | 0 | 250 + 30 | 40 | 30 |
| DIGSA | 125 | 0 | 240 | 30 | 125 + 240 | 45 | 30 |
| DIGSA | 125 | 0 | 120 | 0 | 125 + 120 | 20 | 0 |
| ECHCG | 250 | 70 | 240 | 20 | 250 + 240 | 80 | 76 |
| ECHCG | 250 | 70 | 60 | 0 | 250 + 60 | 80 | 70 |
| ECHCG | 125 | 65 | 60 | 0 | 125 + 60 | 70 | 65 |
| ECHCG | 62.5 | 60 | 120 | 0 | 62.5 + 120 | 70 | 60 |
| ECHCG | 62.5 | 60 | 60 | 0 | 62.5 + 60 | 65 | 60 |
| ECHCG | 62.5 | 60 | 30 | 0 | 62.5 + 30 | 65 | 60 |
| MATCH | 250 | 20 | 120 | 0 | 250 + 120 | 40 | 20 |
| MATCH | 250 | 20 | 60 | 0 | 250 + 60 | 75 | 20 |
| MATCH | 250 | 20 | 30 | 0 | 250 + 30 | 30 | 20 |
| MATCH | 62.5 | 0 | 120 | 0 | 62.5 + 120 | 40 | 0 |
| PAPRH | 250 | 20 | 120 | 0 | 250 + 120 | 40 | 20 |

TABLE X32-continued

Ex. 26 and bentazone, in post-emergence application at 20 DAT, wherein bentazon was used as SL formulation having an active ingredient concentration of 480 g/l.

| | solo application | | | | combination | | |
|---|---|---|---|---|---|---|---|
| | Ex. 26 | | bentazon | | Ex. 26 + bentazon | | COLBY |
| weed | use rate (gai/ha) | % activity | use rate (gai/ha) | % activity | use rate (gai/ha) | % activity | expected % activity |
| PAPRH | 250 | 20 | 60 | 0 | 250 + 60 | 75 | 20 |
| PAPRH | 250 | 20 | 30 | 0 | 250 + 30 | 30 | 20 |
| PAPRH | 62.5 | 0 | 120 | 0 | 62.5 + 120 | 40 | 0 |
| POAAN | 250 | 60 | 60 | 0 | 250 + 60 | 85 | 80 |

TABLE X33

Ex. 26 and bromoxynil, in post-emergence application at 20 DAT, wherein bromoxynil was used as EC formulation having an active ingredient concentration of 235 g/l.

| | solo application | | | | combination | | |
|---|---|---|---|---|---|---|---|
| | Ex. 26 | | Bromoxynil | | Ex. 26 + bromoxynil | | COLBY |
| weed | use rate (gai/ha) | % activity | use rate (gai/ha) | % activity | use rate (gai/ha) | % activity | expected % activity |
| ALOMY | 250 | 75 | 125 | 0 | 250 + 125 | 80 | 75 |
| ALOMY | 250 | 75 | 62.5 | 0 | 250 + 62.5 | 80 | 75 |
| ALOMY | 250 | 75 | 31.25 | 0 | 250 + 31.25 | 80 | 75 |
| ALOMY | 125 | 75 | 250 | 10 | 125 + 250 | 80 | 75 |
| APESV | 125 | 75 | 250 | 0 | 125 + 250 | 80 | 75 |
| BRADC | 125 | 40 | 125 | 10 | 125 + 125 | 60 | 46 |
| BRADC | 125 | 40 | 62.5 | 0 | 125 + 62.5 | 55 | 40 |
| BRADC | 125 | 40 | 31.25 | 0 | 125 + 31.25 | 50 | 40 |
| BROST | 250 | 65 | 31.25 | 0 | 250 + 31.25 | 70 | 65 |
| BROST | 125 | 35 | 250 | 0 | 125 + 250 | 40 | 35 |
| BROST | 125 | 35 | 125 | 0 | 125 + 125 | 50 | 35 |
| BROST | 125 | 35 | 62.5 | 0 | 125 + 62.5 | 50 | 35 |
| BROST | 125 | 35 | 31.25 | 0 | 125 + 31.25 | 55 | 35 |
| DIGSA | 250 | 0 | 250 | 0 | 250 + 250 | 45 | 0 |
| DIGSA | 250 | 0 | 125 | 0 | 250 + 125 | 50 | 0 |
| DIGSA | 250 | 0 | 62.5 | 0 | 250 + 62.5 | 30 | 0 |
| DIGSA | 250 | 0 | 31.25 | 0 | 250 + 31.25 | 30 | 0 |
| DIGSA | 125 | 0 | 250 | 0 | 125 + 250 | 40 | 0 |
| DIGSA | 125 | 0 | 125 | 0 | 125 + 125 | 30 | 0 |
| DIGSA | 125 | 0 | 62.5 | 0 | 125 + 62.5 | 40 | 0 |
| DIGSA | 125 | 0 | 31.25 | 0 | 125 + 31.25 | 40 | 0 |
| GALAP | 250 | 0 | 125 | 80 | 250 + 125 | 100 | 80 |
| GALAP | 250 | 0 | 62.5 | 65 | 250 + 62.5 | 100 | 65 |
| GALAP | 250 | 0 | 31.25 | 65 | 250 + 31.25 | 70 | 65 |
| GALAP | 125 | 0 | 125 | 80 | 125 + 125 | 100 | 80 |
| GALAP | 125 | 0 | 62.5 | 65 | 125 + 62.5 | 100 | 65 |
| LOLMU | 250 | 65 | 250 | 0 | 250 + 250 | 75 | 65 |
| LOLMU | 250 | 65 | 125 | 0 | 250 + 125 | 70 | 65 |
| LOLMU | 250 | 65 | 62.5 | 0 | 250 + 62.5 | 70 | 65 |
| LOLMU | 125 | 55 | 125 | 0 | 125 + 125 | 70 | 55 |
| LOLMU | 125 | 55 | 62.5 | 0 | 125 + 62.5 | 65 | 55 |
| LOLMU | 125 | 55 | 31.25 | 0 | 125 + 31.25 | 60 | 55 |
| POAAN | 125 | 70 | 250 | 0 | 125 + 250 | 75 | 70 |
| POAAN | 125 | 70 | 125 | 0 | 125 + 125 | 75 | 70 |
| POAAN | 125 | 70 | 62.5 | 0 | 125 + 62.5 | 80 | 70 |
| POAAN | 125 | 70 | 31.25 | 0 | 125 + 31.25 | 75 | 70 |
| STEME | 250 | 40 | 125 | 60 | 250 + 125 | 85 | 76 |
| STEME | 250 | 40 | 62.5 | 50 | 250 + 62.5 | 80 | 70 |
| STEME | 250 | 40 | 31.25 | 30 | 250 + 31.25 | 100 | 58 |
| STEME | 125 | 40 | 62.5 | 50 | 125 + 62.5 | 90 | 70 |
| STEME | 125 | 40 | 31.25 | 30 | 125 + 31.25 | 60 | 30 |

TABLE X34

Ex. 26 and chlorotoluron, in post-emergence application at 20 DAT, wherein chlorotoluron was used as SC formulation having an active ingredient concentration of 700 g/l.

| | solo application | | | | combination | | |
| --- | --- | --- | --- | --- | --- | --- | --- |
| | Ex. 26 | | chlortolurom | | Ex. 26 + chlorotoluron | | COLBY |
| weed | use rate (gai/ha) | % activity | use rate (gai/ha) | % activity | use rate (gai/ha) | % activity | expected % activity |
| ALOMY | 250 | 75 | 250 | 40 | 250 + 250 | 95 | 85 |
| ALMOY | 125 | 70 | 500 | 65 | 125 + 500 | 95 | 90 |
| ALOMY | 125 | 70 | 250 | 40 | 125 + 250 | 90 | 82 |
| ALOMY | 125 | 70 | 125 | 30 | 125 + 125 | 85 | 79 |
| APESV | 250 | 75 | 125 | 55 | 250 + 125 | 95 | 89 |
| APESV | 250 | 75 | 62.5 | 25 | 250 + 62.5 | 90 | 81 |
| APESV | 125 | 70 | 125 | 55 | 125 + 125 | 95 | 87 |
| AVEFA | 250 | 75 | 250 | 40 | 250 + 250 | 95 | 85 |
| AVEFA | 250 | 75 | 125 | 0 | 250 + 125 | 90 | 75 |
| AVEFA | 125 | 70 | 500 | 70 | 125 + 500 | 98 | 91 |
| AVEFA | 125 | 70 | 250 | 40 | 125 + 250 | 95 | 82 |
| AVEFA | 125 | 70 | 125 | 0 | 125 + 125 | 85 | 70 |
| BROST | 125 | 40 | 125 | 0 | 125 + 125 | 55 | 40 |
| BROST | 125 | 40 | 62.5 | 0 | 125 + 62.5 | 60 | 40 |
| ECHCG | 250 | 65 | 500 | 65 | 250 + 500 | 95 | 88 |
| GALAP | 250 | 0 | 500 | 70 | 250 + 500 | 85 | 70 |
| GALAP | 250 | 0 | 250 | 65 | 250 + 250 | 70 | 65 |
| GALAP | 125 | 0 | 500 | 70 | 125 + 500 | 85 | 70 |
| GALAP | 125 | 0 | 250 | 65 | 125 + 250 | 75 | 65 |
| LOLMU | 125 | 35 | 500 | 80 | 125 + 500 | 90 | 87 |
| MATCH | 250 | 0 | 125 | 50 | 250 + 125 | 65 | 50 |
| PAPRH | 250 | 45 | 500 | 25 | 250 + 500 | 98 | 59 |
| PAPRH | 250 | 45 | 250 | 20 | 250 + 250 | 85 | 56 |
| PAPRH | 250 | 45 | 125 | 0 | 250 + 125 | 50 | 45 |
| PAPRH | 125 | 0 | 500 | 25 | 125 + 500 | 60 | 25 |
| PAPRH | 125 | 0 | 250 | 25 | 125 + 250 | 30 | 20 |
| PAPRH | 125 | 0 | 125 | 0 | 125 + 125 | 30 | 0 |
| PAPRH | 125 | 0 | 62.5 | 0 | 125 + 62.5 | 20 | 0 |

TABLE X35

Ex. 26 and chlorotoluron, in pre-emergence application at 20 DAT, wherein chlorotoluron was used as SC formulation having an active ingredient concentration of 700 g/l.

| | solo application | | | | combination | | |
| --- | --- | --- | --- | --- | --- | --- | --- |
| | Ex. 26 | | chlorotoluron | | Ex. 26 + chlorotoluron | | COLBY |
| weed | use rate (gai/ha) | % activity | use rate (gai/ha) | % activity | use rate (gai/ha) | % activity | expected % activity |
| ALOMY | 62.5 | 60 | 250 | 0 | 62.5 + 250 | 80 | 60 |
| ALOMY | 62.5 | 60 | 125 | 0 | 62.5 + 125 | 70 | 60 |
| ALOMY | 62.5 | 60 | 62.5 | 0 | 62.5 + 62.5 | 65 | 60 |
| AMBEL | 125 | 0 | 500 | 40 | 125 + 500 | 90 | 40 |
| AMBEL | 125 | 0 | 125 | 0 | 125 + 125 | 30 | 0 |
| AMBEL | 62.5 | 0 | 500 | 40 | 62.5 + 500 | 100 | 40 |
| AMBEL | 31.25 | 0 | 500 | 40 | 31.25 + 500 | 65 | 40 |
| APESV | 125 | 65 | 500 | 65 | 125 + 500 | 95 | 88 |
| APESV | 125 | 65 | 250 | 65 | 125 + 250 | 95 | 88 |
| APESV | 125 | 65 | 62.5 | 55 | 125 + 62.5 | 95 | 84 |
| AVEFA | 62.5 | 40 | 62.5 | 0 | 62.5 + 62.5 | 60 | 40 |
| BRADC | 31.25 | 0 | 500 | 0 | 31.25 + 500 | 30 | 0 |
| BROST | 125 | 30 | 500 | 0 | 125 + 500 | 50 | 30 |
| BROST | 125 | 30 | 250 | 0 | 125 + 250 | 45 | 30 |
| BROST | 125 | 30 | 62.5 | 0 | 125 + 62.5 | 35 | 0 |
| BROST | 62.5 | 20 | 250 | 0 | 62.5 + 250 | 35 | 20 |
| DIGSA | 125 | 60 | 500 | 65 | 125 + 500 | 95 | 86 |
| DIGSA | 125 | 60 | 125 | 0 | 125 + 125 | 65 | 60 |
| DIGSA | 62.5 | 55 | 500 | 65 | 62.5 + 500 | 95 | 84 |

TABLE X35-continued

Ex. 26 and chlorotoluron, in pre-emergence application at 20 DAT, wherein chlorotoluron was used as SC formulation having an active ingredient concentration of 700 g/l.

| | solo application | | | | combination | | |
|---|---|---|---|---|---|---|---|
| | Ex. 26 | | chlorotoluron | | Ex. 26 + chlorotoluron | | COLBY |
| weed | use rate (gai/ha) | % activity | use rate (gai/ha) | % activity | use rate (gai/ha) | % activity | expected % activity |
| DIGSA | 31.25 | 35 | 500 | 65 | 31.25 + 500 | 90 | 77 |
| DIGSA | 62.5 | 55 | 125 | 0 | 62.5 + 125 | 60 | 55 |
| ECHCG | 125 | 90 | 500 | 25 | 125 + 500 | 100 | 93 |
| ECHCG | 125 | 90 | 125 | 0 | 125 + 125 | 95 | 90 |
| ECHCG | 125 | 90 | 62.5 | 0 | 125 + 62.5 | 95 | 90 |
| ECHCG | 62.5 | 70 | 500 | 25 | 62.5 + 500 | 95 | 78 |
| ECHCG | 62.5 | 70 | 250 | 35 | 62.5 + 250 | 90 | 81 |
| ECHCG | 31.25 | 50 | 500 | 25 | 31.25 + 500 | 70 | 63 |
| HELAN | 125 | 0 | 500 | 10 | 125 + 500 | 30 | 10 |
| HELAN | 31.25 | 0 | 500 | 10 | 31.25 + 500 | 20 | 10 |
| LOLMU | 125 | 30 | 500 | 10 | 125 + 500 | 50 | 37 |
| LOLMU | 62.5 | 0 | 500 | 10 | 62.5 + 500 | 60 | 10 |
| LOLMU | 62.5 | 0 | 250 | 0 | 62.5 + 250 | 30 | 0 |
| LOLMU | 31.25 | 0 | 500 | 10 | 31.25 + 500 | 50 | 10 |
| PAPRH | 125 | 0 | 500 | 90 | 125 + 500 | 95 | 90 |
| PAPRH | 125 | 0 | 62.5 | 0 | 125 + 62.5 | 10 | 0 |
| PAPRH | 62.5 | 0 | 500 | 90 | 62.5 + 500 | 95 | 90 |
| PAPRH | 31.25 | 0 | 62.5 | 0 | 31.25 + 62.5 | 35 | 0 |
| POAAN | 62.5 | 75 | 250 | 20 | 62.5 + 250 | 98 | 80 |
| POAAN | 62.5 | 75 | 125 | 0 | 62.5 + 125 | 90 | 75 |
| STEME | 125 | 0 | 250 | 65 | 125 + 250 | 90 | 65 |
| STEME | 62.5 | 0 | 250 | 65 | 62.5 + 250 | 85 | 65 |

TABLE X36

Ex. 26 and dicamba, in post-emergence application at 20 DAT, wherein dicamba was used as SL formulation having an active ingredient concentration of 480 g/l.

| | solo application | | | | combination | | |
|---|---|---|---|---|---|---|---|
| | Ex. 26 | | Dicamba | | Ex. 26 + Dicamba | | COLBY |
| weed | use rate (gai/ha) | % activity | use rate (gai/ha) | % activity | use rate (gai/ha) | % activity | expected % activity |
| ALOMY | 125 | 75 | 140 | 0 | 125 + 140 | 80 | 75 |
| BRADC | 125 | 30 | 140 | 30 | 125 + 140 | 55 | 51 |
| BRADC | 125 | 30 | 35 | 0 | 125 + 35 | 50 | 30 |
| BRADC | 125 | 30 | 17.5 | 0 | 125 + 17.5 | 40 | 30 |
| BROST | 250 | 65 | 140 | 0 | 250 + 140 | 75 | 65 |
| BROST | 250 | 65 | 70 | 0 | 250 + 70 | 70 | 65 |
| BROST | 250 | 65 | 35 | 0 | 250 + 35 | 70 | 65 |
| BROST | 250 | 65 | 17.5 | 0 | 250 + 17.5 | 70 | 65 |
| BROST | 125 | 60 | 140 | 0 | 125 + 140 | 65 | 60 |
| DIGSA | 250 | 30 | 140 | 30 | 250 + 140 | 60 | 51 |
| DIGSA | 250 | 30 | 35 | 0 | 250 + 35 | 60 | 30 |
| DIGSA | 250 | 30 | 17.5 | 0 | 250 + 17.5 | 40 | 30 |
| DIGSA | 125 | 0 | 70 | 0 | 125 + 70 | 20 | 0 |
| DIGSA | 125 | 0 | 35 | 0 | 125 + 35 | 30 | 0 |
| DIGSA | 125 | 0 | 17.5 | 0 | 125 + 17.5 | 20 | 0 |
| ECHCG | 250 | 70 | 35 | 0 | 250 + 35 | 75 | 70 |
| ECHCG | 125 | 65 | 35 | 0 | 125 + 35 | 70 | 65 |
| GALAP | 250 | 0 | 70 | 85 | 250 + 70 | 90 | 85 |
| GALAP | 125 | 0 | 70 | 85 | 125 + 70 | 90 | 85 |
| HELAN | 125 | 0 | 70 | 85 | 125 + 70 | 98 | 85 |
| LOLMU | 125 | 65 | 35 | 0 | 125 + 35 | 70 | 65 |
| LOLMU | 125 | 65 | 17.5 | 0 | 125 + 17.5 | 70 | 65 |
| PAPRH | 250 | 20 | 35 | 30 | 250 + 35 | 55 | 44 |
| PAPRH | 250 | 20 | 17.5 | 20 | 250 + 17.5 | 50 | 36 |
| PAPRH | 125 | 0 | 35 | 30 | 125 + 35 | 40 | 30 |
| PAPRH | 125 | 0 | 17.5 | 20 | 125 + 17.5 | 60 | 20 |

TABLE X36-continued

Ex. 26 and dicamba, in post-emergence application at 20 DAT, wherein dicamba was used as SL formulation having an active ingredient concentration of 480 g/l.

| | solo application | | | | combination | | |
|---|---|---|---|---|---|---|---|
| | | | | | Ex. 26 + Dicamba | | |
| | Ex. 26 | | Dicamba | | | | COLBY |
| weed | use rate (gai/ha) | % activity | use rate (gai/ha) | % activity | use rate (gai/ha) | % activity | expected % activity |
| POAAN | 250 | 80 | 140 | 0 | 250 + 140 | 85 | 80 |
| POAAN | 250 | 80 | 70 | 0 | 250 + 70 | 85 | 80 |
| POAAN | 250 | 80 | 35 | 0 | 250 + 35 | 85 | 80 |
| POAAN | 250 | 80 | 17.5 | 0 | 250 + 17.5 | 85 | 80 |
| POAAN | 125 | 75 | 35 | 0 | 125 + 35 | 80 | 75 |
| STEME | 250 | 60 | 35 | 80 | 250 + 35 | 100 | 92 |
| STEME | 125 | 50 | 35 | 80 | 125 + 35 | 98 | 90 |

TABLE X37

Ex. 26 and flufenacet, in pre-emergence application at 20 DAT, wherein flufenacet was used as SC formulation having an active ingredient concentration of 500 g/l.

| | solo application | | | | combination | | |
|---|---|---|---|---|---|---|---|
| | | | | | Ex. 26 + flufenacet | | |
| | Ex. 26 | | flufenacet | | | | COLBY |
| weed | use rate (gai/ha) | % activity | use rate (gai/ha) | % activity | use rate (gai/ha) | % activity | expected % activity |
| AMBEL | 250 | 0 | 125 | 0 | 250 + 125 | 85 | 0 |
| AMBEL | 250 | 0 | 62.5 | 0 | 250 + 62.5 | 10 | 0 |
| AMBEL | 250 | 0 | 31.25 | 0 | 250 + 31.25 | 20 | 0 |
| AMBEL | 125 | 0 | 125 | 0 | 125 + 125 | 10 | 0 |
| AVEFA | 125 | 65 | 62.5 | 60 | 125 + 62.5 | 90 | 86 |
| GALAP | 250 | 0 | 62.5 | 0 | 250 + 62.5 | 40 | 0 |
| GALAP | 250 | 0 | 31.25 | 0 | 250 + 31.25 | 20 | 0 |
| GALAP | 250 | 0 | 15.6 | 0 | 250 + 15.6 | 20 | 0 |
| GALAP | 125 | 0 | 125 | 40 | 125 + 125 | 65 | 40 |
| GALAP | 125 | 0 | 62.5 | 0 | 125 + 62.5 | 60 | 0 |
| GALAP | 125 | 0 | 31.25 | 0 | 125 + 31.25 | 35 | 0 |
| GALAP | 125 | 0 | 15.6 | 0 | 125 + 15.6 | 10 | 0 |
| POLCO | 250 | 30 | 125 | 0 | 250 + 125 | 60 | 30 |
| POLCO | 125 | 0 | 125 | 0 | 125 + 125 | 15 | 0 |
| POLCO | 125 | 0 | 62.5 | 0 | 125 + 62.5 | 40 | 0 |
| STEME | 250 | 90 | 125 | 0 | 250 + 125 | 98 | 90 |
| STEME | 250 | 90 | 62.5 | 0 | 250 + 62.5 | 98 | 90 |
| STEME | 250 | 90 | 15.6 | 0 | 250 + 15.6 | 98 | 90 |
| STEME | 125 | 20 | 125 | 0 | 125 + 125 | 75 | 20 |
| STEME | 125 | 20 | 62.5 | 0 | 125 + 62.5 | 35 | 20 |
| STEME | 125 | 20 | 31.25 | 0 | 125 + 31.25 | 55 | 20 |
| STEME | 125 | 20 | 15.6 | 0 | 125 + 15.6 | 55 | 20 |

TABLE X38

Ex. 26 and flumioxazin, in pre-emergence application at 20 DAT, wherein flumioxazin was used as WG formulation having an active ingredient concentration of 51%.

| | solo application | | | | combination | | |
|---|---|---|---|---|---|---|---|
| | | | | | Ex. 26 + flumioxazin | | |
| | Ex. 26 | | flumioxazin | | | | COLBY |
| weed | use rate (gai/ha) | % activity | use rate (gai/ha) | % activity | use rate (gai/ha) | % activity | expected % activity |
| AMBEL | 125 | 0 | 7.5 | 0 | 125 + 7.5 | 10 | 0 |
| AMBEL | 125 | 0 | 3.75 | 0 | 125 + 3.75 | 20 | 0 |
| AMBEL | 62.5 | 0 | 7.5 | 0 | 62.5 + 7.5 | 20 | 0 |

TABLE X38-continued

Ex. 26 and flumioxazin, in pre-emergence application at 20 DAT, wherein flumioxazin was used as WG formulation having an active ingredient concentration of 51%.

| | solo application | | | | combination | | |
|---|---|---|---|---|---|---|---|
| | Ex. 26 | | flumioxazin | | Ex. 26 + flumioxazin | | COLBY |
| weed | use rate (gai/ha) | % activity | use rate (gai/ha) | % activity | use rate (gai/ha) | % activity | expected % activity |
| AMBEL | 62.5 | 0 | 3.75 | 0 | 62.5 + 3.75 | 10 | 0 |
| APESV | 125 | 90 | 3.75 | 25 | 125 + 3.75 | 95 | 93 |
| BRADC | 125 | 50 | 15 | 40 | 125 + 40 | 60 | 52 |
| GALAP | 125 | 0 | 30 | 65 | 125 + 30 | 75 | 65 |
| GALAP | 125 | 0 | 7.5 | 0 | 125 + 7.5 | 20 | 0 |
| GALAP | 62.5 | 0 | 7.5 | 0 | 62.5 + 7.5 | 20 | 0 |
| HELAN | 62.5 | 20 | 30 | 50 | 62.5 + 30 | 70 | 60 |
| LOLMU | 62.5 | 10 | 30 | 65 | 62.5 + 30 | 75 | 69 |
| POLCO | 125 | 0 | 7.5 | 65 | 125 + 7.5 | 85 | 65 |

TABLE X39

Ex. 26 and metribuzin, in post-emergence application at 20 DAT, wherein metribuzin was used as WG formulation having an active ingredient concentration of 70%.

| | solo application | | | | combination | | |
|---|---|---|---|---|---|---|---|
| | Ex. 26 | | metribuzin | | Ex. 26 + metribuzin | | COLBY |
| weed | use rate (gai/ha) | % activity | use rate (gai/ha) | % activity | use rate (gai/ha) | % activity | expected % activity |
| ALOMY | 250 | 75 | 35 | 10 | 250 + 35 | 98 | 78 |
| ALOMY | 250 | 75 | 17.5 | 0 | 250 + 17.5 | 85 | 75 |
| ALOMY | 125 | 75 | 35 | 10 | 125 + 35 | 95 | 78 |
| ALOMY | 62.5 | 65 | 35 | 10 | 62.5 + 35 | 95 | 69 |
| ALOMY | 62.5 | 65 | 17.5 | 0 | 62.5 + 17.5 | 90 | 65 |
| AMBEL | 250 | 40 | 70 | 0 | 250 + 70 | 75 | 40 |
| AMBEL | 250 | 40 | 35 | 0 | 250 + 35 | 65 | 40 |
| AMBEL | 250 | 40 | 17.5 | 0 | 250 + 17.5 | 60 | 40 |
| AMBEL | 125 | 0 | 140 | 70 | 125 + 140 | 100 | 70 |
| AMBEL | 125 | 0 | 70 | 0 | 125 + 70 | 70 | 0 |
| AMBEL | 125 | 0 | 35 | 0 | 125 + 35 | 60 | 0 |
| AMBEL | 125 | 0 | 17.5 | 0 | 125 + 17.5 | 60 | 0 |
| AMBEL | 62.5 | 0 | 70 | 0 | 62.5 + 70 | 70 | 0 |
| AMBEL | 62.5 | 0 | 35 | 0 | 62.5 + 35 | 90 | 0 |
| APESV | 250 | 80 | 35 | 55 | 250 + 35 | 100 | 91 |
| APESV | 250 | 80 | 17.5 | 10 | 250 + 17.5 | 95 | 82 |
| APESV | 125 | 75 | 35 | 55 | 125 + 35 | 100 | 89 |
| APESV | 125 | 75 | 17.5 | 10 | 125 + 17.5 | 95 | 78 |
| APESV | 62.5 | 70 | 35 | 55 | 62.5 + 35 | 98 | 87 |
| APESV | 62.5 | 70 | 17.5 | 10 | 62.5 + 17.5 | 85 | 73 |
| AVEFA | 250 | 75 | 70 | 40 | 250 + 70 | 95 | 85 |
| AVEFA | 250 | 75 | 35 | 10 | 250 + 35 | 90 | 78 |
| AVEFA | 125 | 75 | 70 | 40 | 125 + 70 | 95 | 85 |
| AVEFA | 125 | 75 | 35 | 10 | 125 + 35 | 85 | 78 |
| AVEFA | 62.5 | 65 | 70 | 40 | 62.5 + 70 | 95 | 79 |
| AVEFA | 62.5 | 65 | 35 | 10 | 62.5 + 35 | 75 | 69 |
| AVEFA | 62.5 | 65 | 17.5 | 5 | 62.5 + 17.5 | 70 | 67 |
| BRADC | 62.5 | 10 | 17.5 | 50 | 62.5 + 17.5 | 65 | 55 |
| DIGSA | 250 | 0 | 35 | 35 | 250 + 35 | 65 | 35 |
| DIGSA | 250 | 0 | 17.5 | 0 | 250 + 17.5 | 20 | 0 |
| DIGSA | 125 | 0 | 35 | 35 | 125 + 35 | 55 | 35 |
| DIGSA | 125 | 0 | 17.5 | 0 | 125 + 17.5 | 20 | 0 |
| GALAP | 250 | 0 | 140 | 0 | 250 + 140 | 70 | 0 |
| GALAP | 250 | 0 | 70 | 0 | 250 + 70 | 65 | 0 |
| GALAP | 250 | 0 | 35 | 0 | 250 + 35 | 70 | 0 |
| GALAP | 250 | 0 | 17.5 | 0 | 250 + 17.5 | 60 | 0 |
| GALAP | 125 | 0 | 140 | 0 | 125 + 140 | 65 | 0 |
| GALAP | 125 | 0 | 70 | 0 | 125 + 70 | 60 | 0 |
| GALAP | 125 | 0 | 35 | 0 | 125 + 35 | 60 | 0 |
| GALAP | 62.5 | 0 | 140 | 0 | 62.5 + 140 | 70 | 0 |

TABLE X39-continued

Ex. 26 and metribuzin, in post-emergence application at 20 DAT, wherein metribuzin was used as WG formulation having an active ingredient concentration of 70%.

| | solo application | | | | combination | | |
|---|---|---|---|---|---|---|---|
| | Ex. 26 | | metribuzin | | Ex. 26 + metribuzin | | COLBY |
| weed | use rate (gai/ha) | % activity | use rate (gai/ha) | % activity | use rate (gai/ha) | % activity | expected % activity |
| GALAP | 62.5 | 0 | 70 | 0 | 62.5 + 70 | 65 | 0 |
| HELAN | 250 | 10 | 35 | 70 | 250 + 35 | 80 | 73 |
| HELAN | 125 | 10 | 35 | 70 | 125 + 35 | 85 | 73 |
| MATCH | 250 | 0 | 35 | 25 | 250 + 35 | 55 | 25 |
| MATCH | 62.5 | 0 | 35 | 25 | 62.5 + 35 | 30 | 25 |
| MATCH | 62.5 | 0 | 17.5 | 0 | 62.5 + 17.5 | 30 | 0 |
| POAAN | 250 | 80 | 17.5 | 60 | 250 + 17.5 | 98 | 92 |
| POAAN | 125 | 70 | 35 | 70 | 125 + 35 | 100 | 91 |
| POAAN | 125 | 70 | 17.5 | 60 | 125 + 17.5 | 98 | 88 |
| POLCO | 125 | 85 | 35 | 0 | 125 + 35 | 98 | 85 |
| POLCO | 125 | 85 | 17.5 | 0 | 125 + 17.5 | 98 | 85 |
| POLCO | 62.5 | 65 | 140 | 70 | 62.5 + 140 | 98 | 90 |
| POLCO | 62.5 | 65 | 70 | 60 | 62.5 + 70 | 95 | 86 |
| POLCO | 62.5 | 65 | 35 | 0 | 62.5 + 35 | 90 | 65 |
| POLCO | 62.5 | 65 | 17.5 | 0 | 62.5 + 17.5 | 90 | 65 |
| STEME | 125 | 40 | 35 | 80 | 125 + 35 | 100 | 88 |

TABLE X40

Ex. 26 and metribuzin, in pre-emergence application at 20 DAT, wherein metribuzin was used as WG formulation having an active ingredient concentration of 70%.

| | solo application | | | | combination | | |
|---|---|---|---|---|---|---|---|
| | Ex. 26 | | metribuzin | | Ex. 263 + metribuzin | | COLBY |
| weed | use rate (gai/ha) | % activity | use rate (gai/ha) | % activity | use rate (gai/ha) | % activity | expected % activity |
| AVEFA | 125 | 70 | 31.25 | 30 | 125 + 31.25 | 95 | 79 |
| AMBEL | 125 | 0 | 250 | 60 | 125 + 250 | 65 | 60 |
| AMBEL | 62.5 | 0 | 250 | 60 | 62.5 + 250 | 65 | 60 |
| AMBEL | 31.25 | 0 | 250 | 60 | 31.25 + 250 | 70 | 60 |
| BROST | 125 | 35 | 62.5 | 10 | 125 + 62.5 | 55 | 42 |
| BROST | 125 | 35 | 31.25 | 0 | 125 + 31.25 | 50 | 35 |
| BROST | 31.25 | 10 | 250 | 60 | 31.25 + 250 | 70 | 64 |
| ECHCG | 125 | 90 | 62.5 | 30 | 125 + 62.5 | 100 | 93 |
| ECHCG | 31.25 | 50 | 62.5 | 30 | 31.25 + 62.5 | 70 | 65 |
| GALAP | 31.25 | 0 | 250 | 0 | 31.25 + 250 | 20 | 0 |
| HELAN | 125 | 0 | 62.5 | 0 | 125 + 62.5 | 25 | 0 |
| HELAN | 31.25 | 0 | 250 | 50 | 31.25 + 250 | 55 | 50 |
| HELAN | 31.25 | 0 | 125 | 0 | 31.25 + 125 | 20 | 0 |
| PAPRH | 125 | 30 | 31.25 | 80 | 125 + 31.25 | 95 | 86 |
| PAPRH | 62.5 | 0 | 31.25 | 80 | 62.5 + 31.25 | 98 | 80 |
| PAPRH | 31.25 | 0 | 125 | 98 | 31.25 + 125 | 100 | 98 |
| PAPRH | 31.25 | 0 | 31.25 | 80 | 31.25 + 31.25 | 95 | 80 |
| POLCO | 125 | 0 | 250 | 0 | 125 + 250 | 45 | 0 |
| POLCO | 125 | 0 | 125 | 0 | 125 + 125 | 20 | 0 |
| POLCO | 125 | 0 | 62.5 | 0 | 125 + 62.5 | 20 | 0 |
| POLCO | 62.5 | 0 | 62.5 | 0 | 62.5 + 62.5 | 20 | 0 |
| POLCO | 31.25 | 0 | 250 | 0 | 31.25 + 250 | 65 | 0 |

TABLE X41

Ex. 26 and pendimethalin, in post-emergence application at 20 DAT, wherein pendimethalin was used as SC formulation having an active ingredient concentration of 400 g/l.

| | solo application | | | | combination | | |
| --- | --- | --- | --- | --- | --- | --- | --- |
| | Ex. 26 | | pendimethalin | | Ex. 26 + pendimethalin | | COLBY |
| weed | use rate (gai/ha) | % activity | use rate (gai/ha) | % activity | use rate (gai/ha) | % activity | expected % activity |
| ALOMY | 125 | 75 | 125 | 20 | 125 + 125 | 85 | 80 |
| AVEFA | 250 | 75 | 1000 | 0 | 250 + 1000 | 85 | 75 |
| AVEFA | 250 | 75 | 500 | 0 | 250 + 500 | 80 | 75 |
| AVEFA | 250 | 75 | 250 | 0 | 250 + 250 | 85 | 75 |
| AVEFA | 250 | 75 | 125 | 0 | 250 + 125 | 80 | 75 |
| AVEFA | 125 | 75 | 1000 | 0 | 125 + 1000 | 85 | 75 |
| AVEFA | 125 | 75 | 500 | 0 | 125 + 500 | 80 | 75 |
| AVEFA | 125 | 75 | 125 | 0 | 125 + 125 | 80 | 75 |
| BROST | 250 | 65 | 1000 | 0 | 250 + 1000 | 80 | 65 |
| BROST | 250 | 65 | 500 | 0 | 250 + 500 | 75 | 65 |
| BROST | 250 | 65 | 125 | 0 | 250 + 125 | 70 | 65 |
| BROST | 125 | 35 | 1000 | 0 | 125 + 1000 | 70 | 35 |
| BROST | 125 | 35 | 500 | 0 | 125 + 500 | 45 | 35 |
| BROST | 125 | 35 | 250 | 0 | 125 + 250 | 55 | 35 |
| DIGSA | 250 | 10 | 125 | 45 | 250 + 125 | 55 | 51 |
| LOLMU | 250 | 65 | 250 | 20 | 250 + 250 | 80 | 72 |
| LOLMU | 250 | 65 | 125 | 10 | 250 + 125 | 80 | 69 |
| LOLMU | 125 | 55 | 250 | 20 | 125 + 250 | 70 | 64 |
| MATCH | 250 | 0 | 1000 | 0 | 250 + 1000 | 30 | 0 |
| MATCH | 250 | 0 | 500 | 0 | 250 + 500 | 10 | 0 |
| MATCH | 125 | 0 | 1000 | 0 | 125 + 1000 | 10 | 0 |
| MATCH | 125 | 0 | 500 | 0 | 125 + 500 | 10 | 0 |
| POLCO | 125 | 80 | 500 | 60 | 125 + 500 | 98 | 92 |
| POLCO | 125 | 80 | 125 | 40 | 125 + 125 | 98 | 88 |
| STEME | 125 | 20 | 500 | 70 | 125 + 500 | 80 | 76 |
| SETVI | 250 | 20 | 250 | 50 | 250 + 250 | 65 | 60 |

TABLE X42

Ex. 26 and pendimethalin, in pre-emergence application at 21 DAT, wherein pendimethalin was used as SC formulation having an active ingredient concentration of 400 g/l.

| | solo application | | | | combination | | |
| --- | --- | --- | --- | --- | --- | --- | --- |
| | Ex. 26 | | pendimethalin | | Ex. 26 + pendimethalin | | COLBY |
| weed | use rate (gai/ha) | % activity | use rate (gai/ha) | % activity | use rate (gai/ha) | % activity | expected % activity |
| AMBEL | 250 | 0 | 1000 | 0 | 250 + 1000 | 55 | 0 |
| AMBEL | 250 | 0 | 250 | 0 | 250 + 250 | 70 | 0 |
| AVEFA | 250 | 70 | 125 | 0 | 250 + 125 | 80 | 70 |
| BRADC | 250 | 30 | 500 | 0 | 250 + 500 | 35 | 30 |
| BRADC | 125 | 10 | 1000 | 0 | 125 + 1000 | 70 | 10 |
| BRADC | 125 | 10 | 500 | 0 | 125 + 500 | 50 | 10 |
| BRADC | 125 | 10 | 250 | 0 | 125 + 250 | 25 | 10 |
| BROST | 125 | 60 | 1000 | 10 | 125 + 1000 | 70 | 64 |
| BROST | 125 | 60 | 500 | 0 | 125 + 500 | 70 | 60 |
| BROST | 125 | 60 | 250 | 0 | 125 + 250 | 65 | 60 |
| HELAN | 250 | 0 | 100 | 10 | 250 + 100 | 25 | 10 |
| HELAN | 250 | 0 | 500 | 10 | 250 + 500 | 25 | 10 |
| HELAN | 250 | 0 | 250 | 0 | 250 + 250 | 25 | 0 |
| HELAN | 250 | 0 | 125 | 0 | 250 + 125 | 20 | 0 |
| HELAN | 125 | 0 | 125 | 0 | 125 + 125 | 20 | 0 |

TABLE X43

Ex. 26 and picolinafen, in post-emergence application at 20 DAT, wherein picolinafen was used as WG formulation having an active ingredient concentration of 75%.

| | solo application | | | | combination | | |
|---|---|---|---|---|---|---|---|
| | Ex. 26 | | picolinafen | | Ex. 26 + picolinafen | | COLBY |
| weed | use rate (gai/ha) | % activity | use rate (gai/ha) | % activity | use rate (gai/ha) | % activity | expected % activity |
| BRADC | 250 | 60 | 50 | 50 | 250 + 50 | 85 | 80 |
| BRADC | 250 | 60 | 25 | 35 | 250 + 25 | 85 | 74 |
| BRADC | 125 | 55 | 50 | 50 | 125 + 50 | 80 | 78 |
| BRADC | 125 | 55 | 25 | 35 | 125 + 25 | 75 | 71 |
| BRADC | 62.5 | 45 | 25 | 35 | 62.5 + 25 | 70 | 64 |
| SETVI | 250 | 50 | 12.5 | 30 | 250 + 12.5 | 85 | 65 |

TABLE X44

Ex. 26 and picolinafen, in pre-emergence application at 21 DAT, wherein picolinafen was used as WG formulation having an active ingredient concentration of 75%.

| | solo application | | | | combination | | |
|---|---|---|---|---|---|---|---|
| | Ex. 26 | | picolinafen | | Ex. 26 + picolinafen | | COLBY |
| weed | use rate (gai/ha) | % activity | use rate (gai/ha) | % activity | use rate (gai/ha) | % activity | expected % activity |
| AMBEL | 250 | 0 | 50 | 0 | 250 + 50 | 30 | 0 |
| DIGSA | 125 | 45 | 12.5 | 0 | 125 + 12.5 | 65 | 45 |
| HELAN | 250 | 0 | 12.5 | 10 | 250 + 12.5 | 20 | 10 |
| HELAN | 125 | 0 | 50 | 15 | 125 + 50 | 20 | 15 |
| HELAN | 125 | 0 | 12.5 | 10 | 125 + 12.5 | 35 | 10 |
| SETVI | 250 | 25 | 100 | 85 | 250 + 100 | 98 | 89 |
| SETVI | 250 | 25 | 50 | 80 | 250 + 50 | 95 | 85 |
| SETVI | 125 | 20 | 100 | 85 | 125 + 100 | 98 | 88 |
| SETVI | 125 | 20 | 50 | 80 | 125 + 50 | 98 | 84 |
| SETVI | 125 | 20 | 25 | 70 | 125 + 25 | 80 | 76 |
| SETVI | 62.5 | 0 | 100 | 85 | 62.5 + 100 | 95 | 85 |
| SETVI | 62.5 | 0 | 50 | 80 | 62.5 + 50 | 90 | 80 |
| SETVI | 62.5 | 0 | 250 | 70 | 62.5 + 25 | 90 | 70 |
| STEME | 250 | 80 | 100 | 65 | 250 + 100 | 100 | 93 |
| STEME | 250 | 80 | 50 | 50 | 250 + 50 | 100 | 90 |
| STEME | 125 | 30 | 100 | 65 | 125 + 100 | 80 | 76 |
| STEME | 125 | 30 | 50 | 50 | 125 + 50 | 70 | 65 |
| STEME | 125 | 30 | 25 | 20 | 125 + 25 | 50 | 44 |

TABLE X45

Ex. 26 and pinoxaden, in post-emergence application at 20 DAT, wherein pinoxaden was used as EC formulation having an active ingredient concentration of 50 g/l.

| | solo application | | | | combination | | |
|---|---|---|---|---|---|---|---|
| | Ex. 26 | | pinoxaden | | Ex. 26 + pinoxaden | | COLBY |
| weed | use rate (gai/ha) | % activity | use rate (gai/ha) | % activity | use rate (gai/ha) | % activity | expected % activity |
| ALOMY | 125 | 73 | 60 | 94 | 125 + 60 | 100 | 98 |
| ALOMY | 125 | 73 | 7.5 | 75 | 125 + 7.5 | 95 | 93 |

TABLE X46

Ex. 26 and prosulfocarb, in pre-emergence application at 20 DAT, wherein prosulfocarb was used as EC formulation having an active ingredient concentration of 800 g/l.

| | solo application | | | | combination | | |
|---|---|---|---|---|---|---|---|
| | | | | | Ex. 26 + prosulfocarb | | |
| | Ex. 26 | | prosulfocarb | | | | COLBY |
| weed | use rate (gai/ha) | % activity | use rate (gai/ha) | % activity | use rate (gai/ha) | % activity | expected % activity |
| BRADC | 125 | 0 | 500 | 20 | 125 + 500 | 70 | 20 |
| BRADC | 125 | 0 | 250 | 0 | 125 + 250 | 30 | 0 |
| BRADC | 62.5 | 20 | 500 | 20 | 62.5 + 500 | 70 | 36 |
| BROST | 125 | 35 | 1000 | 50 | 125 + 1000 | 75 | 68 |
| BROST | 125 | 35 | 500 | 40 | 125 + 500 | 75 | 61 |
| BROST | 125 | 35 | 250 | 0 | 125 + 250 | 55 | 30 |
| LOLMU | 62.5 | 30 | 250 | 30 | 62.5 + 250 | 60 | 51 |
| MATCH | 125 | 0 | 1000 | 65 | 125 + 1000 | 95 | 65 |
| MATCH | 125 | 0 | 250 | 0 | 125 + 250 | 50 | 0 |
| MATCH | 62.5 | 0 | 250 | 0 | 62.5 + 250 | 50 | 0 |
| PAPRH | 125 | 30 | 1000 | 70 | 125 + 1000 | 95 | 79 |
| PAPRH | 62.5 | 0 | 1000 | 70 | 125 + 1000 | 95 | 70 |
| POAAN | 62.5 | 90 | 125 | 0 | 62.5 + 125 | 95 | 90 |
| POLCO | 125 | 0 | 1000 | 80 | 125 + 1000 | 100 | 80 |
| POLCO | 125 | 0 | 250 | 0 | 125 + 250 | 20 | 0 |
| POLCO | 62.5 | 0 | 1000 | 80 | 62.5 + 1000 | 100 | 80 |
| SETVI | 125 | 0 | 1000 | 85 | 125 + 1000 | 90 | 85 |
| SETVI | 125 | 0 | 250 | 40 | 125 + 250 | 55 | 40 |
| SETVI | 62.5 | 0 | 1000 | 85 | 62.5 + 1000 | 98 | 85 |
| SETVI | 62.5 | 0 | 250 | 40 | 62.5 + 250 | 55 | 40 |

TABLE X47

Ex. 26 and pyridate, in post-emergence application at 20 DAT, wherein pyridate was used as WP formulation having an active ingredient concentration of 45%.

| | solo application | | | | combination | | |
|---|---|---|---|---|---|---|---|
| | | | | | Ex. 26 + pyridate | | |
| | Ex. 26 | | pyridate | | | | COLBY |
| weed | use rate (gai/ha) | % activity | use rate (gai/ha) | % activity | use rate (gai/ha) | % activity | expected % activity |
| ALOMY | 250 | 75 | 900 | 20 | 250 + 900 | 85 | 80 |
| ALOMY | 250 | 75 | 450 | 0 | 250 + 450 | 80 | 75 |
| ALOMY | 250 | 75 | 225 | 0 | 250 + 225 | 80 | 75 |
| ALOMY | 250 | 75 | 112.5 | 0 | 250 + 112.5 | 80 | 75 |
| ALOMY | 125 | 70 | 900 | 20 | 125 + 900 | 80 | 76 |
| ALOMY | 125 | 70 | 450 | 0 | 125 + 450 | 75 | 70 |
| ALOMY | 125 | 70 | 225 | 0 | 125 + 225 | 75 | 70 |
| ALOMY | 125 | 70 | 112.5 | 0 | 125 + 112.5 | 75 | 70 |
| AMBEL | 125 | 0 | 225 | 10 | 125 + 225 | 80 | 10 |
| AMBEL | 125 | 0 | 112.5 | 0 | 125 + 112.5 | 10 | 0 |
| AMBEL | 62.5 | 0 | 450 | 85 | 62.5 + 450 | 100 | 85 |
| AMBEL | 62.5 | 0 | 225 | 10 | 62.5 + 225 | 25 | 10 |
| APESV | 250 | 75 | 900 | 30 | 250 + 900 | 95 | 84 |
| APESV | 250 | 75 | 450 | 0 | 250 + 450 | 85 | 75 |
| APESV | 250 | 75 | 225 | 0 | 250 + 225 | 80 | 75 |
| APESV | 250 | 75 | 112.5 | 0 | 250 + 112.5 | 80 | 75 |
| APESV | 125 | 70 | 450 | 0 | 125 + 450 | 80 | 70 |
| APESV | 125 | 70 | 112.5 | 0 | 125 + 112.5 | 75 | 70 |
| APESV | 62.5 | 60 | 450 | 0 | 62.5 + 450 | 70 | 60 |
| APESV | 62.5 | 60 | 225 | 0 | 62.5 + 225 | 65 | 60 |
| APESV | 62.5 | 60 | 112.5 | 0 | 62.5 + 112.5 | 65 | 60 |
| AVEFA | 250 | 75 | 450 | 10 | 250 + 450 | 85 | 78 |
| AVEFA | 125 | 70 | 225 | 0 | 125 + 225 | 75 | 70 |
| AVEFA | 62.5 | 65 | 450 | 10 | 62.5 + 450 | 70 | 69 |
| AVEFA | 62.5 | 65 | 225 | 0 | 62.5 + 225 | 70 | 65 |
| AVEFA | 62.5 | 65 | 112.5 | 0 | 62.5 + 112.5 | 70 | 65 |
| BRADC | 125 | 40 | 900 | 50 | 125 + 900 | 75 | 70 |
| BRADC | 125 | 40 | 450 | 20 | 125 + 450 | 65 | 52 |
| BRADC | 125 | 40 | 225 | 20 | 125 + 225 | 65 | 52 |

TABLE X47-continued

Ex. 26 and pyridate, in post-emergence application at 20 DAT, wherein pyridate was used as WP formulation having an active ingredient concentration of 45%.

| | solo application | | | | combination | | |
| --- | --- | --- | --- | --- | --- | --- | --- |
| | Ex. 26 | | pyridate | | Ex. 26 + pyridate | | COLBY |
| weed | use rate (gai/ha) | % activity | use rate (gai/ha) | % activity | use rate (gai/ha) | % activity | expected % activity |
| BRADC | 125 | 40 | 112.5 | 0 | 125 + 112.5 | 50 | 40 |
| BRADC | 62.5 | 20 | 900 | 50 | 62.5 + 900 | 65 | 60 |
| BRADC | 62.5 | 20 | 450 | 20 | 62.5 + 450 | 65 | 36 |
| ECHCG | 250 | 65 | 225 | 30 | 250 + 225 | 80 | 76 |
| GALAP | 250 | 0 | 225 | 85 | 250 + 225 | 100 | 85 |
| GALAP | 250 | 0 | 112.5 | 40 | 250 + 112.5 | 50 | 40 |
| GALAP | 125 | 0 | 112.5 | 40 | 125 + 112.5 | 50 | 40 |
| GALAP | 62.5 | 0 | 225 | 85 | 62.5 + 225 | 100 | 85 |
| GALAP | 62.5 | 0 | 112.5 | 40 | 62.5 + 112.5 | 85 | 40 |
| HELAN | 250 | 5 | 450 | 70 | 250 + 450 | 95 | 72 |
| HELAN | 125 | 0 | 450 | 70 | 125 + 450 | 100 | 70 |
| HELAN | 62.5 | 0 | 225 | 60 | 62.5 + 225 | 85 | 60 |
| LOLMU | 250 | 60 | 112.5 | 0 | 250 + 112.5 | 65 | 60 |
| LOLMU | 125 | 35 | 225 | 20 | 125 + 225 | 65 | 48 |
| LOLMU | 125 | 35 | 112.5 | 0 | 125 + 112.5 | 60 | 35 |
| LOLMU | 62.5 | 0 | 225 | 20 | 62.5 + 225 | 65 | 20 |
| LOLMU | 62.5 | 0 | 112.5 | 0 | 62.5 + 112.5 | 30 | 0 |
| MATCH | 250 | 0 | 450 | 40 | 250 + 450 | 100 | 40 |
| MATCH | 250 | 0 | 225 | 0 | 250 + 225 | 65 | 0 |
| MATCH | 250 | 0 | 112.5 | 0 | 250 + 112.5 | 50 | 0 |
| MATCH | 125 | 0 | 450 | 40 | 125 + 450 | 65 | 40 |
| MATCH | 62.5 | 0 | 450 | 40 | 62.5 + 450 | 100 | 40 |
| MATCH | 62.5 | 0 | 225 | 0 | 62.5 + 225 | 40 | 0 |
| MATCH | 62.5 | 0 | 112.5 | 0 | 62.5 + 112.5 | 35 | 0 |
| PAPRH | 250 | 45 | 900 | 70 | 250 + 900 | 100 | 84 |
| PAPRH | 250 | 45 | 450 | 50 | 250 + 450 | 100 | 73 |
| PAPRH | 125 | 0 | 900 | 70 | 125 + 900 | 100 | 70 |
| PAPRH | 125 | 0 | 225 | 10 | 125 + 225 | 40 | 10 |
| PAPRH | 125 | 0 | 112.5 | 0 | 125 + 112.5 | 40 | 0 |
| PAPRH | 62.5 | 0 | 900 | 70 | 62.5 + 900 | 100 | 70 |
| PAPRH | 62.5 | 0 | 450 | 50 | 62.5 + 450 | 65 | 50 |
| PAPRH | 62.5 | 0 | 225 | 10 | 62.5 + 225 | 30 | 10 |
| POLAV | 125 | 90 | 450 | 20 | 125 + 450 | 100 | 92 |
| POLAV | 62.5 | 85 | 900 | 30 | 62.5 + 900 | 98 | 90 |
| POLAV | 62.5 | 85 | 225 | 20 | 62.5 + 225 | 100 | 88 |
| POLAV | 62.5 | 85 | 112.5 | 0 | 62.5 + 112.5 | 95 | 85 |
| POLCO | 125 | 90 | 112.5 | 40 | 125 + 112.5 | 100 | 94 |
| POLCO | 62.5 | 30 | 225 | 50 | 62.5 + 225 | 100 | 65 |
| STEME | 250 | 30 | 900 | 70 | 250 + 900 | 100 | 79 |
| STEME | 250 | 30 | 450 | 55 | 250 + 450 | 100 | 69 |
| STEME | 250 | 30 | 112.5 | 25 | 250 + 112.5 | 60 | 48 |
| STEME | 125 | 55 | 900 | 70 | 125 + 900 | 100 | 87 |
| STEME | 62.5 | 20 | 900 | 70 | 62.5 + 900 | 100 | 76 |
| SETVI | 250 | 25 | 225 | 25 | 250 + 225 | 55 | 44 |
| SETVI | 125 | 20 | 225 | 25 | 125 + 225 | 50 | 40 |
| SETVI | 62.5 | 0 | 900 | 80 | 62.5 + 900 | 85 | 80 |
| SETVI | 62.5 | 0 | 450 | 65 | 62.5 + 450 | 75 | 65 |
| SETVI | 62.5 | 0 | 225 | 25 | 62.5 + 225 | 30 | 25 |

TABLE X48

Ex. 26 and pyroxasulfone, in post-emergence application at 21 DAT, wherein pyroxasulfone was used as WG formulation having an active ingredient concentration of 85%.

| | solo application | | | | combination | | |
| --- | --- | --- | --- | --- | --- | --- | --- |
| | | | | | Ex. 26 + pyroxasulfone | | |
| | Ex. 26 | | pyroxasulfone | | | | COLBY |
| weed | use rate (gai/ha) | % activity | use rate (gai/ha) | % activity | use rate (gai/ha) | % activity | expected % activity |
| ALOMY | 62.5 | 40 | 30 | 65 | 62.5 + 30 | 85 | 79 |
| ALOMY | 62.5 | 40 | 7.5 | 35 | 62.5 + 7.5 | 75 | 61 |
| AMBEL | 250 | 0 | 30 | 20 | 250 + 30 | 30 | 20 |
| AMBEL | 62.5 | 5 | 60 | 60 | 62.5 + 60 | 65 | 60 |
| AVEFA | 62.5 | 50 | 15 | 30 | 62.5 + 30 | 70 | 65 |
| AVEFA | 62.5 | 50 | 7.5 | 25 | 62.5 + 7.5 | 70 | 63 |
| BRADC | 125 | 0 | 60 | 75 | 125 60 | 80 | 75 |
| BRADC | 125 | 0 | 30 | 55 | 125 + 30 | 65 | 55 |
| BRADC | 125 | 0 | 7.5 | 0 | 125 + 7.5 | 20 | 0 |
| BRADC | 62.5 | 0 | 60 | 75 | 62.5 + 60 | 85 | 75 |
| BRADC | 62.5 | 0 | 30 | 55 | 62.5 + 30 | 70 | 55 |
| BROST | 250 | 35 | 15 | 40 | 250 + 15 | 70 | 61 |
| BROST | 250 | 35 | 7.5 | 20 | 250 + 7.5 | 60 | 48 |
| BROST | 125 | 5 | 15 | 40 | 125 + 15 | 55 | 43 |
| BROST | 125 | 5 | 7.5 | 20 | 125 + 7.5 | 40 | 24 |
| ECHCG | 62.5 | 50 | 60 | 80 | 62.5 + 60 | 95 | 90 |
| GALAP | 250 | 0 | 7.5 | 40 | 250 + 7.5 | 65 | 40 |
| GALAP | 125 | 0 | 7.5 | 40 | 125 + 7.5 | 45 | 40 |
| LOLMU | 125 | 10 | 15 | 65 | 125 + 15 | 75 | 69 |
| LOLMU | 125 | 10 | 7.5 | 40 | 125 + 7.5 | 65 | 46 |
| LOLMU | 62.5 | 0 | 30 | 70 | 62.5 + 30 | 80 | 70 |
| LOLMU | 62.5 | 0 | 7.5 | 40 | 62.5 + 7.5 | 65 | 40 |
| MATCH | 250 | 0 | 15 | 0 | 250 + 15 | 30 | 0 |
| PAPRH | 250 | 0 | 60 | 60 | 250 + 60 | 70 | 60 |
| PAPRH | 250 | 0 | 15 | 0 | 250 + 15 | 20 | 0 |
| PAPRH | 62.5 | 0 | 60 | 60 | 62.5 + 60 | 65 | 60 |
| POLCO | 125 | 0 | 60 | 30 | 125 + 60 | 80 | 30 |
| POLCO | 125 | 0 | 30 | 30 | 125 + 30 | 50 | 30 |
| POLCO | 125 | 0 | 15 | 30 | 125 + 15 | 75 | 30 |
| POLCO | 125 | 0 | 7.5 | 30 | 125 + 7.5 | 98 | 30 |
| POLCO | 62.5 | 0 | 60 | 30 | 62.5 + 60 | 65 | 30 |
| POLCO | 62.5 | 0 | 30 | 30 | 62.5 + 30 | 40 | 30 |
| POAAN | 62.5 | 35 | 15 | 70 | 62.5 + 15 | 90 | 81 |
| STEME | 125 | 0 | 30 | 0 | 125 + 30 | 30 | 0 |

TABLE X49

Ex. 26 and pyroxsulam, in post-emergence application at 20 DAT, wherein pyroxsulam was used as SC formulation having an active ingredient concentration of 30 g/l.

| | solo application | | | | combination | | |
| --- | --- | --- | --- | --- | --- | --- | --- |
| | | | | | Ex. 26 + pyroxsulam | | |
| | Ex. 26 | | pyroxsulam | | | | COLBY |
| weed | use rate (gai/ha) | % activity | use rate (gai/ha) | % activity | use rate (gai/ha) | % activity | expected % activity |
| AMBEL | 250 | 20 | 1.875 | 70 | 250 + 1.875 | 98 | 76 |
| AMBEL | 125 | 0 | 1.875 | 70 | 125 + 1.875 | 90 | 70 |
| AMBEL | 62.5 | 0 | 1.875 | 70 | 62.5 + 1.875 | 98 | 70 |
| DIGSA | 125 | 20 | 7.5 | 80 | 250 + 7.5 | 98 | 84 |
| DIGSA | 125 | 0 | 7.5 | 80 | 125 + 7.5 | 85 | 80 |
| DIGSA | 62.5 | 0 | 7.5 | 80 | 62.5 + 7.5 | 90 | 80 |
| DIGSA | 62.5 | 0 | 3.75 | 75 | 62.5 + 3.75 | 80 | 75 |
| DIGSA | 62.5 | 0 | 1.875 | 65 | 62.5 + 1.875 | 70 | 65 |
| BRADC | 250 | 35 | 1.875 | 20 | 250 + 1.875 | 70 | 48 |
| BRADC | 125 | 20 | 3.75 | 75 | 125 + 3.75 | 85 | 80 |
| BRADC | 125 | 20 | 1.875 | 20 | 125 + 1.875 | 65 | 36 |
| BRADC | 62.5 | 0 | 3.75 | 75 | 62.5 + 3.75 | 85 | 75 |
| BRADC | 62.5 | 0 | 1.875 | 20 | 62.5 + 1.875 | 80 | 20 |
| BROST | 62.5 | 0 | 7.5 | 75 | 62.5 + 7.5 | 80 | 75 |
| BROST | 62.5 | 0 | 3.75 | 70 | 62.5 + 3.75 | 75 | 70 |

TABLE X49-continued

Ex. 26 and pyroxsulam, in post-emergence application at 20 DAT, wherein pyroxsulam was used as SC formulation having an active ingredient concentration of 30 g/l.

| | solo application | | | | combination | | |
|---|---|---|---|---|---|---|---|
| | | | | | Ex. 26 + pyroxsulam | | |
| | Ex. 26 | | pyroxsulam | | | | COLBY |
| weed | use rate (gai/ha) | % activity | use rate (gai/ha) | % activity | use rate (gai/ha) | % activity | expected % activity |
| BROST | 62.5 | 0 | 1.875 | 60 | 62.5 + 1.875 | 70 | 60 |
| GALAP | 250 | 30 | 15 | 90 | 250 + 15 | 98 | 93 |
| GALAP | 250 | 30 | 7.5 | 75 | 250 + 7.5 | 95 | 83 |
| GALAP | 125 | 0 | 15 | 90 | 125 + 15 | 95 | 90 |
| GALAP | 125 | 0 | 7.5 | 75 | 125 + 7.5 | 98 | 75 |
| GALAP | 125 | 0 | 3.75 | 65 | 125 + 3.75 | 75 | 65 |
| GALAP | 125 | 0 | 1.875 | 60 | 125 + 1.875 | 65 | 60 |
| GALAP | 62.5 | 0 | 7.5 | 75 | 62.5 + 7.5 | 80 | 75 |
| GALAP | 62.5 | 0 | 3.75 | 65 | 62.5 + 3.75 | 95 | 65 |
| GALAP | 62.5 | 0 | 1.875 | 60 | 62.5 + 1.875 | 80 | 60 |
| LOLMU | 250 | 55 | 3.75 | 65 | 250 + 3.75 | 90 | 84 |
| LOLMU | 250 | 55 | 1.875 | 60 | 250 + 1.875 | 85 | 82 |
| LOLMU | 125 | 35 | 7.5 | 80 | 125 + 7.5 | 95 | 87 |
| LOLMU | 125 | 35 | 3.75 | 65 | 125 + 3.75 | 85 | 77 |
| LOLMU | 62.5 | 10 | 7.5 | 80 | 62.5 + 7.5 | 90 | 82 |
| LOLMU | 62.5 | 10 | 3.75 | 65 | 62.5 + 3.75 | 90 | 69 |
| LOLMU | 62.5 | 10 | 1.875 | 80 | 62.5 + 1.875 | 80 | 64 |
| MATCH | 250 | 30 | 1.875 | 30 | 250 + 1.875 | 98 | 51 |
| MATCH | 125 | 0 | 15 | 80 | 125 + 15 | 85 | 80 |
| MATCH | 125 | 0 | 3.75 | 60 | 125 + 3.75 | 80 | 60 |
| MATCH | 125 | 0 | 1.875 | 30 | 125 + 1.875 | 50 | 30 |
| MATCH | 62.5 | 0 | 3.75 | 60 | 62.5 + 3.75 | 85 | 60 |
| MATCH | 62.5 | 0 | 1.875 | 30 | 62.5 + 1.875 | 70 | 30 |
| PAPRH | 250 | 0 | 15 | 70 | 250 + 15 | 80 | 70 |
| PAPRH | 250 | 0 | 3.75 | 0 | 250 + 3.75 | 60 | 0 |
| PAPRH | 125 | 0 | 15 | 70 | 125 + 70 | 80 | 70 |
| PAPRH | 125 | 0 | 3.75 | 0 | 125 + 3.75 | 60 | 0 |
| PAPRH | 125 | 0 | 1.875 | 0 | 125 + 1.875 | 20 | 0 |
| PAPRH | 62.5 | 0 | 15 | 70 | 62.5 + 15 | 98 | 70 |
| PAPRH | 62.5 | 0 | 7.5 | 30 | 62.5 + 7.5 | 50 | 30 |
| SETVI | 250 | 10 | 1.875 | 75 | 250 + 1.875 | 95 | 78 |
| SETVI | 125 | 0 | 1.875 | 75 | 125 + 1.875 | 95 | 75 |
| SETVI | 62.5 | 0 | 1.875 | 75 | 62.5 + 1.875 | 90 | 75 |

TABLE X50

Ex. 26 and saflufenacil, in pre-emergence application at 20 DAT, wherein saflufenacil was used as SC formulation having an active ingredient concentration of 342 g/l.

| | solo application | | | | combination | | |
|---|---|---|---|---|---|---|---|
| | | | | | Ex. 26 + saflufenacil | | |
| | Ex. 26 | | saflufenacil | | | | COLBY |
| weed | use rate (gai/ha) | % activity | use rate (gai/ha) | % activity | use rate (gai/ha) | % activity | expected % activity |
| AMBEL | 125 | 0 | 6.25 | 45 | 125 + 6.25 | 80 | 45 |
| AMBEL | 62.5 | 0 | 6.25 | 45 | 62.5 + 6.25 | 95 | 45 |
| AMBEL | 31.25 | 0 | 6.25 | 45 | 31.25 + 6.25 | 50 | 45 |
| AVEFA | 125 | 65 | 6.25 | 0 | 125 + 6.25 | 75 | 65 |
| BRADC | 125 | 20 | 12.5 | 20 | 125 + 12.5 | 45 | 36 |
| BRADC | 62.5 | 0 | 6.25 | 10 | 62.5 + 6.25 | 30 | 10 |
| BRADC | 31.25 | 0 | 12.5 | 20 | 31.25 + 12.5 | 25 | 20 |
| DIGSA | 125 | 60 | 25 | 35 | 125 + 25 | 80 | 74 |
| DIGSA | 62.5 | 30 | 6.25 | 10 | 62.5 + 6.25 | 40 | 37 |
| DIGSA | 31.25 | 30 | 25 | 35 | 31.25 + 25 | 60 | 55s |
| GALAP | 125 | 0 | 12.5 | 80 | 125 + 12.5 | 85 | 80 |
| GALAP | 62.5 | 0 | 12.5 | 80 | 62.5 + 12.5 | 90 | 80 |
| GALAP | 31.25 | 0 | 12.5 | 80 | 31.25 + 12.5 | 90 | 80 |
| LOLMU | 31.25 | 10 | 6.25 | 10 | 31.25 + 6.25 | 30 | 19 |
| POLCO | 125 | 0 | 12.5 | 90 | 125 + 12.5 | 100 | 90 |

TABLE X50-continued

Ex. 26 and saflufenacil, in pre-emergence application at 20 DAT, wherein saflufenacil was used as SC formulation having an active ingredient concentration of 342 g/l.

| | solo application | | | | combination | | |
|---|---|---|---|---|---|---|---|
| | | | | | Ex. 26 + saflufenacil | | |
| | Ex. 26 | | saflufenacil | | | | COLBY |
| weed | use rate (gai/ha) | % activity | use rate (gai/ha) | % activity | use rate (gai/ha) | % activity | expected % activity |
| POLCO | 62.5 | 0 | 12.5 | 90 | 62.5 + 12.5 | 100 | 90 |
| SETVI | 125 | 10 | 25 | 65 | 125 + 25 | 85 | 69 |
| SETVI | 125 | 10 | 12.5 | 40 | 125 + 12.5 | 60 | 46 |
| SETVI | 62.5 | 0 | 50 | 90 | 62.5 + 50 | 95 | 90 |
| SETVI | 62.5 | 0 | 25 | 65 | 62.5 + 25 | 80 | 65 |
| SETVI | 62.5 | 0 | 12.5 | 40 | 62.5 + 12.5 | 55 | 40 |
| SETVI | 31.25 | 0 | 50 | 90 | 31.25 + 50 | 95 | 90 |
| SETVI | 31.25 | 0 | 25 | 65 | 31.25 + 25 | 80 | 65 |
| SETVI | 31.25 | 0 | 12.5 | 40 | 31.25 + 12.5 | 60 | 40 |
| SETVI | 31.25 | 0 | 6.25 | 25 | 31.25 + 6.25 | 35 | 25 |

TABLE X51

Ex. 26 and sulfosulfuron, in post-emergence application at 20 DAT, wherein sulfosulfuron was used as WG formulation having an active ingredient concentration of 80%.

| | solo application | | | | combination | | |
|---|---|---|---|---|---|---|---|
| | | | | | Ex. 26 + sulfosulfuron | | |
| | Ex. 26 | | sulfosulfuron | | | | COLBY |
| weed | use rate (gai/ha) | % activity | use rate (gai/ha) | % activity | use rate (gai/ha) | % activity | expected % activity |
| AMBEL | 125 | 0 | 1.5 | 70 | 125 + 1.5 | 90 | 70 |
| AVEFA | 250 | 70 | 3 | 0 | 250 + 3 | 75 | 70 |
| AVEFA | 250 | 70 | 1.5 | 0 | 250 + 1.5 | 75 | 70 |
| BRADC | 250 | 35 | 1.5 | 20 | 250 + 1.5 | 55 | 48 |
| BRADC | 125 | 20 | 12 | 80 | 125 + 12 | 90 | 84 |
| BRADC | 125 | 20 | 1.5 | 20 | 125 + 1.5 | 40 | 36 |
| BROST | 250 | 35 | 1.5 | 0 | 250 + 1.5 | 70 | 35 |
| BROST | 125 | 20 | 12 | 70 | 125 + 12 | 80 | 76 |
| BROST | 125 | 20 | 3 | 50 | 125 + 3 | 65 | 60 |
| BROST | 125 | 20 | 1.5 | 0 | 125 + 1.5 | 60 | 20 |
| DIGSA | 250 | 20 | 12 | 65 | 250 + 12 | 80 | 72 |
| DIGSA | 125 | 0 | 12 | 65 | 125 + 12 | 80 | 65 |
| DIGSA | 125 | 0 | 3 | 20 | 125 + 3 | 30 | 20 |
| DIGSA | 125 | 0 | 1.5 | 0 | 125 + 1.5 | 20 | 0 |
| LOLMU | 250 | 55 | 12 | 35 | 250 + 12 | 75 | 71 |
| LOLMU | 250 | 55 | 6 | 10 | 250 + 6 | 70 | 60 |
| LOLMU | 250 | 55 | 3 | 0 | 250 + 3 | 65 | 55 |
| LOLMU | 250 | 55 | 1.5 | 0 | 250 + 1.5 | 65 | 55 |
| LOLMU | 125 | 35 | 12 | 35 | 125 + 12 | 70 | 58 |
| LOLMU | 125 | 35 | 6 | 10 | 125 + 6 | 50 | 42 |
| LOLMU | 125 | 35 | 3 | 0 | 125 + 3 | 65 | 35 |
| LOLMU | 125 | 35 | 1.5 | 0 | 125 + 1.5 | 60 | 35 |
| PAPRH | 250 | 0 | 3 | 80 | 250 + 3 | 85 | 80 |
| PAPRH | 250 | 0 | 1.5 | 25 | 250 + 1.5 | 55 | 25 |
| PAPRH | 125 | 0 | 3 | 80 | 125 + 3 | 90 | 80 |
| PAPRH | 125 | 0 | 1.5 | 25 | 125 + 1.5 | 30 | 25 |
| SETVI | 250 | 10 | 12 | 75 | 250 + 12 | 95 | 78 |
| SETVI | 250 | 10 | 6 | 65 | 125 + 6 | 80 | 69 |
| SETVI | 125 | 0 | 12 | 75 | 125 + 12 | 90 | 75 |
| SETVI | 125 | 0 | 6 | 65 | 125 + 6 | 80 | 65 |
| SETVI | 125 | 0 | 1.5 | 50 | 125 + 1.5 | 55 | 50 |

TABLE X52

Ex. 26 and topramezone, in post-emergence application at 21 DAT, wherein topramezone was used as SC formulation having an active ingredient concentration of 336 g/l.

| | solo application | | | | combination | | |
|---|---|---|---|---|---|---|---|
| | Ex. 26 | | topramezone | | Ex. 26 + topramezone | | COLBY |
| weed | use rate (gai/ha) | % activity | use rate (gai/ha) | % activity | use rate (gai/ha) | % activity | expected % activity |
| ALOMY | 250 | 75 | 12 | 0 | 250 + 12 | 80 | 75 |
| ALOMY | 250 | 75 | 6 | 0 | 250 + 6 | 80 | 75 |
| ALMOY | 125 | 65 | 24 | 10 | 125 + 24 | 80 | 69 |
| ALMOY | 125 | 65 | 12 | 0 | 125 + 12 | 80 | 65 |
| ALMOY | 125 | 65 | 6 | 0 | 125 + 6 | 75 | 65 |
| ALMOY | 125 | 65 | 3 | 0 | 125 + 3 | 75 | 65 |
| AMBEL | 250 | 0 | 6 | 95 | 250 + 6 | 98 | 85 |
| APESV | 250 | 75 | 6 | 0 | 250 + 6 | 90 | 75 |
| APESV | 250 | 75 | 3 | 0 | 250 + 3 | 85 | 75 |
| APESV | 125 | 65 | 12 | 30 | 125 + 12 | 85 | 76 |
| APESV | 125 | 65 | 6 | 0 | 125 + 6 | 85 | 65 |
| APESV | 125 | 65 | 3 | 0 | 125 + 3 | 80 | 65 |
| BROST | 250 | 35 | 24 | 25 | 250 + 24 | 70 | 51 |
| BROST | 250 | 35 | 12 | 5 | 250 + 12 | 70 | 38 |
| BROST | 250 | 35 | 6 | 0 | 250 + 6 | 60 | 35 |
| BROST | 250 | 35 | 3 | 0 | 250 + 3 | 50 | 35 |
| BROST | 125 | 5 | 24 | 25 | 125 + 24 | 50 | 29 |
| BROST | 125 | 5 | 12 | 5 | 125 + 12 | 50 | 10 |
| BROST | 125 | 5 | 6 | 0 | 125 + 6 | 45 | 5 |
| BROST | 125 | 5 | 3 | 0 | 125 + 3 | 45 | 5 |
| DIGSA | 125 | 0 | 3 | 75 | 125 + 3 | 80 | 75 |
| LOLMU | 250 | 55 | 12 | 10 | 250 + 12 | 65 | 60 |
| LOLMU | 250 | 55 | 6 | 0 | 250 + 6 | 65 | 55 |
| LOLMU | 250 | 55 | 3 | 0 | 250 + 3 | 65 | 55 |
| LOLMU | 125 | 10 | 24 | 20 | 125 + 24 | 60 | 28 |
| LOLMU | 125 | 10 | 12 | 10 | 125 + 12 | 55 | 19 |
| LOLMU | 125 | 10 | 6 | 0 | 125 + 6 | 65 | 10 |
| LOLMU | 125 | 10 | 3 | 0 | 125 + 3 | 55 | 10 |
| MATCH | 250 | 0 | 6 | 30 | 250 + 6 | 40 | 30 |
| PAPRH | 250 | 0 | 24 | 40 | 250 + 24 | 65 | 40 |
| PAPRH | 250 | 0 | 12 | 20 | 250 + 12 | 30 | 20 |
| PAPRH | 125 | 0 | 24 | 40 | 125 + 24 | 75 | 40 |
| POAAN | 250 | 75 | 24 | 0 | 250 + 24 | 95 | 75 |
| POAAN | 250 | 75 | 12 | 0 | 250 + 12 | 90 | 75 |
| POAAN | 250 | 75 | 6 | 0 | 250 + 6 | 80 | 75 |
| POAAN | 250 | 75 | 3 | 0 | 250 + 3 | 85 | 75 |
| POAAN | 125 | 65 | 24 | 0 | 125 + 24 | 80 | 65 |
| POAAN | 125 | 65 | 12 | 0 | 125 + 12 | 80 | 65 |
| POAAN | 125 | 65 | 6 | 0 | 125 + 6 | 70 | 65 |
| POAAN | 125 | 65 | 3 | 0 | 125 + 3 | 70 | 65 |
| POLCO | 125 | 0 | 24 | 85 | 125 + 24 | 100 | 85 |
| POLCO | 125 | 0 | 12 | 30 | 125 + 12 | 98 | 30 |
| POLCO | 125 | 0 | 6 | 30 | 125 + 6 | 98 | 30 |
| POLCO | 125 | 0 | 3 | 0 | 125 + 3 | 75 | 0 |
| SETVI | 250 | 0 | 3 | 70 | 250 + 70 | 75 | 70 |
| SETVI | 125 | 0 | 3 | 70 | 125 + 70 | 85 | 70 |

TABLE X53

Ex. 26 and Mesosulfuron - Methyl, in post-emergence application at 20 DAT, wherein Mesosulfuron - Methyl was used as WG formulation having an active ingredient concentration of 4.5%.

| | solo application | | | | combination | | |
|---|---|---|---|---|---|---|---|
| | Ex. 26 | | mesosulfuron | | Ex. 26 + mesosulfuron | | COLBY |
| weed | use rate (gai/ha) | % activity | use rate (gai/ha) | % activity | use rate (gai/ha) | % activity | expected % activity |
| AMBEL | 250 | 0 | 4 | 85 | 250 + 4 | 95 | 85 |
| AMBEL | 250 | 0 | 2 | 80 | 250 + 2 | 98 | 80 |

TABLE X53-continued

Ex. 26 and Mesosulfuron - Methyl, in post-emergence application at 20 DAT, wherein Mesosulfuron - Methyl was used as WG formulation having an active ingredient concentration of 4.5%.

| | solo application | | | | combination | | |
|---|---|---|---|---|---|---|---|
| | Ex. 26 | | mesosulfuron | | Ex. 26 + mesosulfuron | | COLBY |
| weed | use rate (gai/ha) | % activity | use rate (gai/ha) | % activity | use rate (gai/ha) | % activity | expected % activity |
| AMBEL | 125 | 0 | 4 | 85 | 125 + 4 | 98 | 85 |
| AMBEL | 62.5 | 0 | 4 | 85 | 62.5 + 4 | 100 | 85 |
| DIGSA | 250 | 20 | 2 | 0 | 250 + 2 | 60 | 20 |
| DIGSA | 250 | 20 | 1 | 0 | 250 + 1 | 40 | 0 |
| DIGSA | 125 | 0 | 4 | 20 | 125 + 4 | 25 | 20 |
| DIGSA | 125 | 0 | 2 | 0 | 125 + 2 | 35 | 0 |
| DIGSA | 125 | 0 | 1 | 0 | 125 + 1 | 20 | 0 |
| ECHCG | 250 | 80 | 2 | 0 | 250 + 2 | 85 | 80 |
| GALAP | 125 | 0 | 8 | 75 | 125 + 8 | 80 | 75 |
| GALAP | 125 | 0 | 4 | 65 | 125 + 4 | 80 | 65 |
| LOLMU | 62.5 | 0 | 8 | 90 | 62.5 + 8 | 95 | 90 |
| MATCH | 250 | 0 | 8 | 90 | 250 + 8 | 100 | 90 |
| MATCH | 250 | 0 | 2 | 30 | 250 + 2 | 35 | 30 |
| MATCH | 125 | 0 | 9 | 90 | 125 + 8 | 100 | 90 |
| MATCH | 125 | 0 | 2 | 30 | 125 + 2 | 40 | 30 |
| MATCH | 62.5 | 0 | 2 | 30 | 62.5 + 2 | 40 | 30 |
| MATCH | 62.5 | 0 | 1 | 30 | 62.5 + 1 | 35 | 30 |
| PAPRH | 125 | 0 | 2 | 90 | 125 + 2 | 95 | 90 |
| PAPRH | 125 | 0 | 1 | 70 | 125 + 1 | 90 | 70 |
| PAPRH | 62.5 | 0 | 8 | 98 | 62.5 + 8 | 100 | 98 |
| PAPRH | 62.5 | 0 | 1 | 70 | 62.5 + 1 | 98 | 70 |
| POLCO | 125 | 30 | 2 | 30 | 125 + 2 | 70 | 51 |
| SETVI | 250 | 30 | 8 | 85 | 250 + 8 | 98 | 90 |
| SETVI | 125 | 20 | 8 | 85 | 125 + 8 | 98 | 88 |
| SETVI | 62.5 | 0 | 8 | 85 | 62.5 + 8 | 90 | 85 |
| STEME | 62.5 | 0 | 1 | 95 | 62.5 + 1 | 100 | 95 |

TABLE X54

Ex. 26 and Iodosulfuron-methyl-sodium, in post-emergence application at 20 DAT, wherein Iodosulfuron-methyl-sodium was used as OD formulation having an active ingredient concentration of 100 g/l.

| | solo application | | | | combination | | |
|---|---|---|---|---|---|---|---|
| | Ex. 26 | | iodosulfuron | | Ex. 26 + iodosulfuron | | COLBY |
| weed | use rate (gai/ha) | % activity | use rate (gai/ha) | % activity | use rate (gai/ha) | % activity | expected % activity |
| BRADC | 250 | 50 | 5 | 30 | 250 + 5 | 75 | 65 |
| BRADC | 125 | 25 | 5 | 30 | 125 + 5 | 60 | 48 |
| BRADC | 125 | 25 | 2.5 | 20 | 125 + 2.5 | 45 | 40 |
| BROST | 250 | 55 | 5 | 0 | 250 + 5 | 60 | 55 |
| BROST | 250 | 55 | 2.5 | 0 | 250 + 2.5 | 60 | 55 |
| BROST | 250 | 55 | 1.25 | 0 | 250 + 1.25 | 60 | 55 |
| BROST | 125 | 40 | 2.5 | 0 | 125 + 2.5 | 50 | 40 |
| DIGSA | 250 | 20 | 2.5 | 20 | 250 + 2.5 | 50 | 36 |
| DIGSA | 250 | 20 | 1.25 | 0 | 250 + 1.25 | 40 | 20 |
| DIGSA | 125 | 0 | 5 | 50 | 125 + 5 | 60 | 50 |
| DIGSA | 125 | 0 | 2.5 | 20 | 125 + 2.5 | 50 | 20 |
| DIGSA | 125 | 0 | 1.25 | 0 | 125 + 1.25 | 20 | 0 |

TABLE X55

Ex. 26 and flufenacet, in post-emergence application at 20 DAT, wherein flufenacet was used as SC formulation having an active ingredient concentration of 500 g/l.

| | solo application | | | | combination | | |
| --- | --- | --- | --- | --- | --- | --- | --- |
| | | | | | Ex. 26 + flufenacet | | |
| | Ex. 26 | | flufenacet | | | | COLBY |
| weed | use rate (gai/ha) | % activity | use rate (gai/ha) | % activity | use rate (gai/ha) | % activity | expected % activity |
| AMBEL | 250 | 0 | 125 | 30 | 250 + 125 | 100 | 30 |
| AMBEL | 250 | 0 | 62.5 | 0 | 250 + 62.5 | 65 | 0 |
| AMBEL | 125 | 0 | 250 | 70 | 125 + 250 | 75 | 70 |
| AMBEL | 125 | 0 | 125 | 30 | 125 + 125 | 70 | 30 |
| AMBEL | 62.5 | 0 | 62.5 | 0 | 62.5 + 62.5 | 10 | 0 |
| AVEFA | 62.5 | 35 | 125 | 65 | 62.5 + 125 | 90 | 77 |
| AVEFA | 62.5 | 35 | 62.5 | 65 | 62.5 + 62.5 | 85 | 77 |
| AVEFA | 62.5 | 35 | 31.25 | 30 | 62.5 + 31.25 | 65 | 55 |
| BROST | 250 | 30 | 250 | 80 | 250 + 250 | 95 | 86 |
| BROST | 125 | 5 | 250 | 80 | 125 + 250 | 90 | 81 |
| BROST | 125 | 5 | 125 | 65 | 125 + 125 | 80 | 67 |
| BROST | 62.5 | 0 | 250 | 80 | 62.5 + 250 | 95 | 80 |
| BROST | 62.5 | 0 | 125 | 65 | 62.5 + 125 | 90 | 65 |
| BRADC | 250 | 30 | 250 | 35 | 250 + 250 | 65 | 55 |
| BRADC | 250 | 30 | 125 | 0 | 250 + 125 | 50 | 30 |
| BRADC | 250 | 30 | 62.5 | 0 | 250 + 62.5 | 40 | 30 |
| BRADC | 250 | 30 | 31.25 | 0 | 250 + 31.25 | 40 | 30 |
| BRADC | 125 | 0 | 250 | 35 | 125 + 250 | 65 | 35 |
| BRADC | 125 | 0 | 125 | 0 | 125 + 125 | 30 | 0 |
| BRADC | 125 | 0 | 62.5 | 0 | 125 + 62.5 | 35 | 0 |
| BRADC | 125 | 0 | 31.25 | 0 | 125 + 31.25 | 35 | 0 |
| BRADC | 62.5 | 0 | 250 | 35 | 62.5 + 250 | 65 | 35 |
| BRADC | 62.5 | 0 | 125 | 0 | 62.5 + 125 | 30 | 0 |
| DIGSA | 250 | 30 | 62.5 | 10 | 250 + 62.5 | 50 | 37 |
| DIGSA | 125 | 20 | 62.5 | 10 | 125 + 62.5 | 40 | 28 |
| DIGSA | 62.5 | 0 | 250 | 65 | 31.25 + 250 | 70 | 65 |
| DIGSA | 62.5 | 0 | 125 | 20 | 62.5 + 125 | 25 | 20 |
| ECHCG | 250 | 60 | 31.25 | 25 | 250 + 31.25 | 80 | 70 |
| HELAN | 250 | 0 | 125 | 30 | 250 + 125 | 50 | 30 |
| LOLMU | 250 | 25 | 250 | 85 | 250 + 250 | 98 | 89 |
| LOLMU | 250 | 25 | 125 | 85 | 250 + 125 | 95 | 89 |
| LOLMU | 250 | 25 | 62.5 | 50 | 250 + 62.5 | 70 | 63 |
| LOLMU | 250 | 25 | 31.25 | 20 | 250 + 31.25 | 65 | 40 |
| LOLMU | 125 | 0 | 250 | 85 | 125 + 250 | 98 | 85 |
| LOLMU | 125 | 0 | 125 | 85 | 125 + 125 | 90 | 85 |
| LOLMU | 125 | 0 | 62.5 | 50 | 125 + 62.5 | 65 | 50 |
| LOLMU | 125 | 0 | 31.25 | 20 | 125 + 31.25 | 55 | 20 |
| LOLMU | 62.5 | 0 | 250 | 85 | 62.5 + 250 | 98 | 85 |
| LOLMU | 62.5 | 0 | 125 | 85 | 62.5 + 125 | 95 | 85 |
| LOLMU | 62.5 | 0 | 62.5 | 50 | 62.5 + 62.5 | 60 | 50 |
| POAAN | 250 | 70 | 31.25 | 70 | 250 + 31.25 | 98 | 91 |
| POLAV | 125 | 85 | 250 | 0 | 125 + 250 | 95 | 85 |
| POLAV | 125 | 85 | 125 | 0 | 125 + 125 | 98 | 85 |
| POLAV | 125 | 85 | 62.5 | 0 | 125 + 62.5 | 98 | 85 |
| POLAV | 62.5 | 75 | 62.5 | 0 | 62.5 + 62.5 | 85 | 75 |
| POLCO | 250 | 30 | 125 | 30 | 250 + 125 | 100 | 51 |
| POLCO | 250 | 30 | 62.5 | 30 | 250 + 62.5 | 85 | 51 |
| POLCO | 250 | 30 | 31.25 | 0 | 250 + 31.25 | 98 | 30 |
| POLCO | 125 | 5 | 125 | 30 | 125 + 125 | 50 | 34 |
| POLCO | 125 | 5 | 62.5 | 30 | 125 + 62.5 | 55 | 34 |
| POLCO | 125 | 5 | 31.25 | 0 | 125 + 31.25 | 60 | 5 |
| SETVI | 250 | 0 | 125 | 55 | 250 + 125 | 90 | 55 |
| SETVI | 250 | 0 | 62.5 | 35 | 250 + 62.5 | 50 | 35 |
| SETVI | 125 | 0 | 125 | 55 | 125 + 125 | 80 | 55 |
| SETVI | 62.5 | 0 | 125 | 55 | 62.5 + 125 | 95 | 55 |
| SETVI | 62.5 | 0 | 62.5 | 35 | 62.5 + 62.5 | 50 | 35 |

TABLE X56

Ex.26 and dimethenamid (DMTA), in pre-emergence application at 20 DAT, wherein DMTA was used as EC formulation having an active ingredient concentration of 720 g/l.

| | solo application | | | | combination | | |
| --- | --- | --- | --- | --- | --- | --- | --- |
| | | | | | Ex. 26 + dimethenamid | | |
| | Ex. 26 | | dimethenamid | | | | COLBY |
| weed | use rate (gai/ha) | % activity | use rate (gai/ha) | % activity | use rate (gai/ha) | % activity | expected % activity |
| AMBEL | 125 | 0 | 250 | 30 | 125 + 250 | 70 | 30 |
| AMBEL | 125 | 0 | 125 | 20 | 125 + 125 | 40 | 20 |
| AMBEL | 62.5 | 0 | 250 | 30 | 62.5 + 250 | 40 | 30 |
| AMBEL | 62.5 | 0 | 125 | 20 | 62.5 + 125 | 30 | 20 |
| AMBEL | 31.25 | 0 | 250 | 30 | 31.25 + 250 | 50 | 30 |
| ALOMY | 31.25 | 60 | 250 | 65 | 31.25 + 250 | 98 | 86 |
| ALOMY | 31.25 | 60 | 125 | 60 | 31.25 + 125 | 95 | 84 |
| AVEFA | 62.5 | 55 | 125 | 50 | 62.5 + 125 | 90 | 78 |
| AVEFA | 31.25 | 25 | 250 | 65 | 31.25 + 250 | 90 | 74 |
| AVEFA | 31.25 | 25 | 62.5 | 10 | 31.25 + 62.5 | 55 | 33 |
| BRADC | 31.25 | 0 | 31.25 | 60 | 31.25 + 31.25 | 65 | 60 |
| BROST | 31.25 | 0 | 62.5 | 80 | 31.25 + 62.5 | 85 | 80 |
| GALAP | 125 | 0 | 125 | 50 | 125 + 125 | 100 | 50 |
| GALAP | 125 | 0 | 62.5 | 60 | 125 + 62.5 | 65 | 60 |
| GALAP | 125 | 0 | 31.25 | 50 | 62.5 + 31.25 | 70 | 50 |
| GALAP | 62.5 | 0 | 62.5 | 60 | 62.5 + 62.5 | 70 | 60 |
| GALAP | 31.25 | 0 | 125 | 50 | 31.25 + 125 | 90 | 50 |
| HELAN | 125 | 0 | 250 | 35 | 125 + 250 | 50 | 35 |
| LOLMU | 125 | 0 | 62.5 | 80 | 125 + 62.5 | 90 | 80 |
| LOLMU | 31.25 | 0 | 62.5 | 80 | 31.25 + 62.5 | 95 | 80 |
| PAPRH | 125 | 0 | 125 | 90 | 125 + 125 | 100 | 90 |
| PAPRH | 125 | 0 | 62.5 | 90 | 125 + 62.5 | 100 | 90 |
| PAPRH | 62.5 | 0 | 125 | 90 | 62.5 + 125 | 100 | 90 |
| PAPRH | 62.5 | 0 | 62.5 | 90 | 62.5 + 62.5 | 100 | 90 |
| PAPRH | 31.25 | 0 | 125 | 90 | 31.25 + 125 | 100 | 90 |
| PAPRH | 31.25 | 0 | 62.5 | 90 | 31.25 + 62.5 | 100 | 90 |
| STEME | 125 | 0 | 31.25 | 80 | 125 + 31.25 | 100 | 80 |
| STEME | 62.5 | 0 | 62.5 | 90 | 62.5 + 62.5 | 100 | 90 |

TABLE X57

Ex. 26 and cycloxydim, in post-emergence application at 20 DAT, wherein cycloxydim was used as EC formulation having an active ingredient concentration of 100 g/l.

| | solo application | | | | combination | | |
| --- | --- | --- | --- | --- | --- | --- | --- |
| | | | | | Ex. 26 + cycloxydim | | |
| | Ex. 26 | | cycloxydim | | | | COLBY |
| weed | use rate (gai/ha) | % activity | use rate (gai/ha) | % activity | use rate (gai/ha) | % activity | expected % activity |
| AVEFA | 250 | 85 | 12.5 | 20 | 250 + 12.5 | 98 | 88 |
| AVEFA | 125 | 65 | 12.5 | 20 | 125 + 12.5 | 90 | 72 |
| BRADC | 250 | 30 | 12.5 | 65 | 250 + 12.5 | 95 | 76 |
| BRADC | 125 | 0 | 12.5 | 65 | 125 + 12.5 | 95 | 65 |
| BROST | 125 | 5 | 12.5 | 25 | 125 + 12.5 | 35 | 29 |
| LOLMU | 250 | 25 | 12.5 | 90 | 250 + 12.5 | 98 | 93 |
| LOLMU | 125 | 0 | 12.5 | 90 | 125 + 12.5 | 98 | 90 |
| MATCH | 250 | 0 | 100 | 0 | 250 + 100 | 30 | 0 |
| MATCH | 250 | 0 | 50 | 0 | 250 + 50 | 30 | 0 |
| MATCH | 125 | 0 | 25 | 0 | 125 + 25 | 20 | 0 |
| MATCH | 125 | 0 | 100 | 0 | 125 + 100 | 30 | 0 |
| MATCH | 125 | 0 | 50 | 0 | 125 + 50 | 30 | 0 |
| POAAN | 250 | 70 | 100 | 0 | 250 + 100 | 90 | 70 |
| POAAN | 250 | 70 | 50 | 0 | 250 + 50 | 80 | 70 |
| POAAN | 250 | 70 | 25 | 0 | 250 + 25 | 98 | 70 |
| POAAN | 250 | 70 | 12.5 | 0 | 250 + 12.5 | 98 | 70 |
| POAAN | 125 | 40 | 100 | 0 | 125 + 100 | 70 | 40 |
| POAAN | 125 | 40 | 50 | 0 | 125 + 50 | 75 | 40 |
| POAAN | 125 | 40 | 25 | 0 | 125 + 25 | 75 | 40 |
| POAAN | 125 | 40 | 12.5 | 0 | 125 + 12.5 | 75 | 40 |

TABLE X57-continued

Ex. 26 and cycloxydim, in post-emergence application at 20 DAT, wherein cycloxydim was used as EC formulation having an active ingredient concentration of 100 g/l.

| | solo application | | | | combination | | |
|---|---|---|---|---|---|---|---|
| | Ex. 26 | | cycloxydim | | Ex. 26 + cycloxydim | | COLBY |
| weed | use rate (gai/ha) | % activity | use rate (gai/ha) | % activity | use rate (gai/ha) | % activity | expected % activity |
| POLAV | 125 | 85 | 100 | 0 | 125 + 100 | 90 | 85 |
| POLAV | 125 | 85 | 25 | 0 | 125 + 25 | 90 | 85 |
| POLAV | 125 | 85 | 12.5 | 0 | 125 + 12.5 | 95 | 85 |
| POLCO | 250 | 30 | 100 | 0 | 250 + 100 | 98 | 30 |
| POLCO | 250 | 30 | 50 | 0 | 250 + 50 | 98 | 30 |
| POLCO | 250 | 30 | 25 | 0 | 250 + 25 | 98 | 30 |
| POLCO | 250 | 30 | 12.5 | 0 | 250 + 12.5 | 98 | 30 |
| POLCO | 125 | 5 | 100 | 0 | 125 + 100 | 50 | 5 |
| POLCO | 125 | 5 | 50 | 0 | 125 + 50 | 50 | 5 |
| POLCO | 125 | 5 | 25 | 0 | 125 + 25 | 65 | 5 |
| POLCO | 125 | 5 | 12.5 | 0 | 125 + 12.5 | 65 | 5 |

TABLE X58

Ex. 26 and clomazone, in pre-emergence application at 20 DAT, wherein clomazone was used as CS formulation having an active ingredient concentration of 360 g/l.

| | solo application | | | | combination | | |
|---|---|---|---|---|---|---|---|
| | Ex. 26 | | clomazone | | Ex. 26 + clomazone | | COLBY |
| weed | use rate (gai/ha) | % activity | use rate (gai/ha) | % activity | use rate (gai/ha) | % activity | expected % activity |
| ALOMY | 62.5 | 80 | 30 | 0 | 62.5 + 30 | 90 | 80 |
| AMBEL | 125 | 0 | 120 | 10 | 125 + 120 | 50 | 10 |
| AMBEL | 125 | 0 | 60 | 10 | 125 + 60 | 20 | 10 |
| AMBEL | 62.5 | 0 | 120 | 10 | 62.5 + 120 | 60 | 10 |
| AMBEL | 31.25 | 0 | 120 | 10 | 61.25 + 1250 | 20 | 10 |
| APESV | 125 | 70 | 120 | 65 | 125 + 120 | 95 | 90 |
| APESV | 125 | 70 | 15 | 20 | 125 + 15 | 90 | 76 |
| AVEFA | 31.25 | 20 | 30 | 0 | 31.25 + 30 | 30 | 20 |
| BRADC | 125 | 0 | 120 | 30 | 125 + 120 | 70 | 30 |
| BRADC | 125 | 0 | 60 | 0 | 125 + 60 | 65 | 0 |
| BRADC | 62.5 | 0 | 120 | 30 | 62.5 + 120 | 65 | 30 |
| BRADC | 62.5 | 0 | 60 | 0 | 62.5 + 60 | 55 | 0 |
| BRADC | 31.25 | 0 | 120 | 30 | 31.25 + 120 | 70 | 30 |
| BRADC | 31.25 | 0 | 60 | 0 | 31.25 + 60 | 50 | 0 |
| BRADC | 31.25 | 0 | 30 | 0 | 31.25 + 30 | 40 | 0 |
| BROST | 125 | 30 | 30 | 0 | 125 + 30 | 40 | 30 |
| BROST | 62.5 | 20 | 120 | 30 | 62.5 + 120 | 50 | 44 |
| BROST | 31.25 | 0 | 120 | 30 | 31.25 + 120 | 40 | 30 |
| DIGSA | 125 | 40 | 120 | 30 | 125 + 120 | 70 | 58 |
| DIGSA | 125 | 40 | 15 | 0 | 125 + 15 | 50 | 40 |
| DIGSA | 31.25 | 5 | 120 | 30 | 31.25 + 120 | 65 | 34 |
| ECHCG | 31.25 | 50 | 120 | 90 | 31.25 + 120 | 100 | 95 |
| GALAP | 62.5 | 0 | 30 | 80 | 62.5 + 30 | 85 | 80 |
| HELAN | 62.5 | 0 | 30 | 10 | 62.5 + 30 | 25 | 10 |
| LOLMU | 62.5 | 0 | 120 | 60 | 62.5 + 60 | 65 | 60 |
| LOLMU | 62.5 | 0 | 60 | 40 | 62.5 + 60 | 50 | 40 |
| LOLMU | 31.25 | 0 | 120 | 60 | 31.25 + 120 | 65 | 60 |
| POAAN | 125 | 65 | 60 | 30 | 125 + 60 | 95 | 76 |
| POAAN | 125 | 65 | 30 | 0 | 125 + 30 | 85 | 65 |
| POAAN | 125 | 65 | 15 | 0 | 125 + 15 | 90 | 65 |
| POAAN | 31.25 | 30 | 120 | 80 | 31.25 + 120 | 98 | 90 |
| POLCO | 125 | 0 | 120 | 75 | 125 + 120 | 95 | 75 |
| POLCO | 125 | 0 | 60 | 60 | 125 + 60 | 65 | 60 |
| POLCO | 62.5 | 0 | 120 | 75 | 62.5 + 120 | 95 | 75 |
| SETVI | 125 | 0 | 125 | 65 | 125 + 125 | 70 | 65 |
| SETVI | 125 | 0 | 60 | 30 | 125 + 60 | 65 | 30 |
| SETVI | 62.5 | 0 | 120 | 65 | 62.5 + 120 | 80 | 65 |

TABLE X58-continued

Ex. 26 and clomazone, in pre-emergence application at 20 DAT, wherein clomazone was used as CS formulation having an active ingredient concentration of 360 g/l.

| | solo application | | | | combination | | |
|---|---|---|---|---|---|---|---|
| | | | | | Ex. 26 + clomazone | | |
| | Ex. 26 | | clomazone | | | | COLBY |
| weed | use rate (gai/ha) | % activity | use rate (gai/ha) | % activity | use rate (gai/ha) | % activity | expected % activity |
| SETVI | 62.5 | 0 | 60 | 30 | 62.5 + 60 | 50 | 30 |
| SETVI | 31.25 | 0 | 60 | 30 | 31.25 + 60 | 50 | 30 |

TABLE X59

Ex. 26 and cinmethylin, in post-emergence application at 21 DAT, wherein cinmethylin was used as EC formulation having an active ingredient concentration of 750 g/l.

| | solo application | | | | combination | | |
|---|---|---|---|---|---|---|---|
| | | | | | Ex. 26 + cinmethylin | | |
| | Ex. 26 | | cinmethylin | | | | COLBY |
| weed | use rate (gai/ha) | % activity | use rate (gai/ha) | % activity | use rate (gai/ha) | % activity | expected % activity |
| AMBEL | 250 | 20 | 125 | 0 | 250 + 125 | 40 | 20 |
| AMBEL | 250 | 20 | 62.5 | 0 | 250 + 62.5 | 40 | 0 |
| AMBEL | 125 | 0 | 125 | 0 | 125 + 125 | 35 | 0 |
| AMBEL | 125 | 0 | 62.5 | 0 | 125 + 62.5 | 40 | 0 |
| AVEFA | 125 | 70 | 125 | 10 | 125 + 125 | 90 | 73 |
| BRADC | 250 | 40 | 500 | 20 | 250 + 500 | 75 | 52 |
| BRADC | 250 | 40 | 250 | 10 | 250 + 250 | 60 | 46 |
| BRADC | 250 | 40 | 62.5 | 0 | 250 + 62.5 | 45 | 40 |
| BRADC | 125 | 10 | 500 | 20 | 125 + 500 | 75 | 28 |
| BRADC | 125 | 10 | 250 | 10 | 125 + 250 | 40 | 19 |
| BRADC | 125 | 10 | 125 | 0 | 125 + 125 | 35 | 10 |
| BRADC | 125 | 10 | 62.5 | 0 | 125 + 62.5 | 30 | 10 |
| BROST | 250 | 25 | 250 | 25 | 250 + 250 | 65 | 44 |
| BROST | 250 | 25 | 62.5 | 10 | 250 + 62.5 | 65 | 33 |
| BROST | 125 | 15 | 62.5 | 10 | 125 + 62.5 | 30 | 24 |
| HELAN | 250 | 25 | 500 | 60 | 250 + 500 | 85 | 70 |
| HELAN | 250 | 25 | 62.5 | 30 | 250 + 62.5 | 70 | 48 |
| HELAN | 125 | 10 | 500 | 60 | 125 + 500 | 75 | 64 |
| LOLMU | 250 | 30 | 125 | 30 | 250 + 125 | 80 | 51 |
| LOLMU | 250 | 30 | 62.5 | 0 | 250 + 62.5 | 75 | 30 |
| LOLMU | 125 | 15 | 125 | 30 | 125 + 125 | 80 | 41 |
| LOLMU | 125 | 15 | 62.5 | 0 | 125 + 62.5 | 35 | 15 |
| MATCH | 250 | 20 | 125 | 0 | 250 + 125 | 25 | 20 |
| PAPRH | 250 | 15 | 500 | 55 | 250 + 500 | 80 | 62 |
| PAPRH | 250 | 15 | 250 | 20 | 250 + 250 | 70 | 32 |
| PAPRH | 250 | 15 | 125 | 20 | 250 + 125 | 60 | 32 |
| PAPRH | 125 | 0 | 500 | 55 | 125 + 500 | 70 | 55 |
| PAPRH | 125 | 0 | 250 | 20 | 125 + 250 | 60 | 20 |
| PAPRH | 125 | 0 | 125 | 20 | 125 + 125 | 60 | 20 |
| POAAN | 125 | 40 | 62.5 | 70 | 125 + 62.5 | 90 | 82 |
| POLCO | 250 | 85 | 500 | 0 | 250 + 500 | 90 | 85 |
| POLCO | 250 | 85 | 250 | 0 | 250 + 250 | 98 | 85 |
| POLCO | 250 | 85 | 125 | 0 | 250 + 125 | 98 | 85 |
| POLCO | 250 | 85 | 62.5 | 0 | 250 + 62.5 | 98 | 85 |
| POLCO | 125 | 35 | 500 | 0 | 125 + 500 | 80 | 35 |
| POLCO | 125 | 35 | 250 | 0 | 125 + 250 | 90 | 35 |
| POLCO | 125 | 35 | 125 | 0 | 125 + 125 | 95 | 35 |
| POLCO | 125 | 35 | 62.5 | 0 | 125 + 62.5 | 40 | 35 |
| SETVI | 250 | 15 | 62.5 | 20 | 250 + 62.5 | 60 | 32 |
| SETVI | 125 | 10 | 500 | 85 | 125 + 500 | 98 | 87 |
| SETVI | 125 | 10 | 125 | 55 | 125 + 125 | 65 | 60 |
| SETVI | 125 | 10 | 62.5 | 20 | 125 + 62.5 | 60 | 28 |
| STEME | 250 | 10 | 125 | 10 | 250 + 125 | 70 | 19 |
| STEME | 250 | 10 | 62.5 | 0 | 250 + 62.5 | 55 | 10 |
| STEME | 125 | 0 | 125 | 10 | 125 + 125 | 55 | 10 |
| STEME | 125 | 0 | 62.5 | 0 | 125 + 62.5 | 25 | 0 |

TABLE X60

Ex. 5 and terbuthylazin, in pre-emergence application at 20 DAT, wherein terbuthylazin was used as SC formulation having an active ingredient concentration of 500 g/l.

| | solo application | | | | combination | | |
|---|---|---|---|---|---|---|---|
| | Ex. 5 | | terbuthylazin | | Ex. 5 + therbutylazin | | COLBY |
| weed | use rate (gai/ha) | % activity | use rate (gai/ha) | % activity | use rate (gai/ha) | % activity | expected % activity |
| AMBEL | 62.5 | 70 | 500 | 65 | 62.5 + 500 | 95 | 90 |
| AMBEL | 62.5 | 70 | 62.5 | 0 | 62.5 + 62.5 | 80 | 70 |
| AVEFA | 125 | 90 | 500 | 0 | 125 + 500 | 98 | 90 |
| AVEFA | 125 | 90 | 250 | 0 | 125 + 250 | 95 | 90 |
| AVEFA | 62.5 | 75 | 500 | 0 | 62.5 + 500 | 90 | 75 |
| AVEFA | 62.5 | 75 | 250 | 0 | 62.5 + 250 | 90 | 75 |
| AVEFA | 62.5 | 75 | 125 | 0 | 62.5 + 125 | 80 | 75 |
| ECHCG | 62.5 | 85 | 125 | 0 | 62.5 + 125 | 98 | 85 |
| ECHCG | 62.5 | 85 | 62.5 | 0 | 62.5 + 62.5 | 90 | 85 |
| GALAP | 125 | 0 | 250 | 0 | 125 + 250 | 30 | 0 |
| GALAP | 125 | 0 | 125 | 0 | 125 + 125 | 65 | 0 |
| GALAP | 62.5 | 0 | 250 | 0 | 62.5 + 250 | 50 | 0 |
| GALAP | 62.5 | 0 | 125 | 0 | 62.5 + 125 | 65 | 0 |
| HELAN | 125 | 60 | 125 | 0 | 125 + 125 | 65 | 60 |
| HELAN | 125 | 60 | 62.5 | 0 | 125 + 62.5 | 65 | 60 |
| HELAN | 62.5 | 0 | 125 | 0 | 62.5 + 125 | 65 | 0 |
| HELAN | 62.5 | 0 | 62.5 | 0 | 62.5 + 62.5 | 30 | 0 |
| POLCO | 62.5 | 65 | 500 | 65 | 62.5 + 500 | 100 | 88 |
| POLCO | 62.5 | 65 | 250 | 0 | 62.5 + 250 | 100 | 65 |
| POLCO | 62.5 | 65 | 125 | 0 | 62.5 + 125 | 90 | 65 |
| POLCO | 62.5 | 65 | 62.5 | 0 | 62.5 + 62.5 | 70 | 65 |
| SETVI | 125 | 50 | 250 | 0 | 125 + 250 | 60 | 50 |
| SETVI | 125 | 50 | 125 | 0 | 125 + 125 | 70 | 50 |
| SETVI | 125 | 50 | 62.5 | 0 | 125 + 62.5 | 75 | 50 |

TABLE X61

Ex. 5 and quinmerac, in pre-emergence application at 20 DAT, wherein quinmerac was used as WP formulation having an active ingredient concentration of 50%.

| | solo application | | | | combination | | |
|---|---|---|---|---|---|---|---|
| | Ex. 5 | | quinmerac | | Ex. 5 + quinmerac | | COLBY |
| weed | use rate (gai/ha) | % activity | use rate (gai/ha) | % activity | use rate (gai/ha) | % activity | expected % activity |
| BRADC | 125 | 70 | 250 | 30 | 125 + 250 | 85 | 79 |
| BRADC | 125 | 70 | 125 | 0 | 125 + 125 | 90 | 70 |
| BRADC | 62.5 | 60 | 125 | 0 | 62.5 + 125 | 65 | 60 |
| BRADC | 62.5 | 60 | 62.5 | 0 | 62.5 + 62.5 | 65 | 60 |
| HELAN | 62.5 | 20 | 62.5 | 0 | 62.5 + 62.5 | 35 | 30 |

TABLE X62

Ex. 5 and metazachlor, in post-emergence application at 21 DAT, wherein metazachlor was used as SC formulation having an active ingredient concentration of 500 g/l.

| | solo application | | | | combination | | |
|---|---|---|---|---|---|---|---|
| | Ex. 5 | | metazachlor | | Ex. 5 + metazachlor | | COLBY |
| weed | use rate (gai/ha) | % activity | use rate (gai/ha) | % activity | use rate (gai/ha) | % activity | expected % activity |
| AVEFA | 250 | 85 | 250 | 10 | 250 + 250 | 95 | 87 |
| AVEFA | 250 | 85 | 31.25 | 0 | 250 + 31.25 | 90 | 85 |
| AVEFA | 125 | 80 | 125 | 0 | 125 + 125 | 85 | 80 |

TABLE X62-continued

Ex. 5 and metazachlor, in post-emergence application at 21 DAT, wherein metazachlor was used as SC formulation having an active ingredient concentration of 500 g/l.

| | solo application | | | | combination | | |
|---|---|---|---|---|---|---|---|
| | Ex. 5 | | metazachlor | | Ex. 5 + metazachlor | | COLBY |
| weed | use rate (gai/ha) | % activity | use rate (gai/ha) | % activity | use rate (gai/ha) | % activity | expected % activity |
| AVEFA | 125 | 80 | 31.25 | 0 | 125 + 31.25 | 85 | 80 |
| AVEFA | 62.5 | 80 | 250 | 10 | 62.5 + 250 | 95 | 82 |
| DIGSA | 62.5 | 35 | 31.25 | 10 | 62.5 + 31.25 | 50 | 42 |
| GALAP | 250 | 25 | 250 | 85 | 250 + 250 | 95 | 89 |
| GALAP | 31.25 | 10 | 250 | 85 | 31.25 + 250 | 95 | 87 |
| GALAP | 31.25 | 10 | 125 | 80 | 31.25 + 125 | 90 | 82 |
| MATCH | 250 | 60 | 125 | 0 | 250 + 125 | 65 | 60 |
| MATCH | 125 | 30 | 62.5 | 0 | 125 + 62.5 | 60 | 30 |
| MATCH | 62.5 | 30 | 125 | 0 | 62.5 + 125 | 65 | 30 |
| PAPRH | 62.5 | 60 | 125 | 20 | 62.5 + 125 | 90 | 68 |
| POLAV | 62.5 | 90 | 31.25 | 20 | 62.5 + 31.25 | 98 | 92 |

TABLE X63

Ex. 5 and Mesosulfuron - Methyl, in post-emergence application at 20 DAT, wherein Mesosulfuron - Methyl was used as WG formulation having an active ingredient concentration of 4.5%.

| | solo application | | | | combination | | |
|---|---|---|---|---|---|---|---|
| | Ex. 5 | | mesosulfuron | | Ex. 5 + mesosulfuron | | COLBY |
| weed | use rate (gai/ha) | % activity | use rate (gai/ha) | % activity | use rate (gai/ha) | % activity | expected % activity |
| GALAP | 62.5 | 0 | 8 | 75 | 62.5 + 8 | 85 | 75 |
| GALAP | 62.5 | 0 | 4 | 65 | 62.5 + 4 | 85 | 65 |
| GALAP | 62.5 | 0 | 2 | 65 | 62.5 + 2 | 70 | 65 |
| GALAP | 62.5 | 0 | 1 | 55 | 62.5 + 1 | 60 | 55 |
| MATCH | 62.5 | 40 | 2 | 30 | 62.5 + 2 | 75 | 58 |
| PAPRH | 62.5 | 25 | 1 | 70 | 62.5 + 1 | 85 | 78 |
| SETVI | 62.5 | 55 | 8 | 85 | 62.5 + 8 | 98 | 93 |

TABLE X64

Ex. 5 and flufenacet, in post-emergence application at 20 DAT, wherein flufenacet was used as SC formulation having an active ingredient concentration of 500 g/l.

| | solo application | | | | combination | | |
|---|---|---|---|---|---|---|---|
| | Ex. 5 | | flufenacet | | Ex. 5 + flufenacet | | COLBY |
| weed | use rate (gai/ha) | % activity | use rate (gai/ha) | % activity | use rate (gai/ha) | % activity | expected % activity |
| BRADC | 125 | 40 | 125 | 0 | 125 + 125 | 45 | 40 |
| BRADC | 62.5 | 35 | 250 | 35 | 62.5 + 250 | 75 | 58 |
| BRADC | 62.5 | 35 | 125 | 0 | 62.5 + 125 | 75 | 35 |
| BRADC | 62.5 | 35 | 62.5 | 0 | 62.5 + 62.5 | 60 | 35 |
| BRADC | 62.5 | 35 | 31.25 | 0 | 62.5 + 31.25 | 60 | 35 |
| BROST | 62.5 | 35 | 250 | 80 | 62.5 + 250 | 95 | 87 |
| BROST | 62.5 | 35 | 125 | 65 | 62.5 + 125 | 90 | 77 |
| MATCH | 250 | 30 | 62.5 | 0 | 250 + 62.5 | 80 | 30 |
| MATCH | 250 | 30 | 31.25 | 0 | 250 + 31.25 | 65 | 30 |
| MATCH | 125 | 40 | 125 | 50 | 125 + 125 | 50 | 40 |

TABLE X64-continued

Ex. 5 and flufenacet, in post-emergence application at 20 DAT, wherein flufenacet was used as SC formulation having an active ingredient concentration of 500 g/l.

| | solo application | | | | combination | | |
|---|---|---|---|---|---|---|---|
| | Ex. 5 | | flufenacet | | Ex. 5 + flufenacet | | COLBY |
| weed | use rate (gai/ha) | % activity | use rate (gai/ha) | % activity | use rate (gai/ha) | % activity | expected % activity |
| MATCH | 125 | 40 | 62.5 | 0 | 125 + 62.5 | 65 | 40 |
| MATCH | 125 | 40 | 31.25 | 0 | 125 + 31.25 | 65 | 40 |
| PAPRH | 125 | 65 | 250 | 0 | 125 + 250 | 100 | 65 |
| PAPRH | 125 | 65 | 125 | 0 | 125 + 125 | 100 | 65 |
| PAPRH | 62.5 | 70 | 250 | 0 | 62.5 + 250 | 100 | 70 |
| PAPRH | 62.5 | 70 | 125 | 0 | 62.5 + 125 | 90 | 70 |
| PAPRH | 62.5 | 70 | 62.5 | 0 | 62.5 + 62.5 | 90 | 70 |
| PAPRH | 62.5 | 70 | 31.25 | 0 | 62.5 + 31.25 | 98 | 70 |
| POLAV | 125 | 90 | 250 | 0 | 125 + 250 | 98 | 90 |
| POLAV | 125 | 90 | 125 | 0 | 125 + 125 | 98 | 90 |
| POLAV | 125 | 90 | 62.5 | 0 | 125 + 62.5 | 95 | 90 |
| POLAV | 125 | 90 | 31.25 | 0 | 125 + 31.25 | 98 | 90 |
| POLAV | 62.5 | 90 | 250 | 0 | 62.5 + 250 | 95 | 90 |
| POLAV | 62.5 | 90 | 125 | 0 | 62.5 + 125 | 95 | 90 |
| POLAV | 62.5 | 90 | 62.5 | 0 | 62.5 + 62.5 | 98 | 90 |
| POLAV | 62.5 | 90 | 31.25 | 0 | 62.5 + 31.25 | 95 | 90 |
| POLCO | 62.5 | 60 | 250 | 50 | 62.5 + 250 | 100 | 80 |
| POLCO | 62.5 | 60 | 125 | 30 | 62.5 + 125 | 100 | 72 |
| POLCO | 62.5 | 60 | 62.5 | 30 | 62.5 + 62.5 | 100 | 72 |
| POLCO | 62.5 | 60 | 31.25 | 0 | 62.5 + 31.25 | 100 | 60 |
| SETVI | 125 | 40 | 125 | 55 | 125 + 125 | 80 | 73 |
| SETVI | 62.5 | 30 | 125 | 55 | 62.5 + 125 | 90 | 69 |
| SETVI | 62.5 | 30 | 62.5 | 35 | 62.5 + 62.5 | 98 | 55 |

TABLE X65

Ex. 5 and dimethenamid (DMTA), in pre-emergence application at 20 DAT, wherein DMTA was used as EC formulation having an active ingredient concentration of 720 g/l.

| | solo application | | | | combination | | |
|---|---|---|---|---|---|---|---|
| | Ex. 5 | | dimethenamid | | Ex. 5 + dimethenamid | | COLBY |
| weed | use rate (gai/ha) | % activity | use rate (gai/ha) | % activity | use rate (gai/ha) | % activity | expected % activity |
| AMBEL | 62.5 | 70 | 250 | 30 | 62.5 + 250 | 100 | 79 |
| AMBEL | 62.5 | 70 | 125 | 20 | 62.5 + 125 | 100 | 76 |
| AMBEL | 62.5 | 70 | 62.5 | 0 | 62.5 + 62.5 | 85 | 70 |
| AMBEL | 62.5 | 70 | 31.25 | 0 | 62.5 + 31.25 | 100 | 70 |
| AMBEL | 31.25 | 10 | 250 | 30 | 31.25 + 250 | 90 | 37 |
| AMBEL | 31.25 | 10 | 125 | 20 | 31.25 + 125 | 75 | 28 |
| AMBEL | 31.25 | 10 | 62.5 | 0 | 31.25 + 62.5 | 60 | 10 |
| AMBEL | 31.25 | 10 | 31.25 | 0 | 31.25 + 31.25 | 30 | 10 |
| AVEFA | 62.5 | 75 | 62.5 | 10 | 62.5 + 62.5 | 85 | 78 |
| BROST | 31.25 | 5 | 62.5 | 80 | 31.25 + 62.5 | 85 | 81 |
| GALAP | 125 | 0 | 125 | 50 | 125 + 125 | 85 | 50 |
| GALAP | 125 | 0 | 62.5 | 60 | 125 + 62.5 | 100 | 60 |
| GALAP | 125 | 0 | 31.25 | 50 | 125 + 31.25 | 100 | 50 |
| GALAP | 62.5 | 0 | 125 | 50 | 62.5 + 125 | 95 | 50 |
| GALAP | 62.5 | 0 | 62.5 | 60 | 62.5 + 62.5 | 100 | 60 |
| GALAP | 31.25 | 0 | 125 | 50 | 31.25 + 625 | 100 | 50 |
| HELAN | 62.5 | 0 | 250 | 35 | 62.5 + 250 | 60 | 35 |
| HELAN | 62.5 | 0 | 125 | 0 | 62.5 + 125 | 30 | 0 |
| HELAN | 62.5 | 0 | 62.5 | 0 | 62.5 + 62.5 | 30 | 0 |
| HELAN | 31.25 | 0 | 125 | 0 | 31.25 + 125 | 20 | 0 |
| PAPRH | 31.25 | 0 | 62.5 | 90 | 31.25 + 62.5 | 100 | 90 |

TABLE X66

Ex. 5 and cycloxydim, in post-emergence application at 20 DAT, wherein cycloxydim was used as EC formulation having an active ingredient concentration of 100 g/l.

| | solo application | | | | combination | | |
|---|---|---|---|---|---|---|---|
| | | | | | Ex. 5 + cycloxydim | | COLBY |
| | Ex. 5 | | cycloxydim | | | | |
| weed | use rate (gai/ha) | % activity | use rate (gai/ha) | % activity | use rate (gai/ha) | % activity | expected % activity |
| AVEFA | 250 | 85 | 12.5 | 20 | 250 + 12.5 | 98 | 88 |
| AVEFA | 125 | 85 | 12.5 | 20 | 125 + 12.5 | 98 | 88 |
| BRADC | 250 | 60 | 12.5 | 65 | 250 + 12.5 | 95 | 86 |
| BRADC | 125 | 40 | 12.5 | 65 | 125 + 12.5 | 95 | 79 |
| BROST | 250 | 80 | 12.5 | 25 | 250 + 12.5 | 90 | 85 |
| MATCH | 250 | 30 | 100 | 0 | 250 + 100 | 60 | 30 |
| MATCH | 250 | 30 | 12.5 | 0 | 250 + 12.5 | 50 | 30 |
| PAPRH | 125 | 65 | 100 | 0 | 125 + 100 | 85 | 65 |
| PAPRH | 125 | 65 | 12.5 | 0 | 125 + 12.5 | 95 | 65 |
| POLAV | 125 | 90 | 100 | 0 | 125 + 100 | 98 | 90 |
| POLAV | 125 | 90 | 50 | 0 | 125 + 50 | 95 | 90 |
| POLAV | 125 | 90 | 25 | 0 | 125 + 25 | 98 | 90 |
| POLAV | 125 | 90 | 12.5 | 0 | 125 + 12.5 | 95 | 90 |

TABLE X67

Ex. 26 and terbuthylazin, in pre-emergence application at 20 DAT, wherein terbuthylazin was used as SC formulation having an active ingredient concentration of 500 g/l.

| | solo application | | | | combination | | |
|---|---|---|---|---|---|---|---|
| | | | | | Ex. 26 + therbutylazin | | COLBY |
| | Ex. 26 | | terbuthylazin | | | | |
| weed | use rate (gai/ha) | % activity | use rate (gai/ha) | % activity | use rate (gai/ha) | % activity | expected % activity |
| ALOMY | 62.5 | 85 | 250 | 40 | 62.5 + 250 | 98 | 91 |
| APESV | 125 | 75 | 125 | 50 | 125 + 125 | 98 | 88 |
| APESV | 125 | 75 | 62.5 | 0 | 125 + 62.5 | 85 | 75 |
| AVEFA | 125 | 75 | 500 | 0 | 125 + 500 | 80 | 75 |
| AVEFA | 125 | 75 | 250 | 0 | 125 + 250 | 80 | 75 |
| AVEFA | 125 | 75 | 125 | 0 | 125 + 125 | 98 | 75 |
| AVEFA | 62.5 | 55 | 500 | 0 | 62.5 + 500 | 90 | 55 |
| BROST | 125 | 35 | 250 | 0 | 125 + 250 | 40 | 35 |
| BROST | 125 | 35 | 62.5 | 0 | 125 + 62.5 | 45 | 35 |
| DIGSA | 125 | 45 | 500 | 20 | 125 + 500 | 65 | 56 |
| DIGSA | 125 | 45 | 250 | 0 | 125 + 250 | 60 | 45 |
| DIGSA | 125 | 45 | 125 | 0 | 125 + 125 | 50 | 45 |
| DIGSA | 62.5 | 20 | 250 | 0 | 62.5 + 250 | 30 | 20 |
| ECHCG | 62.5 | 60 | 500 | 0 | 62.5 + 500 | 70 | 60 |
| ECHCG | 62.5 | 60 | 250 | 0 | 62.5 + 250 | 65 | 60 |
| LOLMU | 125 | 0 | 500 | 35 | 125 + 500 | 55 | 35 |
| LOLMU | 125 | 0 | 250 | 10 | 125 + 250 | 20 | 10 |
| LOLMU | 125 | 0 | 125 | 0 | 125 + 125 | 20 | 0 |
| LOLMU | 62.5 | 0 | 500 | 35 | 62.5 + 500 | 40 | 35 |
| POAAN | 62.5 | 70 | 250 | 70 | 62.5 + 250 | 98 | 91 |
| POAAN | 62.5 | 70 | 125 | 30 | 62.5 + 125 | 95 | 79 |
| POAAN | 62.5 | 70 | 62.5 | 0 | 62.5 + 62.5 | 80 | 70 |
| POLCO | 125 | 0 | 250 | 0 | 125 + 250 | 50 | 0 |
| POLCO | 62.5 | 0 | 500 | 65 | 62.5 + 500 | 70 | 65 |
| STEME | 125 | 0 | 62.5 | 70 | 125 + 62.5 | 95 | 70 |
| SETVI | 125 | 0 | 250 | 0 | 125 + 250 | 20 | 0 |

TABLE X68

Ex. 26 and quinmerac, in pre-emergence application at 20 DAT, wherein quinmerac was used as WP formulation having an active ingredient concentration of 50%.

| | solo application | | | | combination | | |
|---|---|---|---|---|---|---|---|
| | Ex. 26 | | quinmerac | | Ex. 26 + quinmerac | | COLBY |
| weed | use rate (gai/ha) | % activity | use rate (gai/ha) | % activity | use rate (gai/ha) | % activity | expected % activity |
| AMBEL | 125 | 0 | 250 | 0 | 125 + 250 | 30 | 0 |
| AMBEL | 62.5 | 0 | 250 | 0 | 62.5 + 250 | 30 | 0 |
| APESV | 125 | 70 | 250 | 25 | 125 + 250 | 85 | 78 |
| APESV | 125 | 70 | 62.5 | 0 | 125 + 362.5 | 75 | 70 |
| AVEFA | 125 | 65 | 125 | 0 | 125 + 125 | 70 | 65 |
| AVEFA | 125 | 65 | 31.25 | 0 | 125 + 31.25 | 70 | 65 |
| AVEFA | 62.5 | 45 | 125 | 0 | 125 + 62.5 | 50 | 45 |
| BROST | 125 | 30 | 62.5 | 0 | 125 + 62.5 | 35 | 30 |
| DIGSA | 125 | 40 | 125 | 0 | 125 + 125 | 65 | 40 |
| DIGSA | 125 | 40 | 62.5 | 0 | 125 + 62.5 | 50 | 40 |
| DIGSA | 125 | 40 | 31.25 | 0 | 125 + 31.25 | 50 | 40 |
| GALAP | 125 | 0 | 125 | 95 | 125 + 125 | 100 | 95 |
| HELAN | 62.5 | 0 | 125 | 0 | 62.5 + 125 | 25 | 0 |
| LOLMU | 62.5 | 0 | 250 | 0 | 62.5 + 250 | 10 | 0 |
| PAPRH | 62.5 | 0 | 250 | 95 | 62.5 + 250 | 100 | 95 |
| POAAN | 125 | 65 | 250 | 0 | 125 + 250 | 85 | 65 |
| POAAN | 125 | 65 | 125 | 0 | 125 + 125 | 80 | 65 |
| POAAN | 125 | 65 | 62.5 | 0 | 125 + 62.5 | 85 | 65 |
| STEME | 15 | 40 | 250 | 0 | 125 + 250 | 55 | 40 |
| STEME | 62.5 | 30 | 250 | 0 | 62.5 + 250 | 45 | 30 |

TABLE X69

Ex. 26 and metazachlor, in post-emergence application at 21 DAT, wherein metazachlor was used as SC formulation having an active ingredient concentration of 500 g/l.

| | solo application | | | | combination | | |
|---|---|---|---|---|---|---|---|
| | Ex. 26 | | metazachlor | | Ex. 26 + metazachlor | | COLBY |
| weed | use rate (gai/ha) | % activity | use rate (gai/ha) | % activity | use rate (gai/ha) | % activity | expected % activity |
| AVEFA | 125 | 70 | 250 | 10 | 125 + 250 | 95 | 73 |
| AVEFA | 125 | 70 | 62.5 | 10 | 125 + 62.5 | 80 | 73 |
| AVEFA | 62.5 | 70 | 250 | 10 | 62.5 + 250 | 95 | 73 |
| AVEFA | 62.5 | 70 | 125 | 0 | 62.5 + 125 | 95 | 70 |
| BRADC | 250 | 40 | 125 | 25 | 250 + 125 | 75 | 55 |
| BRADC | 250 | 40 | 62.5 | 20 | 250 + 62.5 | 65 | 52 |
| BRADC | 125 | 10 | 125 | 25 | 125 + 125 | 45 | 33 |
| BRADC | 125 | 10 | 31.25 | 10 | 125 + 31.25 | 30 | 19 |
| BRADC | 62.5 | 0 | 250 | 60 | 62.5 + 250 | 75 | 60 |
| DIGSA | 250 | 20 | 31.25 | 0 | 250 + 31.25 | 25 | 20 |
| DIGSA | 125 | 20 | 250 | 75 | 125 + 250 | 85 | 80 |
| DIGSA | 125 | 20 | 31.25 | 0 | 125 + 31.25 | 25 | 20 |
| DIGSA | 62.5 | 20 | 250 | 75 | 62.5 + 250 | 90 | 80 |
| GALAP | 250 | 25 | 250 | 85 | 250 + 250 | 95 | 89 |
| LOLMU | 250 | 30 | 250 | 85 | 250 + 250 | 95 | 90 |
| LOLMU | 250 | 30 | 31.25 | 30 | 250 + 31.25 | 65 | 51 |
| LOLMU | 125 | 15 | 250 | 85 | 125 + 250 | 95 | 87 |
| LOLMU | 125 | 15 | 31.25 | 30 | 125 + 31.25 | 50 | 41 |
| LOLMU | 62.5 | 0 | 250 | 85 | 62.5 + 250 | 90 | 85 |
| LOLMU | 62.5 | 0 | 125 | 85 | 62.5 + 125 | 90 | 85 |
| MATCH | 62.5 | 0 | 250 | 20 | 62.5 + 250 | 30 | 20 |
| MATCH | 62.5 | 0 | 62.5 | 0 | 62.5 + 62.5 | 10 | 0 |
| MATCH | 62.5 | 0 | 31.25 | 0 | 62.5 + 31.25 | 10 | 0 |
| POAAN | 62.5 | 30 | 250 | 85 | 62.5 + 250 | 95 | 90 |
| POLAV | 125 | 90 | 125 | 25 | 125 + 125 | 98 | 93 |
| POLCO | 250 | 85 | 250 | 20 | 250 + 250 | 95 | 88 |
| POLCO | 250 | 85 | 62.5 | 0 | 250 + 62.5 | 98 | 85 |
| POLCO | 250 | 85 | 31.25 | 0 | 250 + 31.25 | 98 | 85 |
| POLCO | 125 | 35 | 250 | 20 | 125 + 250 | 90 | 48 |
| POLCO | 125 | 35 | 125 | 10 | 125 + 125 | 65 | 42 |

TABLE X69-continued

Ex. 26 and metazachlor, in post-emergence application at 21 DAT, wherein metazachlor was used as SC formulation having an active ingredient concentration of 500 g/l.

| | solo application | | | | combination | | |
|---|---|---|---|---|---|---|---|
| | Ex. 26 | | metazachlor | | Ex. 26 + metazachlor | | COLBY |
| weed | use rate (gai/ha) | % activity | use rate (gai/ha) | % activity | use rate (gai/ha) | % activity | expected % activity |
| POLCO | 125 | 35 | 62.5 | 0 | 125 + 62.5 | 90 | 35 |
| POLCO | 125 | 35 | 31.25 | 0 | 125 + 31.25 | 80 | 35 |
| POLCO | 62.5 | 0 | 250 | 20 | 62.5 + 250 | 30 | 20 |
| POLCO | 62.5 | 0 | 125 | 10 | 62.5 + 125 | 60 | 10 |
| POLCO | 62.5 | 0 | 31.25 | 0 | 62.5 + 31.25 | 30 | 0 |
| SETVI | 125 | 10 | 31.25 | 65 | 125 + 31.25 | 90 | 69 |
| SETVI | 62.5 | 10 | 31.25 | 65 | 62.5 + 31.25 | 80 | 69 |
| STEME | 250 | 10 | 250 | 35 | 250 + 250 | 75 | 42 |
| STEME | 250 | 10 | 125 | 25 | 250 + 125 | 65 | 33 |
| STEME | 250 | 10 | 62.5 | 0 | 250 + 62.5 | 65 | 10 |
| STEME | 250 | 10 | 31.25 | 0 | 250 + 31.25 | 30 | 10 |
| STEME | 125 | 0 | 250 | 35 | 125 + 250 | 65 | 35 |
| STEME | 125 | 0 | 125 | 25 | 125 + 125 | 40 | 25 |
| STEME | 125 | 0 | 62.5 | 0 | 125 + 62.5 | 20 | 0 |
| STEME | 125 | 0 | 31.25 | 0 | 125 + 31.25 | 15 | 0 |
| STEME | 62.5 | 0 | 250 | 35 | 62.5 + 250 | 70 | 35 |
| STEME | 62.5 | 0 | 125 | 25 | 62.5 + 125 | 50 | 25 |
| STEME | 62.5 | 0 | 62.5 | 0 | 62.5 + 62.5 | 35 | 0 |

TABLE X70

Ex. 5 and clomazone, in pre-emergence application at 20 DAT, wherein clomazone was used as CS formulation having an active ingredient concentration of 360 g/l.

| | solo application | | | | combination | | |
|---|---|---|---|---|---|---|---|
| | Ex. 5 | | clomazone | | Ex. 5 + clomazone | | COLBY |
| weed | use rate (gai/ha) | % activity | use rate (gai/ha) | % activity | use rate (gai/ha) | % activity | expected % activity |
| AMBEL | 125 | 85 | 120 | 10 | 125 + 120 | 100 | 87 |
| AMBEL | 125 | 85 | 60 | 10 | 125 + 60 | 100 | 87 |
| AMBEL | 125 | 85 | 15 | 0 | 125 + 15 | 98 | 85 |
| AMBEL | 31.25 | 20 | 1250 | 10 | 31.25 + 120 | 35 | 28 |
| BRADC | 125 | 70 | 120 | 30 | 125 + 120 | 98 | 79 |
| BRADC | 125 | 70 | 60 | 0 | 125 + 60 | 100 | 70 |
| BRADC | 125 | 70 | 15 | 0 | 125 + 15 | 85 | 70 |
| BRADC | 62.5 | 60 | 120 | 30 | 62.5 + 120 | 80 | 72 |
| BRADC | 62.5 | 60 | 60 | 0 | 62.5 + 60 | 70 | 60 |
| BRADC | 62.5 | 60 | 30 | 0 | 62.5 + 30 | 70 | 60 |
| BRADC | 31.25 | 20 | 30 | 0 | 31.25 + 30 | 30 | 20 |
| DIGSA | 31.25 | 40 | 120 | 30 | 31.25 + 120 | 75 | 58 |
| DIGSA | 31.25 | 40 | 60 | 0 | 31.25 + 60 | 50 | 40 |
| SETVI | 125 | 50 | 30 | 0 | 125 + 30 | 60 | 50 |
| SETVI | 62.5 | 30 | 30 | 0 | 62.5 + 30 | 35 | 30 |

TABLE X71

Ex. 5 and cinmethylin, in post-emergence application at 21 DAT, wherein cinmethylin was used as EC formulation having an active ingredient concentration of 750 g/l.

| | solo application | | | | combination | | |
|---|---|---|---|---|---|---|---|
| | | | | | Ex. 5 + cinmethylin | | |
| | Ex. 5 | | cinmethylin | | | | COLBY |
| weed | use rate (gai/ha) | % activity | use rate (gai/ha) | % activity | use rate (gai/ha) | % activity | expected % activity |
| BRADC | 250 | 70 | 125 | 0 | 250 + 125 | 75 | 70 |
| BRADC | 125 | 60 | 500 | 20 | 125 + 500 | 85 | 68 |
| BRADC | 125 | 60 | 125 | 0 | 125 + 125 | 70 | 60 |
| DIGSA | 250 | 80 | 250 | 20 | 250 + 250 | 95 | 84 |
| DIGSA | 250 | 80 | 125 | 15 | 250 + 125 | 95 | 83 |
| DIGSA | 250 | 80 | 62.5 | 0 | 250 + 62.5 | 85 | 80 |
| DIGSA | 125 | 60 | 250 | 20 | 125 + 250 | 90 | 68 |
| DIGSA | 125 | 60 | 125 | 15 | 125 + 125 | 90 | 66 |
| DIGSA | 125 | 60 | 62.5 | 0 | 125 + 62.5 | 80 | 60 |
| LOLMU | 250 | 85 | 62.5 | 0 | 250 + 62.5 | 90 | 85 |
| LOLMU | 125 | 85 | 125 | 30 | 125 + 125 | 95 | 90 |
| MATCH | 125 | 30 | 125 | 0 | 125 + 125 | 60 | 30 |
| PAPRH | 250 | 80 | 62.5 | 0 | 250 + 62.5 | 85 | 80 |
| PAPRH | 125 | 60 | 62.5 | 0 | 125 + 62.5 | 65 | 60 |
| SETVI | 125 | 70 | 125 | 55 | 125 + 125 | 98 | 87 |

The invention claimed is:
1. A herbicidal composition comprising
A) a phenylpyrimidine of formula (I)

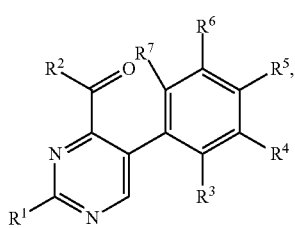

(I)

wherein in formula (I) the variables have the following meanings:

$R^1$ $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_3$-$C_6$-haloalkynyl, $C_3$-$C_6$-cycloalkyl, $C_3$-$C_6$-cycloalkenyl, $C_3$-$C_6$-halocycloalkyl, $C_3$-$C_6$-halocycloalkenyl, [1-($C_1$-$C_6$-alkyl)]-$C_3$-$C_6$-cycloalkyl, [1-($C_2$-$C_6$-alkenyl)]-$C_3$-$C_6$-cycloalkyl, [1-($C_2$-$C_6$-alkynyl)]-$C_3$-$C_6$-cycloalkyl, [1-($C_1$-$C_6$-haloalkyl)]-$C_3$-$C_6$-cycloalkyl, [1-($C_2$-$C_6$-haloalkenyl)]-$C_3$-$C_6$-cycloalkyl, [1-($C_3$-$C_6$-haloalkynyl)]-$C_3$-$C_6$-cycloalkyl, $C_3$-$C_6$-cycloalkyl-$C_1$-$C_6$-alkyl, $C_3$-$C_6$-cycloalkyl-$C_1$-$C_6$-haloalkyl;

$R^2$ H, halogen, $C_1$-$C_6$-alkyl, $C_1$-$C_6$-haloalkyl, OH, $C_1$-$C_6$-alkoxy, $C_1$-$C_6$-alkoxy-$C_1$-$C_6$-alkoxy, $C_1$-$C_6$-haloalkoxy-$C_1$-$C_6$-alkoxy, $C_1$-$C_6$-alkoxy-$C_1$-$C_6$-haloalkoxy, $C_1$-$C_6$-haloalkoxy-$C_1$-$C_6$-haloalkoxy, $C_1$-$C_6$-alkoxy-$C_1$-$C_6$-alkoxy-$C_1$-$C_6$-alkoxy, $C_1$-$C_6$-haloalkoxy, $C_1$-$C_6$-hydroxyalkoxy, $C_3$-$C_6$-alkenyloxy, $C_3$-$C_6$-alkenyloxy-$C_1$-$C_6$-alkoxy, $C_3$-$C_6$-haloalkenyloxy-$C_1$-$C_6$-haloalkoxy, $C_3$-$C_6$-alkenyloxy-$C_1$-$C_6$-haloalkoxy, $C_3$-$C_6$-haloalkenyloxy, $C_3$-$C_6$-alkynyloxy, $C_3$-$C_6$-haloalkynyloxy, $C_3$-$C_6$-alkynyloxy-$C_1$-$C_6$-alkoxy, $C_3$-$C_6$-haloalkynyloxy-$C_1$-$C_6$-haloalkoxy, $C_3$-$C_6$-alkynyloxy-$C_1$-$C_6$-haloalkoxy, $C_3$-$C_6$-alkynyloxy-$C_3$-$C_6$-alkenyloxy, $C_3$-$C_6$-haloalkynyloxy-$C_3$-$C_6$-alkenyloxy, $C_3$-$C_6$-alkynyloxy-$C_3$-$C_6$-haloalkenyloxy, $C_3$-$C_6$-haloalkynyloxy-$C_3$-$C_6$-haloalkenyloxy, $C_3$-$C_6$-alkynyloxy-$C_3$-$C_6$-alkynyloxy, $C_3$-$C_6$-haloalkynyloxy-$C_3$-$C_6$-alkynyloxy, $C_3$-$C_6$-alkynyloxy-$C_3$-$C_6$-haloalkynyloxy, $C_3$-$C_6$-haloalkynyloxy-$C_3$-$C_6$-haloalkynyloxy, $C_3$-$C_6$-cycloalkoxy, $C_3$-$C_6$-halocycloalkoxy, ($C_3$-$C_6$-cycloalkyl)$C_1$-$C_6$-alkoxy, ($C_3$-$C_6$-halocycloalkyl)$C_1$-$C_6$-alkoxy, ($C_3$-$C_6$-cycloalkyl)$C_1$-$C_6$-haloalkoxy, ($C_3$-$C_6$-halocycloalkyl)$C_1$-$C_6$-haloalkoxy, $C_1$-$C_6$-alkylthio, $C_1$-$C_6$-haloalkylthio, $C_2$-$C_6$-alkenylthio, $C_2$-$C_6$-haloalkenylthio, $C_2$-$C_6$-alkynylthio, $C_2$-$C_6$-haloalkynylthio, $C_1$-$C_6$-haloalkylthio, $C_3$-$C_6$-cycloalkylthio, $C_3$-$C_6$-halocycloalkylthio, ($C_3$-$C_6$-cycloalkyl)$C_1$-$C_6$-alkylthio, ($C_3$-$C_6$-cycloalkyl)$C_1$-$C_6$-haloalkylthio, ($C_3$-$C_6$-halocycloalkyl)$C_1$-$C_6$-alkylthio, $R^3$ halogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy, $C_1$-$C_6$-haloalkoxy, $C_3$-$C_6$-alkenyloxy, $C_3$-$C_6$-haloalkenyloxy, $C_3$-$C_6$-alkynyloxy, $C_3$-$C_6$-haloalkynyloxy, $C_1$-$C_6$-alkoxy-$C_1$-$C_6$-alkoxy, $C_3$-$C_6$-cycloalkyl; and $R^4$, $R^5$, $R^6$ and $R^7$ independently of one another
H, halogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl;

including agriculturally acceptable salts or derivatives of the compounds of formula (I) having a carboxyl group;

and an herbicide B selected from the group consisting of cinmethylin, trifludimoxazin, bentazone, bromoxynil, saflufenacil, dicamba, diflufenican, flufenacet, flumioxazin, isoproturon, metazachlor, metribuzin, pendimethalin, picolinafen, pinoxaden, prosulfocarb, pyridate, pyroxasulfone, pyroxsulam, saflufenazil, sulfosulfuron, terbutylazin, dimethenamid, mesosulfuron, iodosulfuron, cycloxydim, clomazone, quinmerac, and topramezone;

including their agriculturally acceptable salts or derivatives.

2. The composition according to claim 1 wherein in compound of formula (I) $R^1$ is $C_1$-$C_6$-alkyl, or $C_3$-$C_6$-cycloalkyl, wherein the cycloalkyl substituent is unsubstituted.

3. The composition according to claim 1, wherein in compound of formula (I) $R^2$ is OH, $C_1$-$C_6$-alkoxy, $C_1$-$C_6$-haloalkoxy, $C_3$-$C_6$-alkynyloxy, or $C_1$-$C_6$-alkylthio.

4. The composition according to claim 1, wherein in compound of formula (I) $R^3$ is halogen, $C_1$-$C_6$-alkyl, $C_1$-$C_6$-haloalkyl, or $C_3$-$C_6$-cycloalkyl.

5. The composition according to claim 1, wherein in compound of formula (I) $R^4$, $R^5$, $R^6$ and $R^7$ independently of one another are H, halogen, $C_1$-$C_6$-alkyl, $C_1$-$C_6$-haloalkyl, $C_2$-$C_6$-alkenyl, or $C_3$-$C_6$-cycloalkyl.

6. The composition according to claim 1, wherein in compound of formula (I)
$R^1$ is $C_3$-$C_6$-cycloalkyl;
$R^2$ is OH or $C_1$-$C_6$-alkoxy;
$R^3$ is halogen;
$R^4$, $R^6$ and $R^7$ are H;
$R^5$ is H or halogen.

7. The composition according to claim 1, wherein in compound of formula (I)
$R^1$ is c-$C_3H_5$;
$R^2$ is OH or $OCH_3$;
$R^3$ is Cl;
$R^4$, $R^6$ and $R^7$ are H;
$R^5$ is H or F.

8. The composition according to claim 1 wherein the weight ratio of component A to component B is in the range of from 1:500 to 500:1.

9. The composition according to claim 1 additionally comprises safener as component C.

10. The composition according claim 9 wherein the weight ratio of component A to component C is in the range of from 1:500 to 500:1.

11. A herbicidal composition comprising a composition as claimed in claim 1 and at least one inert liquid and/or solid carrier and optionally at least one surface-active substance.

12. A method of controlling undesired vegetation, which comprises allowing a herbicidal composition as claimed in claim 1 to act on plants, their environment or on seed.

13. The method of claim 12, wherein in the compound of formula (I) $R^1$ is $C_1$-$C_6$-alkyl or $C_3$-$C_6$-cycloalkyl, wherein the cycloalkyl substituent is unsubstituted.

14. The method of claim 12, wherein in the compound of formula (I) $R^2$ is OH, $C_1$-$C_6$-alkoxy, $C_1$-$C_6$-haloalkoxy, or $C_3$-$C_6$-alkynyloxy.

15. The method of claim 12, wherein in the compound of formula (I) $R^3$ is halogen, $C_1$-$C_6$-alkyl, $C_1$-$C_6$-haloalkyl, $C_1$-$C_6$-alkoxy or $C_3$-$C_6$-cycloalkyl.

16. The method of claim 12, wherein in compound of formula (I) $R^4$, $R^5$, $R^6$ and $R^7$ independently of one another are H, halogen, $C_1$-$C_6$-alkyl, $C_1$-$C_6$-haloalkyl, $C_2$-$C_6$-alkenyl, or $C_3$-$C_6$-cycloalkyl;
wherein the cycloalkyl substituents independently from one another are unsubstituted or substituted by one to five substituents selected from the group consisting of halogen, CN, $NO_2$, $C_1$-$C_6$-alkyl, $C_1$-$C_6$-haloalkyl, $C_1$-$C_6$-alkoxy or $C_1$-$C_6$-haloalkoxy.

17. The method of claim 12, wherein in compound of formula (I)
$R^1$ is $C_3$-$C_6$-cycloalkyl;
$R^2$ is OH or $C_1$-$C_6$-alkoxy;
$R^3$ is halogen;
$R^4$, $R^6$ and $R^7$ are H;
$R^5$ is H or halogen.

18. The method of claim 12, wherein in compound of formula (I)
$R^1$ is c-$C_3H_5$;
$R^2$ is OH or $OCH_3$;
$R^3$ is Cl;
$R^4$, $R^6$ and $R^7$ are H;
$R^5$ is H or F.

* * * * *